US010696631B2

(12) United States Patent
Chen et al.

(10) Patent No.: US 10,696,631 B2
(45) Date of Patent: Jun. 30, 2020

(54) CHEMICAL CONJUGATES OF EVANS BLUE DERIVATIVES AND THEIR USE AS RADIOTHERAPY AND IMAGING AGENTS

(71) Applicant: THE UNITED STATES OF AMERICA, AS REPRESENTED BY THE SECRETARY, DEPARTMENT OF HEALTH AND HUMAN SERVICES, Bethesda, MD (US)

(72) Inventors: Xiaoyuan Chen, Potomac, MD (US); Orit Jacobson Weiss, Silver Spring, MD (US)

(73) Assignee: THE UNITED STATES OF AMERICA, AS REPRESENTED BY THE SECRETARY, DEPARTMENT OF HEALTH AND HUMAN SERVICES, Bethesda, MD (US)

( * ) Notice: Subject to any disclaimer, the term of this patent is extended or adjusted under 35 U.S.C. 154(b) by 0 days.

(21) Appl. No.: 16/099,488

(22) PCT Filed: May 9, 2017

(86) PCT No.: PCT/US2017/031696
§ 371 (c)(1),
(2) Date: Nov. 7, 2018

(87) PCT Pub. No.: WO2017/196806
PCT Pub. Date: Nov. 16, 2017

(65) Prior Publication Data
US 2019/0084931 A1 Mar. 21, 2019

Related U.S. Application Data

(60) Provisional application No. 62/333,427, filed on May 9, 2016.

(51) Int. Cl.
| | | |
|---|---|---|
| *C07D 207/452* | (2006.01) |
| *C07D 207/444* | (2006.01) |
| *A61K 51/04* | (2006.01) |
| *A61K 51/08* | (2006.01) |
| *C07B 59/00* | (2006.01) |
| *A61P 35/00* | (2006.01) |

(52) U.S. Cl.
CPC ...... *C07D 207/452* (2013.01); *A61K 51/0497* (2013.01); *A61K 51/082* (2013.01); *A61K 51/088* (2013.01); *C07B 59/002* (2013.01); *C07D 207/444* (2013.01); *A61P 35/00* (2018.01); *C07B 2200/05* (2013.01)

(58) Field of Classification Search
CPC .............. A61K 51/0497; A61K 51/088; A61K 51/082; C07D 207/444; C07D 207/452; C07B 59/002; C07B 2200/05; A61P 35/00

See application file for complete search history.

(56) References Cited

U.S. PATENT DOCUMENTS

| 7,368,099 B2 | 5/2008 | Katayama et al. |
| 2016/0287730 A1 | 10/2016 | Chen et al. |

FOREIGN PATENT DOCUMENTS

| CN | 103242255 | * | 1/2015 | .......... C07D 255/02 |
| CN | 104650217 | A | 5/2015 | |
| WO | 2004075925 | A1 | 9/2004 | |
| WO | 2006025304 | A1 | 3/2006 | |
| WO | 2016209795 | A1 | 12/2016 | |
| WO | 2017192874 | A1 | 11/2017 | |
| WO | 2019070236 | A1 | 4/2019 | |
| WO | 2019165200 | A1 | 8/2019 | |

OTHER PUBLICATIONS

Haojun Chen et al., "Chemical Conjugation of Evans Blue Derivative: A Strategy to Develop Long-Acting Therapeutics through Albumin Binding", Theranostics, vol. 6, Issue 2, Jan. 1, 2016, 11 pages.
Haojun Chen et al., "Novel molecular "add-on" based on Evans Blue confers superior pharmacokinetics and transforms drugs to theranostic agents", Journal of Nuclear Medicine, vol. 58, No. 4, Nov. 22, 2016, 10 pages.
International Search Report issued in International Application No. PCT/US2017/031696 dated Aug. 18, 2017, 7 pages.
Satheesh Chandran M. et al., "Preparation and Characterization of Chain-Extended Bismaleimide/Carbon Fibre Composites" International Journal of Polymer Science, vol. 2010, 2010, 9 pages.
Written Opinion issued in International Application No. PCT/US2017/031696 dated Aug. 18, 2017, 9 pages.
Yi Liu et al., "Stable Evans Blue Derived Exendin-4 Peptide for Type 2 Diabetes Treatment", Bioconjugate Chemistry, vol. 27, No. 1, Jan. 20, 2016, 12 pages.
Zhibo Liu et al., "Simple bioconjugate chemistry serves great clinical advances: albumin as a versatile platform for diagnosis and precision therapy", Chemical Society Reviews, vol. 45, No. 5, Mar. 7, 2016, 48 pages.
International Preliminary Report on Patentability issued in Application No. PCT/US2017/031696 dated Nov. 13, 2018, 10 pages.
Gang Niu. et al., "In Vivo Labeling of Serum Albumin for PET" The Journal of Nuclear Medicine (2014), vol. 55, No. 7, pp. 1150-1156.
Kaspar, A., Reicher, J., "Future directions for peptide therapeutics development" Drug Discovery Today (2013) vol. 18, No. 17, pp. 807-817.
Wang, Y. et al., "In vivo albumin labeling and lymphatic imaging" PNAS (2015) vol. 112, No. 1, pp. 208-213.
Extended European Search Report issued in EP Application No. 17796666.0 dated Oct. 10, 2019, 5 pages.

* cited by examiner

*Primary Examiner* — Michael G. Hartley
*Assistant Examiner* — Leah H Schlientz
(74) *Attorney, Agent, or Firm* — Cantor Colburn LLP

(57) ABSTRACT

The present invention is directed to a compound of Formula I or Formula III or a pharmaceutically acceptable ester, amide, solvate, or salt thereof, or a salt of such an ester or amide or a solvate of such an ester amide or salt: wherein the definitions $R_1$-$R_{13}$ and $L_1$-$L_4$ are provided in the disclosure, and wherein R14 is a peptide. The compounds of Formula I may be covalently bonded to a peptide via a linker to provide a compound of Formula III and thereby extend the half-life of the therapeutic compound. The invention is also directed to pharmaceutical compositions of the disclosed compounds, as well as their use in the diagnosis or treatment of diseases.

46 Claims, 80 Drawing Sheets

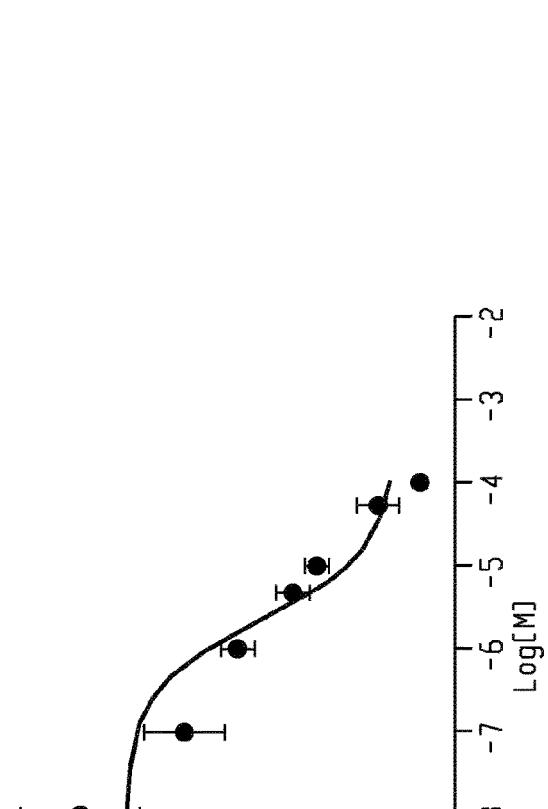
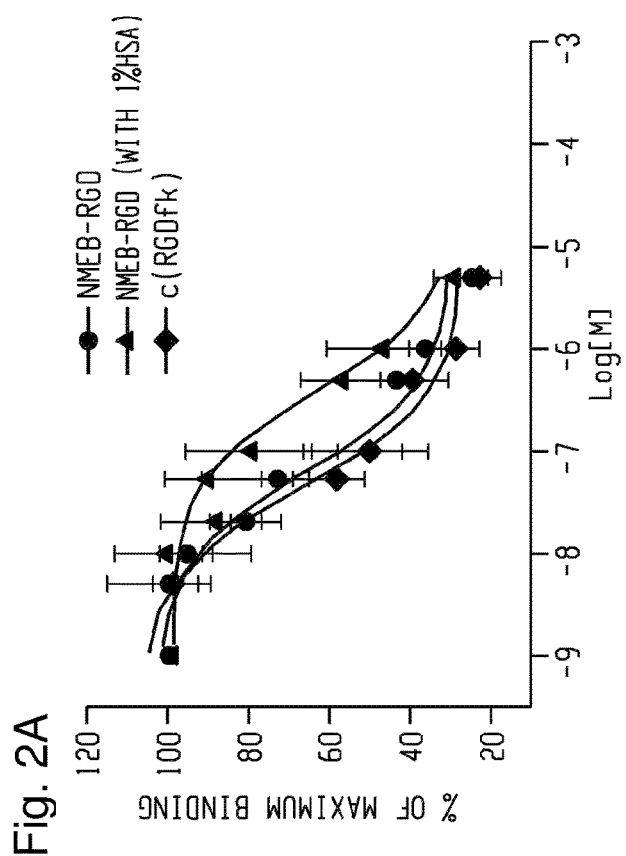

$K_{on}$ 58233; $K_{off}$ 0.2843; $K_d$ 4.8 μM

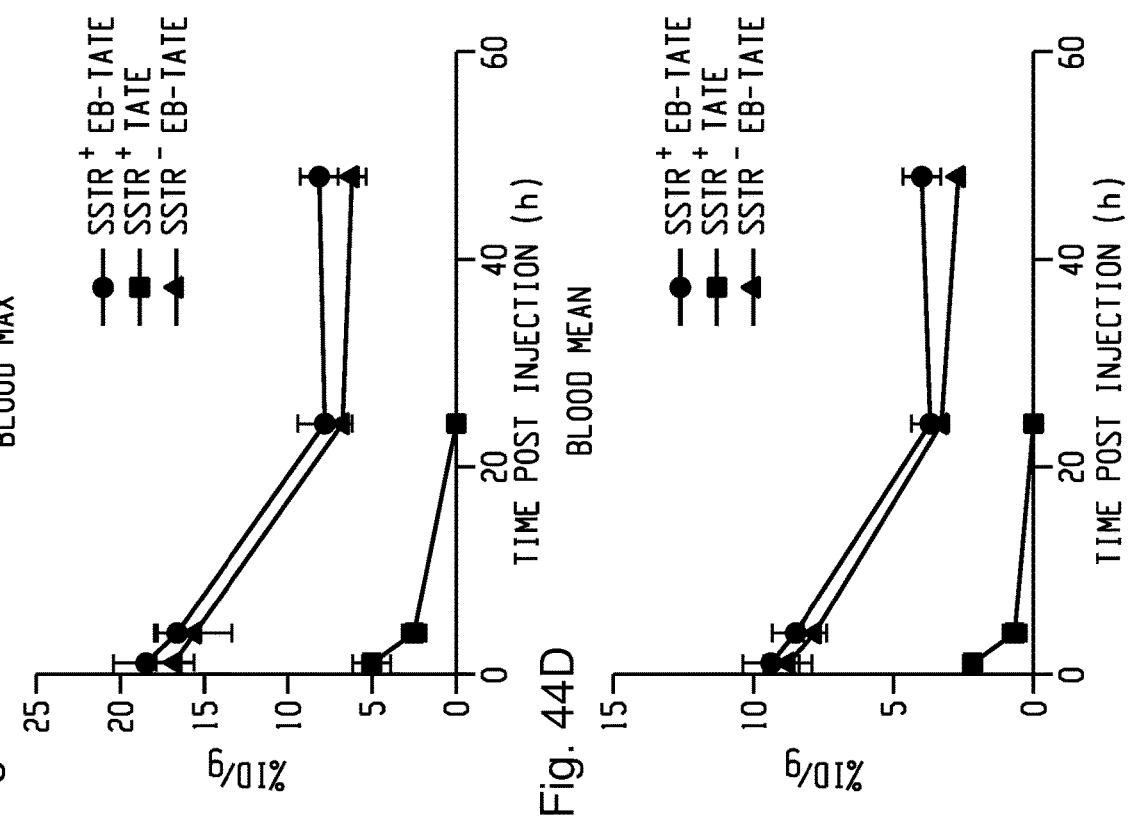
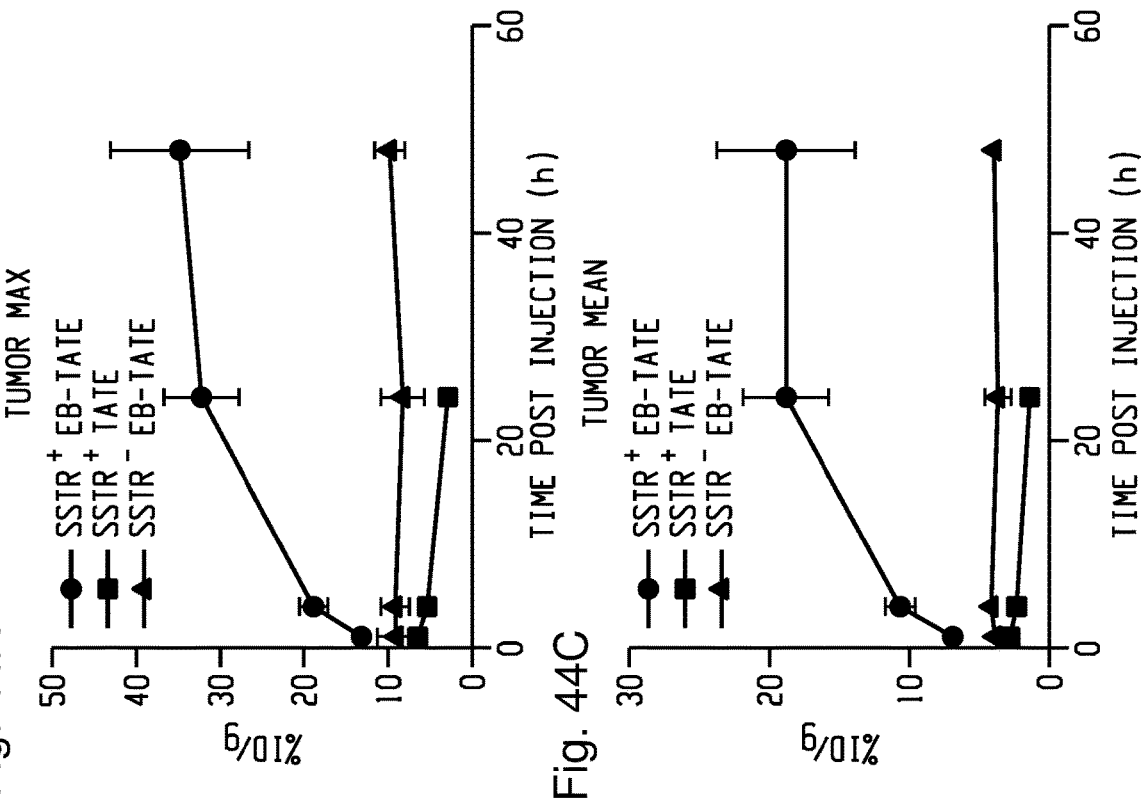
Fig. 44A, Fig. 44B, Fig. 44C, Fig. 44D

NO TREATMENT  AFTER TREATMENT

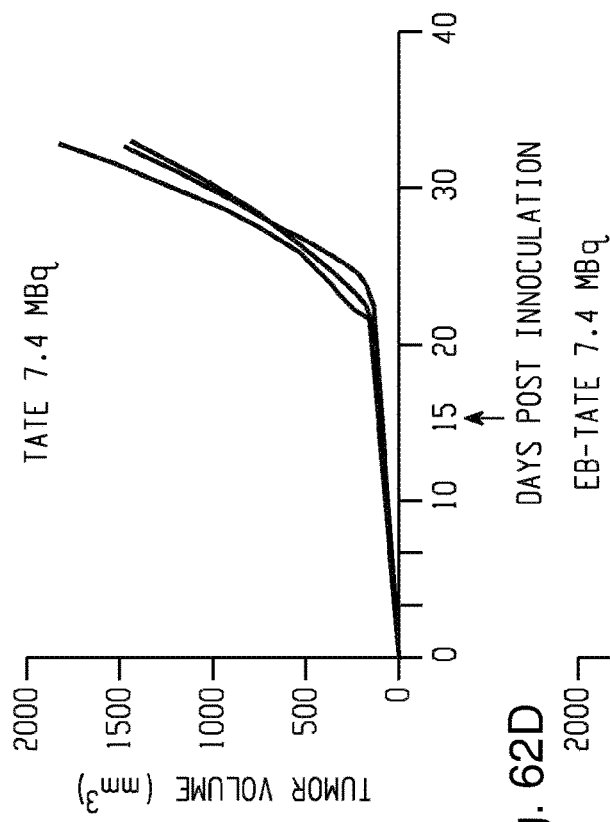
Fig. 62A
Fig. 62B
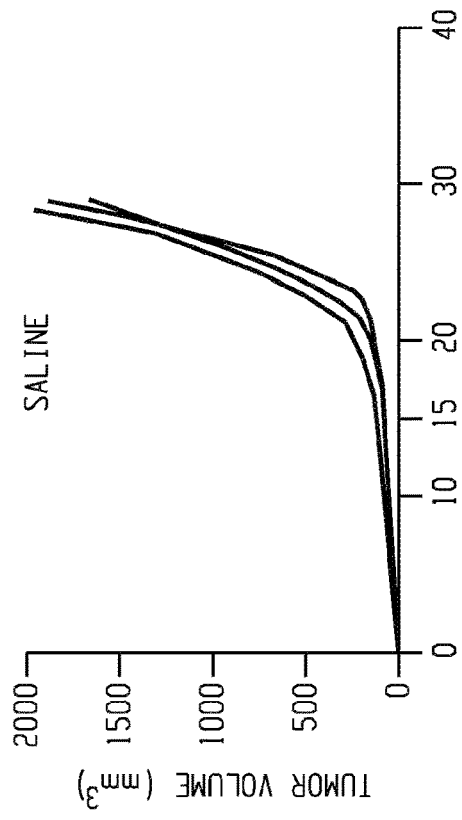
Fig. 62C
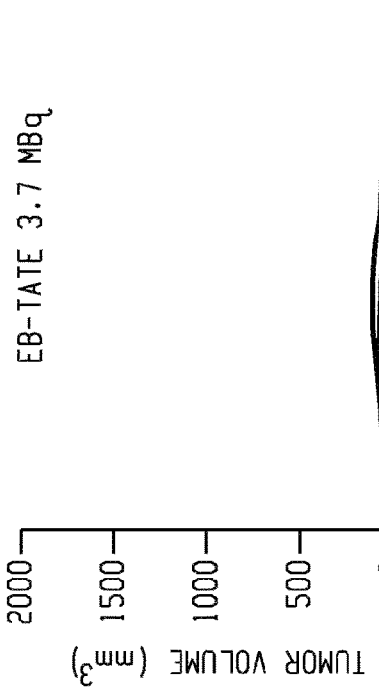
Fig. 62D

A. SALINE
B. $^{90}$Y-EB-TATE SSTR2$^+$ 7.4MBq
C. $^{90}$Y-EB-TATE SSTR2$^+$ 3.9MBq
D. $^{90}$Y-TATE SSTR2$^+$ 7.4MBq
E. $^{90}$Y-EB-TATE SSTR2$^-$ 7.4MBq

CHEMICAL CONJUGATES OF EVANS BLUE DERIVATIVES AND THEIR USE AS RADIOTHERAPY AND IMAGING AGENTS

CROSS-REFERENCE TO RELATED APPLICATION

This application is a § 371 US National Stage application of International Application No. PCT/US2017/031696 filed 9 May 2017, which claims priority to U.S. Provisional Patent Application No. 62/333,427, filed on 9 May 2016. Each of these applications are incorporated herein by reference in their entireties.

STATEMENT OF GOVERNMENT SUPPORT

This invention was made in part with government support from the National Institutes of Health. The United States government has certain rights in the invention.

FIELD OF THE INVENTION

The present invention relates to functionalized derivatives of Evans Blue dye, and more particularly to functionalized derivatives of Evans Blue dye that are useful as radiotherapy and imaging agents.

BRIEF DESCRIPTION OF THE ART

The effectiveness of pharmaceuticals depends heavily on pharmacokinetics. In particular, compounds for pharmaceutical use must have sufficient half-life to exert the desired effect on the patient. Various approaches have been used to increase the half-life of pharmaceutical compounds in the body. One method of increasing half-life is to reduce the rate of clearance of the drug from the body, which can be done by inhibition of clearance mechanisms, either through direct modification of the drug, or by addition of other agents which act on the clearance pathways. Reduction of clearance is particularly desired for protein drugs, as they are highly vulnerable to degradation by proteases.

As the kidney generally filters out molecules below 60 kDa, one method of clearance rate reduction is to increase the molecular size of the protein drug through, for example, protein fusions, glycosylation, or the addition of polyethylene glycol polymers (PEG). However, some of these approaches have disadvantages. For example, one common strategy to improve the pharmacokinetics of pharmaceutical agents is to attach poly(ethylene glycol) (PEG) moieties to therapeutic compounds, a process known as PEGylation. However, the covalent attachment of PEG to a drug or therapeutic protein can mask the agent from the host's immune system to reduce immunogenicity and antigenicity, and increase the hydrodynamic size of the agent which prolongs its circulatory time by reducing renal clearance. PEGylation can also provide water solubility to hydrophobic drugs and proteins. However, due to the bulky size of PEG chain, the biological activity is inevitably compromised after PEGylation.

Fusion of small molecule or protein drugs with large proteins such as albumin or the Fc domain of immunoglobulin G (IgG) can increase drug half-life by increasing the molecular size of the drug and in turn reducing renal clearance. In addition to increasing size, fusion with either albumin or the IgG Fc domain adds functionality to the fused complex and enables interaction with the neonatal Fc receptor (FcRn), which salvages bound ligands from intracellular catabolism by recycling them back to circulation. This interaction with FcRn contributes to the extraordinarily long 21 day serum half-life of albumin and IgG in humans. Therefore, engineering proteins or small molecule drugs to interact with albumin or serum IgG has the potential to significantly increase half-life by reducing both renal clearance and intracellular catabolism. Through these methods the in vivo exposure of the therapeutics can be extended.

As the most abundant protein in blood plasma (around 50 mg/ml), human serum albumin (HSA) with a molecular weight of 66.5 kDa is the chief carrier protein in the blood. It acts as the chief solubilizing agent for long chain fatty acids, a detoxifying protein through its binding of bilirubin, and the transport vehicle for heavy metal ions in the blood. Since the mid-1990s albumin has been studied as a carrier protein, either for targeting drugs to inflamed or malignant tissue or for extending their half-life. Two principal albumin-based technologies have been developed for therapeutic use. One method is to pass lipophilic drugs and HSA under high pressure through a jet to form albumin-drug nanoparticles. The other is to develop albumin-binding peptides or prodrugs that bind in situ to circulating albumin, either covalently or non-covalently, after intravenous injection.

Due to the extreme abundance in the blood circulation, albumin has advantages over immunoglobulin G (IgG) as the drug carrier. Taking drug release into consideration, physical binding is preferred to covalent binding since there is a need for a balance between albumin binding affinity and efficient drug release from the binding. To make a prodrug covalently bind to albumin, the cysteine-34 position of albumin is commonly used, since the free thiol group of cysteine-34 is a unique feature of an extracellular protein and accounts for approximately 90% of the thiol concentration in blood plasma. For example, the first and most advanced prototype of these types of prodrugs is the (6-maleimidocaproyl)hydrazone derivative of doxorubicin (DOXO-EMCH), an acid-sensitive prodrug of doxorubicin that is rapidly and selectively bound to the cysteine-34 position of endogenous albumin after intravenous administration. Aldoxorubicin contains an acid-sensitive hydrazone linker allowing doxorubicin to be released either extracellularly in the slightly acidic environment often present in tumor tissue or intracellularly in acidic endosomal or lysosomal compartments after cellular uptake of the albumin conjugate by the tumor cell.

One example of physical interaction with albumin is the development of Levemir® (Novo Nordisk), an insulin analog for treating diabetes, in which myristic acid (tetradecanoic acid) is bound to the lysine amino acid at position B29. The fatty acid on the Levemir attach to serum albumin makes it a long-acting form of insulin. Besides insulin administration, another other option of controlling glucose levels in diabetes is to stimulate insulin secretion. The peptide hormone GLP-1-(7-37) results from selective cleavage of the proglucagon molecule and increases insulin secretion in pancreatic cells but only has a half-life of 1.5-2 min due to degradation by ubiquitous enzymes. In analogy to Levemir®, GLP-1-(7-37) is derivatized with a fatty acid, for example palmitic acid, at the ε-amino position of lysine introduced at the N-terminal position of glutamic acid in the GLP-1 peptide sequence. The resulting new drug liraglutide (Victoza®) is an albumin-binding derivative of GLP-1 stable against metabolic degradation due to albumin-binding, and has a plasma half-life of 11-15 h after subcutaneous administration. Additional examples of anti-diabetic peptides modified for better drug-like properties are disclosed by Kaspar, et al. "Future Directions for Peptide Therapeutics Development", *Drug Discovery Today*, 18(17):807-817 (2013).

Albumin-based drug delivery systems are not only important treatment options for metabolic disorders such as diabetes but are also useful for cancer therapy. Using albumin as a drug carrier has several unique advantages for drug delivery to solid tumors. First, albumin-based drug carriers offer enhanced permeability and retention of macromolecules in relation to passive tumor targeting (EPR effect). Moreover, two albumin-binding proteins were found to be overexpressed in tumor environment including the gp60 receptor on tumor endothelium and SPARC, a secreted glycoprotein with high binding affinity to albumin in the tumor interstitium. Besides the EPR effect, the interplay of two albumin-binding proteins facilitates the uptake and retention of albumin in the tumor.

Evans Blue (EB) is an azo dye with a high affinity for serum albumin. It is frequently used in the measurement of blood volume, but it can also be used to show permeability to macromolecules. Because EB strongly binds to albumin, it can serve as a marker of where the large albumin molecules are localized, and thus it can be used to assess permeability of barriers, such as of the blood-brain barrier (BBB). Because albumin cannot cross the BBB and virtually all EB is bound to albumin, EB will only enter the CNS if the BBB has been compromised. EB has also been used in a viability assay, as the EB bound to albumin will enter damaged or non-viable cells, but not healthy cells.

Derivatives of Evans Blue dye are known in the art. For example, Chinese patent CN103242255 to Zhang, et al. discloses imaging agents in which a truncated version of EB which binds to albumin is linked with a macrocyclic chelating group (NOTA, 1,4,7-triazacyclononane-N,N',N''-triacetic acid) that can bind a radionuclide or other labels. Such derivatives made with macrocyclic chelating groups make an agent useful in blood pool imaging. Similarly, International patent application WO2004075925 to Katayama et al. discloses an agent useful for imaging of an exfoliated vascular endothelial site in which a truncated version of EB which binds to albumin is linked to a linear chelating group that binds to a radionuclide. The synthesis and use of EB-NOTA has been disclosed (see Niu et al., "In Vivo Labeling of Serum Albumin for PET", *J. Nucl. Med.* 55:1150-1156 (2014)).

The drug-albumin conjugates discussed above can increase half-life of the bound drug, but do not have improved targeting to specific tissues unless those tissues bind albumin. Ability to specifically target certain cells or tissues might improve therapeutic effect of the conjugates.

Because of the broad potential for albumin-based therapeutics, there is a need for improved drug-albumin conjugates. The present invention is believed to be an answer to that need.

SUMMARY OF THE INVENTION

In one aspect, the present invention is directed to a compound of Formula I or a pharmaceutically acceptable ester, amide, solvate, or salt thereof, or a salt of such an ester or amide or a solvate of such an ester amide or salt:

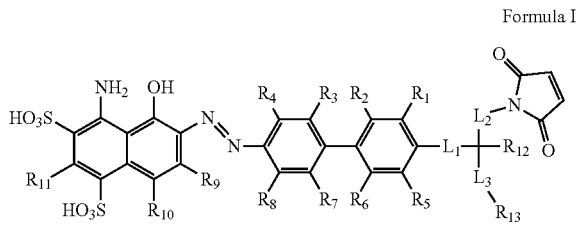

Formula I wherein: $R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy;

$R_{12}$ is hydrogen, $C_1$-$C_6$alkyl, or $C_1$-$C_6$haloalkyl;

$L_1$ is —(CH$_2$)$_m$— wherein m is an integer from 0 to 12, wherein each CH$_2$ can be individually replaced with —O—, —NH(CO)—, or —(CO)—NH—, providing no two adjacent CH$_2$ groups are replaced;

$L_2$ is —(CH$_2$)$_n$— wherein n is an integer from 0 to 12, wherein each CH$_2$ can be individually replaced with —O—, —NH(CO)—, or —(CO)—NH—, providing no two adjacent CH$_2$ groups are replaced;

$L_3$ is —(CH$_2$)$_p$— wherein p is an integer from 0 to 12, wherein each CH$_2$ can be individually replaced with —O—, —NH(CO)—, or —(CO)—NH—, providing no two adjacent CH$_2$ groups are replaced; and $R_{13}$ is a chelating group.

In another aspect, the present invention is directed to a compound of Formula III or a pharmaceutically acceptable ester, amide, solvate, or salt thereof, or a salt of such an ester or amide or a solvate of such an ester amide or salt:

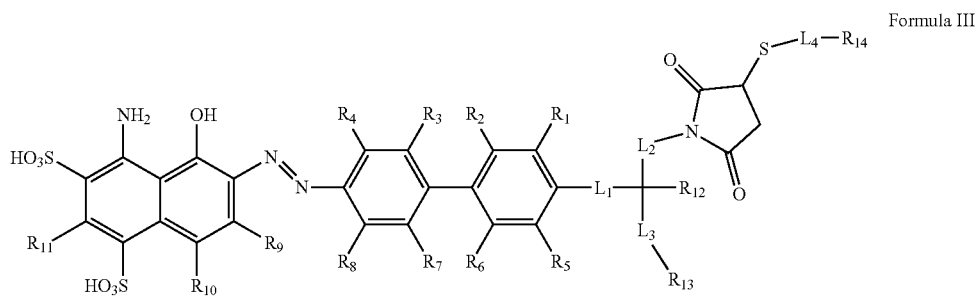

Formula III wherein:

$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy;

$R_{12}$ is hydrogen, $C_1$-$C_6$alkyl, or $C_1$-$C_6$haloalkyl;

$R_{14}$ is a peptide;

$L_1$ is —$(CH_2)_m$— wherein m is an integer from 0 to 12, wherein each $CH_2$ can be individually replaced with —O—, —NH(CO)—, or —(CO)—NH—, providing no two adjacent $CH_2$ groups are replaced;

$L_2$ is —$(CH_2)_n$— wherein n is an integer from 0 to 12, wherein each $CH_2$ can be individually replaced with —O—, —NH(CO)—, or —(CO)—NH—, providing no two adjacent $CH_2$ groups are replaced;

$L_3$ is —$(CH_2)_p$— wherein p is an integer from 0 to 12, wherein each $CH_2$ can be individually replaced with —O—, —NH(CO)—, or —(CO)—NH—, providing no two adjacent $CH_2$ groups are replaced; and $L_4$ is —$(CH_2)_q$— wherein q is an integer from 0 to 12, wherein each $CH_2$ can be individually replaced with —O—, —NH(CO)—, or —(CO)—NH—, providing no two adjacent $CH_2$ groups are replaced; and $R_{13}$ is a chelating group.

In yet another aspect, the present invention is directed to a pharmaceutical composition comprising one of the above-described compounds, the compound further comprising a radionuclide, together with a pharmaceutically acceptable carrier.

In yet another aspect, the present invention is directed to a method of treating or diagnosing cancer in a mammal, comprising administering to said mammal a therapeutically effective amount of one of the above-described compounds, optionally in combination with one or more additional active ingredients.

These and other aspects will become apparent upon reading the following detailed description of the invention.

BRIEF DESCRIPTION OF THE DRAWINGS

The following description of the invention will be better understood when taken in conjunction with the following drawings in which:

FIGS. 2A-2C are plots of % maximum binding versus concentration (Log molar, Log [M]) for compounds to integrin $\alpha_v\beta_3$ without competitor (FIG. 2A), for compounds to integrin $\alpha_v\beta_3$ with $^{64}$Cu-NOTA-c(RGDfk) competition (FIG. 2B), and for compounds to albumin (FIG. 2C);

FIGS. 44A, 44B, 44C, and 44D are plots showing tumor and blood TACs of $^{86}$Y-EB-TATE and $^{86}$Y-TATE;

FIGS. 62A, 62B, 62C, and 62D are plots showing $^{90}$Y radiotherapy in AR42J xenografts tumor growth curves;

DETAILED DESCRIPTION OF THE INVENTION

Terminology

Figure 1:
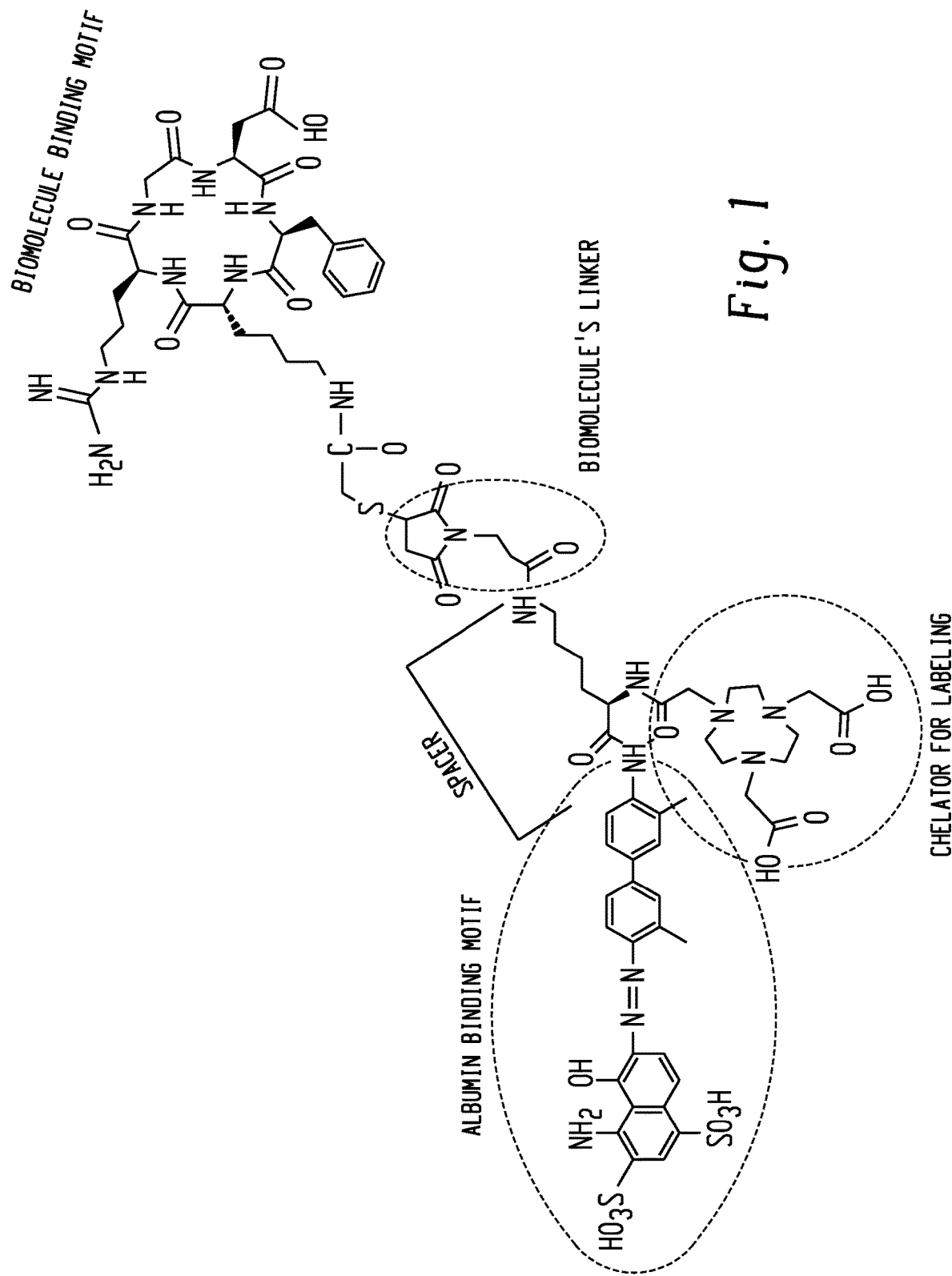
FIG. 1 is a diagram of a compound useful as a therapeutic or imaging agent according to an embodiment.

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced items. The term "or" means "and/or". The terms "comprising," "having," "including," and "containing" are to be construed as open-ended terms (i.e., meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art of this disclosure.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group.

All compounds are understood to include all possible isotopes of atoms occurring in the compounds. Isotopes include those atoms having the same atomic number but different mass numbers and encompass heavy isotopes and radioactive isotopes. By way of general example, and without limitation, isotopes of hydrogen include tritium and deuterium, and isotopes of carbon include $^{11}$C, $^{13}$C, and $^{14}$C. Accordingly, the compounds disclosed herein may include heavy or radioactive isotopes in the structure of the compounds or as substituents attached thereto. Examples of useful heavy or radioactive isotopes include $^{18}$F, $^{15}$N, $^{18}$O, $^{76}$Br, $^{125}$I and $^{131}$I.

Formulae I, II, III and IV include all pharmaceutically acceptable salts of Formulae I, II, III, and IV.

The opened ended term "comprising" includes the intermediate and closed terms "consisting essentially of" and "consisting of."

The term "substituted" means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent.

"Alkyl" includes both branched and straight chain saturated aliphatic hydrocarbon groups, having the specified number of carbon atoms, generally from 1 to about 8 carbon atoms. The term $C_1$-$C_6$alkyl as used herein indicates an alkyl group having from 1, 2, 3, 4, 5, or 6 carbon atoms. Other embodiments include alkyl groups having from 1 to 8 carbon atoms, 1 to 4 carbon atoms or 1 or 2 carbon atoms, e.g. $C_1$-$C_5$alkyl, $C_1$-$C_4$alkyl, and $C_1$-$C_2$alkyl. When $C_0$-$C_n$ alkyl is used herein in conjunction with another group, for example, —$C_0$-$C_2$alkyl(phenyl), the indicated group, in this case phenyl, is either directly bound by a single covalent bond ($C_0$alkyl), or attached by an alkyl chain having the specified number of carbon atoms, in this case 1, 2, 3, or 4 carbon atoms. Alkyls can also be attached via other groups such as heteroatoms as in —O—$C_0$-$C_4$alkyl($C_3$-$C_7$cycloalkyl). Examples of alkyl include, but are not limited to, methyl, ethyl, n-propyl, isopropyl, n-butyl, 3-methylbutyl, t-butyl, n-pentyl, and sec-pentyl.

"Alkoxy" is an alkyl group as defined above with the indicated number of carbon atoms covalently bound to the group it substitutes by an oxygen bridge (—O—). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy. Similarly an "Alkylthio" or a "thioalkyl" group is an alkyl group as defined above with the indicated number of carbon atoms covalently bound to the group it substitutes by a sulfur bridge (—S—). Similarly, "alkenyloxy", "alkynyloxy", and "cycloalkyloxy" refer to alkenyl, alkynyl, and cycloalkyl groups, in each instance covalently bound to the group it substitutes by an oxygen bridge (—O—).

"Halo" or "halogen" means fluoro, chloro, bromo, or iodo, and are defined herein to include all isotopes of same, including heavy isotopes and radioactive isotopes. Examples of useful halo isotopes include $^{18}$F, $^{76}$Br, and $^{131}$I. Additional isotopes will be readily appreciated by one of skill in the art.

"Haloalkyl" means both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" is a haloalkyl group as defined above attached through an oxygen bridge (oxygen of an alcohol radical).

"Peptide" means a molecule which is a chain of amino acids linked together via amide bonds (also called peptide bonds).

"Pharmaceutical compositions" means compositions comprising at least one active agent, such as a compound or salt of Formula II, and at least one other substance, such as a carrier. Pharmaceutical compositions meet the U.S. FDA's GMP (good manufacturing practice) standards for human or non-human drugs.

"Carrier" means a diluent, excipient, or vehicle with which an active compound is administered. A "pharmaceutically acceptable carrier" means a substance, e.g., excipient, diluent, or vehicle, that is useful in preparing a pharmaceutical composition that is generally safe, non-toxic and neither biologically nor otherwise undesirable, and includes a carrier that is acceptable for veterinary use as well as human pharmaceutical use. A "pharmaceutically acceptable carrier" includes both one and more than one such carrier.

A "patient" means a human or non-human animal in need of medical treatment. Medical treatment can include treatment of an existing condition, such as a disease or disorder or diagnostic treatment. In some embodiments the patient is a human patient.

"Providing" means giving, administering, selling, distributing, transferring (for profit or not), manufacturing, compounding, or dispensing.

"Treatment" or "treating" means providing an active compound to a patient in an amount sufficient to measurably reduce any disease symptom, slow disease progression or cause disease regression. In certain embodiments treatment of the disease may be commenced before the patient presents symptoms of the disease.

A "therapeutically effective amount" of a pharmaceutical composition means an amount effective, when administered to a patient, to provide a therapeutic benefit such as an amelioration of symptoms, decrease disease progression, or cause disease regression.

A "therapeutic compound" means a compound which can be used for diagnosis or treatment of a disease. The compounds can be small molecules, peptides, proteins, or other kinds of molecules.

A significant change is any detectable change that is statistically significant in a standard parametric test of statistical significance such as Student's T-test, where p<0.05.

Chemical Description

Compounds of Formulae I, II, III, and IV may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

The term "chiral" refers to molecules, which have the property of non-superimposability of the mirror image partner.

"Stereoisomers" are compounds, which have identical chemical constitution, but differ with regard to the arrangement of the atoms or groups in space.

A "diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

A "chelating group" or "chelator" is a ligand group which can form two or more separate coordinate bonds to a single central atom, which is usually a metal ion. Chelating groups as disclosed herein are organic groups which possess multiple N, O, or S heteroatoms, and have a structure which allows two or more of the heteroatoms to form bonds to the same metal ion.

"Pharmaceutically acceptable salts" include derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media such as ether, ethyl acetate, ethanol, isopropanol, or acetonitrile are used, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in G. Steffen Paulekuhn, et al., *Journal of Medicinal Chemistry* 2007, 50, 6665 and *Handbook of Pharmaceutically Acceptable Salts: Properties, Selection and Use*, P. Heinrich Stahl and Camille G. Wermuth, Editors, Wiley-VCH, 2002.

As indicated above, in one aspect the present invention encompasses chemical conjugates of Evans Blue dye having the compound of Formula I illustrated below, or a pharmaceutically acceptable ester, amide, solvate, or salt thereof, or a salt of such an ester or amide or a solvate of such an ester amide or salt:

Formula I

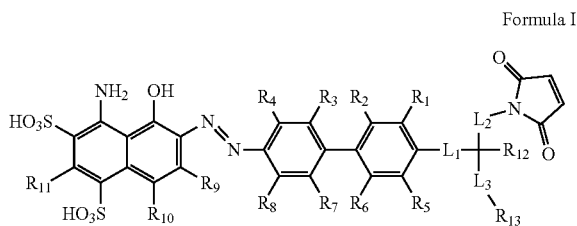

In Formula I, the substituents $R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy. $R_{12}$ is hydrogen, $C_1$-$C_6$alkyl, or $C_1$-$C_6$haloalkyl. $R_{13}$ is a chelating group. In some embodiments the chelating group may be a macrocyclic moiety, such as a NOTA group, a DOTA group, mercaptoacetyltriglycine ($MAG_3$), dipicolylamine ethanoic acid (DPA), cyclodextrin, crown ether, or porphyrin, or may be a linear moiety such as a 1,4,7-triazaheptane-1,4,7,7-tetracetic acid group. Chemical structures of several of these compounds are shown below.

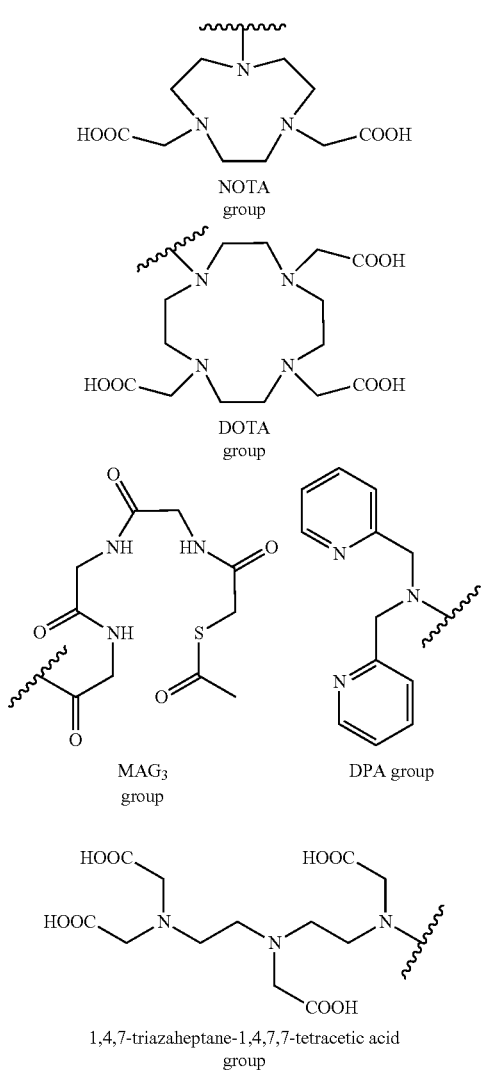

NOTA group

DOTA group

MAG₃ group

DPA group 1,4,7-triazaheptane-1,4,7,7-tetracetic acid group

Formula I may also include linking group $L_1$ which is —(CH$_2$)$_m$— wherein m is an integer from 0 to 12; linking group $L_2$ which is —(CH$_2$)$_n$— wherein n is an integer from 0 to 12; and linking group $L_3$ which is —(CH$_2$)$_p$— wherein p is an integer from 0 to 12. In each of $L_1$, $L_2$, $L_3$, and $L_4$, each CH$_2$ can be individually replaced with —O—, —NH(CO)—, or —(CO)—NH—, providing no two adjacent CH$_2$ groups are replaced.

In some embodiments, the linking groups $L_1$-$L_3$ include polyethylene glycol segments —CH$_2$CH$_2$O—.

In one embodiment of Formula I, $L_1$ is —NH(CO). In another embodiment of Formula I, $L_2$ is —(CH$_2$)$_4$—NH(CO)—(CH$_2$)$_2$—. In yet another embodiment of Formula I, $L_3$ is —NH(CO)CH$_2$—.

In yet another embodiment of Formula I, $R_1$ and $R_4$ are chosen independently from halogen, hydroxyl, cyano, C$_1$-C$_6$alkyl, C$_1$-C$_6$alkoxy, C$_1$-C$_6$haloalkyl, and C$_1$-C$_6$haloalkoxy.

In yet another embodiment of Formula I, $R_2$, $R_3$, $R_5$, $R_6$, $R_7$, $R_8$, $R_9$, $R_{10}$, and $R_{11}$ are each hydrogen.

In yet another embodiment of Formula I, $R_1$ and $R_4$ are chosen independently from C$_1$-C$_6$alkyl.

In yet another embodiment of Formula I, $R_1$ and $R_4$ are each methyl.

In yet another embodiment of Formula I, $R_{12}$ is hydrogen.

In yet another embodiment of Formula I, $R_{13}$ is selected from

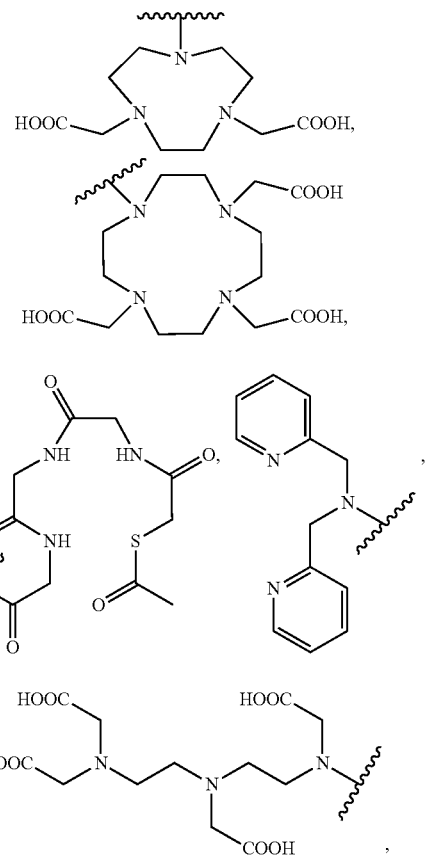

a crown ether, a cyclodextrin, or a porphyrin.

In yet another embodiment of Formula I, $R_{13}$ is

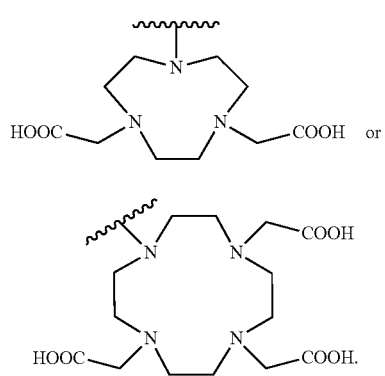

In another aspect, the present invention encompasses chemical conjugates of Evans Blue dye having the compound of Formula II illustrated below, or a pharmaceutically acceptable ester, amide, solvate, or salt thereof, or a salt of such an ester or amide or a solvate of such an ester amide or salt:

Formula II

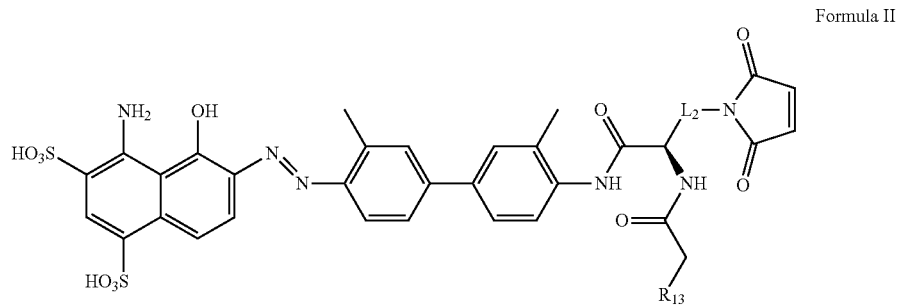

In Formula II, linking group $L_2$ is —$(CH_2)_n$— wherein n is an integer from 0 to 12, wherein each $CH_2$ can be individually replaced with —O—, —NH(CO)—, or —(CO)—NH—, providing no two adjacent $CH_2$ groups are replaced. In Formula II, $R_{13}$ is a chelating group.

In some embodiments of Formula II, $R_{13}$ is selected from

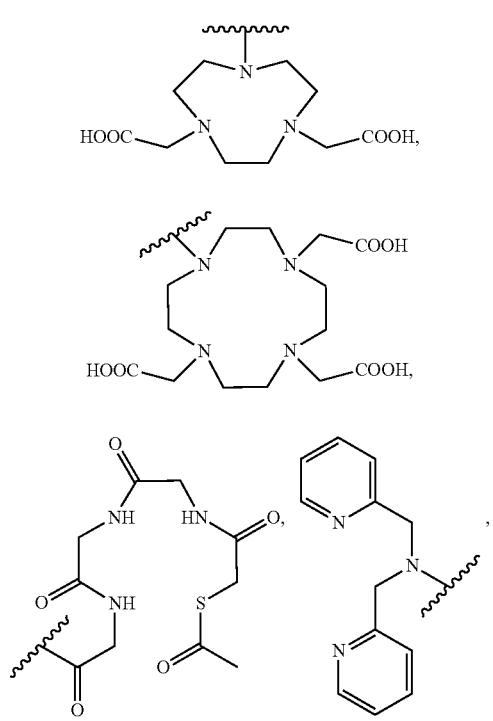

-continued

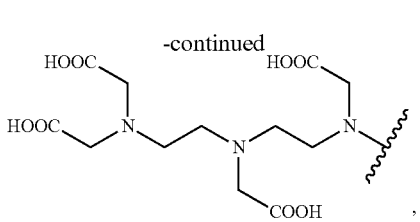

a crown ether, a cyclodextrin, or a porphyrin.

In yet another embodiment of Formula II, $R_{13}$ is

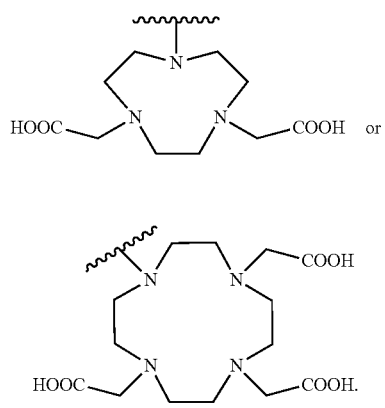 [SMILES: *N1CCN(CC(=O)O)CCN(CC(=O)O)CC1 ; "or" ; *N1CCN(CC(=O)O)CCN(CC(=O)O)CCN(CC(=O)O)CC1]

In yet another embodiment of Formula II, $L_2$ is —$(CH_2)_4$—NH(CO)—$(CH_2)_2$—.

In another aspect, the present invention encompasses chemical conjugates of Evans Blue dye having the compound of Formula III illustrated below, or a pharmaceutically acceptable ester, amide, solvate, or salt thereof, or a salt of such an ester or amide or a solvate of such an ester amide or salt:

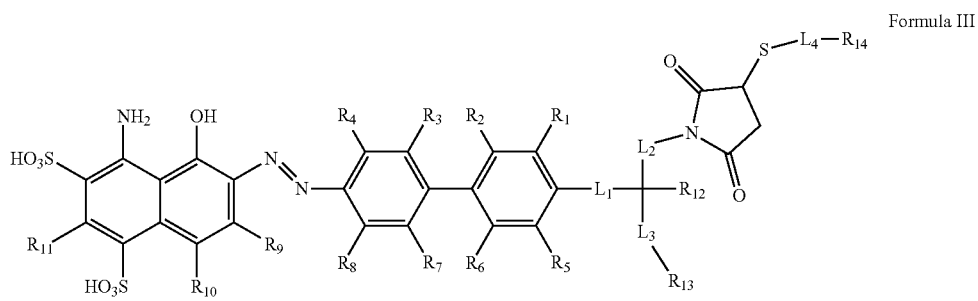

Formula III

In Formula III, the substituents $R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkyl, $C_1$-$C_6$alkoxy, $C_1$-$C_6$haloalkyl, and $C_1$-$C_6$haloalkoxy; $R_{12}$ is hydrogen, $C_1$-$C_6$alkyl, or $C_1$-$C_6$haloalkyl; and $R_{14}$ is a peptide.

Formula III may also include linking group $L_1$ which —$(CH_2)_m$— wherein m is an integer from 0 to 12; linking group $L_2$ which is —$(CH_2)_n$— wherein n is an integer from 0 to 12; linking group $L_3$ which is —$(CH_2)_p$— wherein p is an integer from 0 to 12; and linking group $L_4$ which is —$(CH_2)_q$— wherein q is an integer from 0 to 12. In each of $L_1$, $L_2$, $L_3$, and $L_4$, each $CH_2$ can be individually replaced with —O—, —NH(CO)—, or —(CO)—NH—, providing no two adjacent $CH_2$ groups are replaced. In Formula III $R_{13}$ is a chelating group.

In one embodiment of Formula III, $L_1$ is —NH(CO)—, $R_1$ and $R_4$ are each methyl, and $R_2$, $R_3$, $R_5$, $R_6$, $R_7$, $R_8$, $R_9$, $R_{10}$, $R_{11}$, and $R_{12}$ are each hydrogen.

The peptide of $R_{14}$ may be a therapeutic peptide, such as a peptide which can treat a disease or a peptide which can be used to diagnose a disease. The peptide of $R_{14}$ may include, for example, peptides such as interferon alpha, GCSF, octreotate, bombesin, RGD, alpha-MSH, CTT1298, or aptamers. The peptide may act to cause a biological effect while still attached as part of Formula III, or the peptide may be cleaved from Formula III, for example by a peptidase enzyme. The peptide may be a peptide which is capable of binding to a target cell or tissue, for example, the peptide may be capable of binding to a tumor. The binding may be via covalent or non-covalent binding.

For example, the peptide of $R_{14}$ may be the cyclic peptide Arg-Gly-Asp-Phe-Lys. The peptide of $R_{14}$ may be

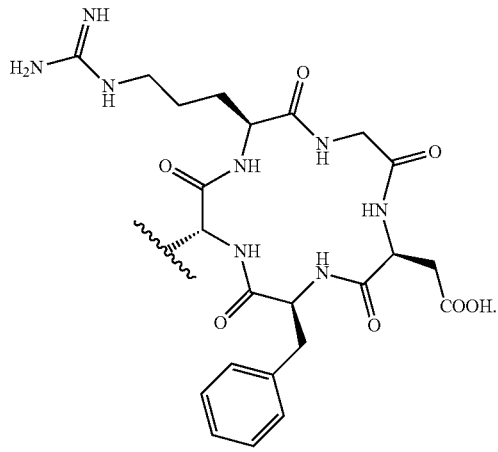 [SMILES: *[C@H]1NC(=O)[C@H](Cc2ccccc2)NC(=O)[C@H](CC(=O)O)NC(=O)CNC(=O)[C@H](CCCNC(=N)N)NC1=O]

In another embodiment, the peptide of $R_{14}$ may be

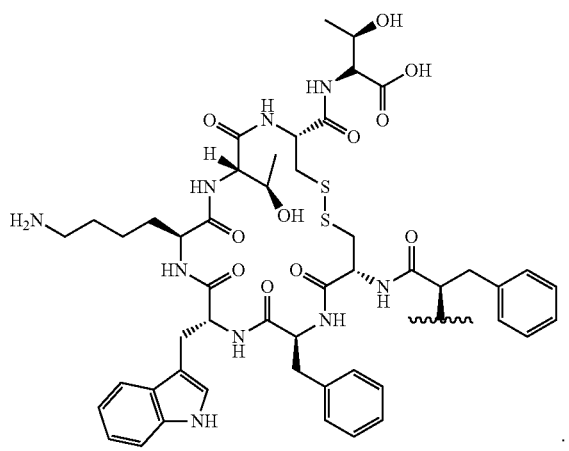

In yet another embodiment, the peptide of $R_{14}$ may be

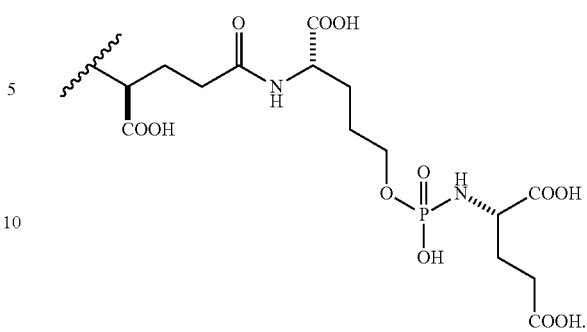

In some embodiments, $R_{14}$ is a therapeutic compound. The therapeutic compound may be any compound having therapeutic properties, and may encompass small molecular therapeutic molecules, peptidic drugs, or protein-based therapeutics. Examples of suitable small molecular therapeutic molecules useful in Formula III include, but are not limited to, doxorubicin, paclitaxel, gemcitabine, camptothecin, temozolomide, and the like. Examples of suitable peptidic drugs useful in Formula III include, but are not limited to insulin, GLP-1, exendin-4, octreotide, bombesin, RGD peptide (arginylglycylaspartic acid), and the like, or a therapeutic fragment thereof. Examples of suitable therapeutic proteins useful in Formula III include, but are not limited to vascular endothelial growth factor (VEGF), interferon (IFN), tumor necrosis factor (TNF), asparaginase, adenosine deaminase, and the like, or a therapeutic fragment thereof. Preferably, the therapeutic compound R in Formula III is capable of treating or diagnosing diseases or conditions in mammals, and preferably humans. For example, in one embodiment, R is selected for its ability to treat or diagnose cancer or diabetes.

It should be understood that $R_{14}$ can be a native therapeutic molecule, or a therapeutically active fragment thereof. Preferably, $R_{14}$ contains a sulfhydryl moiety that facilitates conjugation or cross-linking between it and the maleimide moiety of Formula I to form the conjugated complex of Formula III. The active sulfhydryl moiety on the therapeutic compound may be naturally occurring (for example, Cys-40 in exendin-4), or may be artificially introduced into the therapeutic compound or fragment by methods well known in the art such as amino acid substitution or chemical modification.

In some embodiments, $R_{14}$ further comprises a radionuclide such as $^{18}F$, $^{76}Br$, $^{124}I$, $^{125}I$, or $^{131}I$. An example of a useful substituent of $R_{14}$ that contains a radionuclide is

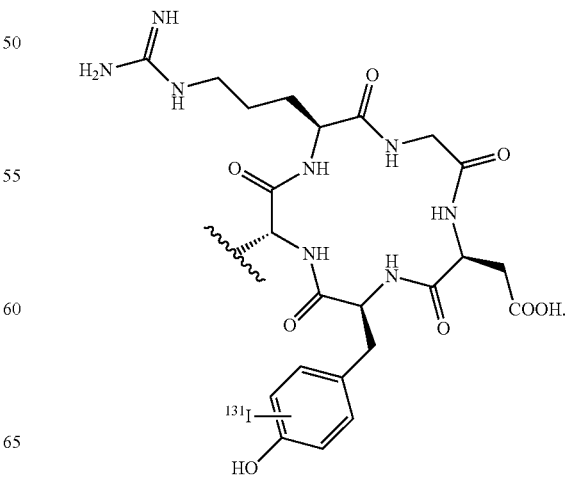

In some embodiments, $R_{13}$ is selected from

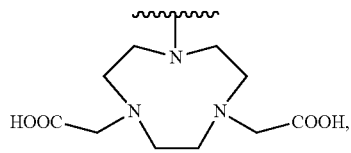

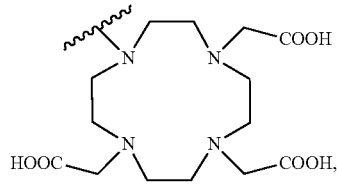

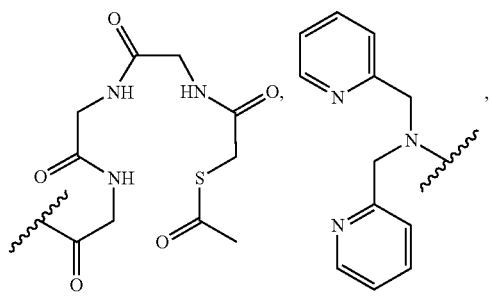

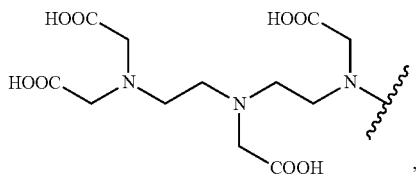

a crown ether, a cyclodextrin, or a porphyrin.

In some embodiments, $R_{13}$ is

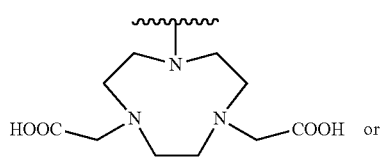  or

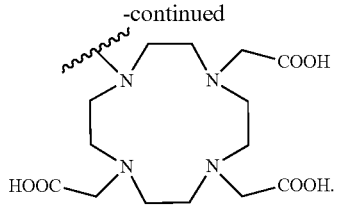

In some embodiments, the $R_{13}$ group in Formula III further includes a radionuclide such as $^{64}Cu$, $^{67}Cu$, $^{90}Y$, $^{86}Y$, $^{111}In$, $^{186}Re$, $^{188}Re$, $^{89}Zr$, $^{99}Tc$, $^{153}Sm$, $^{213}Bi$, $^{225}Ac$, $^{223}Ra$, or the like. In some embodiments, the radionuclide included in $R_{13}$ is $^{64}Cu$ or $^{90}Y$. The radionuclide may be bound to $R_{13}$ by chelation, or by other means such as conventional covalent or ionic bonds known in the chemical arts. The radionuclide may be suitable purposes such as imaging or scanning, for example PET imaging, and the compound of Formula III may be a PET imaging agent. The radionuclide may be suitable for purposes of patient treatment, for example radiation treatment, and the compound of Formula III may be an agent for treatment of cancer.

In another aspect, the present invention encompasses chemical conjugates of Evans Blue dye having the compound of Formula IV illustrated below, or a pharmaceutically acceptable ester, amide, solvate, or salt thereof, or a salt of such an ester or amide or a solvate of such an ester amide or salt:

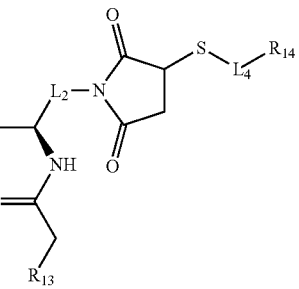

Formula IV

In Formula IV, $R_{14}$ is a peptide, and $R_{13}$ is a chelating group.

Formula IV may also include linking group $L_2$ which is —$(CH_2)_n$— wherein n is an integer from 0 to 12; and linking group $L_4$ which is —$(CH_2)_q$— wherein q is an integer from 0 to 12. In each of $L_2$ and $L_4$, each $CH_2$ can be individually replaced with —O—, —NH(CO)—, or —(CO)—NH—, providing no two adjacent $CH_2$ groups are replaced.

In some embodiments, the linking groups $L_1$-$L_4$ include polyethylene glycol segments —$CH_2CH_2O$—.

In one embodiment, $L_2$ is —$(CH_2)_4$—NH(CO)—$(CH_2)_2$—; and $L_4$-$R_{14}$ is

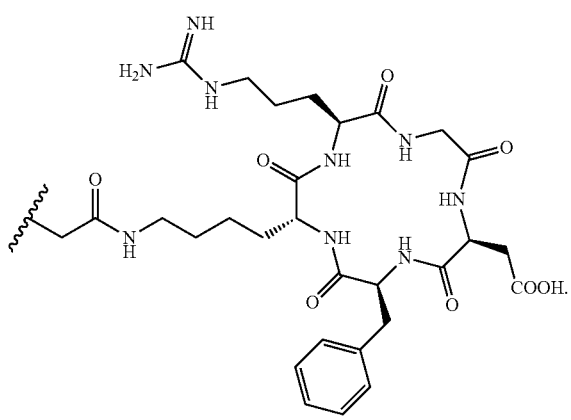 [SMILES: *CC(=O)NCCCC[C@H]1NC(=O)[C@H](Cc2ccccc2)NC(=O)[C@H](CC(=O)O)NC(=O)CNC(=O)[C@H](CCCNC(=N)N)NC1=O]

In another embodiment, $R_{13}$ is selected from

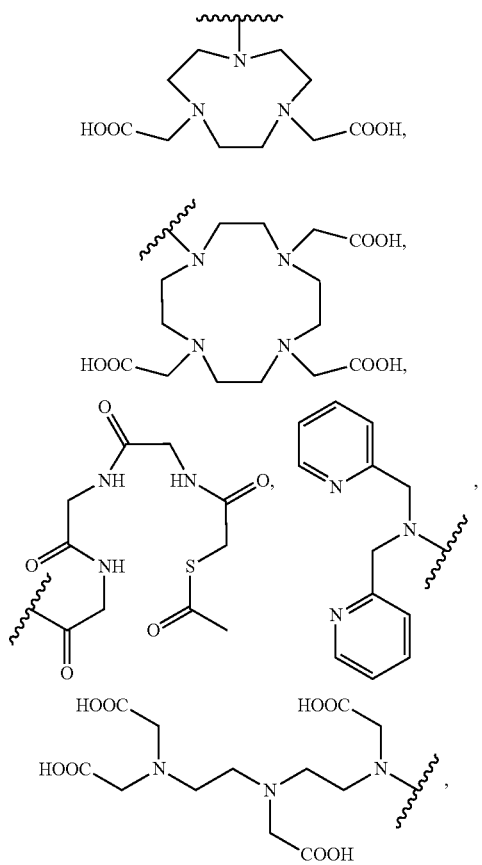

a crown ether, a cyclodextrin, or a porphyrin.

In another embodiment, $R_{13}$ is

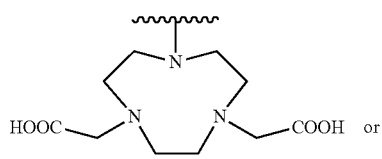

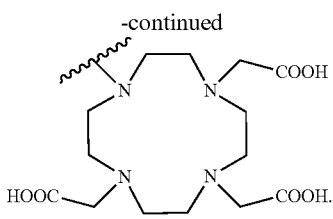

The description of embodiments of $R_{14}$ as given for compounds of Formula III also applies to compounds of Formula IV. Also, $R_{13}$ and/or $R_{14}$ of Formula IV may further include a radionuclide as described above, and the description of radionuclide embodiments as given for compounds of Formula III also applies to compounds of Formula IV.

In some embodiments, the novel molecules in the disclosure include the truncated Evans Blue domain as an Albumin-binding motif, a chelator for labeling with radionuclide, a spacer, a residue derived from maleimide as a linker, and a biomolecule binding motif. (FIG. 1).

Pharmaceutical Preparations

Reference to a formula includes references to all subformulae, for example, Formula III includes compounds of Formula IV. Compounds disclosed herein can be administered as the neat chemical, but are preferably administered as a pharmaceutical composition. Accordingly, the invention encompasses pharmaceutical compositions comprising a compound or pharmaceutically acceptable salt of a compound, such as a compound of Formula III, together with at least one pharmaceutically acceptable carrier. The pharmaceutical composition may contain a compound or salt of Formula III as the only active agent, but is preferably contains at least one additional active agent. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula III and optionally from about 0.1 mg to about 2000 mg, from about 10 mg to about 1000 mg, from about 100 mg to about 800 mg, or from about 200 mg to about 600 mg of an additional active agent in a unit dosage form. The pharmaceutical composition may also include a molar ratio of a compound, such as a compound of Formula III, and an additional active agent. For example the pharmaceutical composition may contain a molar ratio of about 0.5:1, about 1:1, about 2:1, about 3:1 or from about 1.5:1 to about 4:1 of an additional active agent to a compound of Formula III.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin, talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula III and usually at least about 5 wt. % of a compound of Formula III. Some embodiments contain from about 25 wt % to about 50 wt % or from about 5 wt % to about 75 wt % of the compound of Formula III.

Treatment Methods

The compounds of Formula III, as well as pharmaceutical compositions comprising the compounds, are useful for diagnosis or treatment of diseases such as diabetes or cancer. According to the present invention, a method of treating diabetes comprises providing to a patient in need of such treatment a therapeutically effective amount of a compound of Formula III. In one embodiment, the patient is a mammal, and more specifically a human. As will be understood by one skilled in the art, the invention also encompasses methods of treating non-human patients such as companion animals, e.g. cats, dogs, and livestock animals.

A therapeutically effective amount of a pharmaceutical composition is preferably an amount sufficient to reduce or ameliorate the symptoms of a disease or condition. In the case of diabetes for example, a therapeutically effective amount may be an amount sufficient to reduce or ameliorate high blood sugar. A therapeutically effective amount of a compound or pharmaceutical composition described herein will also provide a sufficient concentration of a compound of Formula III when administered to a patient. A sufficient concentration is preferably a concentration of the compound in the patient's body necessary to prevent or combat the disorder. Such an amount may be ascertained experimentally, for example by assaying blood concentration of the compound, or theoretically, by calculating bioavailability.

According to the invention, the methods of treatment disclosed herein include providing certain dosage amounts of a compound of Formula III to a patient. Dosage levels of each compound of from about 0.1 mg to about 140 mg per kilogram of body weight per day are useful in the treatment of the above-indicated conditions (about 0.5 mg to about 7 g per patient per day). The amount of compound that may be combined with the carrier materials to produce a single dosage form will vary depending upon the patient treated and the particular mode of administration. Dosage unit forms will generally contain between from about 1 mg to about 500 mg of each active compound. In certain embodiments 25 mg to 500 mg, or 25 mg to 200 mg of a compound of Formula I are provided daily to a patient. Frequency of dosage may also vary depending on the compound used and the particular disease treated. However, for treatment of most diseases and disorders, a dosage regimen of 4 times daily or less can be used and in certain embodiments a dosage regimen of 1 or 2 times daily is used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A compound of Formula III may be administered singularly (i.e., sole therapeutic agent of a regime) to treat or prevent diseases and conditions such as diabetes, or may be administered in combination with another active agent. One or more compounds of Formula III may be administered in coordination with a regime of one or more other active agents such as anticancer cytotoxic agents. In an embodiment, a method of treating or diagnosing cancer in a mammal includes administering to said mammal a therapeutically effective amount of a compound of Formula III, optionally in combination with one or more additional active ingredients.

As will be appreciated by one skilled in the art, the methods of treatment provided herein are also useful for treatment of mammals other than humans, including for veterinary applications such as to treat horses and livestock, e.g. cattle, sheep, cows, goats, swine and the like, and pets (companion animals) such as dogs and cats.

For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids (e.g. blood, plasma, serum, cellular interstitial fluid, saliva, feces, and urine) and cell and tissue samples of the above subjects will be suitable for use.

In one embodiment, the invention provides a method of treating a diabetes disorder in a patient identified as in need of such treatment, the method comprising providing to the patient an effective amount of a compound of Formula III. The compounds of Formula III provided herein may be administered alone, or in combination with one or more other active agents.

In another embodiment, the method of treating diabetes may additionally comprise administering the compound of Formula III in combination with one or more additional compounds, wherein at least one of the additional compounds is an active agent, to a patient in need of such treatment. The one or more additional compounds may include additional therapeutic compounds, including anti-cancer therapeutic compounds such as doxorubicin, paclitaxel, docetaxel, cisplatin, camptothecin, temozolomide, avastin, Herceptin, Erbitux, and the like.

The compositions of the present invention offer the advantage that many small molecules and biologics can be easily modified in one step with high yield and high purity. Due to the relatively strong binding of EB moiety with albumin, the in vivo biodistribution can be easily controlled to adjust the number of EB moieties and linkers. In addition, the relative small size of the EB moiety reduces the likelihood of any interference with the biological function of the small molecule or biologic. The addition of a chelator, such as NOTA or DOTA linked to the EB moiety allows for facile addition of further groups such as radionuclides, which can allow the present molecules to act as imaging agents and/or radiotherapeutic agents. The present invention therefore provides an efficient system for developing long lasting and long acting therapeutic and imaging agents with high efficacy.

EXAMPLES

The present invention is further described in detail by means of the following Examples. All parts and percentages are by weight and all temperatures are degrees Celsius unless explicitly stated otherwise.

Abbreviations
Boc tert-butoxycarbonyl
BSA Bovine Serum Albumin
CT Computerized Tomography
DIPEA diisopropylethylamine
DMF N,N-Dimethylformamide
DMSO Dimethyl Sulfoxide
DOTA 1,4,7,10-tetraazacyclododecane-1,4,7,10-tetraacetic acid
HATU 1-[Bis(dimethylamino)methylene]-1H-1,2,3-triazolo[4,5-b]pyridinium 3-oxid hexafluorophosphate
HPLC High Performance Liquid Chromatography
HRMS High Resolution Mass Spectrometry
LC/MS Liquid Chromatography/Mass Spectrometry
NOTA 1,4,7-triazacyclononane-N,N',N''-triacetic acid
PBS Phosphate Buffered Saline
PET Positron Emission Tomography
RT Room Temperature
SATA N-Succinimidyl S-acetylthioacetate
TFA Trifluoroacetic acid
THF Tetrahydrofuran General Methods Boc-Lysine-Fmoc amino acid was purchased from Bachem. NOTA-bis(t-Bu ester) and DOTA-tris (t-Bu ester) were purchased from Macrocyclics. N-succinimidyl S-acetylthioacetate (SATA) and PEG4 biotinylation reagent were purchased from Thermo Fisher Scientific. Avidin-sepharose beads acquired from GE Healthcare. Arg-Gly-Asp (RGD) peptide was purchased from C.S. Bio. All other solvents and chemicals were purchased from Sigma-Aldrich.

Analytical high performance liquid chromatography (HPLC) was done on Phenomenex Luna C8 column (5 μm, 4.60×150 mm) with two gradient systems; system 1—gradient starting from 80% of solvent A (50 mM NH$_4$OAc) and 20% of solvent B (CH$_3$CN) for 2 min and increasing to 90% of solvent B in 15 min at flow rate of 1 mL/min. System 2—gradient starting from 95% solvent A and 5% solvent B and changing to 65% solvent B at 35 min at flow rate of 1 mL/min. The ultraviolet (uv) absorbance was monitored at 254 and 600 nm. Compounds were purified on either Biotage purification system (C-18, 210×25 mm) or Higgins column (C-18, 5 μm, 250×20 mm) using gradient system 2 and flow rates of 25 or 12 mL/min respectively using a gradient similar to system 2 except change in the solvents [solvent A: 0.1% trifluoroacetic acid (TFA)/H$_2$O, solvent B: 0.1% TFA/CH$_3$CN]. LC-MS analysis was done similar to the reported procedure (1). $^{64}$CuCl$_2$ was acquired from the NIH Cyclotron Facility. Radio-TLC was performed on an AR-2000 Bioscan scanner, using iTLC plates and 0.1M Citric acid pH 5 as a developing solvent. $^{18}$F-FGD was purchased from Cardinal Health. $^{18}$F-FLT was synthesized according to the known procedure (2).

Example 1: Preparation of Evans Blue Amine (EB-NH$_2$)

To a 100 ml round bottom flask containing 2-tolidine (4.3 g) and methylene chloride (40 ml) was added di-t-butyldicarbonate (4.4 g). The mixture was stirred at room temperature overnight. The reaction was concentrated and the residue was purified by chromatography on silica gel to give 3.2 g of N-Boc-2-tolidine. LC-MS: [MH]$^+$=313.4135 (m/z), calc: 312.1838.

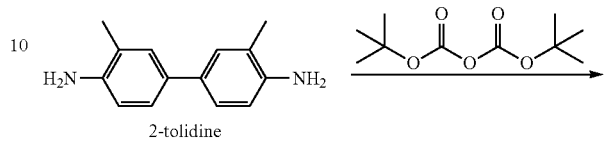

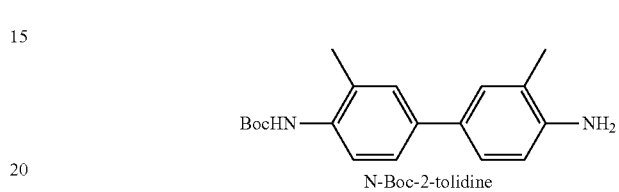

N-Boc-2-tolidine (0.46 g, 1.47 mmol) was dissolved in acetonitrile (10 ml) in a glass vial, was cooled to 0° C., then hydrochloric acid (0.3 M, 15 ml) was added. Cold sodium nitrite solution (0.31 g in 5 ml water) was added dropwise and stirred for 20 min, and the solution turned bright yellow. This solution was added dropwise to another glass vial containing 1-amino-8-naphthol-2,4-disulfonic acid monosodium salt (0.59 g) and sodium bicarbonate (0.49 g) in water (20 ml) at 0° C. The reaction was deemed complete by LC/MS and the reaction was lyophilized without further purification to provide the Boc-EB product. [M-H]$^-$= 541.4425, calc: 542.0930.

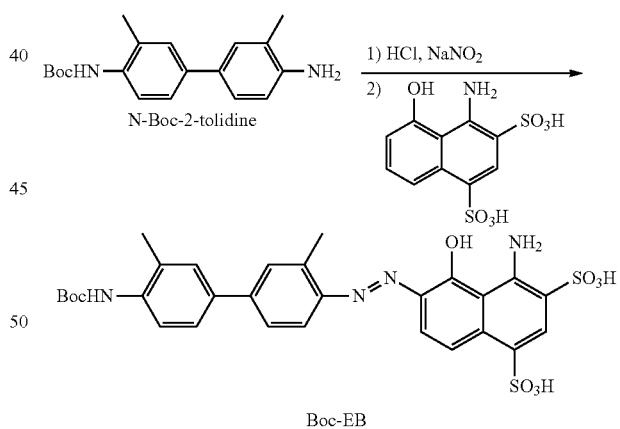

The Boc EB product was added to a solution of 80% TFA, 10% 1,2-ethanedithiol and 10% thioanisole and stirred until reaction was complete. The mixture was diluted with water (100 ml) and loaded on a C-18 chromatography cartridge (3×15 cm). The column was washed with water and then with 80% ethanol to elute the desired product. After evaporation of the solvent in the eluent, 0.6 g of 80% pure product EB-NH$_2$ was obtained. A small amount of product was further purified by HPLC. LC-MS: [M-H]$^-$=541.4425, calc: 542.0930.

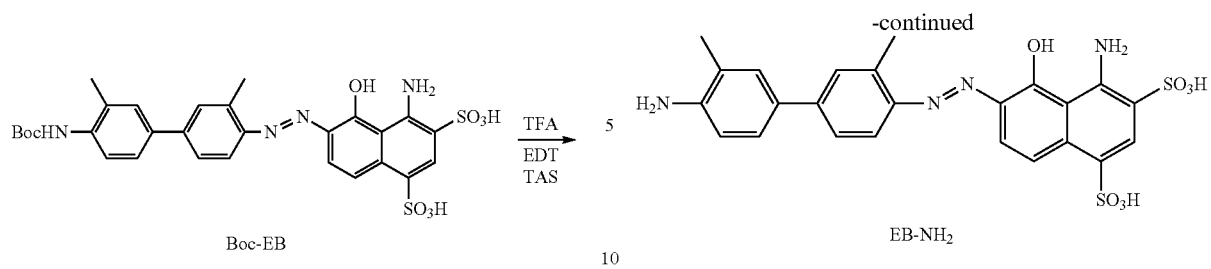

-continued

Example 2: Synthesis of EB-Lys-Boc

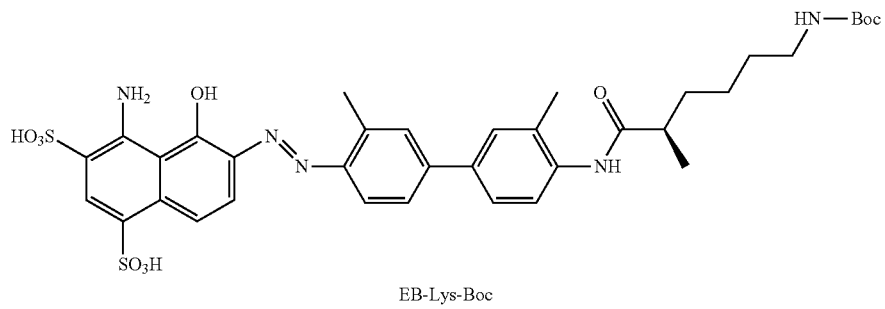 [SMILES: Cc1cc(-c2ccc(NC(=O)[C@H](C)CCCCNC(=O)OC(C)(C)C)c(C)c2)ccc1/N=N/c1ccc2c(S(=O)(=O)O)cc(S(=O)(=O)O)c(N)c2c1O ; "EB-Lys-Boc"]

To a solution of Boc-Lys-Fmoc (3.6 eq) in anhydrous N,N-dimethylformamide (DMF) (2-3 mL) were added (1-[Bis(dimethylamino)methylene]-1H-1,2,3-triazolo[4,5-b]pyridinium 3-oxid hexafluorophosphate) (HATU, 4.2 eq) under Argon. The solution was stirred for 10 min at room temperature (RT). Then 10 eq of diisopropylethylamine (DIPEA) were added followed by addition of EB-NH$_2$ in 5-7 mL DMF. The reaction was stirred over-night at RT. Conversion of the EB-NH$_2$ to EB-conjugated to protected Fmoc-Lys-Boc was monitored using analytical HPLC system 1. Retention time of EB-NH$_2$ was 7.7 min and conjugated EB-protected Lys was 11 min. After conversion completion, 20% of piperidine (v/v) were added and the reaction was stirred for an additional hour. DMF was removed by high vacuum oil pump and the reaction was re-dissolved in methanol/H$_2$O (2:1) and purified on Biotage system. The collected HPLC fractions were re-injected onto an analytical HPLC to determine purity greater than 90% and were further lyophilized. EB-Lys-Boc retention time (r.t.) was 8.3 min (system 1) or 23.2 min (system 2). LC-MS analysis confirmed mass of 769 [MH]$^-$.

Example 3: Synthesis of NOTA-EB-Lys-Boc

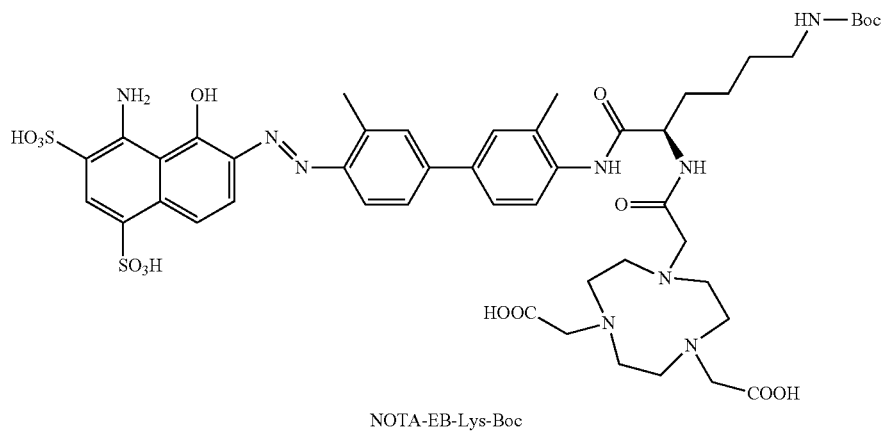 [SMILES: Cc1cc(-c2ccc(NC(=O)[C@@H](CCCCNC(=O)OC(C)(C)C)NC(=O)CN3CCN(CC(=O)O)CCN(CC(=O)O)CC3)c(C)c2)ccc1/N=N/c1ccc2c(S(=O)(=O)O)cc(S(=O)(=O)O)c(N)c2c1O ; "NOTA-EB-Lys-Boc"]

Reaction between EB-Lys-Boc and NOTA-bis(t-Bu ester) was done similar to the conditions described above. Analytical HPLC system 2 confirmed purity >90% with a r.t. of 29.3 min and mass of 1167 [MH]⁻.

Example 4: Synthesis of NOTA-EB-Lys

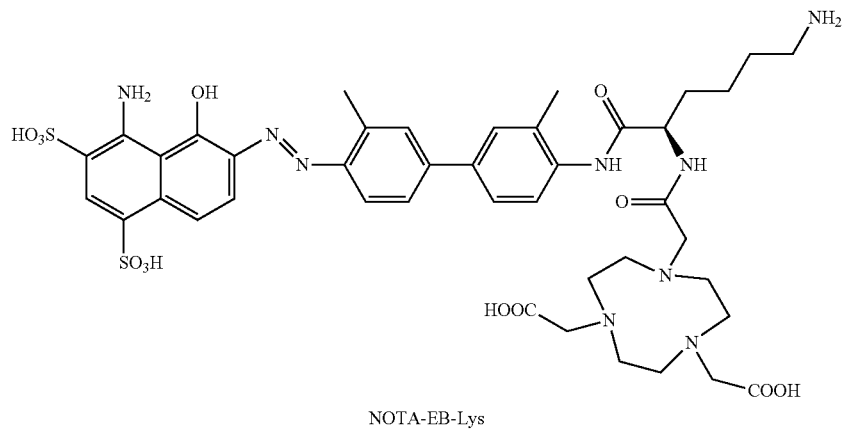 [SMILES: Cc1cc(-c2ccc(NC(=O)[C@@H](CCCCN)NC(=O)CN3CCN(CC(=O)O)CCN(CC(=O)O)CC3)c(C)c2)ccc1/N=N/c1ccc2c(S(=O)(=O)O)cc(S(=O)(=O)O)c(N)c2c1O ; "NOTA-EB-Lys"]

NOTA-EB-Lys

Deprotection was done at RT using thioanisole: 1,2-ethanedithiol:anisole:TFA (5:3:2:90). Completion of deprotection was monitored by HPLC (r.t. of 17.1 min). TFA was removed by Argon flow before purification. NOTA-EB-Lys was purified on Biotage system. LC-MS analysis confirmed mass of 954[MH]⁻.

Example 5: Synthesis of NOTA-Maleimide-EB (NMEB)

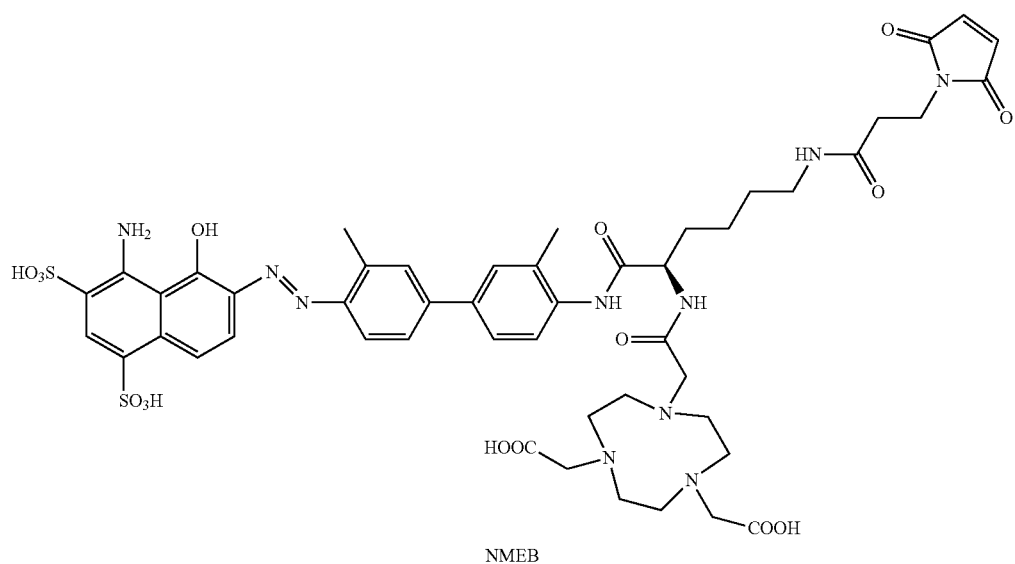 [SMILES: Cc1cc(-c2ccc(NC(=O)[C@@H](CCCCNC(=O)CCN3C(=O)C=CC3=O)NC(=O)CN3CCN(CC(=O)O)CCN(CC(=O)O)CC3)c(C)c2)ccc1/N=N/c1ccc2c(S(=O)(=O)O)cc(S(=O)(=O)O)c(N)c2c1O ; "NMEB"]

NMEB

NOTA-EB-Lys was dissolved in 0.5 mL DMF. Then 1.26 eq of trimethylamine were added, followed by 1.26 eq of 3-(Maleimido)propionic acid N-hydroxysuccinimide ester in 0.2 mL DMF. The reaction was stirred for 2 h at RT. Purification was done on Higgins column. Analytical HPLC injection (system 2) showed purity >90% with a r.t. of 17.4 min and mass of 1105 [MH]$^-$.

Example 6: Synthesis of RGD-SH

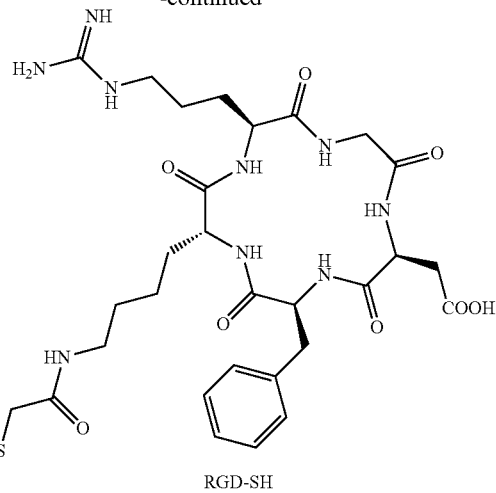

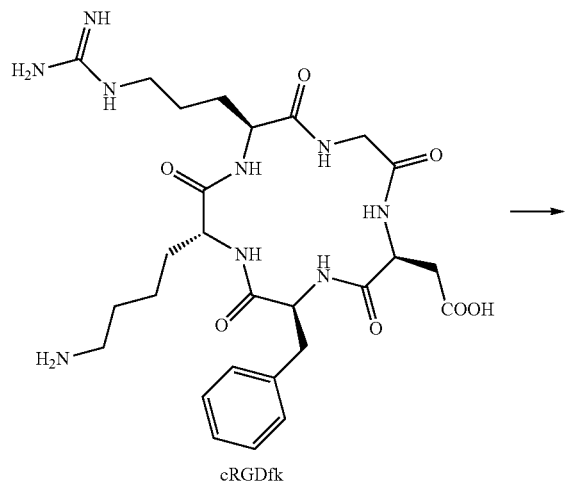

20-30 mg of c(RGDfk) was dissolved in 1.5 mL of Na$_2$HPO$_4$ pH 7.5. 1.3 eq of SATA were dissolved in dimethylsulfoxide and were added to the peptide. The solution was stirred for 1-1.5 h until HPLC showed complete conversion to the conjugated peptide. The solvent was removed by lyophilization over-night. De-protection of the acetyl group was done using 70 mg hydroxylamine and 20 mg ethylenediaminetetraacetic acid in 0.1M borate buffer pH 8.6 and H$_2$O (1:1) for 1 h at RT. Purification of RGD-SH was done on Higgins column. Re-injection of the pure peptide onto analytical HPLC showed purity greater than 90% with a r.t. of 17.3 min. LC-MS analysis was confirmed mass of 676 [MH]$^-$.

Example 7: Synthesis of NMEB-RGD

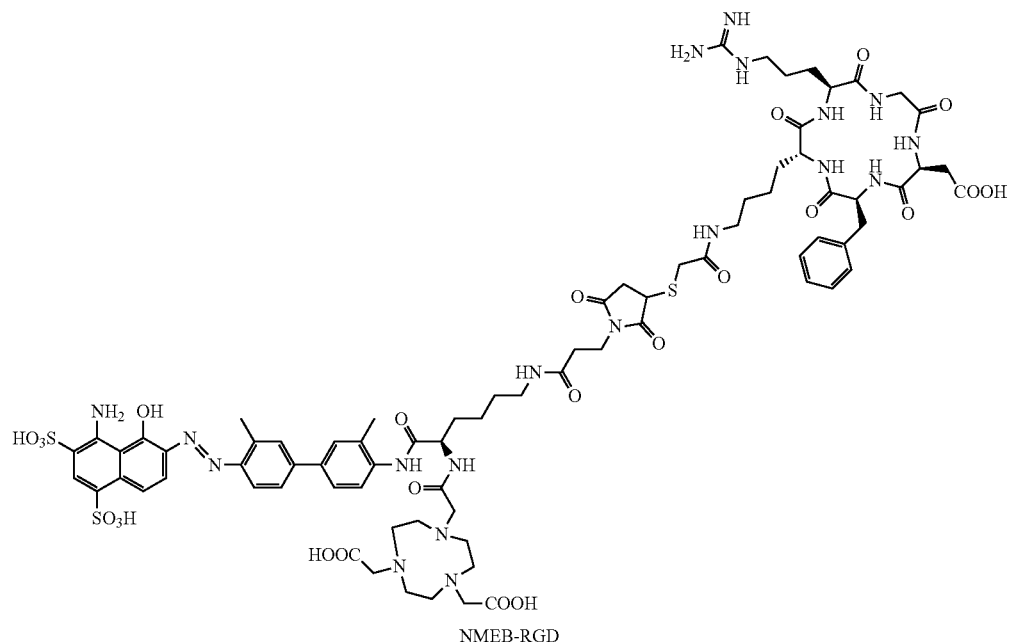 [SMILES: Cc1cc(-c2ccc(NC(=O)[C@@H](CCCCNC(=O)CCN3C(=O)CC(SCC(=O)NCCCC[C@H]4NC(=O)[C@H](Cc5ccccc5)NC(=O)[C@H](CC(=O)O)NC(=O)CNC(=O)[C@H](CCCNC(=N)N)NC4=O)C3=O)NC(=O)CN3CCN(CC(=O)O)CCN(CC(=O)O)CC3)c(C)c2)ccc1/N=N/c1ccc2c(S(=O)(=O)O)cc(S(=O)(=O)O)c(N)c2c1O]

NMEB was dissolved in 0.3 mL of de-gassed 0.1% sodium ascorbate (w/v) in phosphate buffer-saline (PBS). RGD-SH (1.1 eq) was dissolved in 50 μL of DMF and added to the NMEB solution. The reaction was stirred at RT for 2 h. Purification was done on Higgins system. NMEB-RGD r.t. was 17.54 min, chemical purity >90% and mass of 1783 [MH]⁻.

Example 8: Synthesis of DOTA-Maleimide-EB-RGD (DEB-RGD)

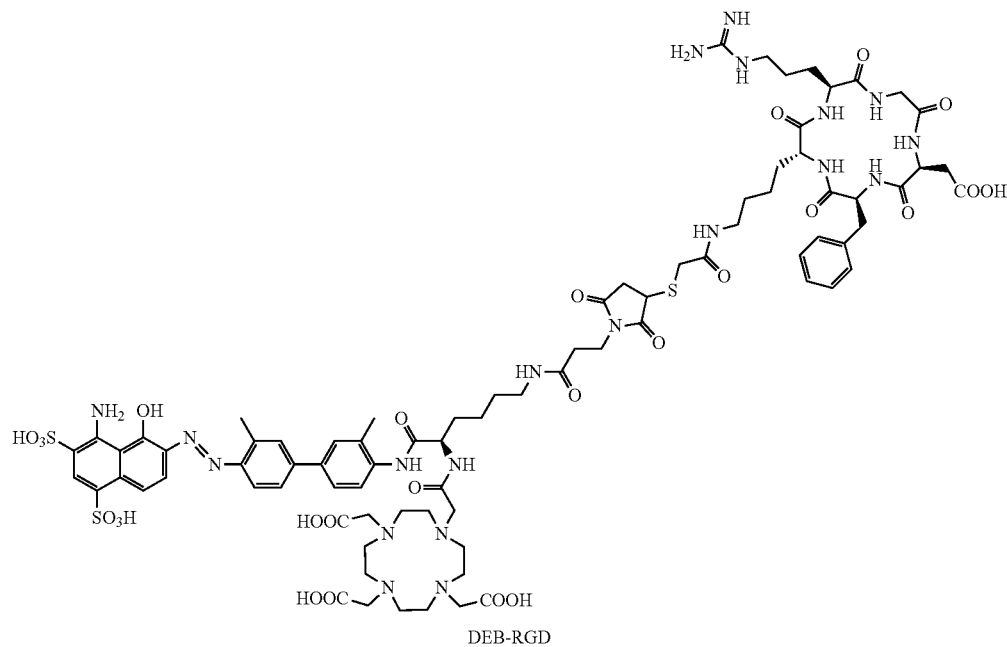 [SMILES: Cc1cc(-c2ccc(NC(=O)[C@@H](CCCCNC(=O)CCN3C(=O)CC(SCC(=O)NCCCC[C@H]4NC(=O)[C@H](Cc5ccccc5)NC(=O)[C@H](CC(=O)O)NC(=O)CNC(=O)[C@H](CCCNC(=N)N)NC4=O)C3=O)NC(=O)CN3CCN(CC(=O)O)CCN(CC(=O)O)CCN(CC(=O)O)CC3)c(C)c2)ccc1/N=N/c1ccc2c(S(=O)(=O)O)cc(S(=O)(=O)O)c(N)c2c1O]

DEB-RGD

Synthesis of DOTA-maleimide-EB conjugated to thiolated RGD, was done in the same manner as in Example 7 but using DOTA-tris (t-Bu ester) as a chelator, with HPLC r.t. of 17.8 min and mass of 1883.9 [MH]⁻.

Example 9: Synthesis of DOTA-Maleimide-EB Conjugated to Thiolated Octreotate (EB-TATE)

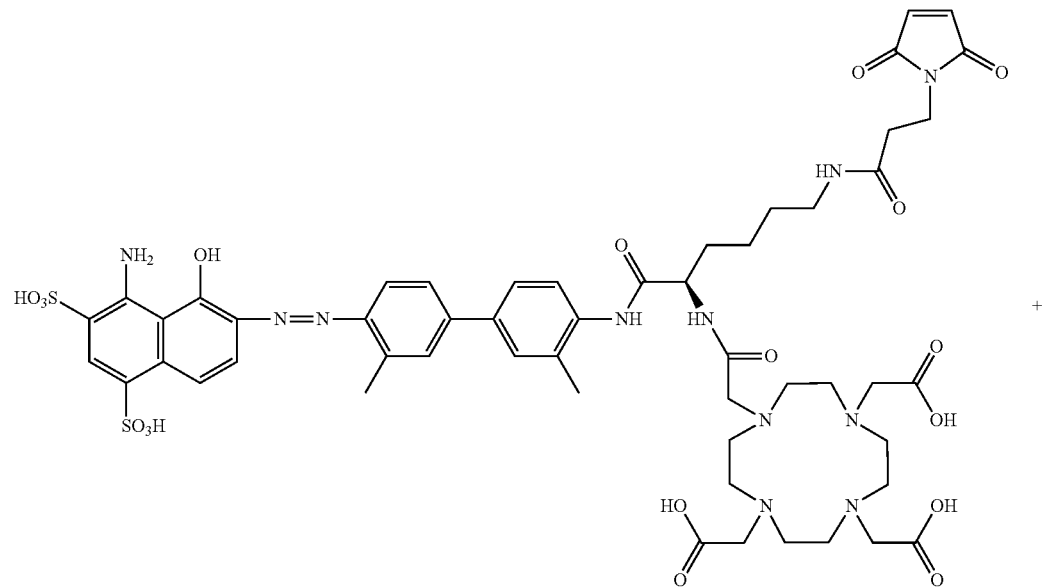

-continued
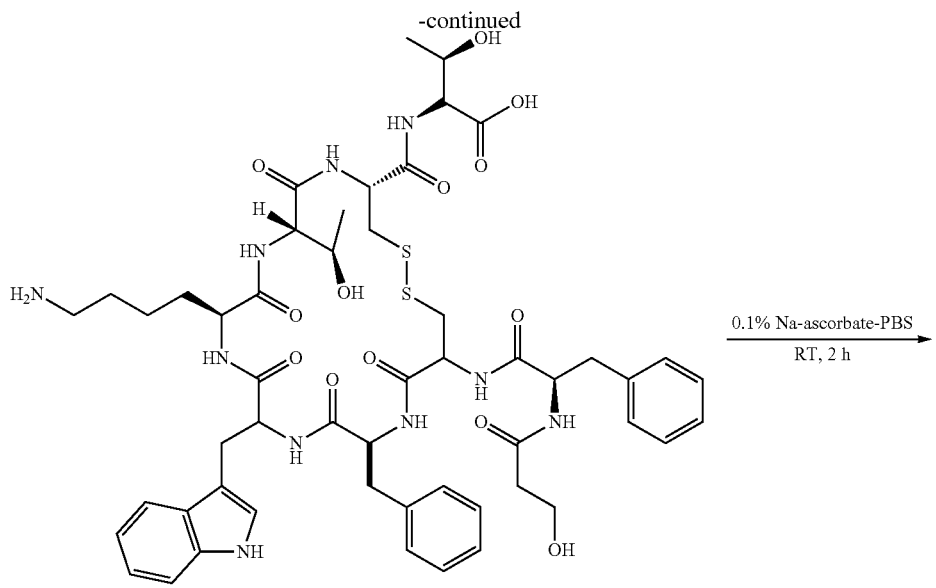
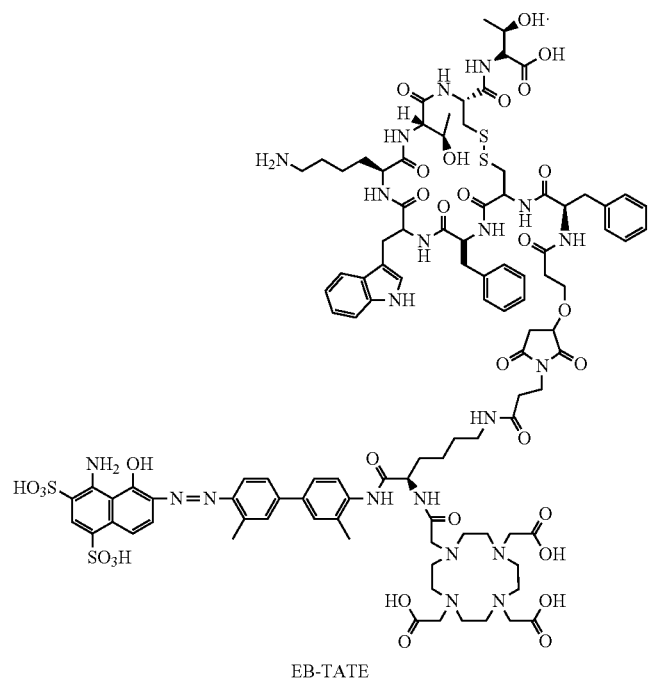
EB-TATE
Synthesis of DOTA-maleimide-EB conjugated to thiolated Octreotate, was done in the same manner as in Example 7 but using DOTA-tris (t-Bu ester) as a chelator, with HPLC r.t. of 3.35 min and mass of 1862.58 [MH]⁻.
Example 10: Synthesis of DOTA-Maleimide-EB Conjugated to CTT1298 (DMEB-CTT)

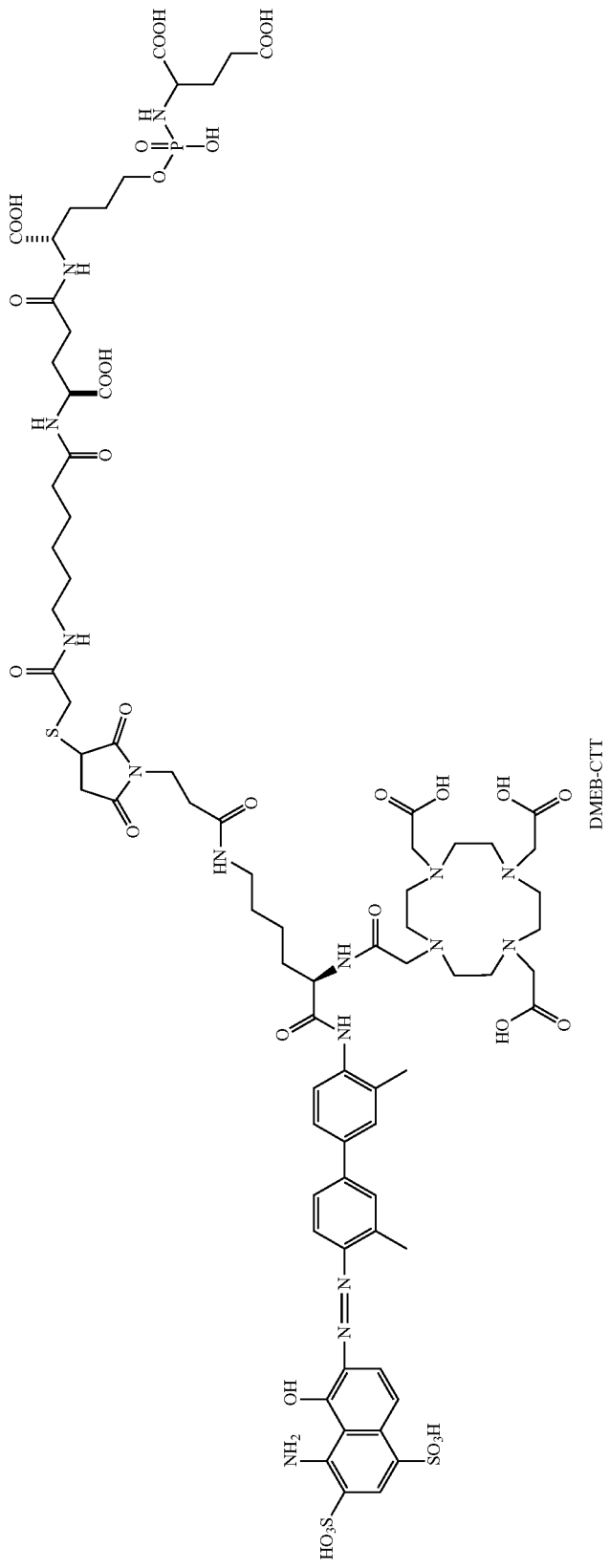

Synthesis of DOTA-maleimide-EB conjugated to CTT1298, a prostate specific membrane antigen (PSMA) ligand, was done in the same manner as in Example 7 but using DOTA-tris (t-Bu ester) as a chelator, with HPLC r.t. of 2.32 min and mass of 1865.38 [MH]⁻.
Example 9: Comparative Compounds
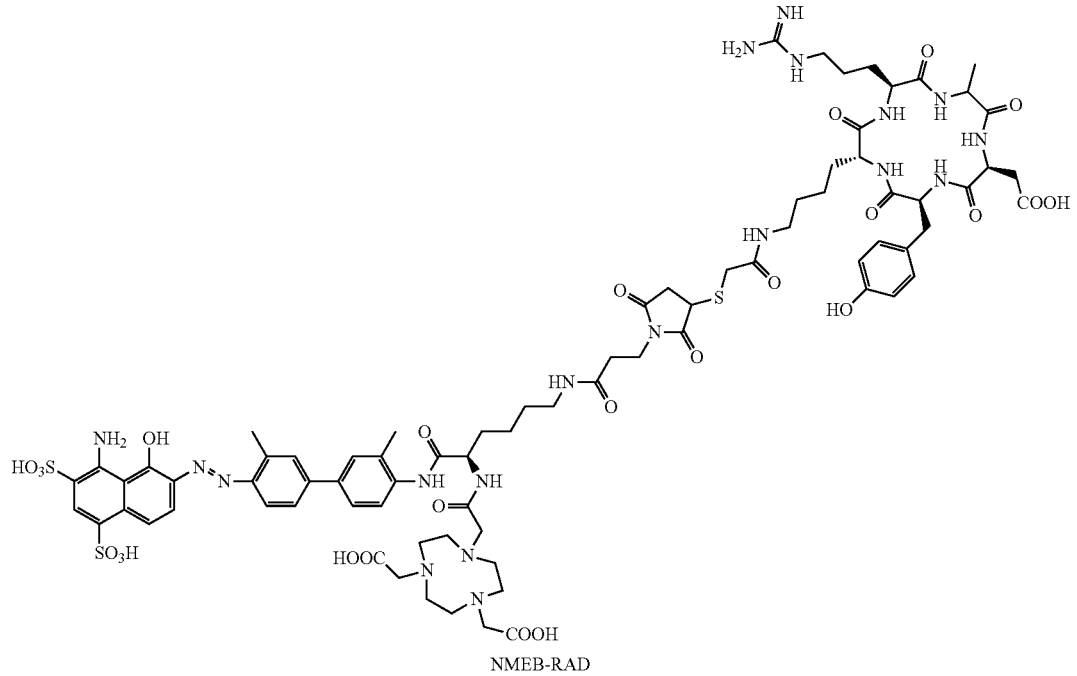
NMEB-RAD
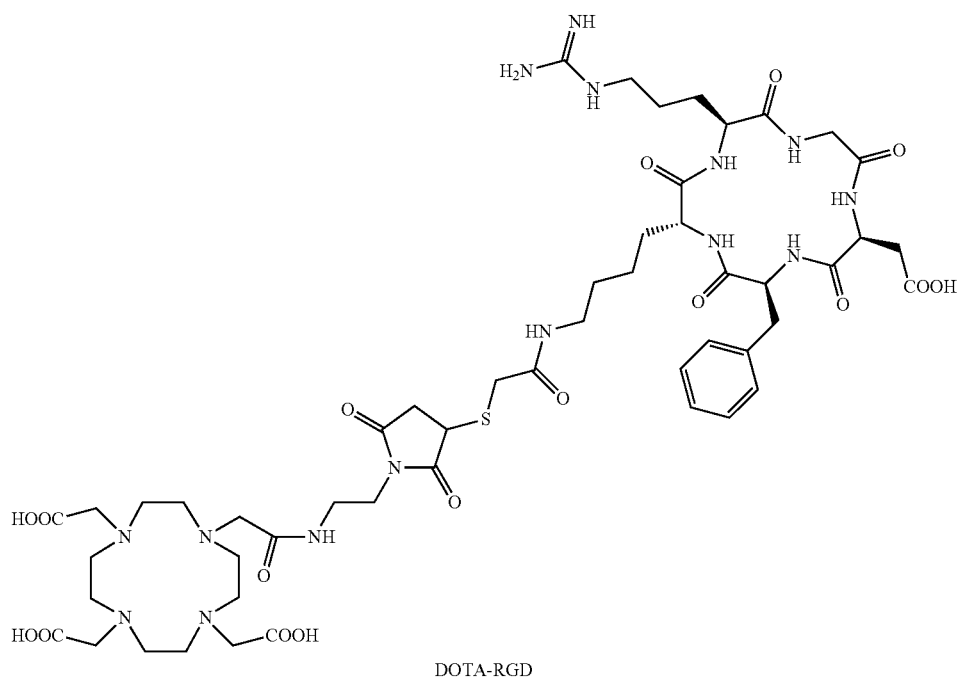
DOTA-RGD

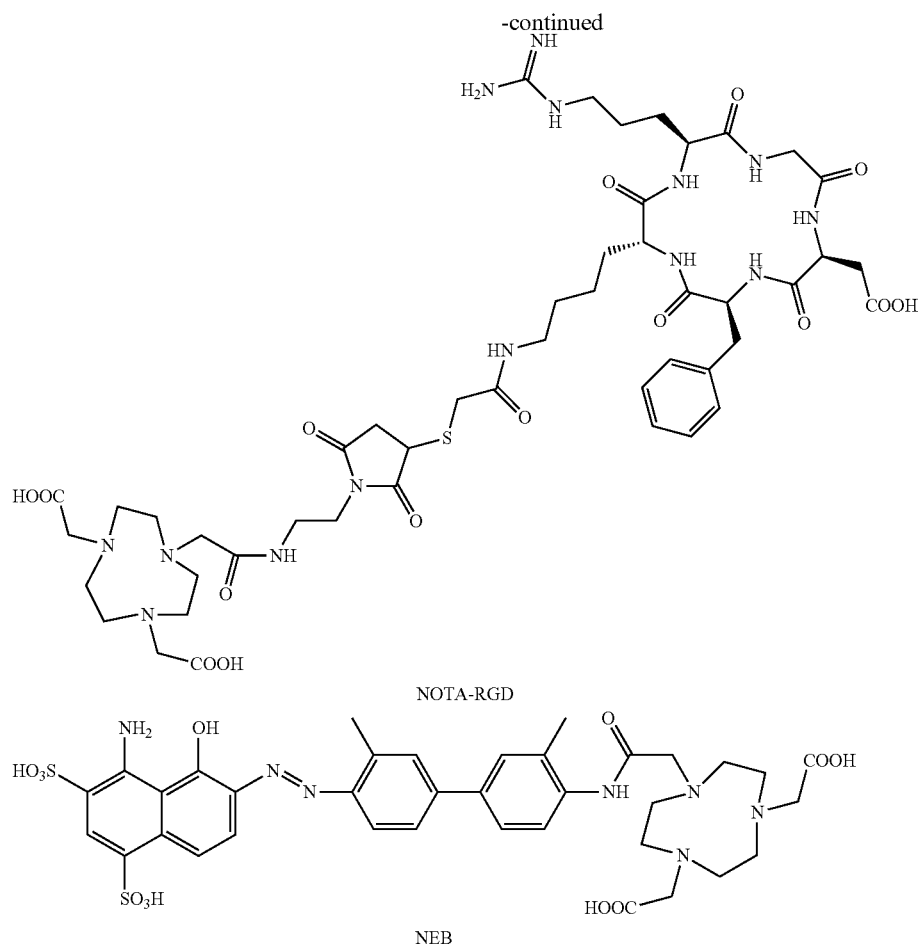

NOTA-RGD

NEB

The compounds NMEB-RAD, DOTA-RGD, NOTA-RGD, and NEB, with structures as shown above, were synthesized by methods similar to the methods in examples 2-8.

Example 10: Labeling of Compounds

10 μL of $^{64}CuCl_2$ (1.5-2.2 GBq, 42-60 mCi) were diluted with 0.5 mL 0.4M ammonium acetate pH 5.6. Then 0.37-0.74 GBq (10-20 mCi) were transferred into a vial containing the peptide (100 μg). The reaction was mixed for 30 min at 37° C. and then tested for purity by either, analytical HPLC system 1 (r.t. 6.37) and radioTLC (AR-2000 Bioscan scanner) using iTLC plates and 0.1M Citric acid as developing solvent pH 5. Rf of free $^{64}$Cu ~0.9 and Rf of $^{64}$Cu-NMEB-RGD ~0.1. Labeling of $^{64}$Cu-c(RGDfk), $^{64}$Cu-NMEB, $^{64}$Cu-EB-TATE, and $^{64}$Cu-DMEB-CTT was done at the same manner. Y-90 (Perkin-Elmer) labeling was done similarly to the conditions described above for $^{64}$Cu using 370-444 mBq (10-12 mCi).

Example 11: Stability Studies in Mouse Serum 7.4-11.1 MBq (0.2-0.3 mCi) of 6Cu-NMEB-RGD were incubated with 0.5 mL of mouse serum for 1, 4, 8 and 24 h at 37° C. At each time point, an aliquot was taken and loaded on iTLC plate and developed in for RadioTLC measurements.

Example 12: Cell Culture

U87MG human glioblastoma, MDA-MB-435 human melanoma and HT-29 human colorectal adenocarcinoma cell lines were purchased from ATCC, and was grown in Minimum Essential Medium, Leibovitz's L-15 Medium and McCoy's 5A Medium, respectively. All the cells were supplemented with 10% fetal bovine serum, 100 IU/mL penicillin, and 100 mg/mL streptomycin. Cells were grown in humidified atmosphere containing 5% $CO_2$ at 37° C.

Example 13: Cell Uptake of NMEB-RGD and FTIC-Albumin $10^5$ cells were incubated in triplicates with a constant amount of FITC-albumin and increasing amounts of NMEB-RGD for 2 h. Thereafter, cells were washed with PBS and acquired using and LSR II flow cytometer. Cell fluorescence was expressed as mean fluorescent intensity (MFI).

Example 14: Histopathologic Staining

For visualization of endothelial cells, integrin expression on both tumor vasculature and tumor cells, CD31, CD61 (murine integrin $3_3$) or human integrin $α_vβ_3$ immunofluoresence staining was chosen, respectively. The mouse anti-human integrin $α_vβ_3$ antibody we used only recognizes human integrin $α_vβ_3$, which does not cross-react with murine integrin $α_vβ_3$ of the tumor cells. Briefly, frozen tissue sections (5 μm) were fixed with cold acetone, rinsed with PBS and blocked with 1% bovine serum albumin solution for an hour at RT. The slides were incubated with 1:100 dilution of rat anti-mouse CD31, hamster anti-rat CD61 or mouse anti-human integrin $\alpha_v\beta_3$ monoclonal antibody at room temperature overnight, and then incubated with 1:200 Alexa Fluor 488-labeled donkey anti-rat, Alexa Fluor 647-labeled anti-hamster and Alexa Fluor 488-labeled anti-mouse secondary antibody, respectively. Samples were mounted with DAPI for staining of cell nuclei. Fluorescence images were acquired with an epifluorescence microscope (200×; Olympus, X81). Images were acquired under the same conditions and displayed at the same scale.

Example 15: Histopathologic Staining after Targeted Radiotherapy

U87MG tumor samples from Groups A-F were collected and sectioned after the animals were sacrificed. The CD31 staining procedure was the same as previously described. For Ki-67 staining, frozen tumor sections were fixed with cold acetone for 20 min and dried in the air for 30 min at room temperature. After blocking with 1% bovine serum albumin (BSA) for 30 min, slides were stained with Ki-67-specific monoclonal antibody (1:1000, Abcam) and then incubated with Cy-3-conjugated donkey anti-rabbit secondary antibody (1:200, Thermo Fisher Scientific). After being washed three times with PBS, samples were mounted with DAPI for staining of cell nuclei (Vector). Fluorescence images were acquired with an epifluorescence microscope (200×; Olympus, X81).

Immunofluorescent terminal deoxynucleotidetransferase-mediated biotin-dUTP labeling (TUNEL) analysis was done by use of a commercial available kit (Roche Applied Science). According to the manufacture's specifications, samples were fixed with 10% formalin and permeabilized by incubation with 0.1% Triton for 2 min on ice. After fixation and permeabilization, 50 μL of TUNEL reaction mixture were added on the samples. The slides were then incubated in a humidified atmosphere for 60 min at 37° C. in the dark. After rinsing with PBS and mounting with DAPI (Vector), samples were observed under an epifluorescence microscope using GFP channel. Staining of human tissue was done by Histoserv, Inc. using sc-7312 antibody (Santa Cruz biotechnology, Inc.) H&E staining for mice tissues was also conducted by Histoserv, Inc.

Example 16: Stability Assays in FVB Mice

FVB mice were injected with 3.7 MBq (100 μCi) of $^{64}$Cu-NMEB-RGD. At 1 and 4 h, mice (n=2) were euthanized and blood was withdrawn from the heart. The red blood cells were separated from the plasma using centrifugation (3500 rpm for 5 min). Then after, 0.2 mL from the plasma were diluted with cold methanol (1:1), vortex for 30 second and centrifuged for 5 min at 10,600 g. The extracted soup was taken, filter on 0.45 μm filter and injected into an analytical HPLC using system 1.

$^{64}$Cu-NMEB-RGD was stable in mouse serum for up to 24 h; no significant de-metalation was observed. In vivo, $^{64}$Cu-NMEB-RGD was stable up to 4 h in the blood with only a small amount of a more polar component apparent. Over 90% of the radioactivity extraction was bound to the blood proteins fraction. Evaluation of stability in vivo was limited to 4 h because at 24 h the amount of $^{64}$Cu-NMEB-RGD that extracted from the albumin/blood was too low for HPLC analysis.

Example 17: Tumor Model

Female athymic nude mice (Harlan Laboratories) were housed in an animal facility under pathogen-free conditions. Tumor model was developed in 5 to 6 weeks old female athymic nude mice by injection of 5×10$^6$ cells into their right shoulders. The mice underwent small-animal PET studies when the tumor volume reached 300 mm$^3$ (14-20 days after inoculation), and received $^{90}$Y radionuclide therapy when the tumor volume reached 150 mm$^3$ (10-14 days after inoculation).

Example 18: Biodistribution

U87MG tumor xenografts injected with $^{64}$Cu-NMEB-RGD were sacrificed after 24 h time-point PET imaging. Blood, muscle, bone, liver, kidneys, spleen, intestine, heart and tumor were collected and wet-weighed. For mice bearing MDA-MB-435 and HT-29 tumor xenografts, injected with $^{64}$Cu-NMEB-RGD, blood, tumor and heart were collected. Radioactivity was measured in a γ-counter. The results were expressed % ID/g.

Example 19: In Vitro Characterization of NMEB-RGD

The binding affinity of NMEB-RGD to integrin $\alpha_v\beta_3$ was compared to c(RGDfK) in competition assays using U87MG cells. The IC$_{50}$ values for NMEG-RGD and c(RGDfK) were 59.88±13.95 nM and 46.61±18.77 nM, respectively (FIG. 2A), when competed with $^{18}$F-NOTA-c(RGDfK) at 1 h and 74.07±28.24 nM and 85.21±13.99 nM, respectively (FIG. 2B) against $^{64}$Cu-NOTA-c(RGDfK) at 4 h. The specific activity for both tracers was similar (6.66 GBq/μmol) which allowed one to assume that the difference in binding of both tracers was not due to receptor saturation.

In the presence of human serum albumin (HSA), the binding affinity of NMEB-RGD was lower (higher numerically) at 1 h incubation time (412.03±371.38 nM, FIG. 2B). In contrast, the NMEB-RGD binding affinity of NMEB-RGD to albumin (2.34±1.38 μM, FIG. 2C) was 39 fold lower (higher numerically) than to integrin $\alpha_v\beta_3$. This low affinity to albumin was comparable to the published binding affinity of Evans Blue (EB) to albumin (~2.5 μM). To test whether the lower binding affinity of NMEB-RGD to integrin $\alpha_v\beta_3$ in the presence of albumin is due to lower free NMEB-RGD concentration in the buffer or a significantly slower association rate of the EB-RGD-albumin complex, the binding of NMEB-RGD to integrin $\alpha_v\beta_3$ was evaluated in the presence of albumin over 4 h. Competition with $^{64}$Cu-NOTA-c(RGDfk) as a competitor with these conditions reduced the IC$_{50}$ to 221.13±77.02 nM (FIG. 2B).

Figure 3B:
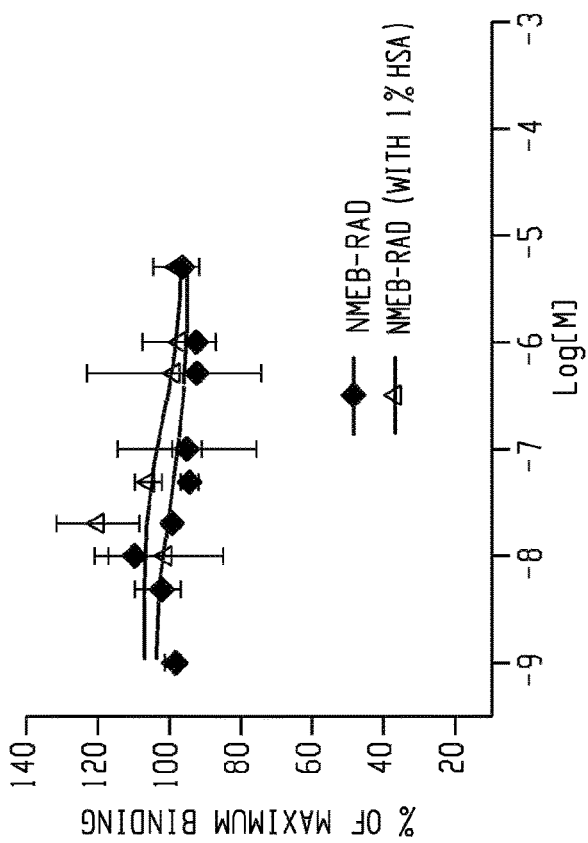
FIGS. 3A and 3B are plots of % of maximum binding versus concentration (Log molar, Log [M]) for the listed compounds binding to integrin $\alpha_v\beta_3$.
Figure 3A:
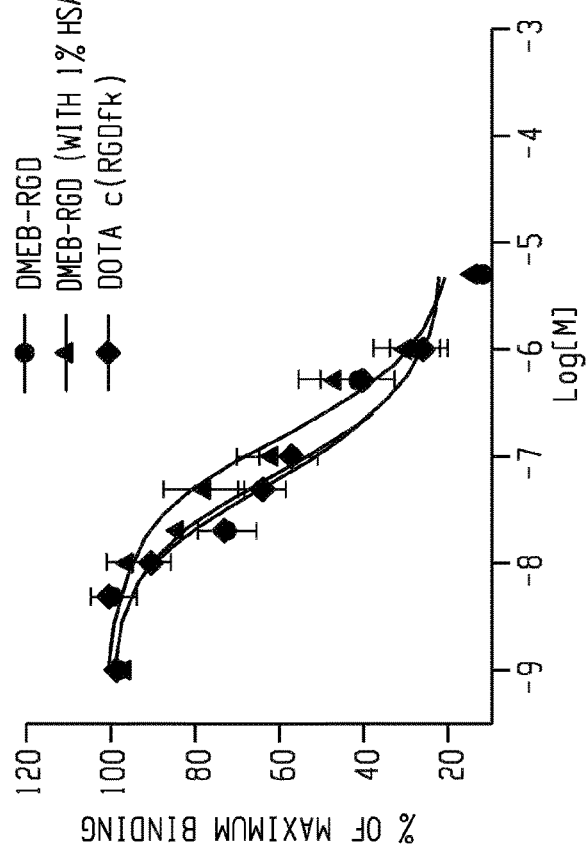

Replacing the chelator from NOTA to DOTA for c(RGDfk) and EB-RGD derivative, did not change the binding affinity towards integrin $\alpha_v\beta_3$ (IC$_{50}$ of 67.79±33.63 nM for DOTA-c(RGDfk) vs. 76.61±31 nM for DMEB-RGD without addition of HSA and 185.23±121.28 nM in the presence of 1% HSA, FIG. 3A) after 4 h incubation. Replacement of Glycine residue in RGD peptide to Alanine abolished the binding to the receptor (FIG. 3B).

Figure 2D:
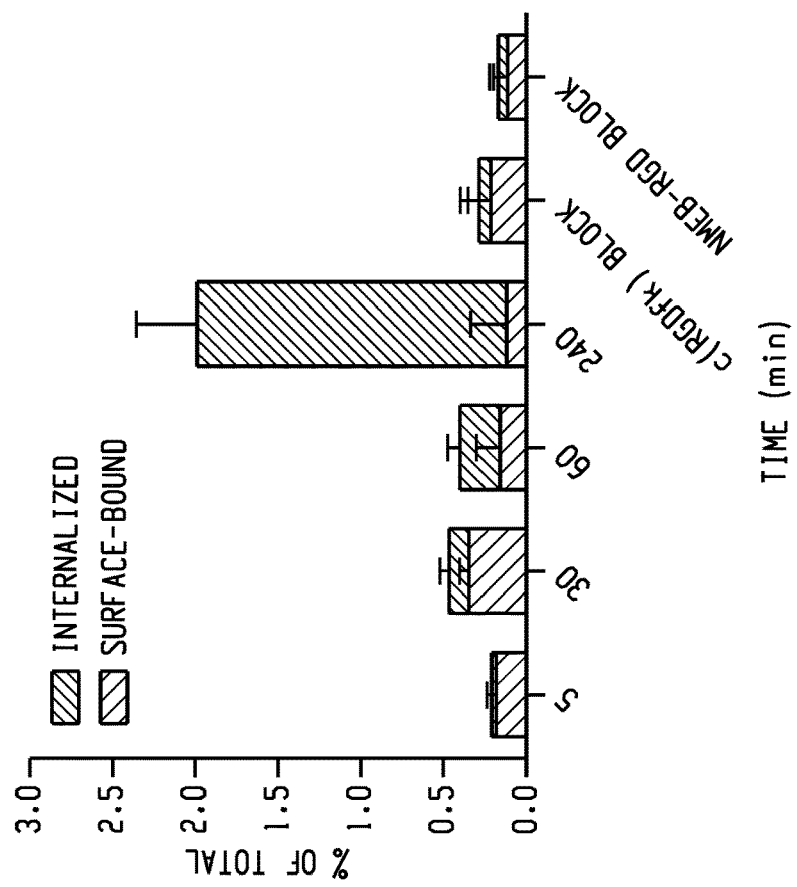
FIGS. 2D and 2E are plots of % of total versus time (minutes, min) showing uptake (FIG. 2D) and internalization (FIG. 2E) of $^{64}$Cu-NMEB-RGD.
Figure 2E:
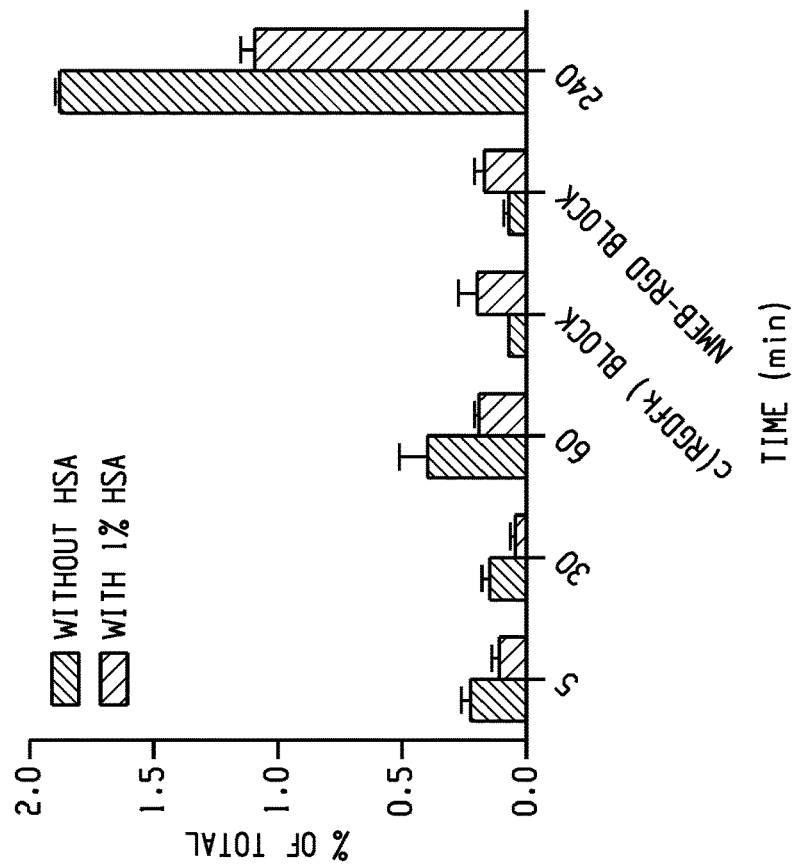
Figure 4A:
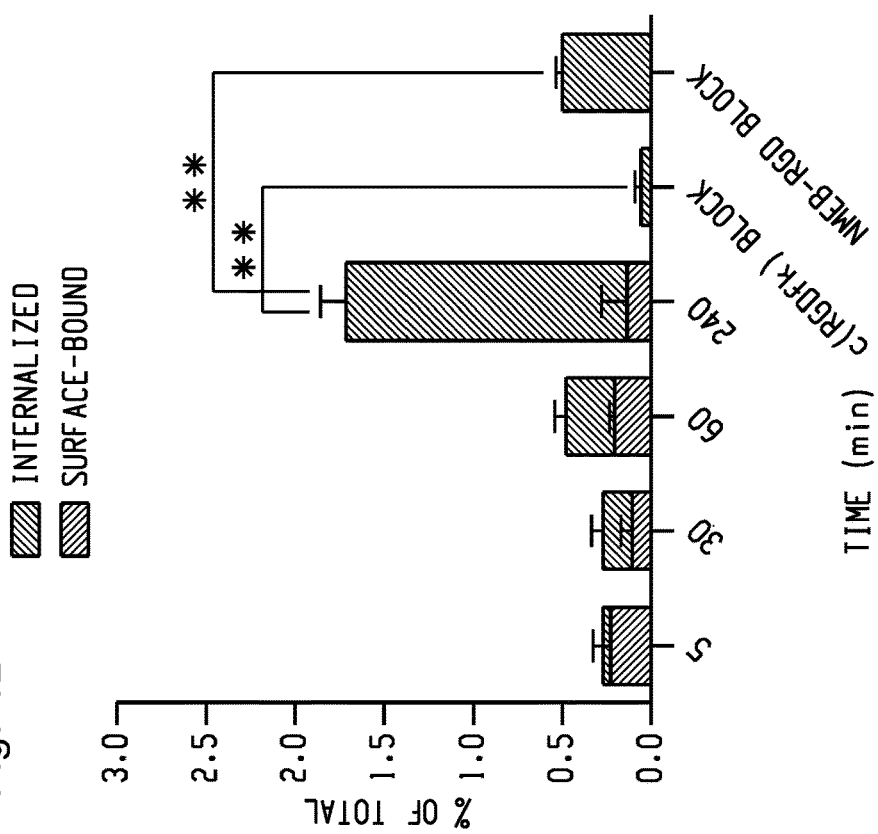
FIGS. 4A and 4B are plots of % of total versus time (minutes, min) for $^{64}$Cu-NMEB-RGD uptake in MDA-MB-435 and HT-29 cells (FIG. 4A) and internalization in MDA-MB-435 cells (FIG. 4B) in the listed cell types.
Figure 4B:
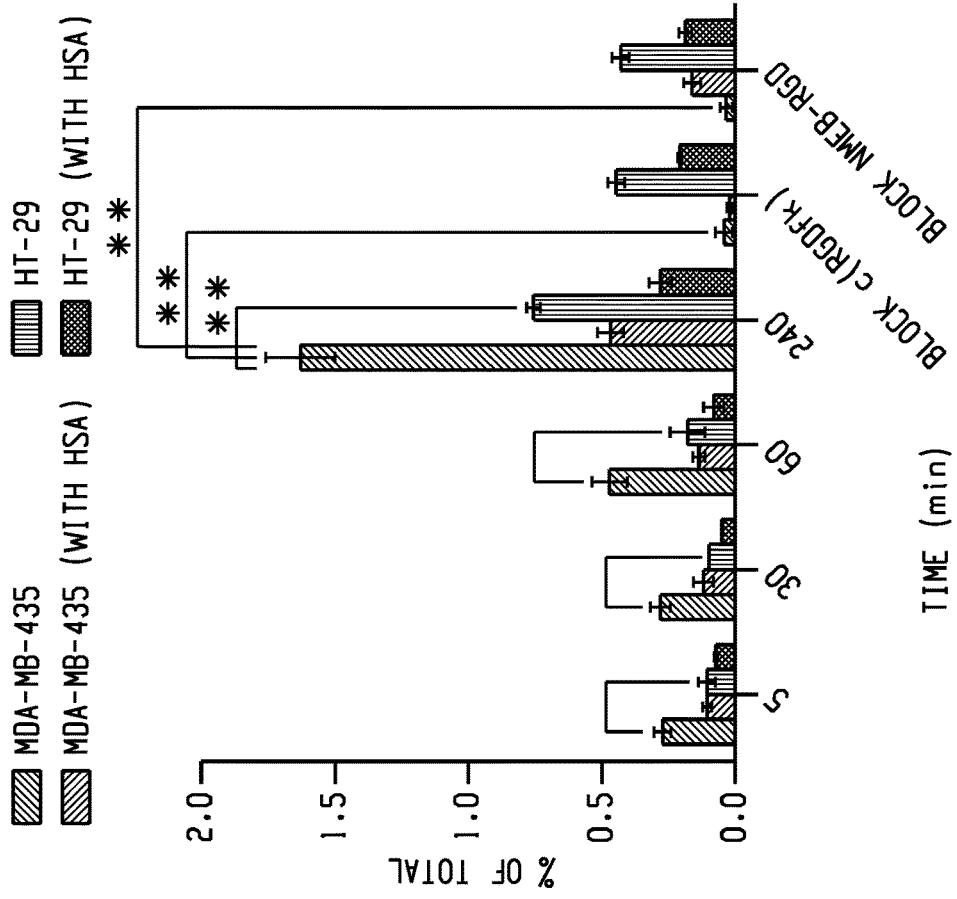
Figure 5:
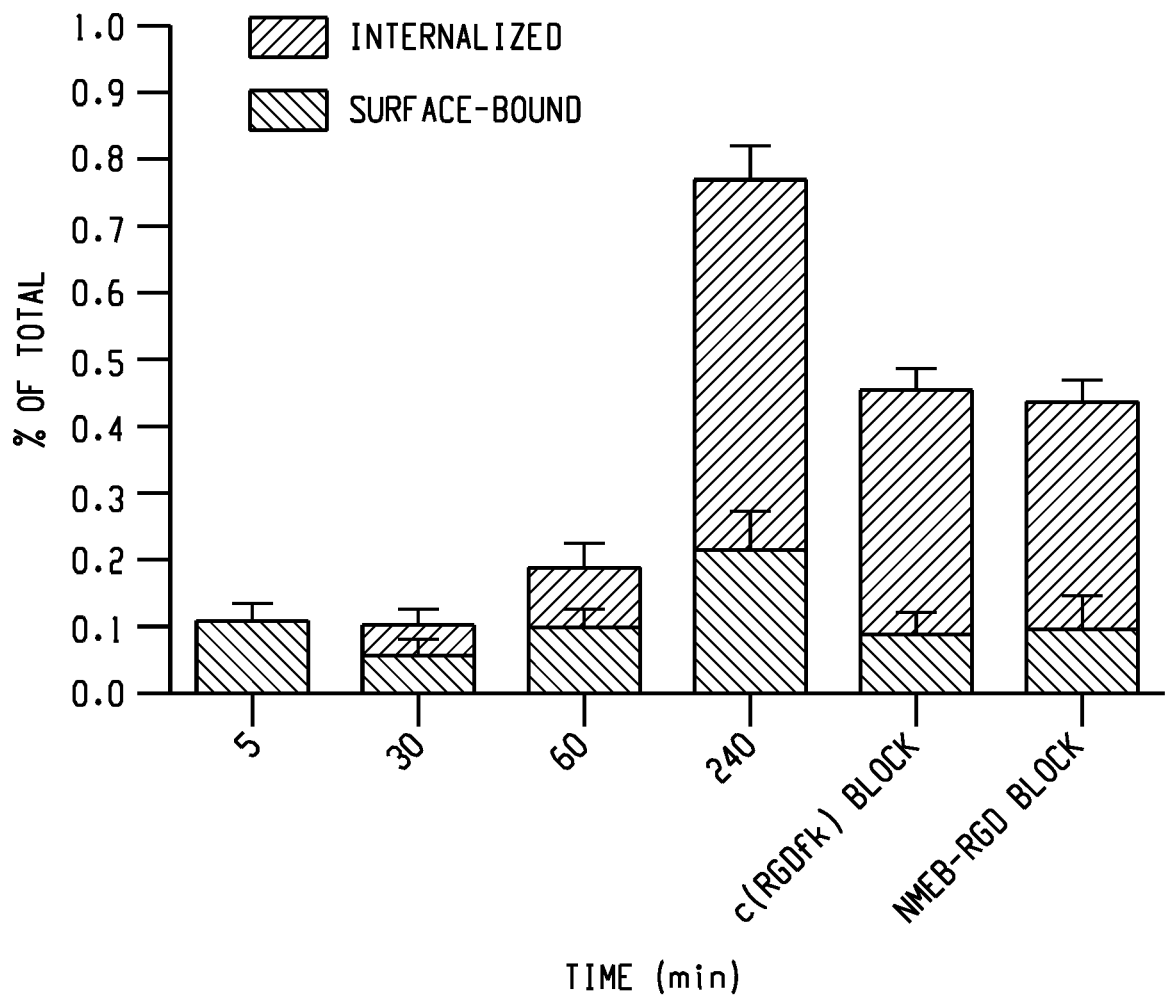
FIG. 5 is a plot of % of total versus time (minutes, min) for internalization of $^{64}$Cu-NMEB-RGD in HT-29 cells.

Example 20: Cellular Uptake and Internalization $^{64}$Cu-NMEB-RGD cell uptake and internalization was tested using three cell lines (U87MG, MDA-MB-435 and HT29) which are known and evaluated by us to express different levels of integrin $\alpha_v\beta_3$ (high, medium and low, respectively. $^{64}$Cu-NMEB-RGD uptake at all time points was significantly higher in the absence of albumin in the medium (FIG. 2D). $^{64}$Cu-NMEB-RGD uptake by U87MG cells, which express highest levels of integrin $\alpha_v\beta_3$, increased with longer incubation times, reaching 1.86±0.22% of total input at 4 h. For HT29 cells, which express the lowest integrin levels, the uptake was significantly lower (0.76±0.03%, FIG. 4A). The specificity of $^{64}$Cu-NMEB-RGD to integrin $\alpha_v\beta_3$ was tested by co-incubation with excess of either c(RGDfk) or NMEB-RGD (FIG. 2D). At 5 min, $^{64}$Cu-NMEB-RGD uptake was not due to internalization, however at later time points; most of $^{64}$Cu-NMEB-RGD uptake was internalized (FIG. 2E). This phenomenon was also seen in MDA-MB-435 and HT29 cell lines (FIGS. 4A-B, FIG. 5). To test if the internalization of NMEB-RGD also internalized albumin bound to NMEB-RGD, U87MG cells were incubated with fluorescently labeled albumin at increasing concentrations of NMEB-RGD, and the overall fluorescence of the cells was measured. No increase in cellular fluorescence over the baseline was observed with fitc-Albumin alone at any concentration of EB-RDG. The cells' fluorescence did not elevate with increased quantities of NMEB-RGD and suggested that the NMEB-RGD does not induce internalization of albumin, and it is likely to be released from the albumin prior to binding to integrin $\alpha_v\beta_3$.

Example 21: Micropet Imaging of Tumor Xenografts with 64CU-NMEB-RGD

Figure 6:
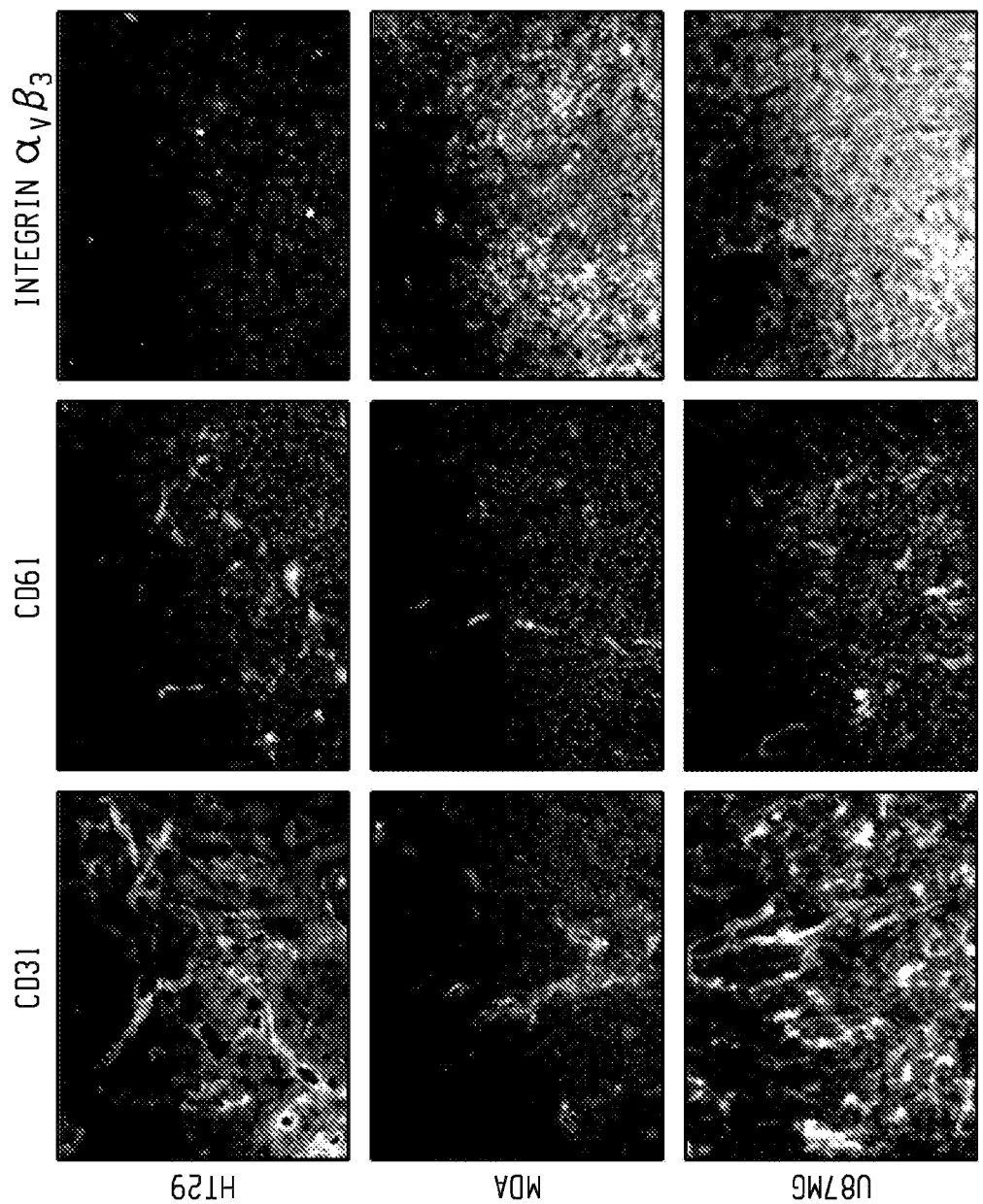
FIG. 6 is a set of micro PET images of $^{64}$Cu-NMEB-RGD bound to human tumor tissues.

The tumor vascularization and integrin $\alpha_v\beta_3$ expression levels in U87MG, MDA-MB-435 and HT29 tumor tissues was visualized using fluorescent antibodies for CD31, CD61 (murine integrin 13) and human integrin $\alpha_v\beta_3$. Both U87MG and HT29 tumors showed elevated vascularity shown by high CD31 staining while MDA-MB-435 tumor had relatively weaker staining (FIG. 6). U87MG tumor tissue showed the highest human integrin $\alpha_v\beta_3$ expression (FIG. 6). MDA-MB-435 had lower integrin expression but much higher than HT29 (FIG. 6). Murine integrin $3_3$ (CD61) expression levels were in agreement with CD31 staining, with the cells order of U87MG>HT29>MDA-MB-435 (FIG. 6).

Figure 7:
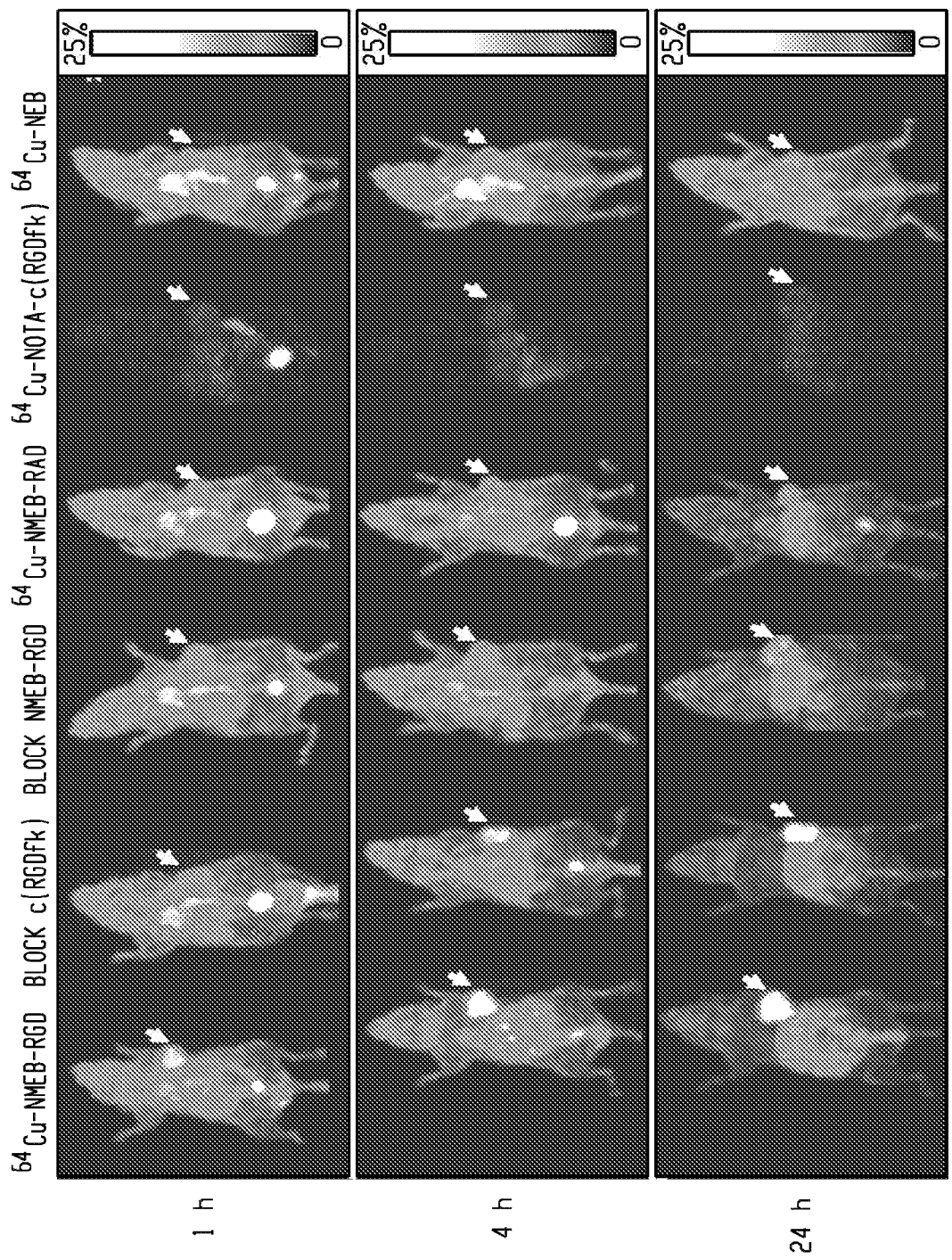
FIG. 7 is a set of micro PET images of $^{64}$Cu-NMEB-RGD in mouse tumor xenografts.
Figure 8:
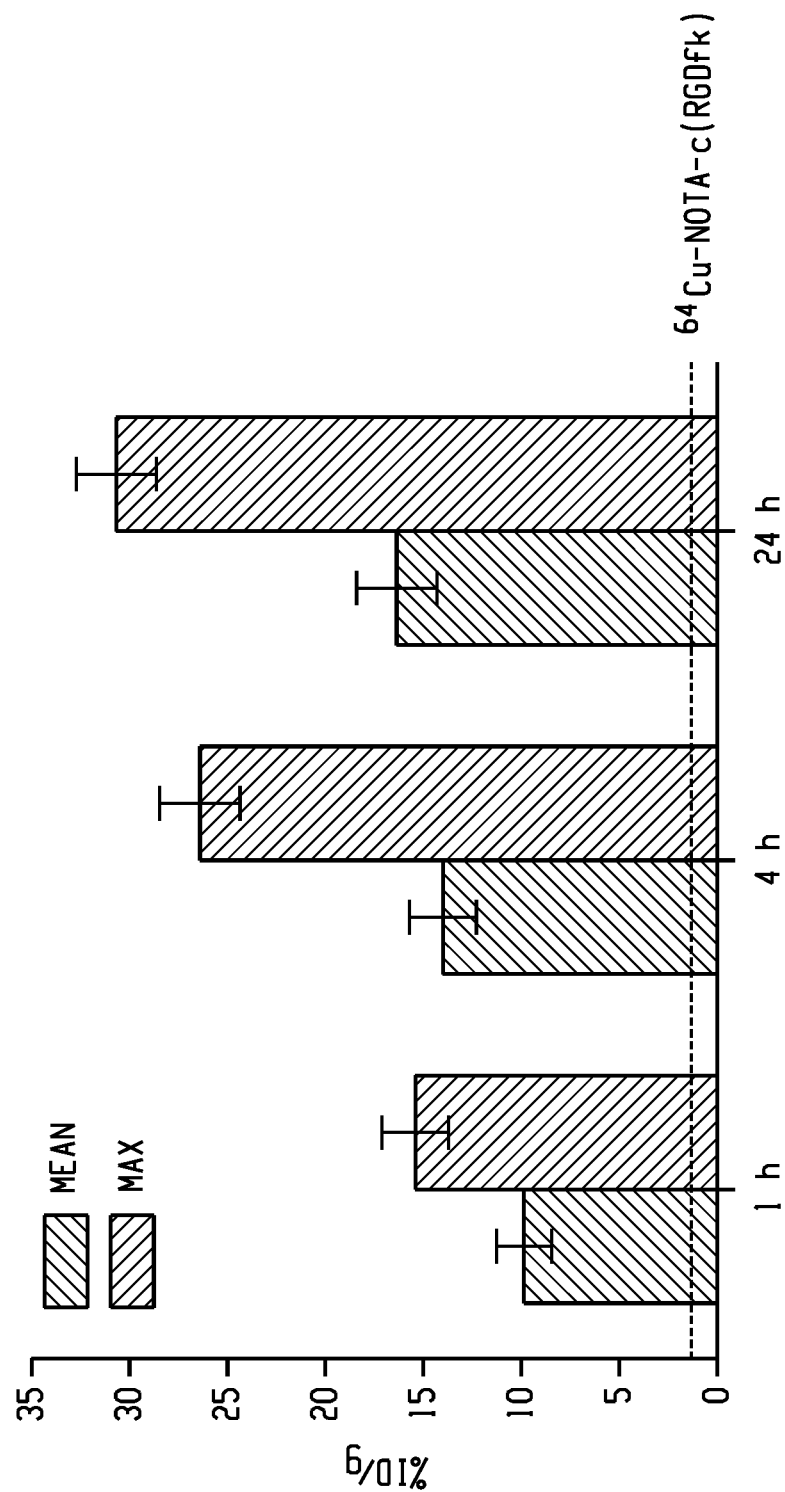
FIG. 8 is a plot of % injected dose per gram (% ID/g) versus time (hours, h) for uptake of $^{64}$Cu-NMEB-RGD in mouse tumor xenografts.
Figure 9:
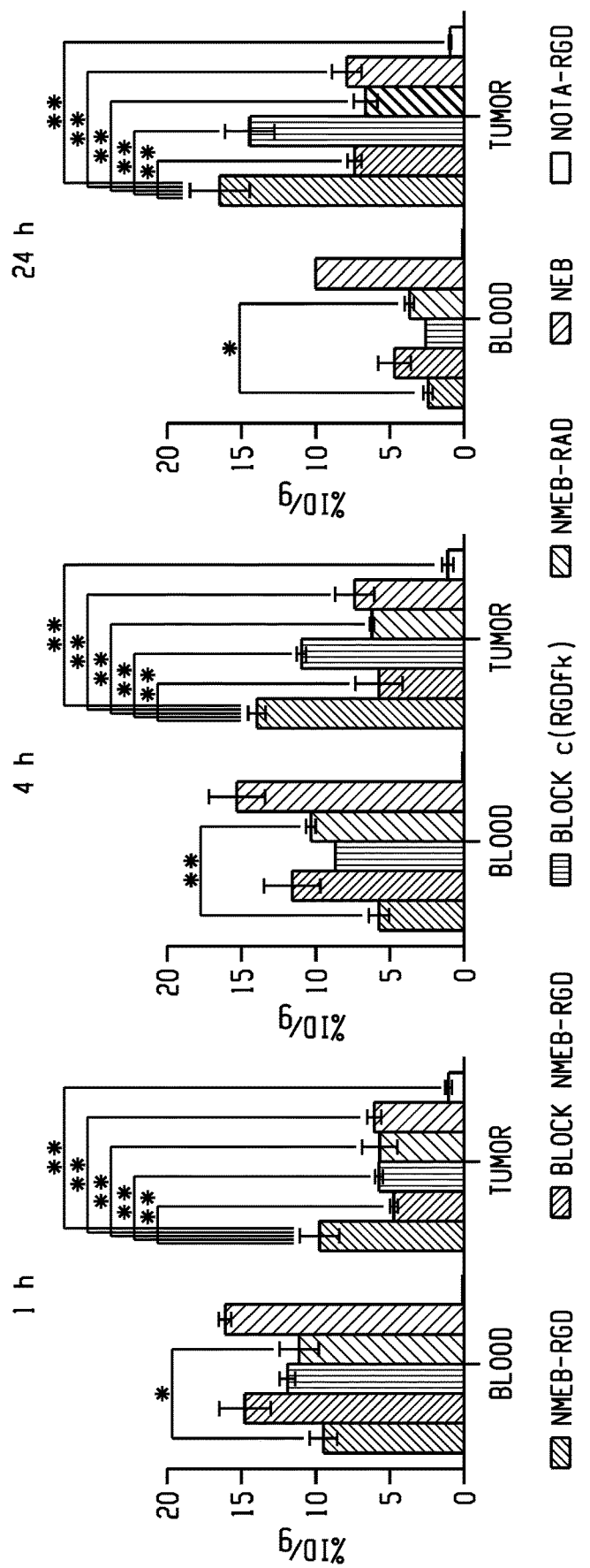
FIG. 9 is a set of plots of % injected dose per gram (% ID/g) versus time (hours, h) for uptake of $^{64}$Cu-NMEB-RGD in blood and tumor.
Figure 10:
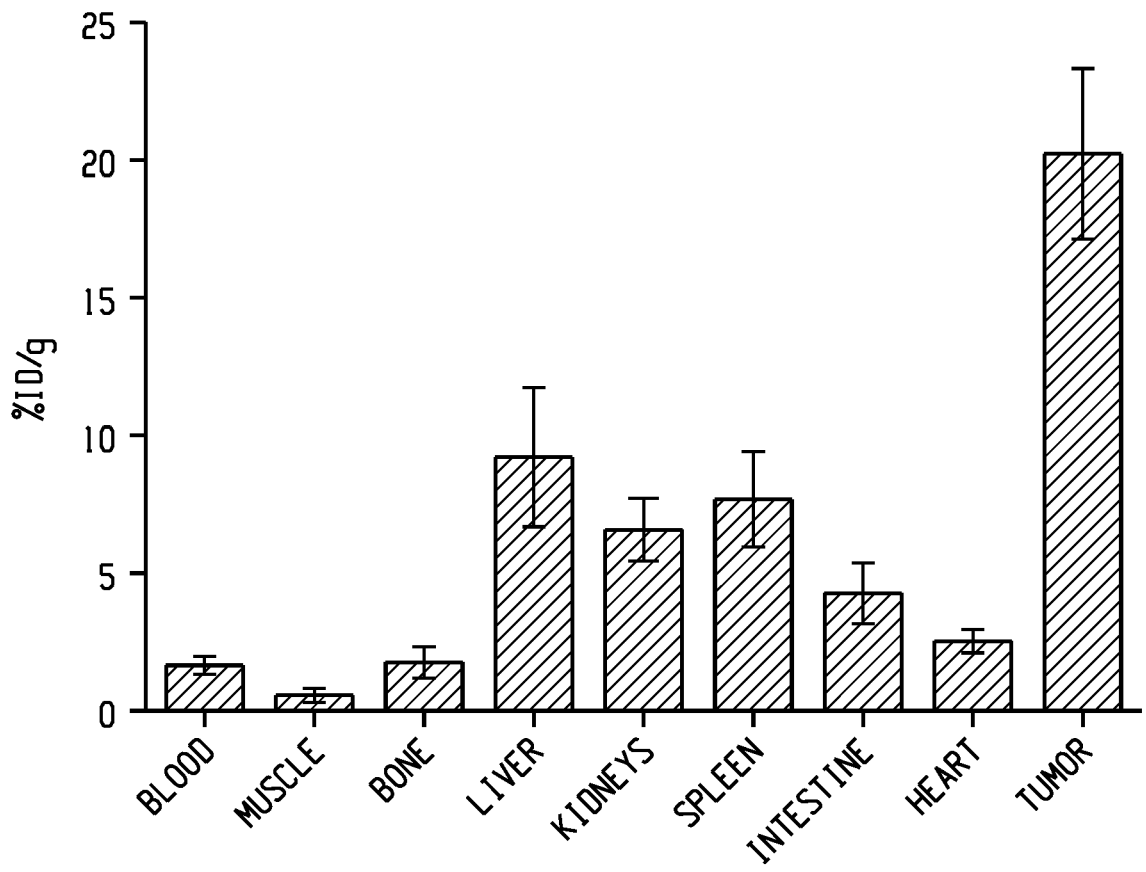
FIG. 10 is a plot of % injected dose per gram (% ID/g) for uptake of $^{64}$Cu-NMEB-RGD in various tissue types.

All the four radiotracers were first evaluated in U87MG xenografts (high integrin $\alpha_v\beta_3$ and high vascularity). $^{64}$Cu-NMEB-RGD had significantly higher uptake than all the tracers at all time points (9.87±1.40, 14.09±1.62 and 16.64±1.99% ID/g at 1, 4 and 24 h post-injection (p.i.) respectively, FIG. 7). Comparison between the % ID/g mean to max gave even higher accumulation in the tumor that reached 27-30% ID/g at 4 and 24 h p.i., which was 15 times higher than the uptake of $^{64}$Cu-NOTA-c(RGDfk) (FIG. 8). $^{64}$Cu-NMEB-RGD uptake in the blood was relatively high at 1 h p.i. (9.58±0.84% ID/g) but significantly decreased at 4 and 24 h p.i. to 5.73±0.67 and 2.46±0.25% ID/g, respectively, and resulted in high tumor to background ratio (FIGS. 7 and 9). Binding specificity of $^{64}$Cu-NMEB-RGD to integrin $\alpha_v\beta_3$ was tested by co-injection of either c(RGDfk) or unlabeled NMEB-RGD. When an excess of monomer was co-injected, the tumor uptake was decreased significantly at 1 h p.i. to about 25% of the uptake without blocking (5.77±0.08% ID/g, P=0.017). At 4 h p.i. the tumor uptake was increased to 11.1±0.05% ID/g and this uptake was slightly increased at 24 h p.i. to similar values as $^{64}$Cu-NMEB-RGD (FIG. 7). Co-injection using excess of unlabeled NMEB-RGD successfully blocked tumor uptake at all time points by 55-65% (FIGS. 7 and 9). In order to further confirm the validation of PET quantification, biodistribution study was performed right after PET imaging at 24 h p.i. and confirmed the high $^{64}$Cu-NMEB-RGD uptake in the tumor (FIG. 10).

$^{64}$Cu-NOTAc(RGDfk) was rapidly cleared from the blood through the urinary tract and depicted low accumulation in the tumor (1.29±0.17, 1.15±0.07, 1.06±0.03% ID/g at 1, 4 and 24 h p.i. correspondingly, FIGS. 7 and 9). The non-specific tracer, $^{64}$Cu-NMEB-RAD had low tumor accumulation at all time points (approximately 6% ID/g). Its uptake in the blood was significantly higher than $^{64}$Cu-NMEB-RGD at all time points (10-12% ID/g up to 4 h p.i and 3.7±0.3% ID/g at 24 h p.i. FIGS. 7 and 9). $^{64}$Cu-NEB had the highest accumulation in the blood at all time points while uptake in the tumor was slightly higher than $^{64}$Cu-NMEB-RAD (6-7% ID/g up to 4 h p.i and approximately 8% ID/g at 24 h p.i. FIGS. 7 and 9).

Figure 11:
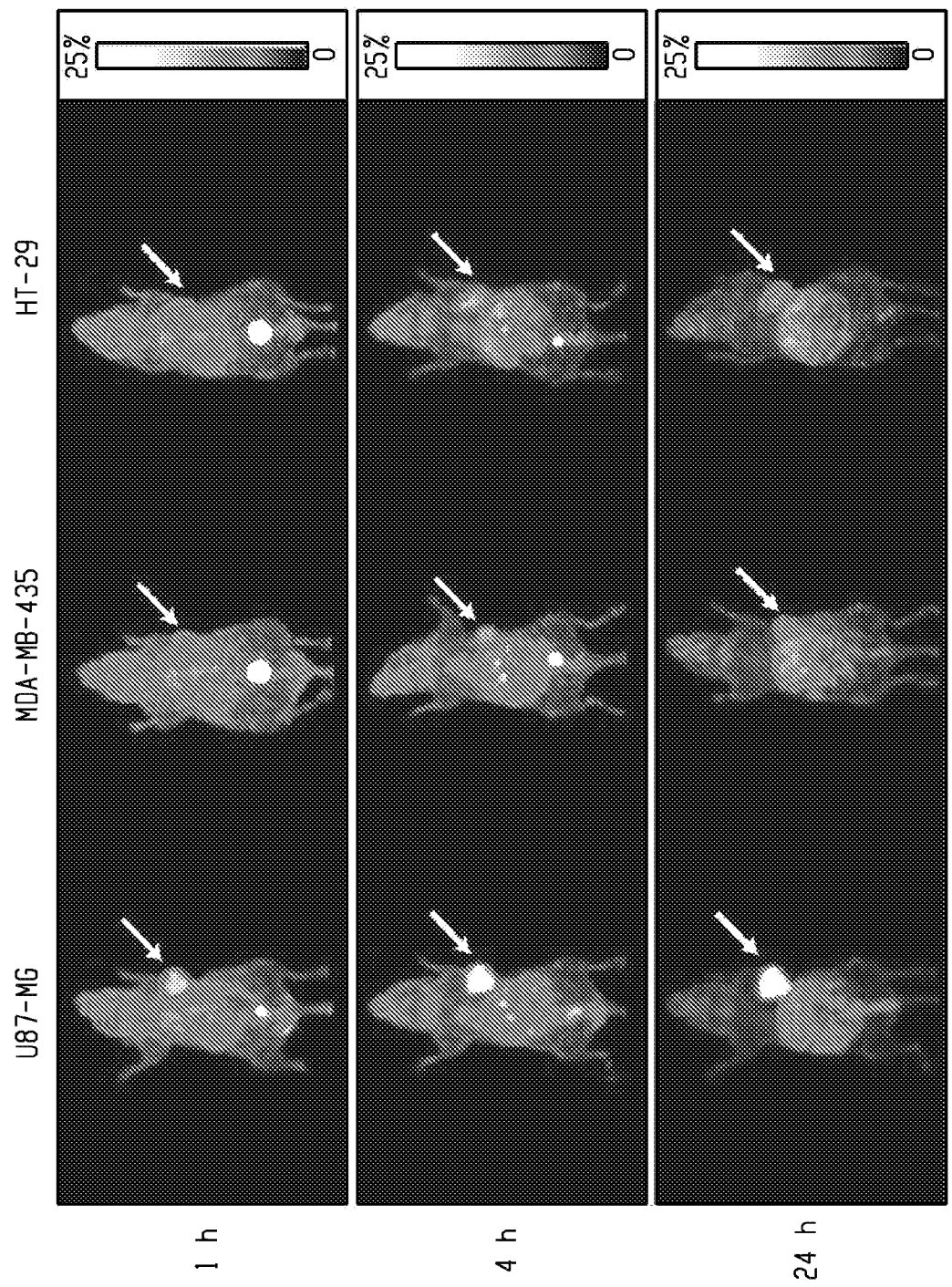
FIG. 11 is a set of micro PET images of $^{64}$Cu-NMEB-RGD in mouse tumor xenografts.
Figure 12:
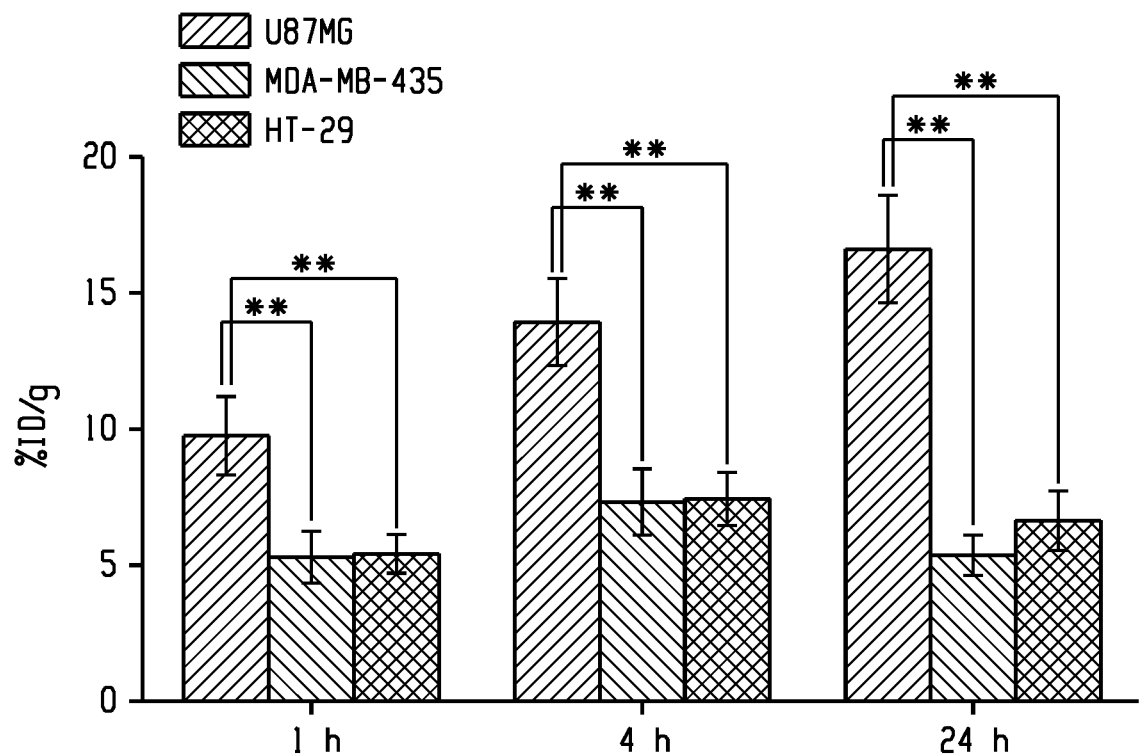
FIG. 12 is a plot of % injected dose per gram (% ID/g) versus time (hours, h) for uptake of $^{64}$Cu-NMEB-RGD in mouse tumor xenografts.
Figure 13:
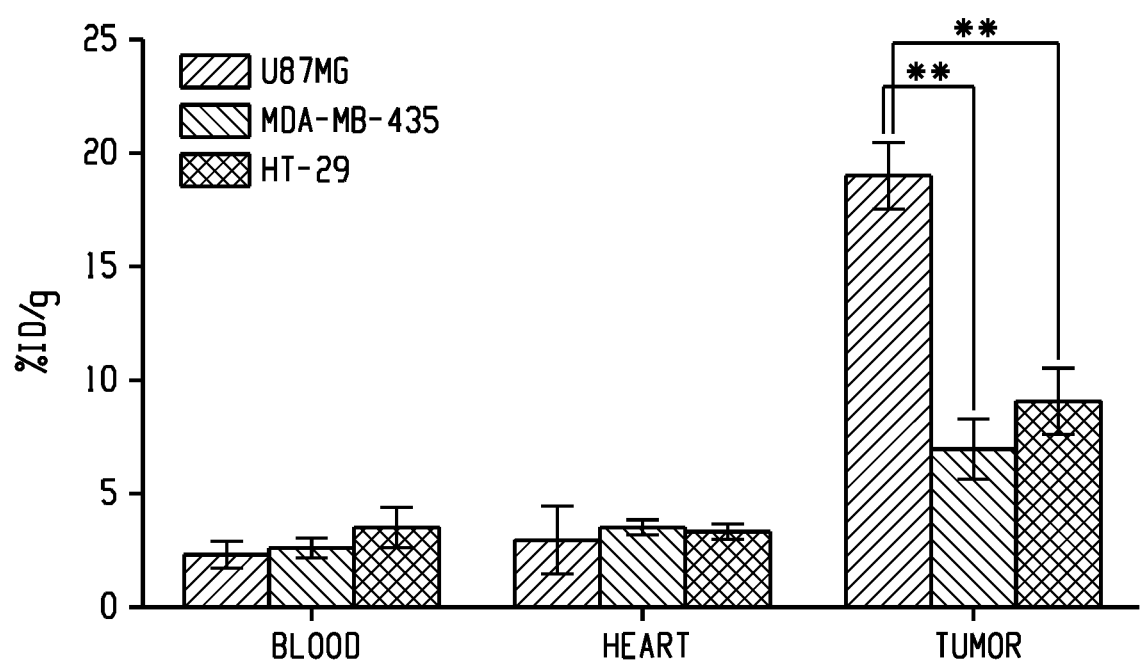
FIG. 13 is a plot of % injected dose per gram (% ID/g) for uptake in different tissue types of $^{64}$Cu-NMEB-RGD in mouse tumor xenografts.
Figure 14:
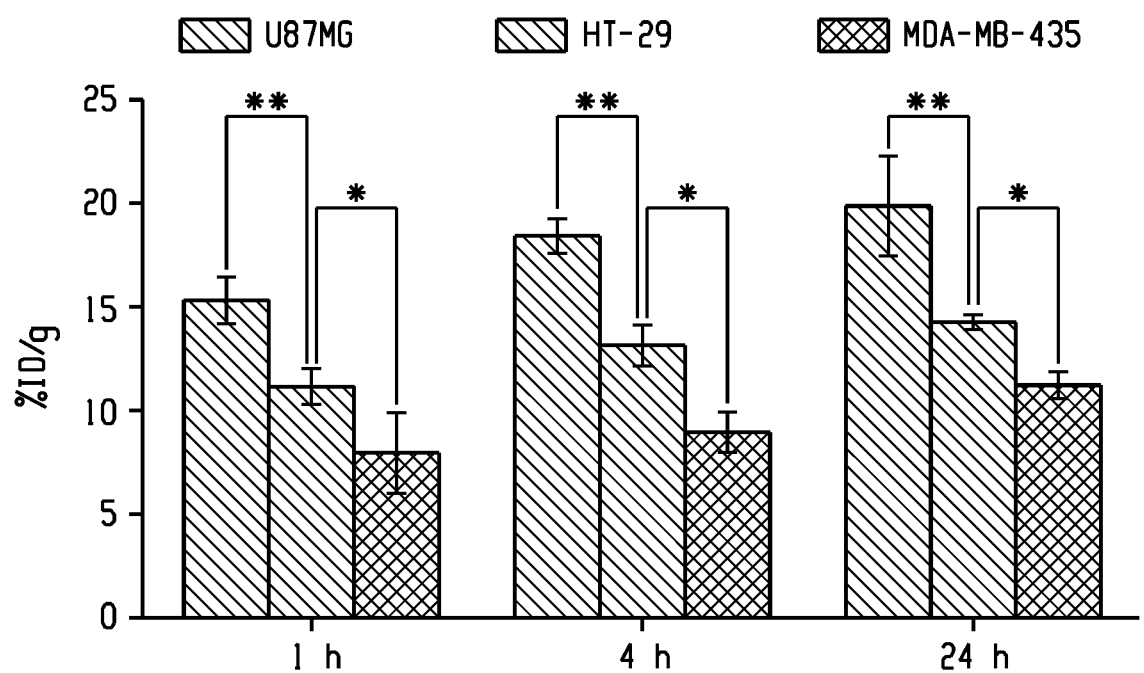
FIG. 14 is a plot of % injected dose per gram (% ID/g) versus time (hours, h) for uptake of $^{64}$Cu-NMEB in mouse tumor xenografts.

$^{64}$Cu-NMEB-RGD uptake in U87MG xenografts was compared to MDA-MB-435 and HT29 xenografts which have different integrin and vascularity levels (FIGS. 11-12). $^{64}$Cu-NMEB-RGD uptake in both MDA-MB-435 and HT29 xenografts was significantly lower than U87MG at all time points (FIGS. 11-12). The blood and heart uptake was the same with all the three models (FIG. 13 In order to assess the portion of the tumor uptake is mainly due to specific receptor binding but not vascularity and enhanced permeability and retention (EPR) effect, we injected the blood pool imaging tracer, $^{64}$Cu-NEB, to MDA-MB-435 and HT29 xenografts. $^{64}$Cu-NEB uptake was in correlation to CD31 and CD61 staining, follow the order of U87MG>HT29>MDA-MB-435 (FIG. 14).

Example 22: Radiotherapy

Figure 15:
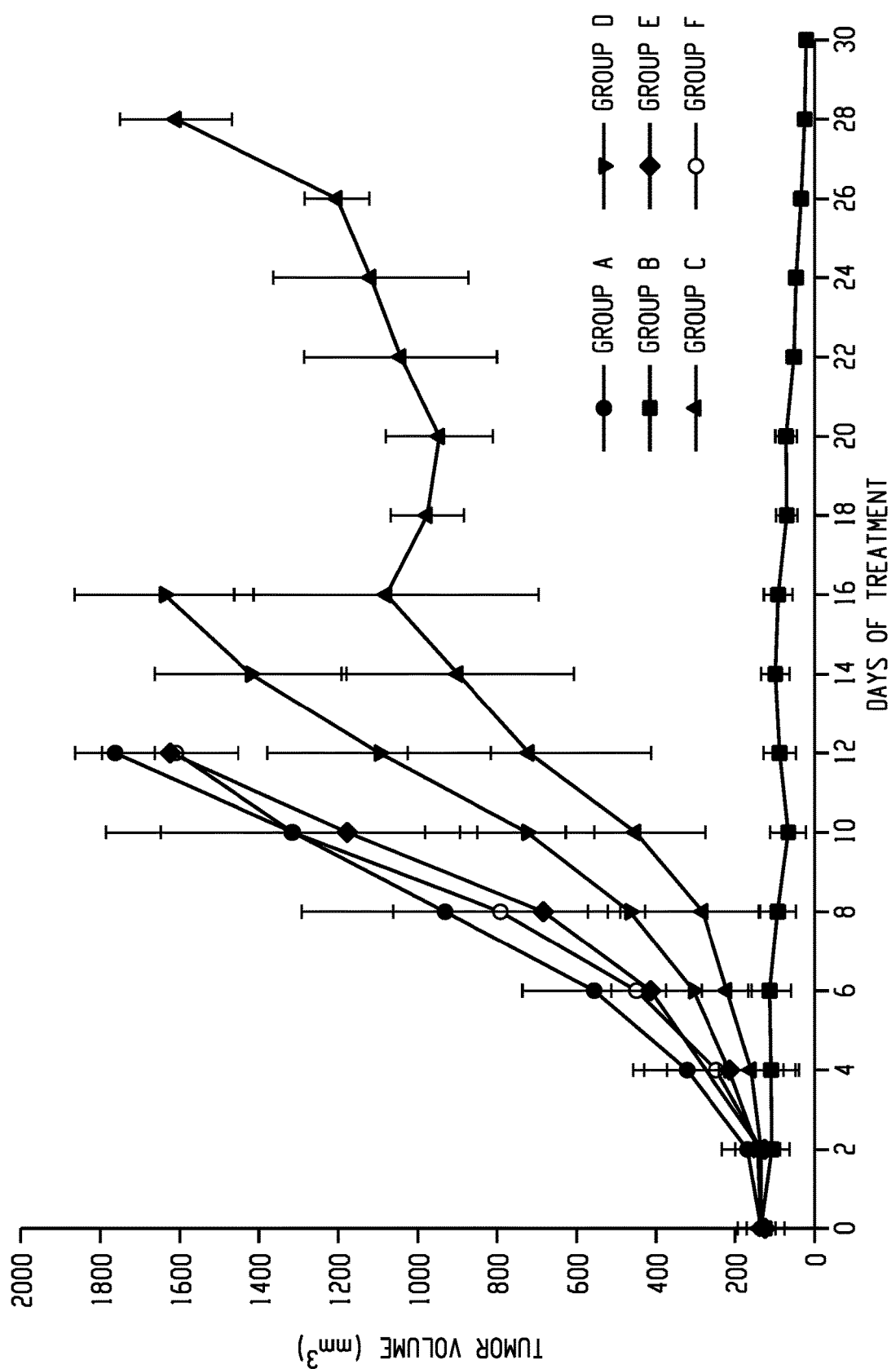
FIG. 15 is a plot of tumor volume (millimeters, mm) versus days of treatment for various treatment arms.
Figure 16:
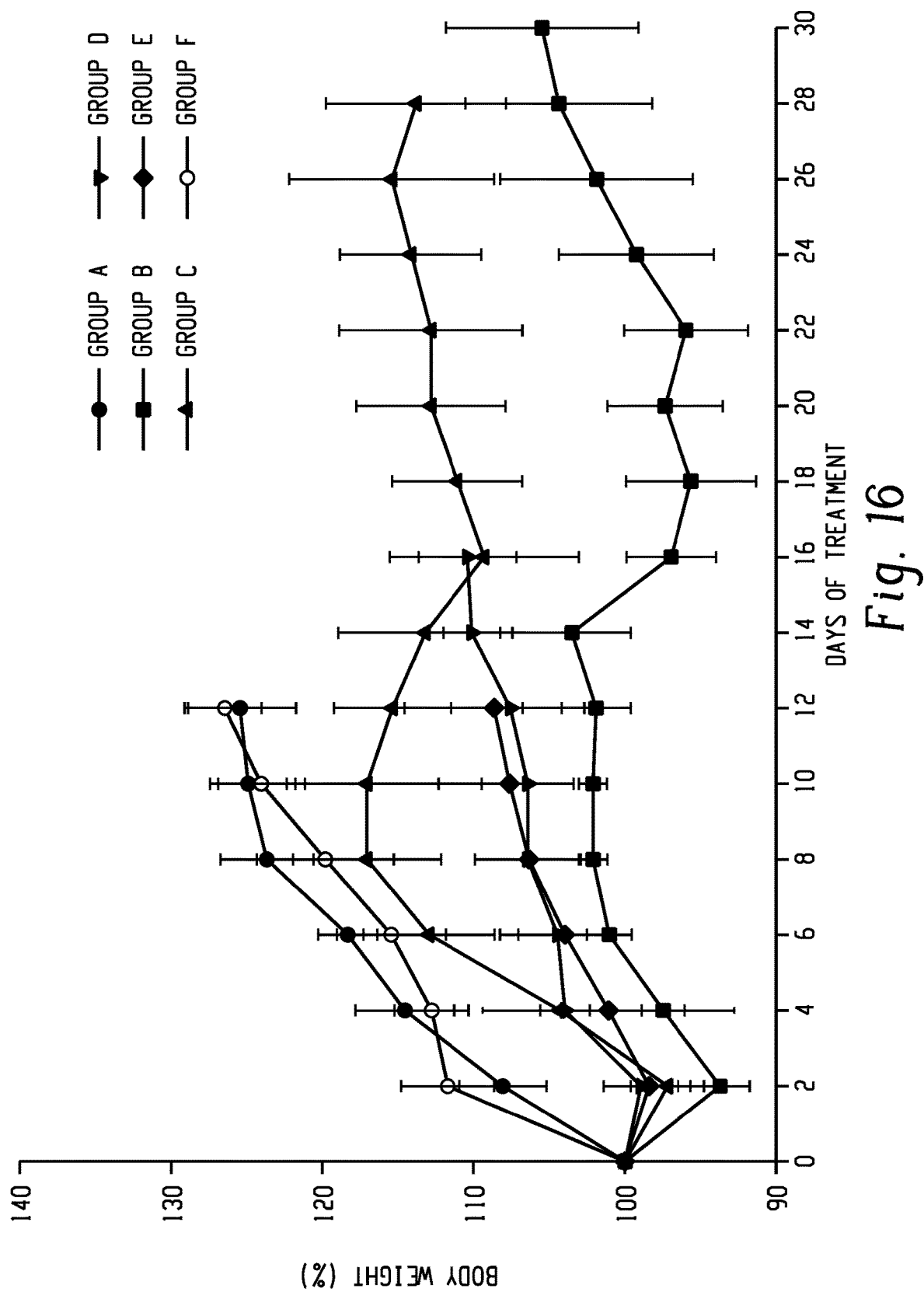
FIG. 16 is a plot of body weight (% of starting weight, %) versus days of treatment for various treatment arms.
Figure 17:
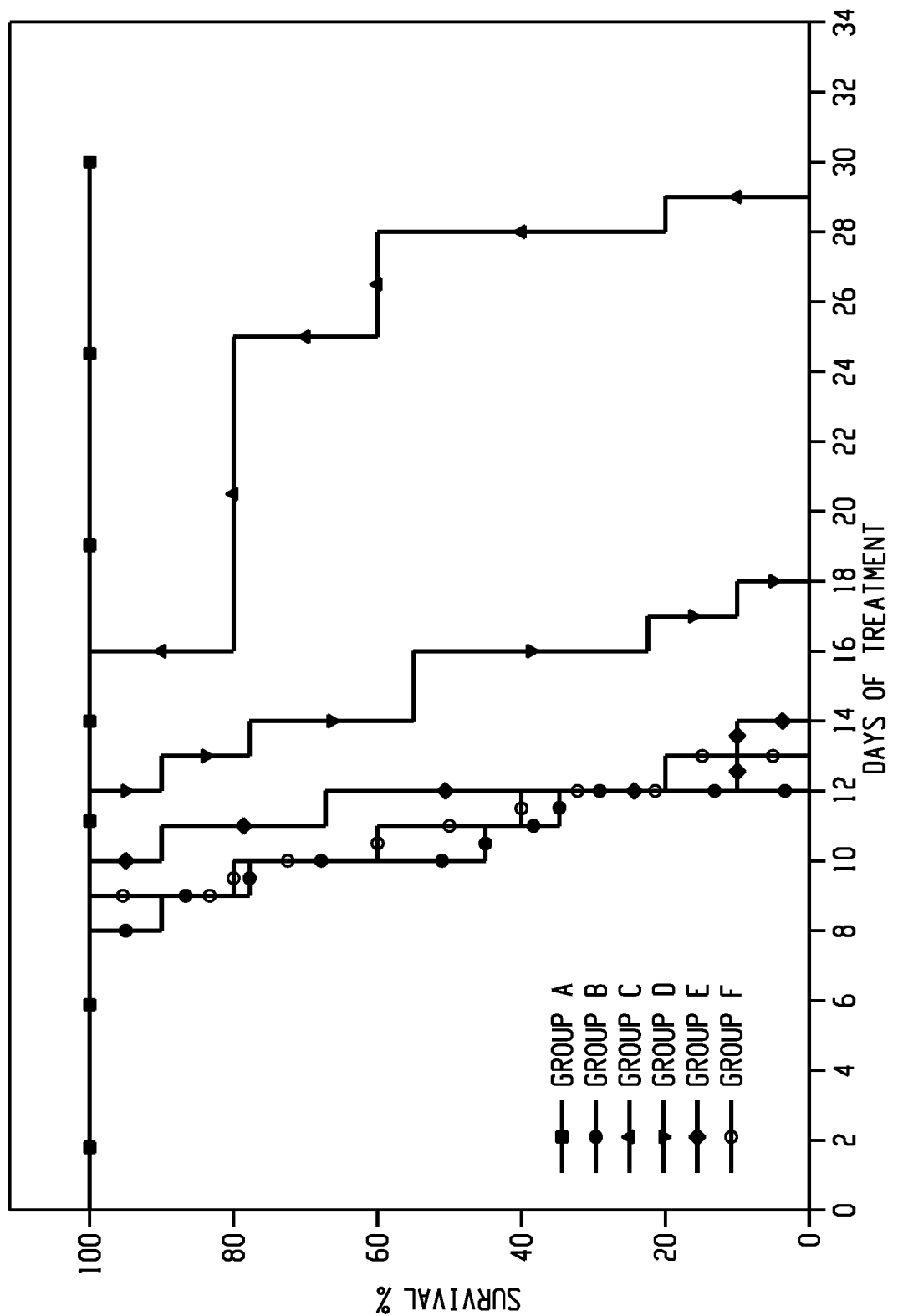
FIG. 17 is a plot of % survival versus days of treatment for various treatment arms.

NMEB-RGD was applied to integrin $\alpha_v\beta_3$ targeted radiotherapy. NMEB was altered to encompass DOTA (named hereafter DMEB), which can chelate the radiotherapeutic isotope $^{90}$Y. Radiotherapy efficacy on tumor growth was evaluated in U87MG tumor bearing mice (initial tumor size ranging from 150 to 200 mm$^3$) as follows: group A injected with Saline; group B was treated with 7.4 MBq (200 µCi) of $^{90}$Y-DMEB-RGD; group C treated with 3.7 MBq (100 µCi) of $^{90}$Y-DMEB-RGD; group D treated with 1.75 MBq (50 µCi) of $^{90}$Y-DMEB-RGD; group E treated with 7.4 MBq of $^{90}$Y-DOTA-c(RGDfK) and group F treated with 1.75 MBq of $^{90}$Y-DOTA-c(RGDfK) (FIGS. 15-17). The day of the first injection is referred as day 0. At day 6 post treatment, significant differences between the groups were evident (FIG. 15). The tumor volume from all $^{90}$Y-DMEB-RGD treated mice (groups B-D) were significantly lower (p<0.01) than that in saline injected group A (FIG. 15). Moreover, starting from day 8 after the treatment, significant differences in the tumor volume were observed between all three groups of $^{90}$Y-DMEB-RGD and groups E-F (FIG. 15). These differences increased over time, and tumors of mice injected with 7.4 MBq of $^{90}$Y-DMEB-RGD showed reduction of volume by day 8 (group B, FIG. 15). In order to test whether an additional injection of $^{90}$Y-DMEB-RGD will eliminate the tumor, we re-injected 7.4, 3.7 or 1.75 MBq of $^{90}$Y-DOTA-c(RGDfK) to groups B-D respectively 14 days post initial treatment. Second injection of $^{90}$Y-DMEB-RGD in dose of 7.4 MBq, shrank the tumor volume significantly (P=0.01 at day 20 and decreased to 0.0003 at day 22, FIG. 15) and the tumors almost disappeared up to 30 days post initial treatment. Minor tumor shrink was detected in group C (3.7 MBq dose), which lasted for several days after the second injection and then the tumor volume increased once more (FIG. 15). No effect on the tumor volume was observed for group D (received dose of 1.75 MBq). The systemic toxicity of the radiotherapy was evaluated by monitoring animal body weight. Only group B showed statistically significant, but minor (5%), weight loss at day 2, but regained their weight at day 4 (FIG. 16). Animal body weight for all other groups continued to increase after treatment (FIG. 16). Similar pattern was observed after the second injection. End point of the radiotherapy, which was used for survival analysis, was determined to be when the tumor volume reached 1600 mm$^3$, the tumor has ulcer or the mice died. Survival analysis showed significant differences (p<0.01) for groups B-D in comparison to groups A, E and F. For group B the survival was 100% up to 30 days post initial treatment, and for groups B, C, and D the % survival was dose dependent (FIG. 17).

Figure 18A:
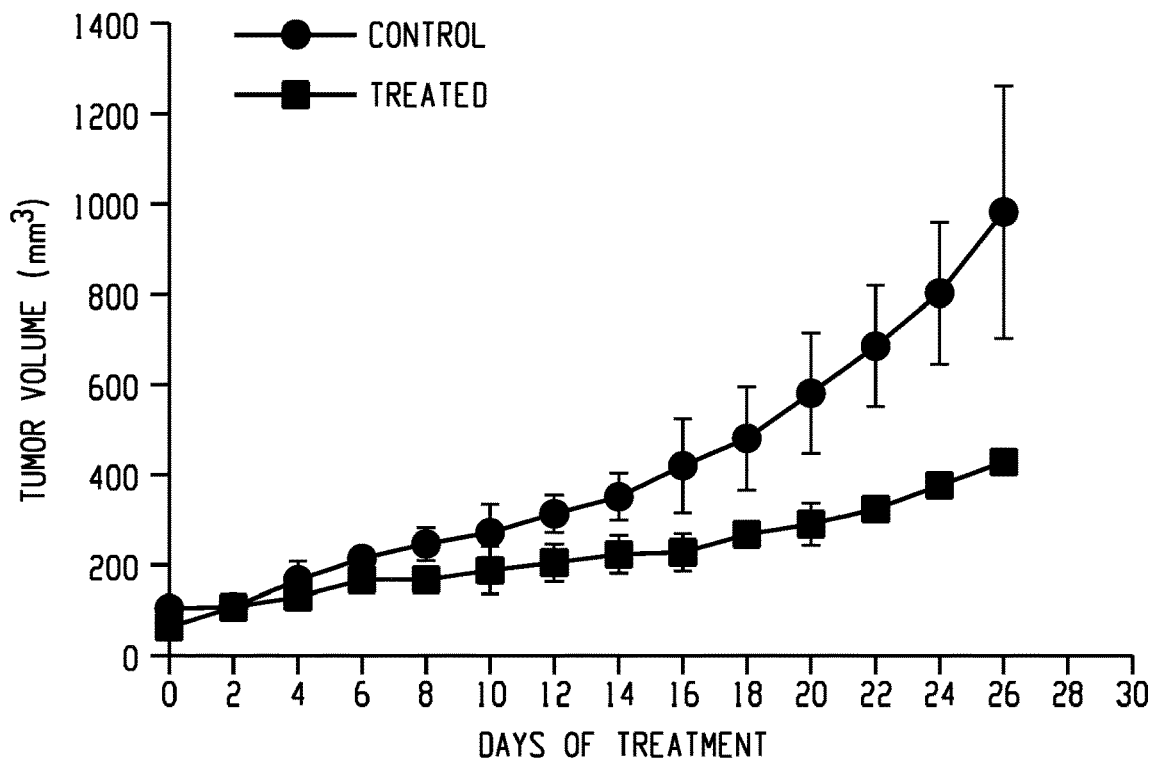
FIGS. 18A and 18B are plots of tumor volume (FIG. 18A, millimeters, mm) and body weight (FIG. 18B, % of starting weight, %) versus days of treatment for various treatment arms.
Figure 18B:
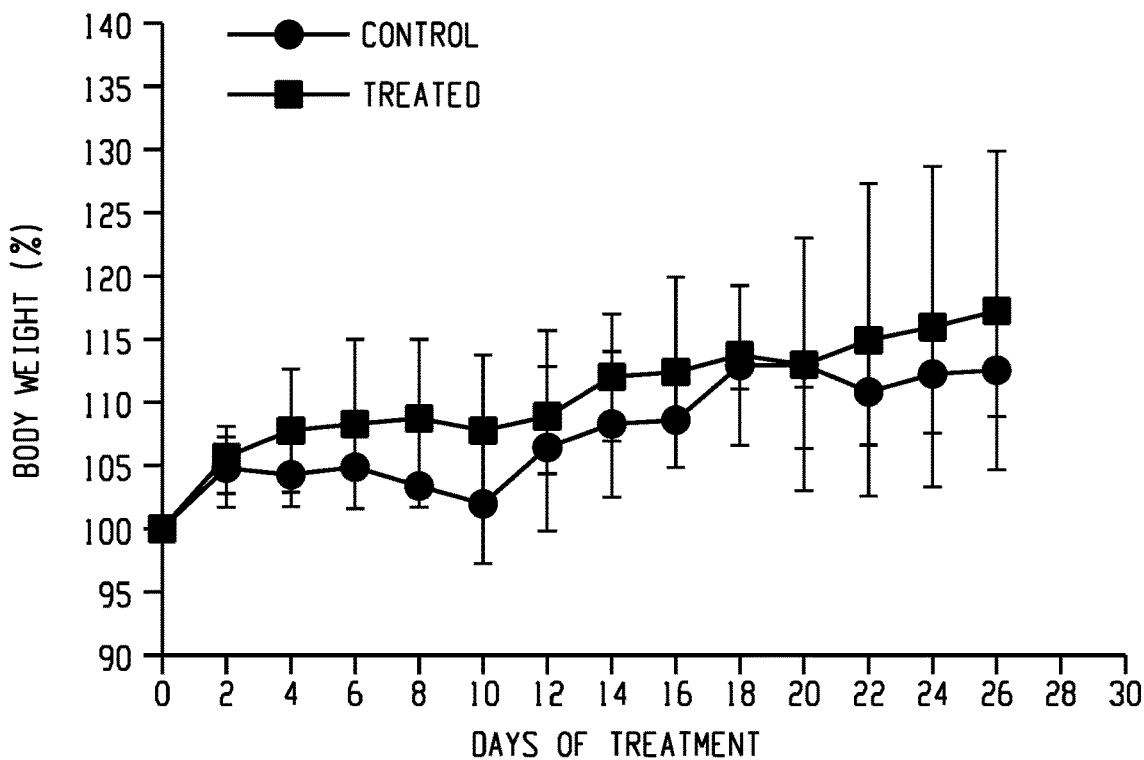

In order to test the specificity of $^{90}$Y-DMEB-RGD radiotherapy to integrin $\alpha_v\beta_3$, the efficacy of 7.4 MBq $^{90}$Y-DMEB-RGD in HT29 that expresses lower human integrin levels but has moderate expression of mouse integrin was tested (FIG. 6). Despite the high vascularity of this tumor xenograft, it grows much slower than U87MG model. Injection of HT29 tumor bearing mice with 7.4 MBq $^{90}$Y-DMEB-RGD was compared in the same model to injection of saline (FIG. 18A). The tumor volume between the treated group and the control was similar up to 8 days post treatment and then the treated tumor started to grow in a slower speed as compared to the control. As a result, $^{90}$Y-DMEB-RGD targeted radiotherapy lead to a delay of tumor growth in HT-29 tumor xenografts, rather than tumor shrinkage as shown in U87MG (FIGS. 16 and 18A). Body weight of HT-29 treated mice did not change drastically in comparison to the control group (FIG. 18B). HT-29 treated and non-treated mice were sacrificed at day 26 post injection due to tumors ulcer.

Figure 19:
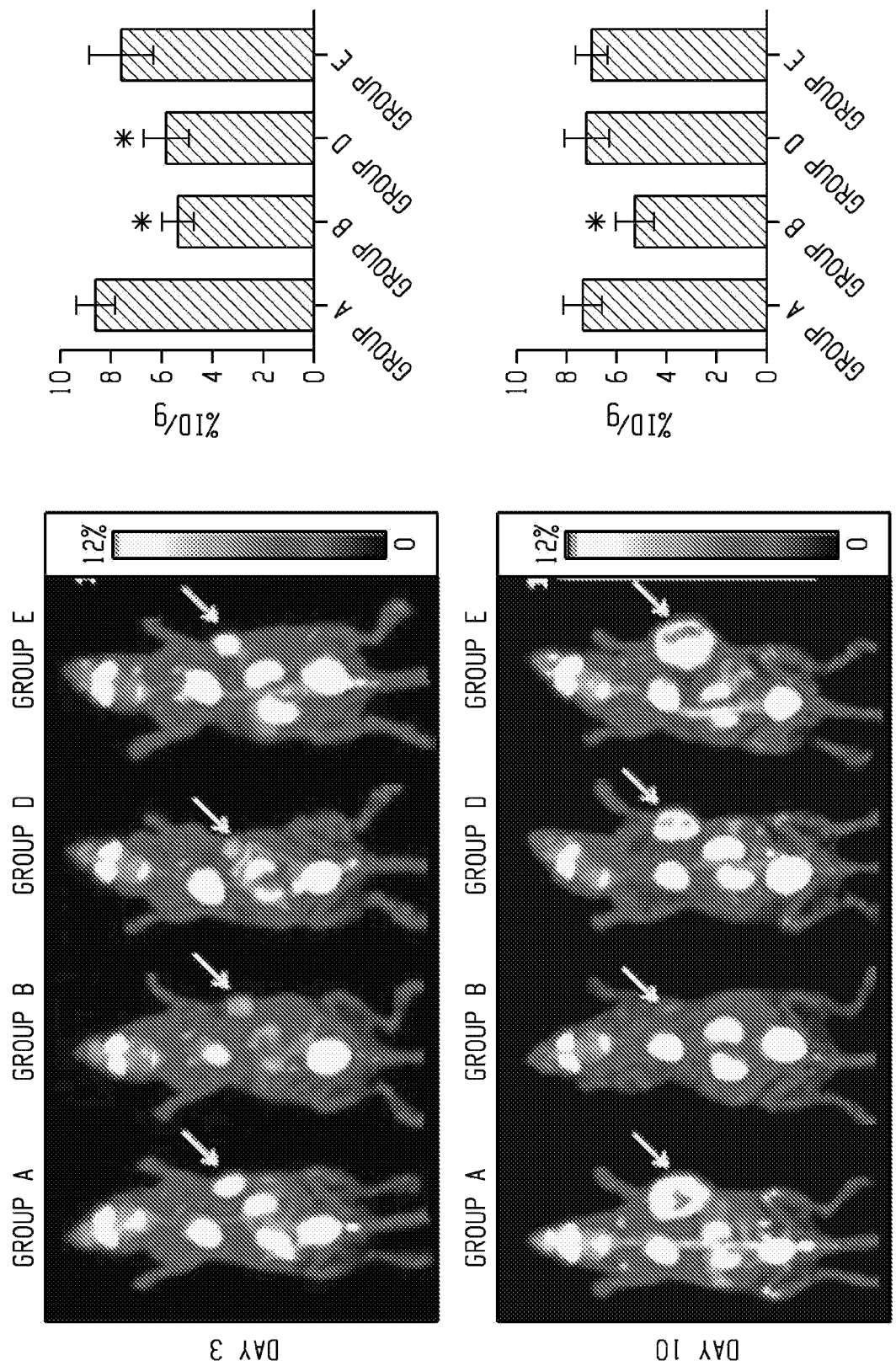
FIG. 19 is a set of micro PET images and a set of plots of % injected dose per gram (% ID/g) of tumor xenografts for various treatment arms 3 days post injection.
Figure 20:
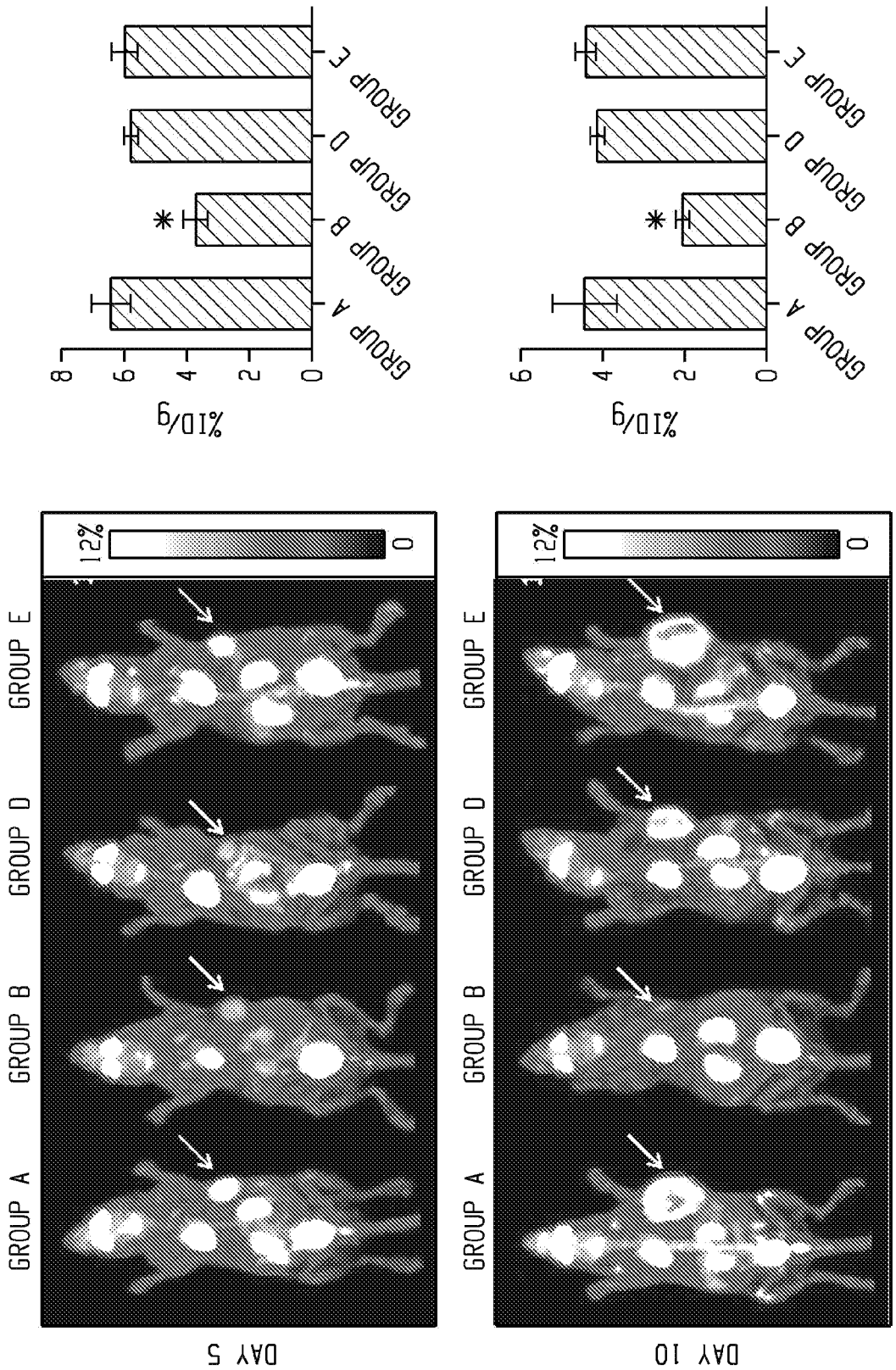
FIG. 20 is a set of micro PET images and a set of plots of % injected dose per gram (% ID/g) of tumor xenografts for various treatment arms 10 days post injection.

$^{18}$F-FDG PET imaging 3 days post-injection of $^{90}$Y, showed decreased metabolism only for the groups injected with $^{90}$Y-DMEB-RGD (FIG. 19). However, repeating this scan 10 days post-treatment showed significant decreased metabolism only for group B (FIG. 20). $^{18}$F-FLT PET imaging was conducted 5 and 12 days post initial treatment and showed a significant less 18F-FLT uptake for group B suggesting lower proliferation of the tumor of these mice. This uptake was decreased between day 5 and 12 (FIG. 20).

Example 23: Tumor Biology after 90Y Radiotherapy

Figure 21:
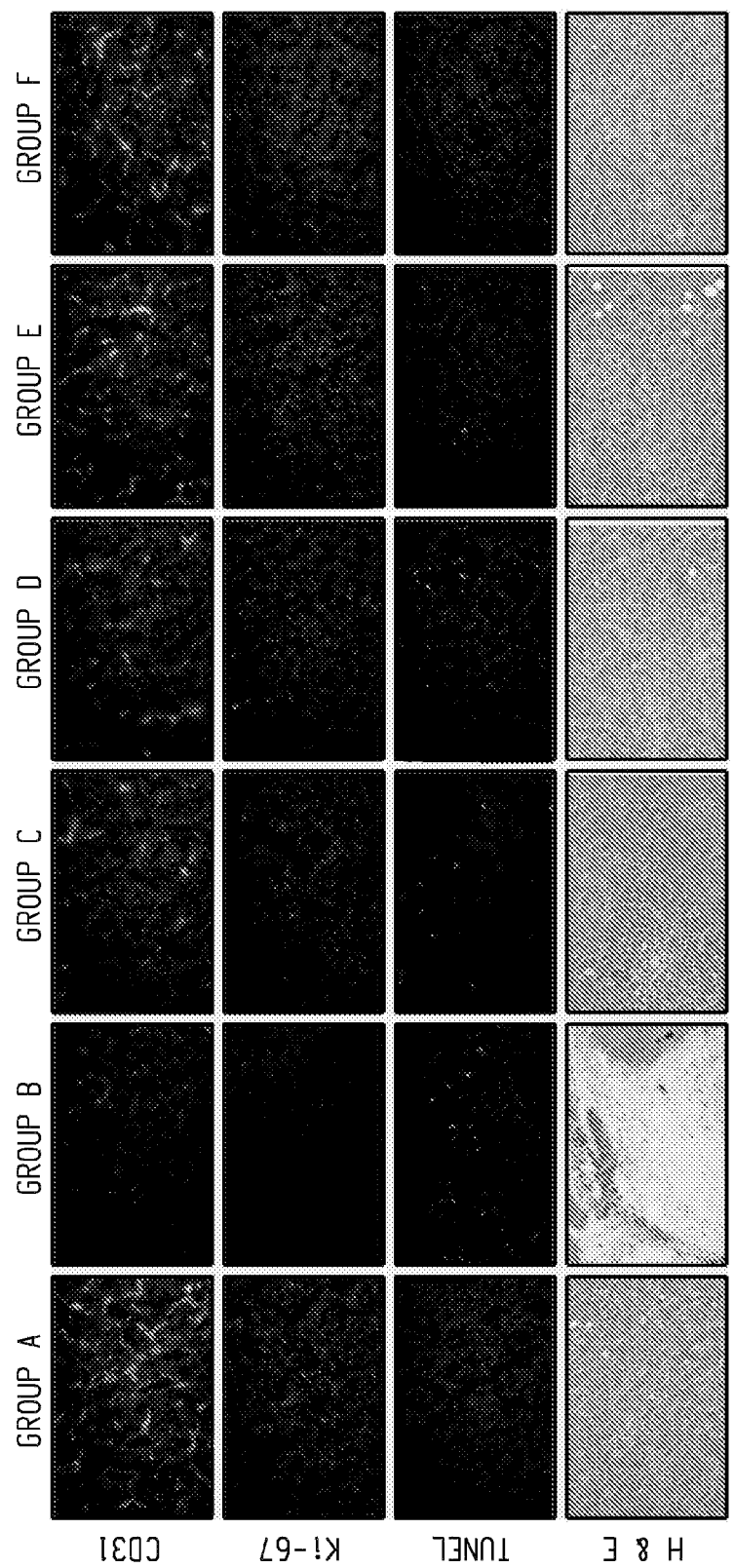
FIG. 21 is a set of images of stained cells of different types after treatment in various treatment arms.

CD31 staining to evaluate tumor vasculature, Ki-67 staining to evaluate tumor proliferation and TUNEL staining to determine the DNA damage were done for all the six groups (A-F). For groups A, E and F that had large necrotic area, staining was focused on the tumor rim where tumor cells were alive. As shown in FIG. 21, the tumor vasculature in Group B (injected with 7.4 MBq of $^{90}$Y-DMEB-RGD) was lesser than that in the other groups. Consistent with $^{18}$F-FLT PET imaging, a relatively high percentage of cells were stained positively for Ki-67 in Group A and Group C-F, while significantly reduced cell proliferation was observed in the Group B (FIG. 21). Compared with the other 5 groups, group B showed considerably more cell apoptosis, envisioned by TUNEL staining (FIG. 21). Hematoxylin and eosin staining showed that most of the tumor area in Group B was already necrotic after two doses of $^{90}$Y-DMEB-RGD treatment, whereas tumors from other 5 groups were almost entirely viable (FIG. 21).

Example 24: Evaluation of 64CU-NMEB-RGD in Human Subjects

Figure 22:
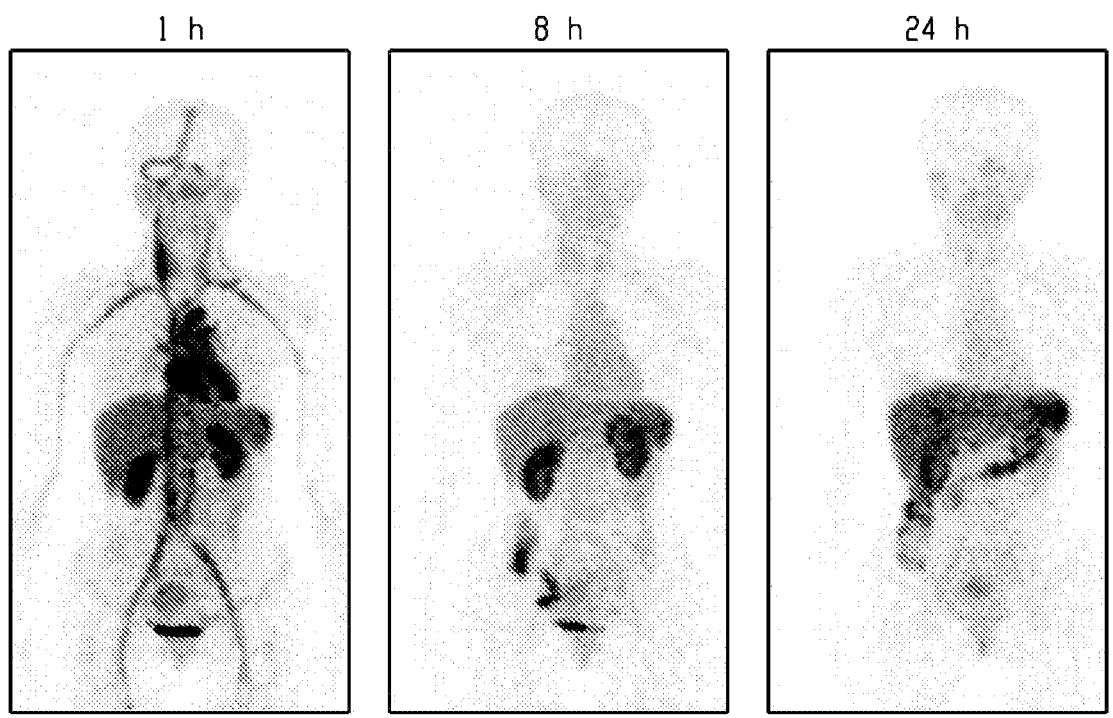
FIG. 22 is a set of PET images of 3 healthy human volunteers after injection with $^{64}$Cu-NMEB-RGD.

Three healthy volunteers were injected with 148-296 MBq (4-8 mCi) of $^{64}$Cu-NMEB-RGD and scanned by PET/CT at 1, 8 and 24 h post-injection (FIG. 22). $^{64}$Cu-NMEB-RGD uptake at 1 h p.i. was seen in the blood pool, kidneys and secreted via the bladder, with no undesired accumulation in normal organs. Dosimetry calculation are presented in Table 1, with low accumulation in normal organs, effective dose of 0.0315 mSv/MBq (0.1166 Rem/mCi), and exposure of 0.933 Rem for a subject injected with 8 mCi, which is very similar to an $^{18}$F-FDG PET scan.

TABLE 1

Dosimetry Calculation for $^{64}$Cu-NMEB-RGD. Estimated absorbed dose after intravenous administration of $^{64}$Cu-NMEB-RGD (milliSieverts/megaBecquerel, mSv/MBq, n = 3).

| Target Organ | Mean (mSv/MBq) | Standard Deviation |
|---|---|---|
| Adrenals | 0.0319 | 0.0051 |
| Brain | 0.0077 | 0.0007 |
| Breasts | 0.0241 | 0.0032 |
| Gallbladder Wall | 0.0346 | 0.0042 |
| Lower Large Intestine Wall | 0.0291 | 0.0041 |
| Small Intestine | 0.0545 | 0.0043 |
| Stomach Wall | 0.0301 | 0.0041 |
| Upper Large Intestine Wall | 0.0317 | 0.0042 |
| Heart Wall | 0.0298 | 0.0041 |
| Kidneys | 0.0994 | 0.0425 |
| Liver | 0.1012 | 0.0228 |
| Lungs | 0.0200 | 0.0046 |
| Muscle | 0.0127 | 0.0017 |
| Ovaries | 0.0294 | 0.0036 |
| Pancreas | 0.0647 | 0.0185 |
| Red Marrow | 0.0230 | 0.0027 |
| Osteogenic Cells | 0.0528 | 0.0087 |
| Skin | 0.0219 | 0.0030 |
| Spleen | 0.1293 | 0.0265 |
| Testes | 0.0229 | NA |
| Thymus | 0.0261 | 0.0039 |
| Thyroid | 0.0248 | 0.0030 |
| Urinary Bladder Wall | 0.0268 | 0.0015 |
| Uterus | 0.0334 | NA |
| Total Body | 0.0299 | 0.0045 |
| Effective Dose Equivalent | 0.0454 | 0.0088 |
| Effective Dose | 0.0315 | 0.0052 |

NA = Not Available

Figure 23:
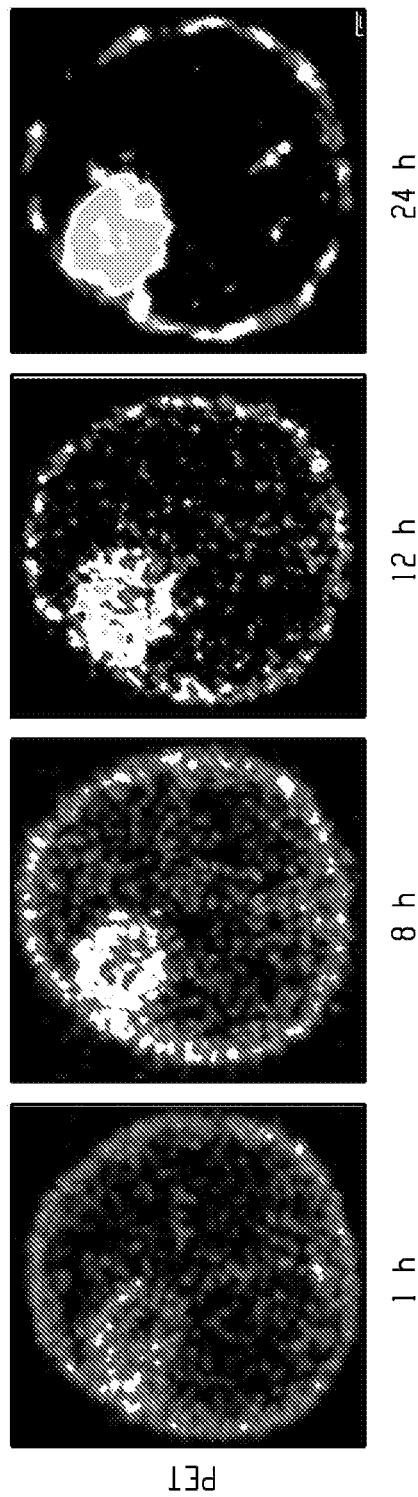
FIG. 23 is a set of PET images of a glioblastoma in a human patient after injection with $^{64}$Cu-NMEB-RGD.
Figure 24:
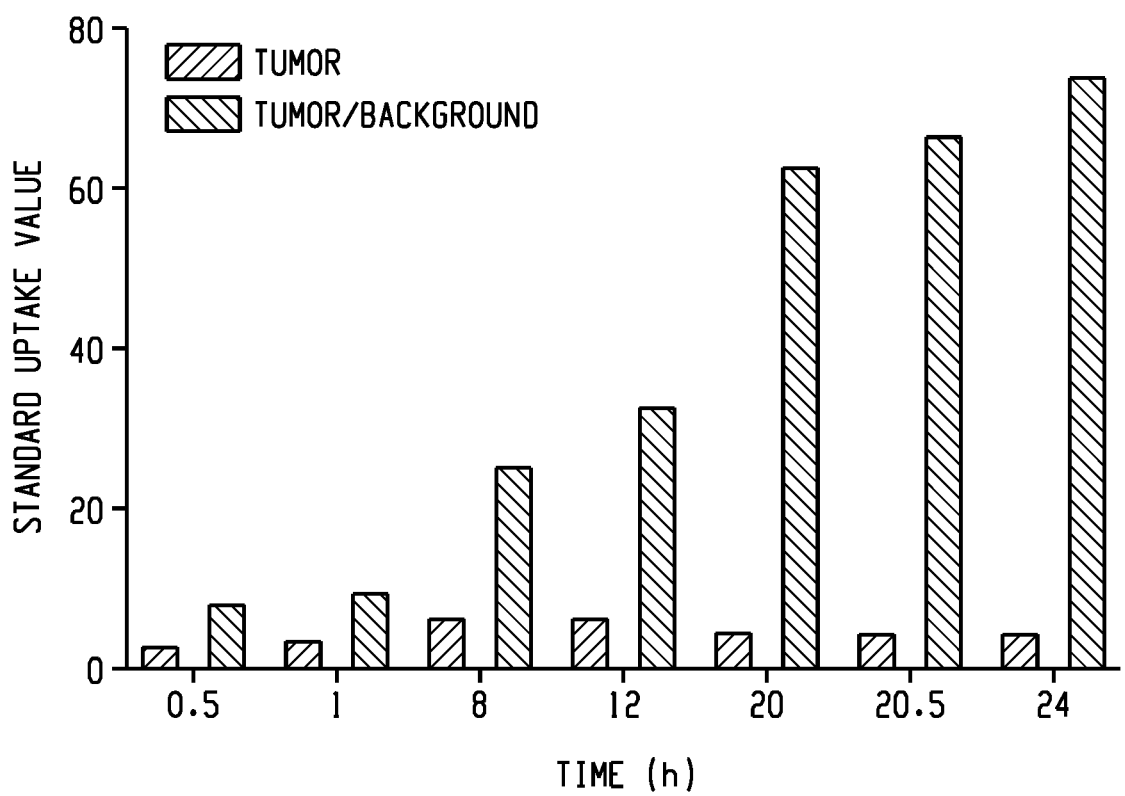
FIG. 24 is a plot of standard uptake value (SUV) versus time (hours, h) of a glioblastoma in a human patient after injection with $^{64}$Cu-NMEB-RGD.

Injection of $^{64}$Cu-NMEB-RGD in a patient with WHO stage IV glioblastoma showed high accumulation at the tumor which increased over time (FIG. 23) reaching SUV max of 6.25 at 12 h p.i. and slight decrease at 24 h (FIG. 24 and Table 2). Tumor/non-tumor ratio also increased over time and reached to a maximum of 73.4 (FIG. 24 and Table 2). Tumor biopsy showed moderate expression of integrin $\alpha_v\beta_3$.

TABLE 2

$^{64}$Cu-NMEB-RGD Distribution in GBM Patient

| | 0.5 h | 1 h | 8 h | 12 h | 20 h | 20.5 h | 24 h |
|---|---|---|---|---|---|---|---|
| Tumor-SUV$_{max}$ | 1.84 | 2.74 | 5.07 | 6.25 | 3.8 | 3.97 | 3.67 |
| Tumor-SUV$_{mean}$ | 0.91 | 1.39 | 2.61 | 3.27 | 2.07 | 2.07 | 2.01 |
| Background | 0.22 | 0.28 | 0.2 | 0.19 | 0.06 | 0.06 | 0.05 |
| T(max/N) | 8.36 | 9.78 | 25.35 | 32.89 | 63.33 | 66.16 | 73.4 |
| T(mean/N) | 4.13 | 4.96 | 13.05 | 17.21 | 34.5 | 34.5 | 40.2 |

Example 25: Evaluation of 64CU-EB-TATE in Human Subjects

Figure 25:
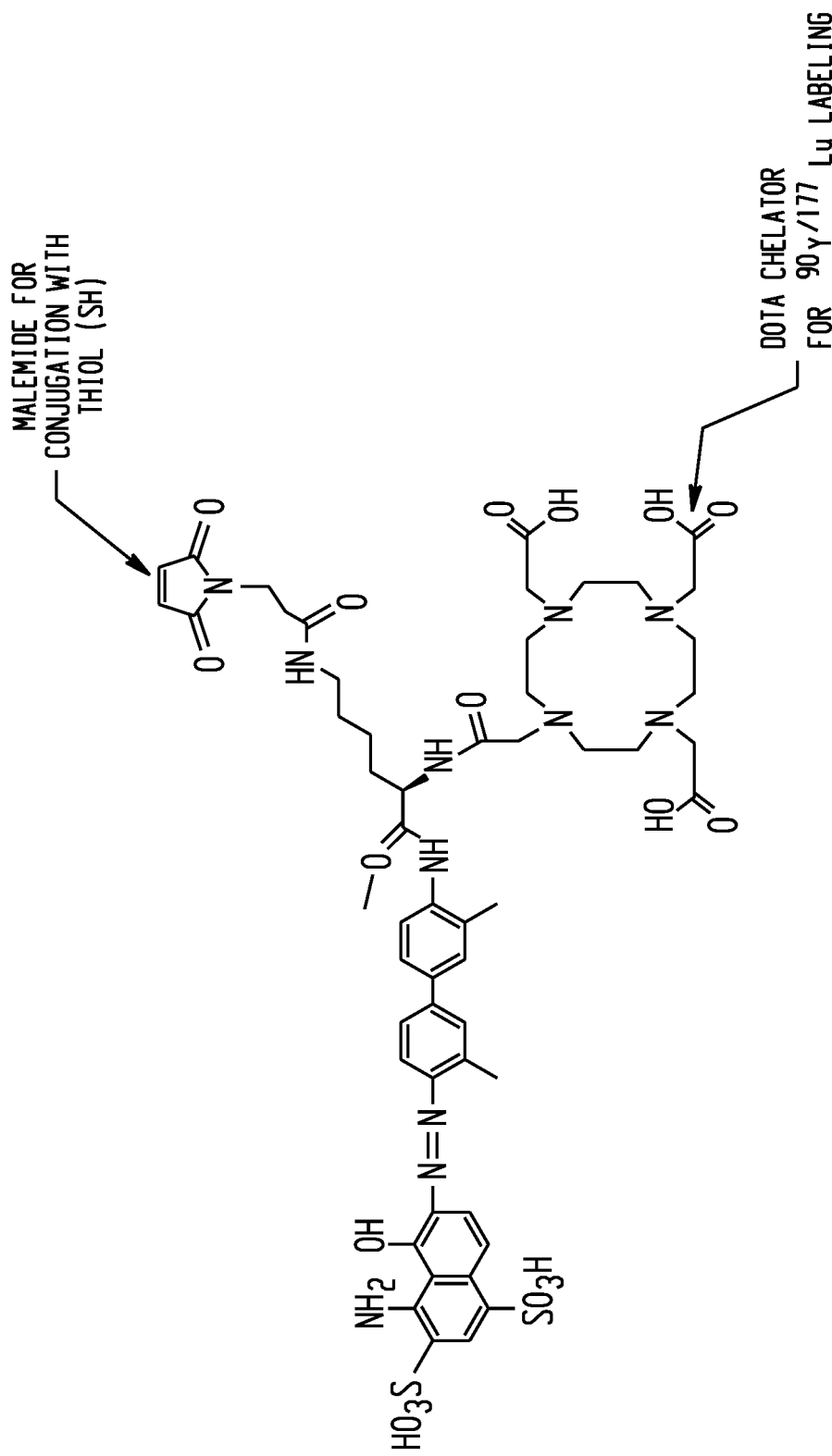
FIG. 25 shows design of the add-on molecule featuring (i) truncated Evans blue (EB) dye molecule, (ii) a metal chelate, and (iii) a maleimide.
Figure 26A:
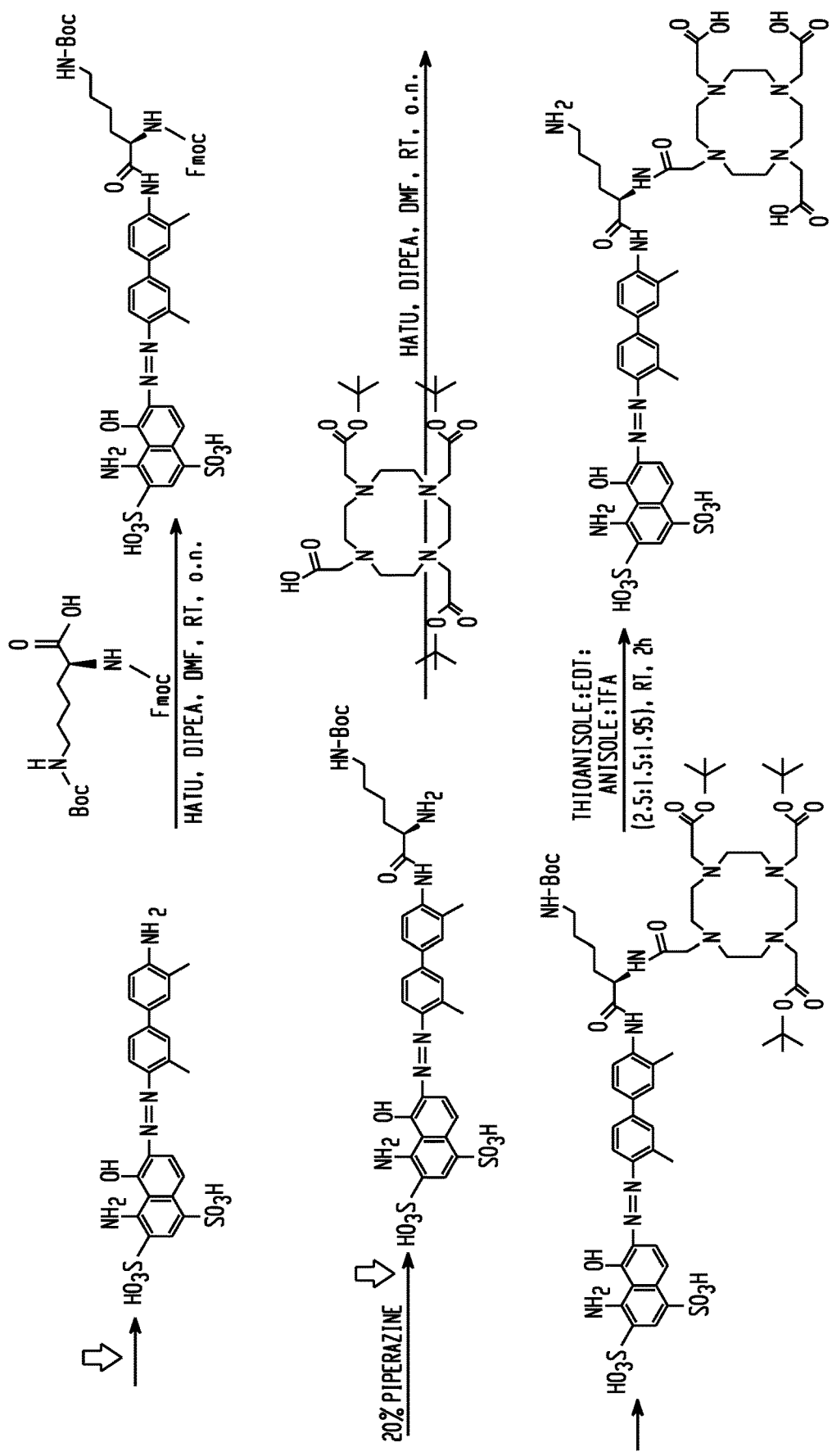
FIGS. 26A and 26B shows the synthesis of the truncated EB derivative.
Figure 26B:
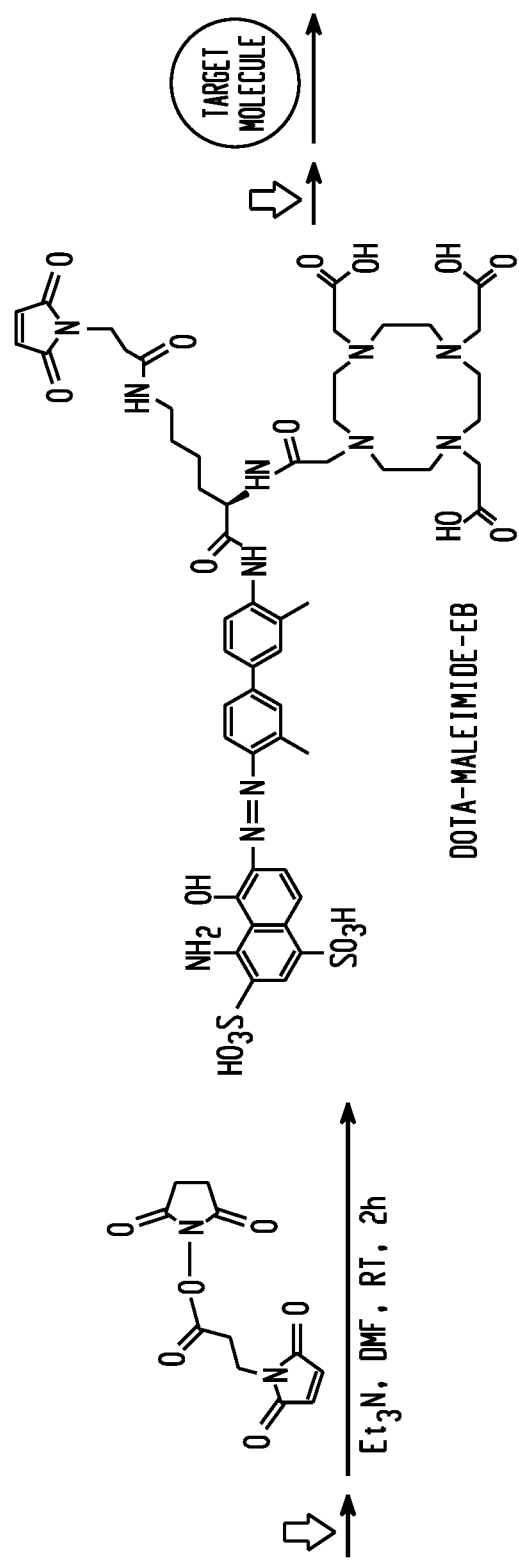
Figure 27A:
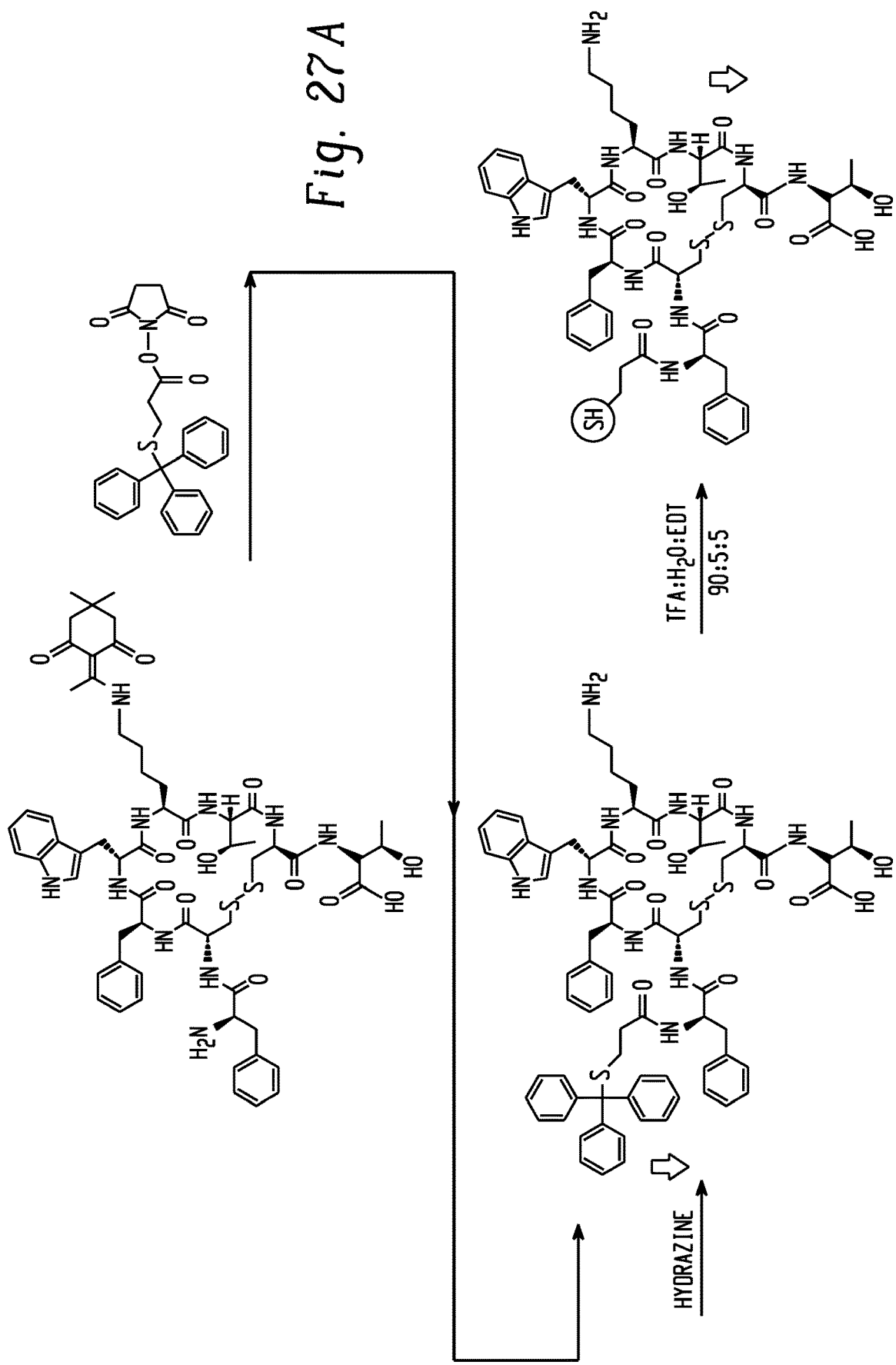
FIGS. 27A and 27B shows the synthesis of TATE-SH and the HPLC analysis of the reaction mixture containing the same.
Figure 27B:
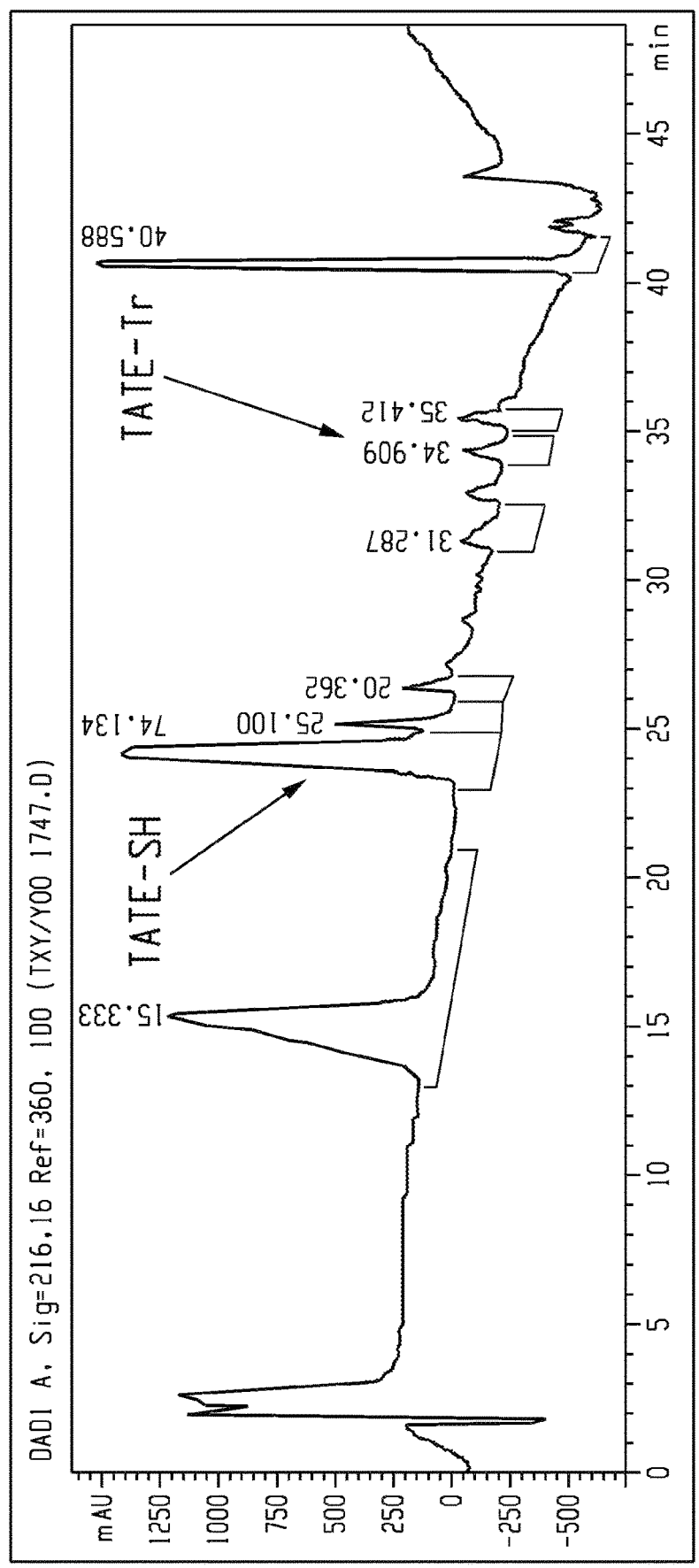

In order to extend blood half-life of drugs using albumin as a carrier molecule, an "add-on" molecule featuring (i) truncated Evans blue (EB) dye molecule (ii) a metal chelate and (iii) a maleimide (FIG. 25) was developed. The "add-on" molecule can be easily conjugated to targeting molecules containing a free thiol group to prolong the half-life in the blood by the moderate binding of EB to albumin, and allows radiolabeling for imaging and radiotherapy. The synthesis of the truncated EB derivative is described in FIGS. 26A and 26B and was previously reported (*J Nucl Med.* 2017 April; 58(4):590-597). To conjugate it to Octreotate (TATE), a somatostatin receptor-binding peptide, a free thiol group on the alpha amine of the phenylalanine residue needed to be inserted. The synthesis of TATE-SH is described in FIGS. 27A-B.

Figure 28A:
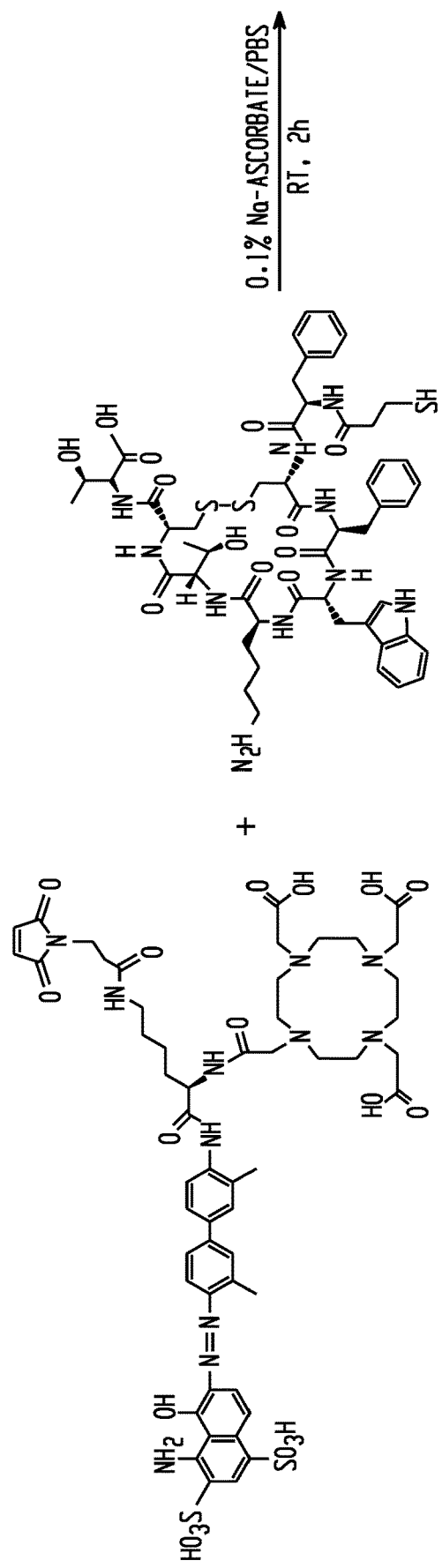
FIGS. 28A and 28B shows the synthesis of EB-TATE.
Figure 28B:
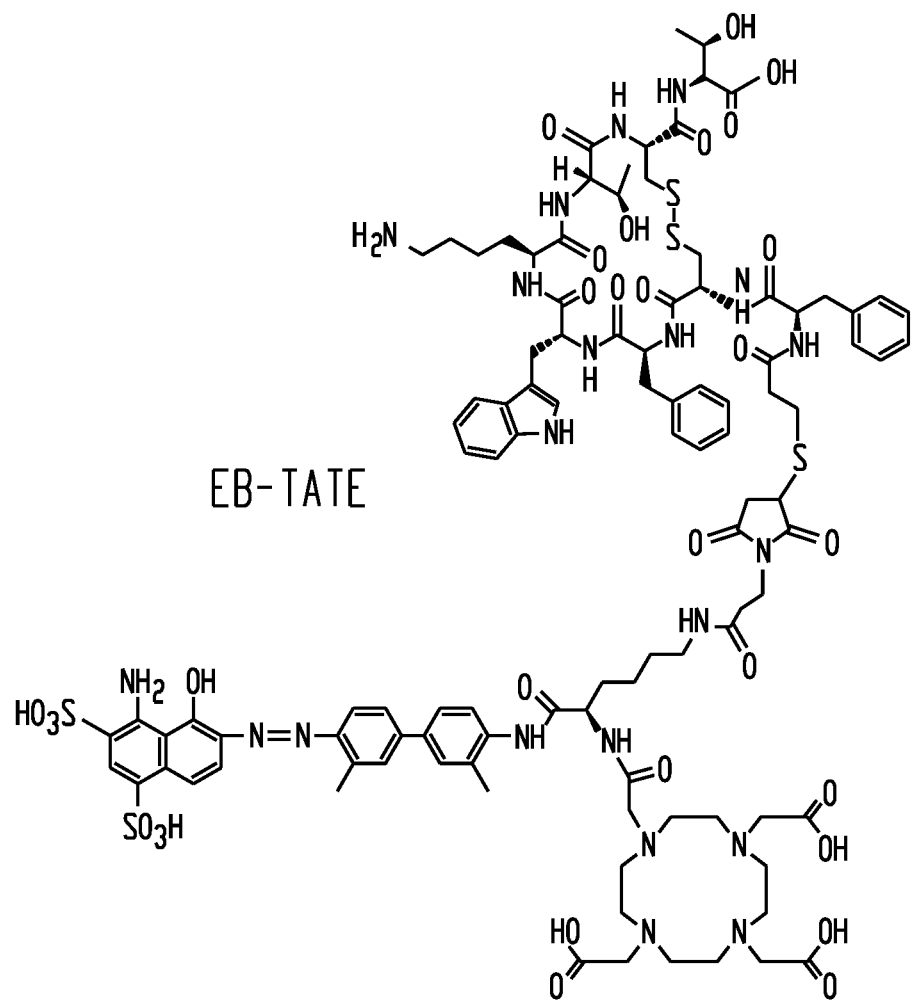
Figure 29:
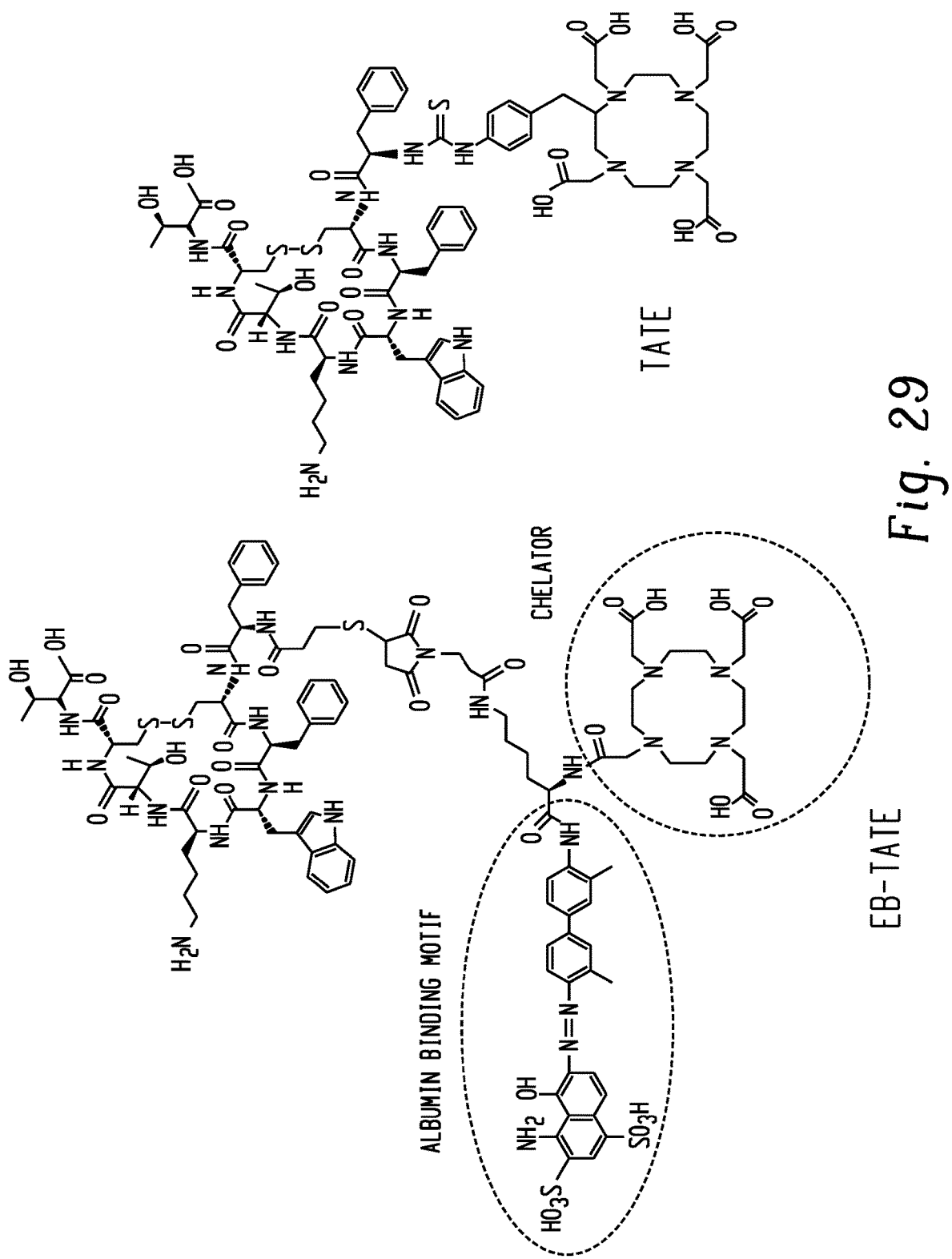
FIG. 29 shows the structures of EB-TATE and TATE.

The truncated EB was conjugated with DOTA chelator, and thereafter, coupled to TATE-SH, to give EB-TATE, FIGS. 28A and 28B). As a comparison, TATE was conjugated to DOTA without the EB moiety, denoted as TATE (FIG. 29). Both TATE and EB-TATE were radiolabeled with either Cu-64, Y-86 or Y-90 for imaging or radiotherapy, respectively, and compared in mouse xenograft models.

Figure 30:
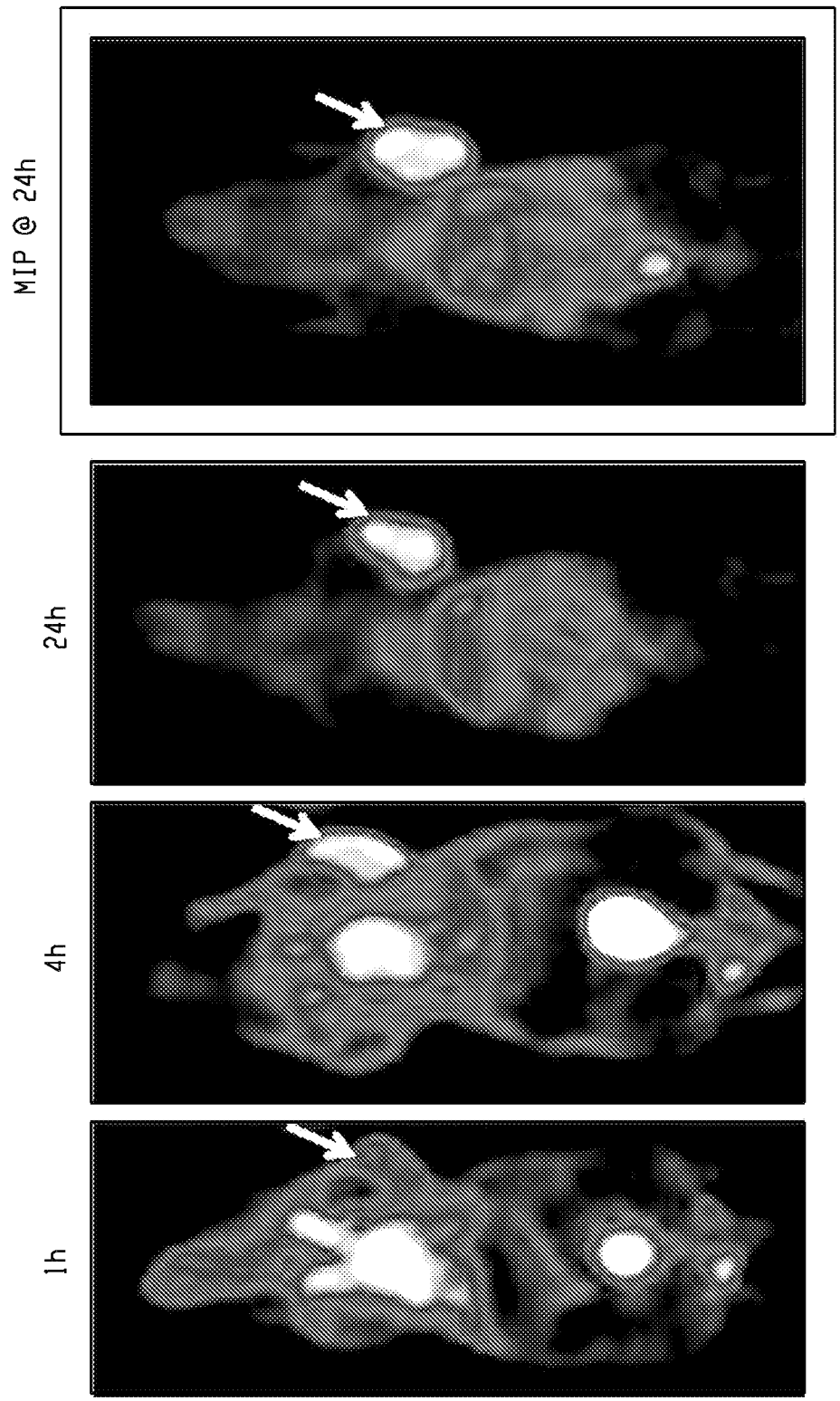
FIG. 30 is a set of PET images showing evaluation of $^{64}$Cu-EB-TATE in a model of AR42J rat pancreas neuroendocrine tumor xenografts.
Figure 31:
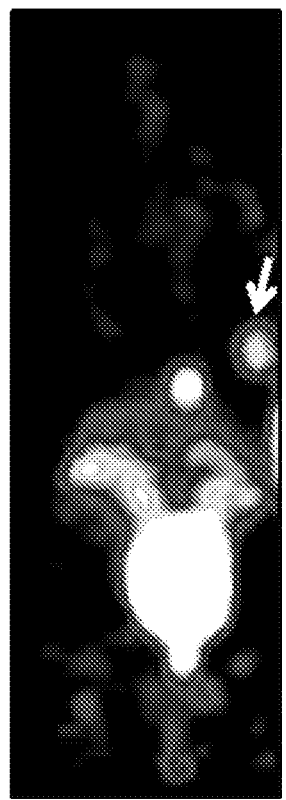
FIG. 31 is a set of PET images showing evaluation of $^{64}$Cu-TATE in a model of AR42J rat pancreas neuroendocrine tumor xenografts.
Figure 31:
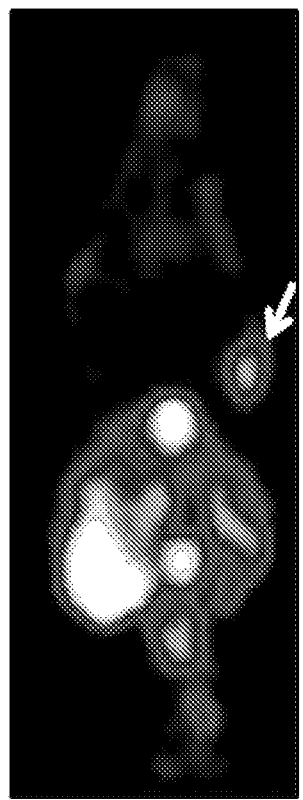
Figures 32A, 32B:
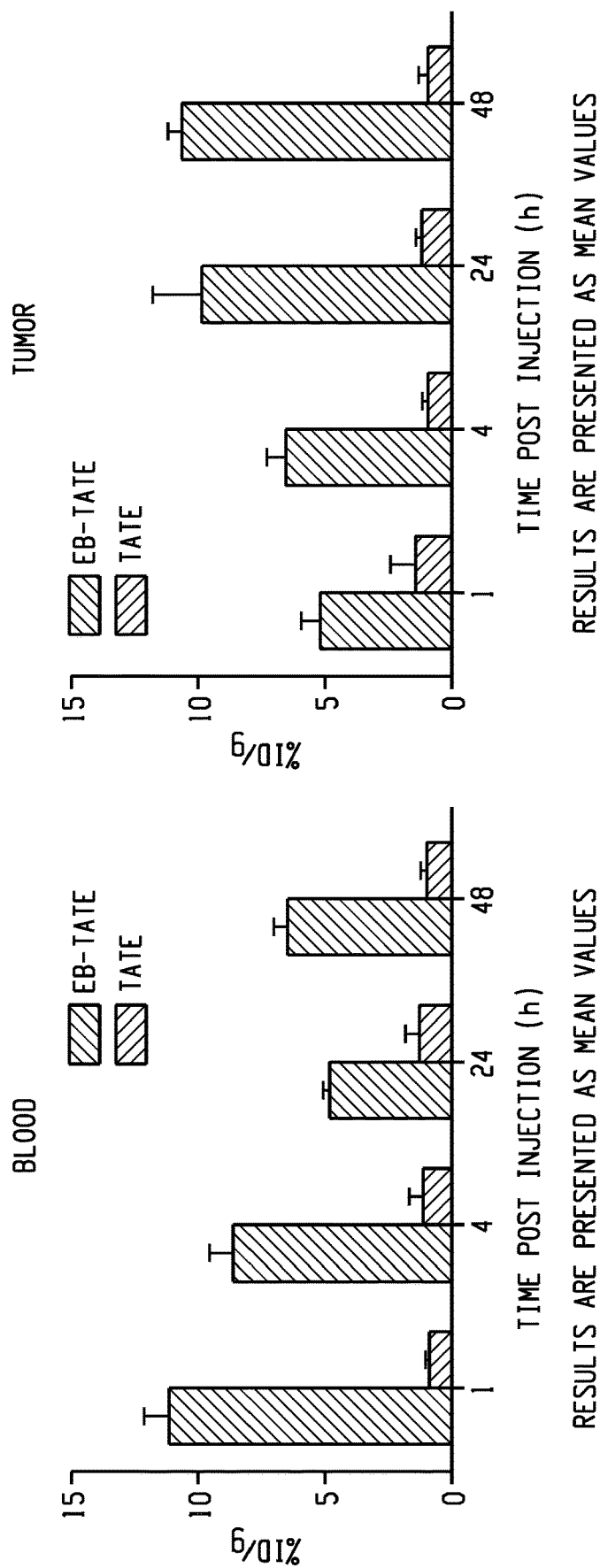
FIGS. 32A and 32B are diagrams showing time-dependent blood and tumor uptake of $^{64}$Cu-EB-TATE vs. $^{64}$Cu-TATE.
Figure 33A:
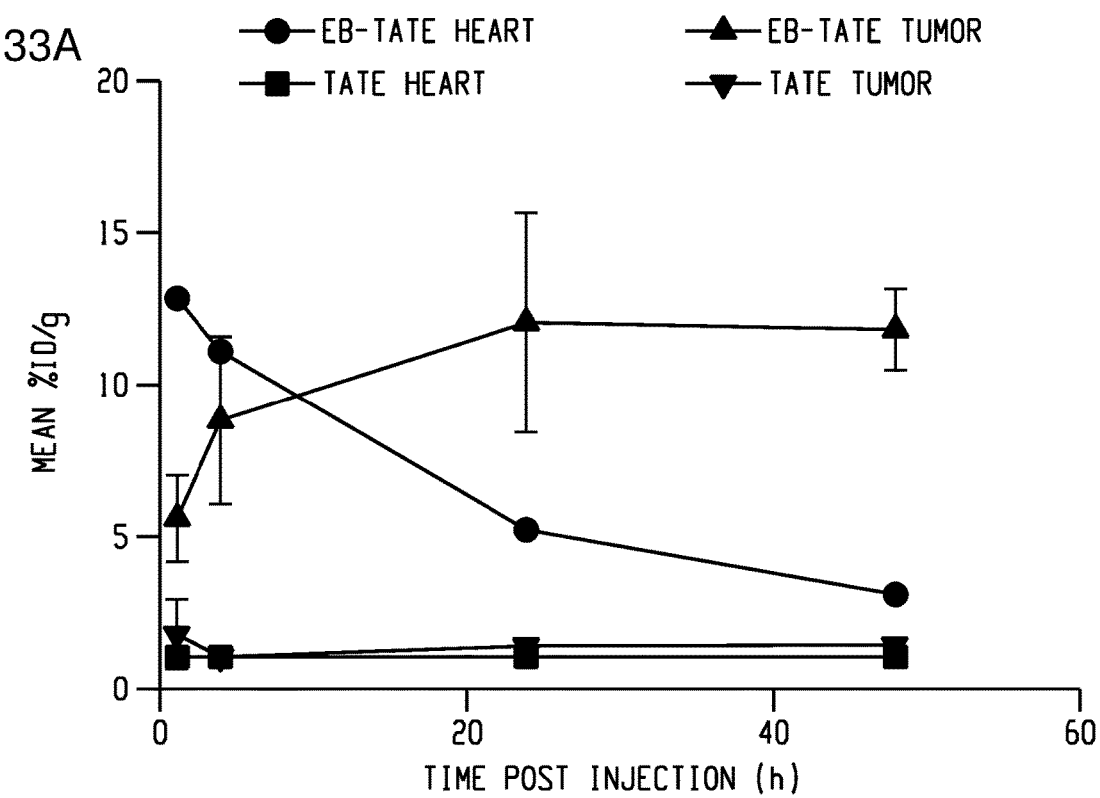
FIGS. 33A and 33B are plots showing time-dependent blood and tumor uptake of $^{64}$Cu-EB-TATE vs. $^{64}$Cu-TATE (mean vs. max)
Figure 33B:
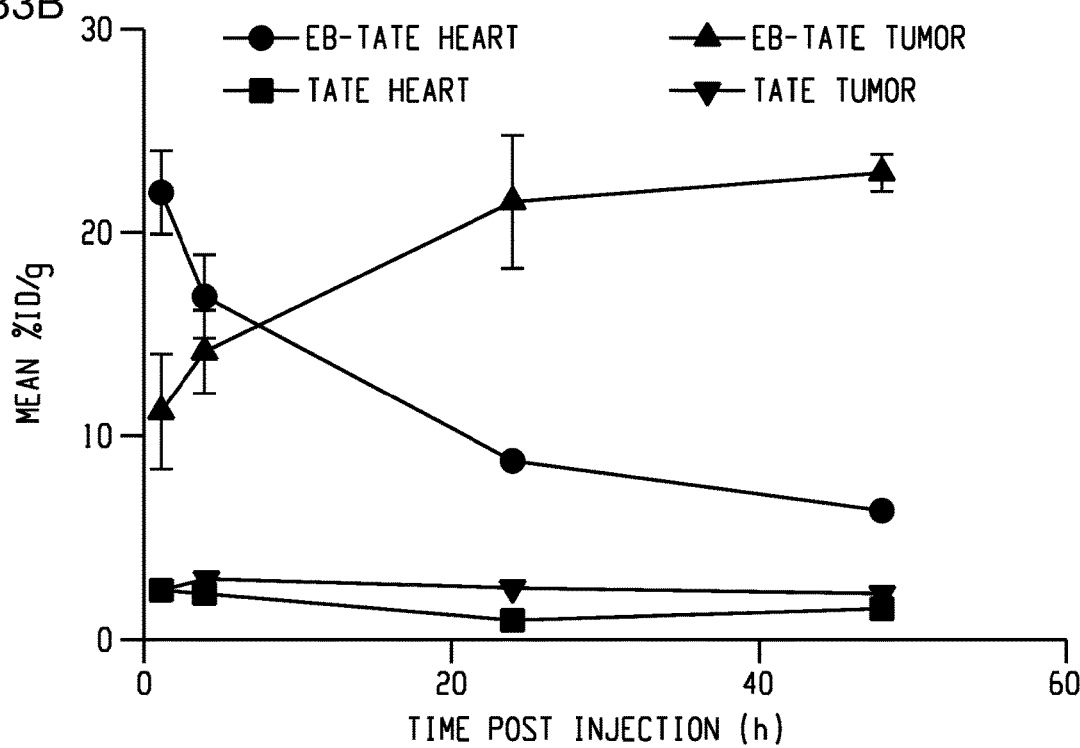
Figure 34B:
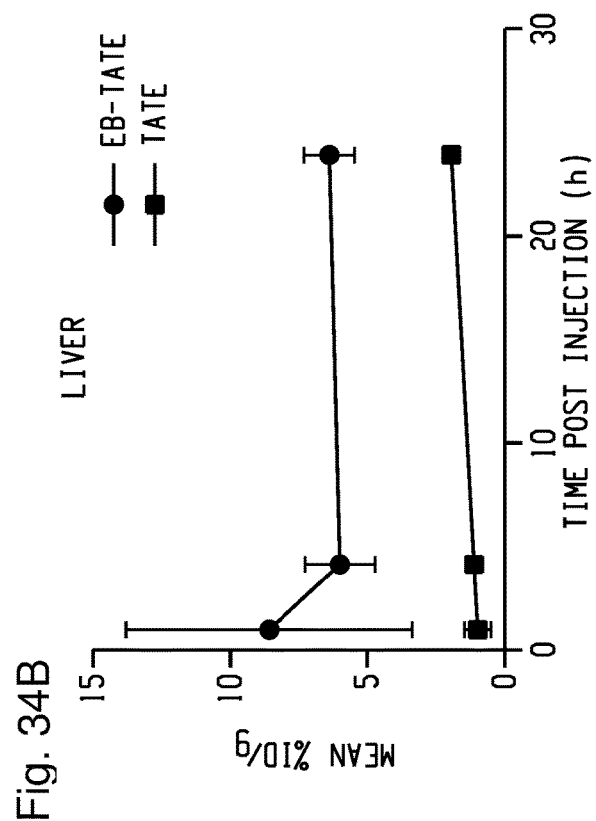
FIGS. 34A, 34B, and 34C are plots showing time-dependent bladder, liver, and kidney uptake of $^{64}$Cu-EB-TATE vs. $^{64}$Cu-TATE.
Figure 34A:
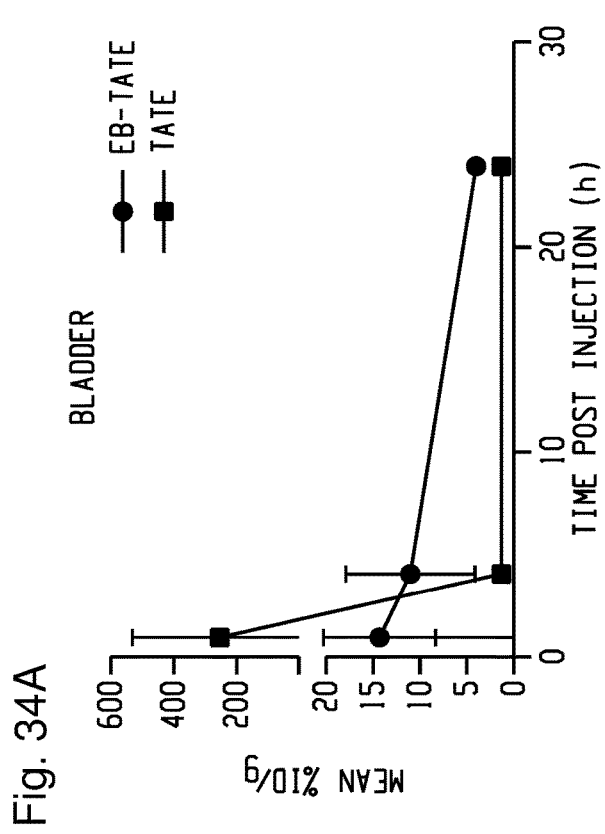
Figure 34C:
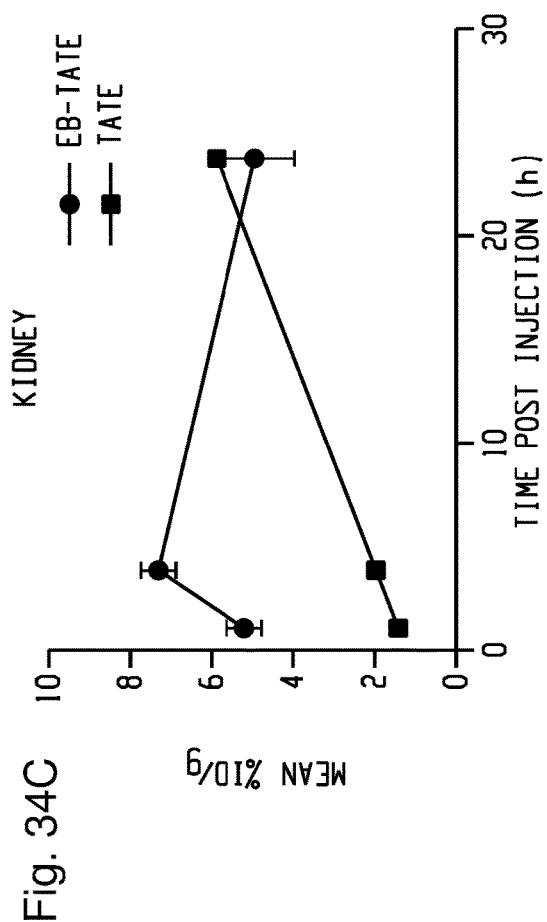
Figure 35B:
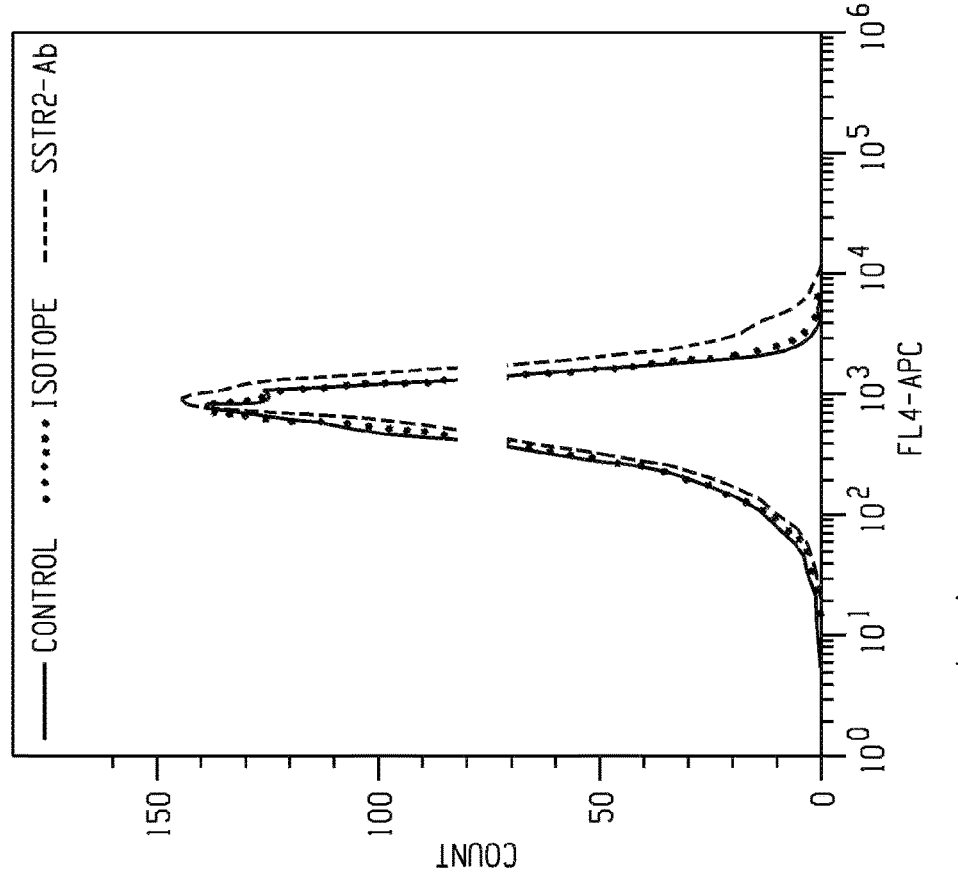
FIGS. 35A and 35B are plots showing the results of a FACS analysis of HCT116 SSTR2 positive/negative cells.
Figure 35A:
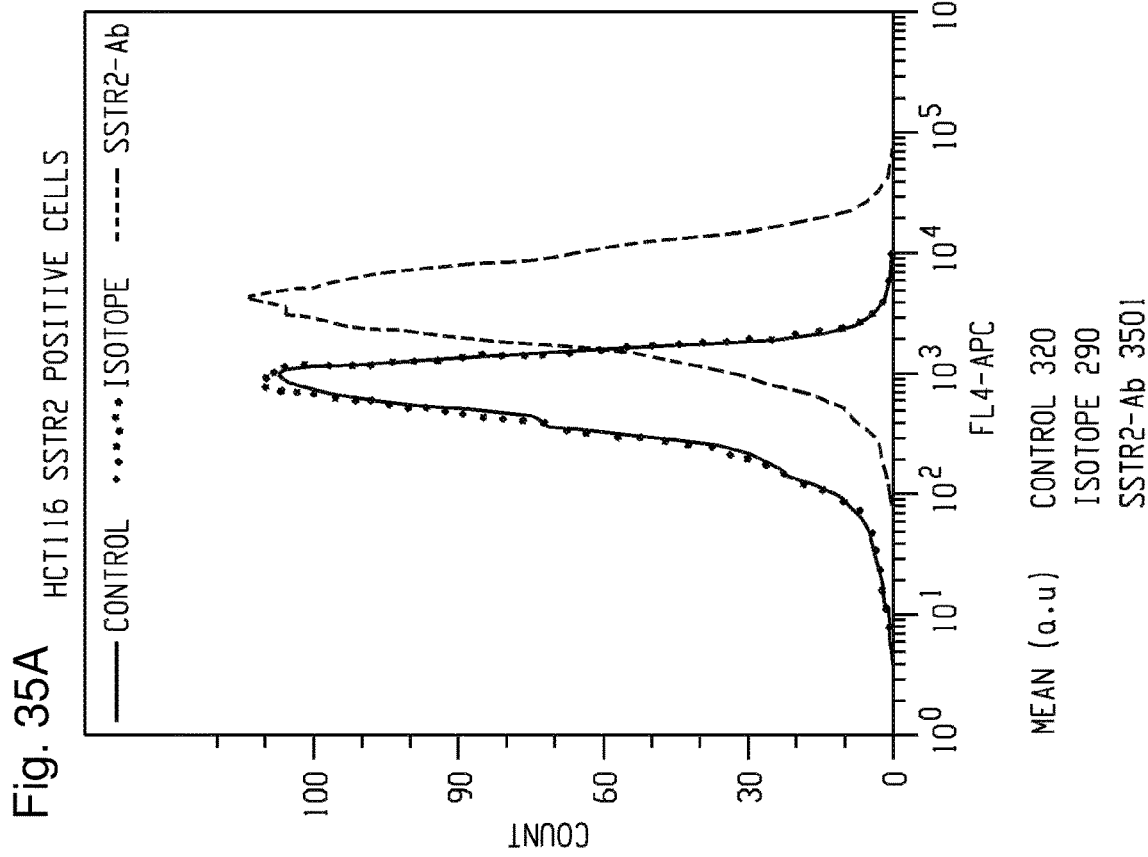
Figure 36:
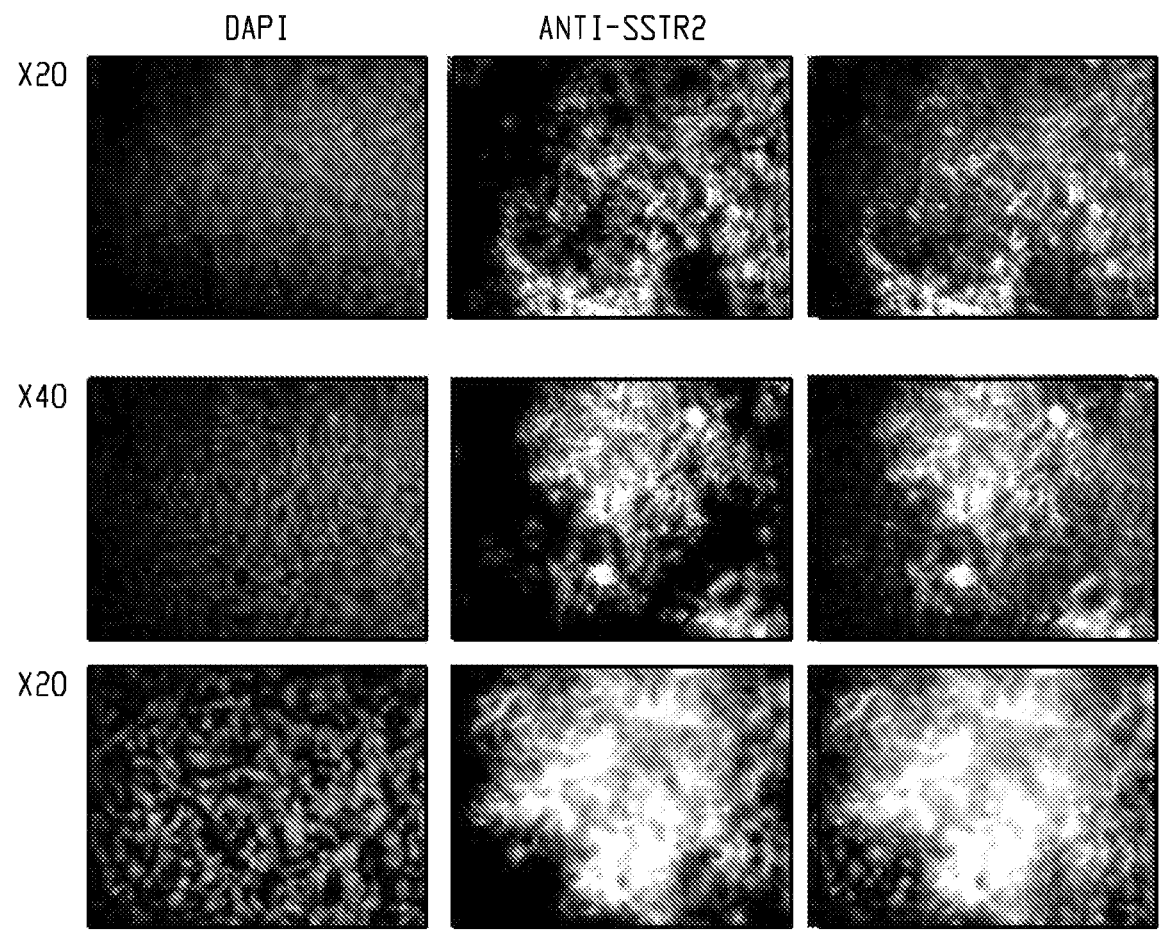
FIG. 36 is an image showing the results of immunofluorescent staining for HCT116 positive cells.
Figure 37:
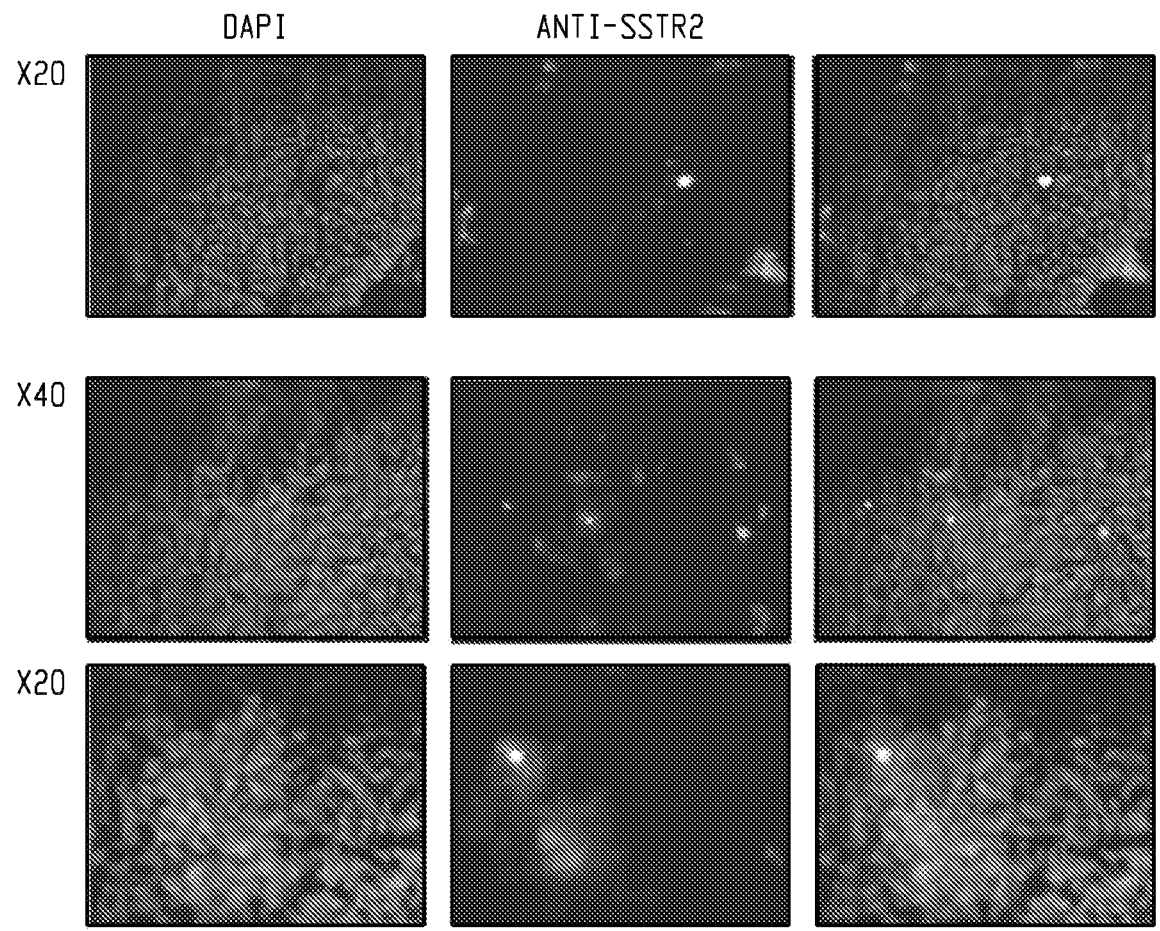
FIG. 37 is an image showing the results of immunofluorescent staining for HCT116 negative cells.
Figure 38A:
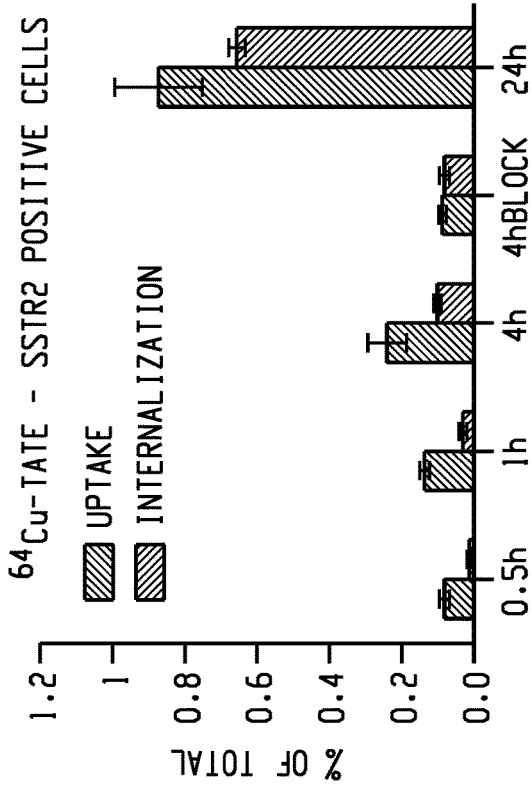
FIGS. 38A, 38B, 38C, and 38D are diagrams showing the results of $^{64}$Cu-EB-TATE cell uptake/internalization study.
Figure 38B:
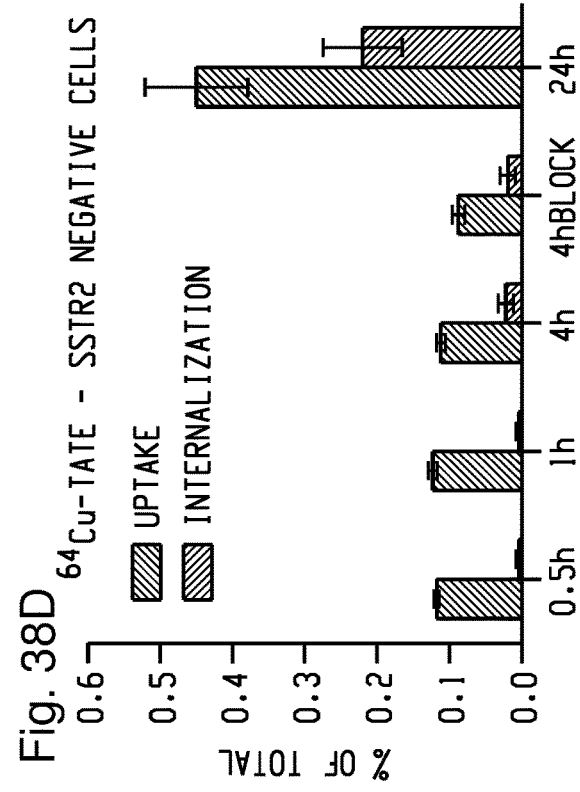
Figure 38C:
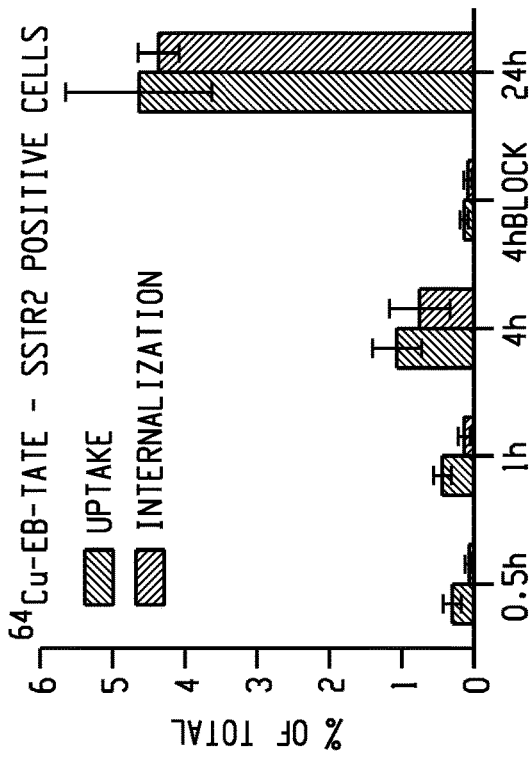
Figure 38D:
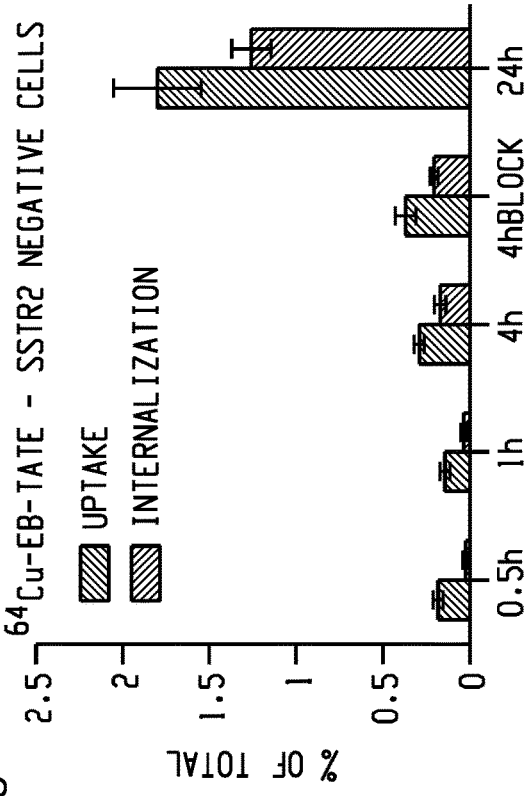
Figure 39B:
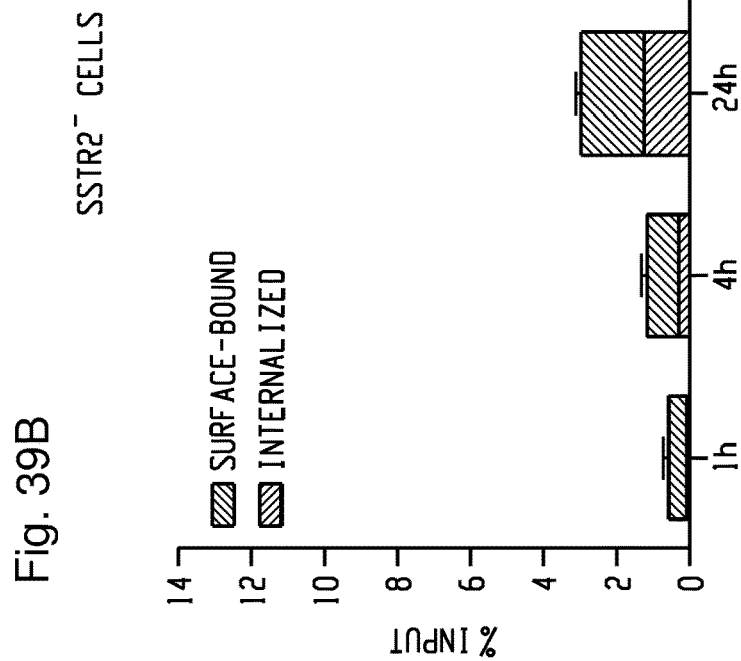
FIGS. 39A and 39B are diagrams showing the results of $^{86}$Y-EB-TATE cell uptake/internalization study in HCT116 SSTR2$^{+/-}$ cells.
Figure 39A:
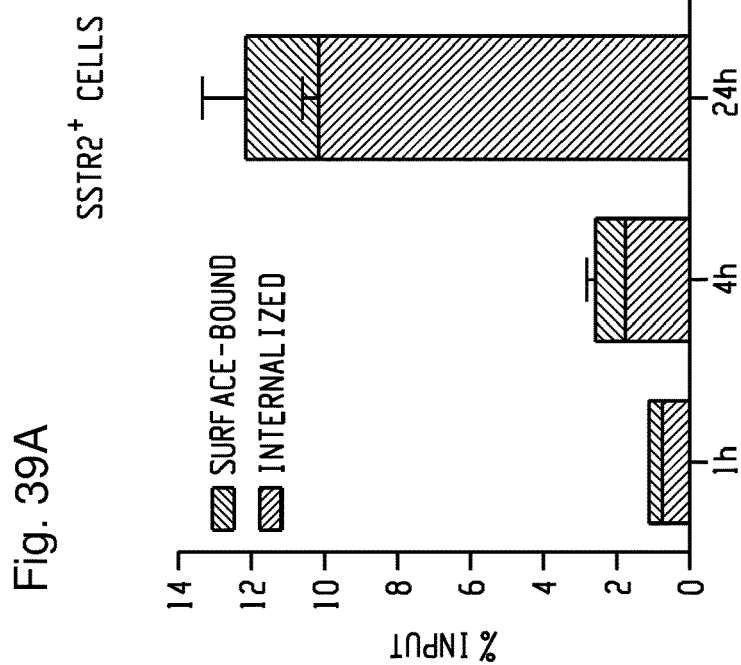
Figures 40A, 40B:
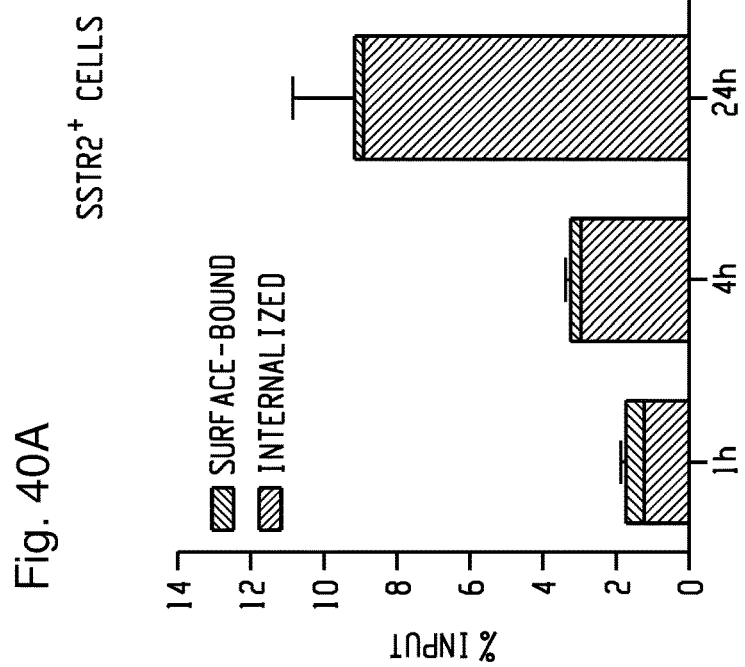
FIGS. 40A and 40B are diagrams showing the results of $^{86}$Y-TATE cell uptake/internalization study in HCT116 SSTR2$^{+/-}$ cells.

The two compounds in a model of AR42J rat pancreas neuroendocrine tumor xenografts, which is a well-established model in the literature and was reported to have high SSTR2 expression, were first evaluated (FIGS. 30 and 31). EB-TATE and TATE were first labeled with Cu-64 and the mice underwent PET scans at different time points post-injection (p.i.) of identical radioactive doses. $^{64}$Cu-EB-TATE had a significant higher tumor uptake at all time points with high tumor to background ratio at 24 h p.i. (FIGS. 30-31, 32A-B, and 33A-B). As expected, addition of EB moiety to Octreotate, significantly decreased its excretion through the bladder (FIGS. 34A-C). Next, these two tracers in human HCT116 colon xenograft transfected with SSTR2 were evaluated. FACS analysis and immunofluorescence staining were performed to determine the SSTR2 expression differences between HCT116 and SSTR2-HCT116 transfected cells (FIGS. 35A-B and 36-37). Cell uptake/internalization studies of both $^{64}$Cu-EB-TATE and $^{64}$Cu-TATE in positive and negative HCT116 SSTR2 cells were also investigated. $^{64}$Cu-EB-TATE cell uptake was significantly higher at all time points and most of the uptake was related to internalization (FIG. 38A-D). Moreover, $^{64}$Cu-EB-TATE cell uptake and internalization could be blocked by addition of unlabeled EB-TATE which implies on its specificity to SSTR2 (FIG. 38A-D).

A potential future application of EB-TATE is radiotherapy using Y-90. To allow a better understanding of $^{90}$Y-EB-TATE distribution and accumulation in different organs, EB-TATE was labelled with the PET isotope Y-86. Moreover, Y-86 is better chelated by DOTA isotope therefor using Y-86 as an imaging isotope will reduce the accumulation of radioactivity that is due to transchelation or another phenomenon that are not related specifically to EB-TATE.

Figure 41:
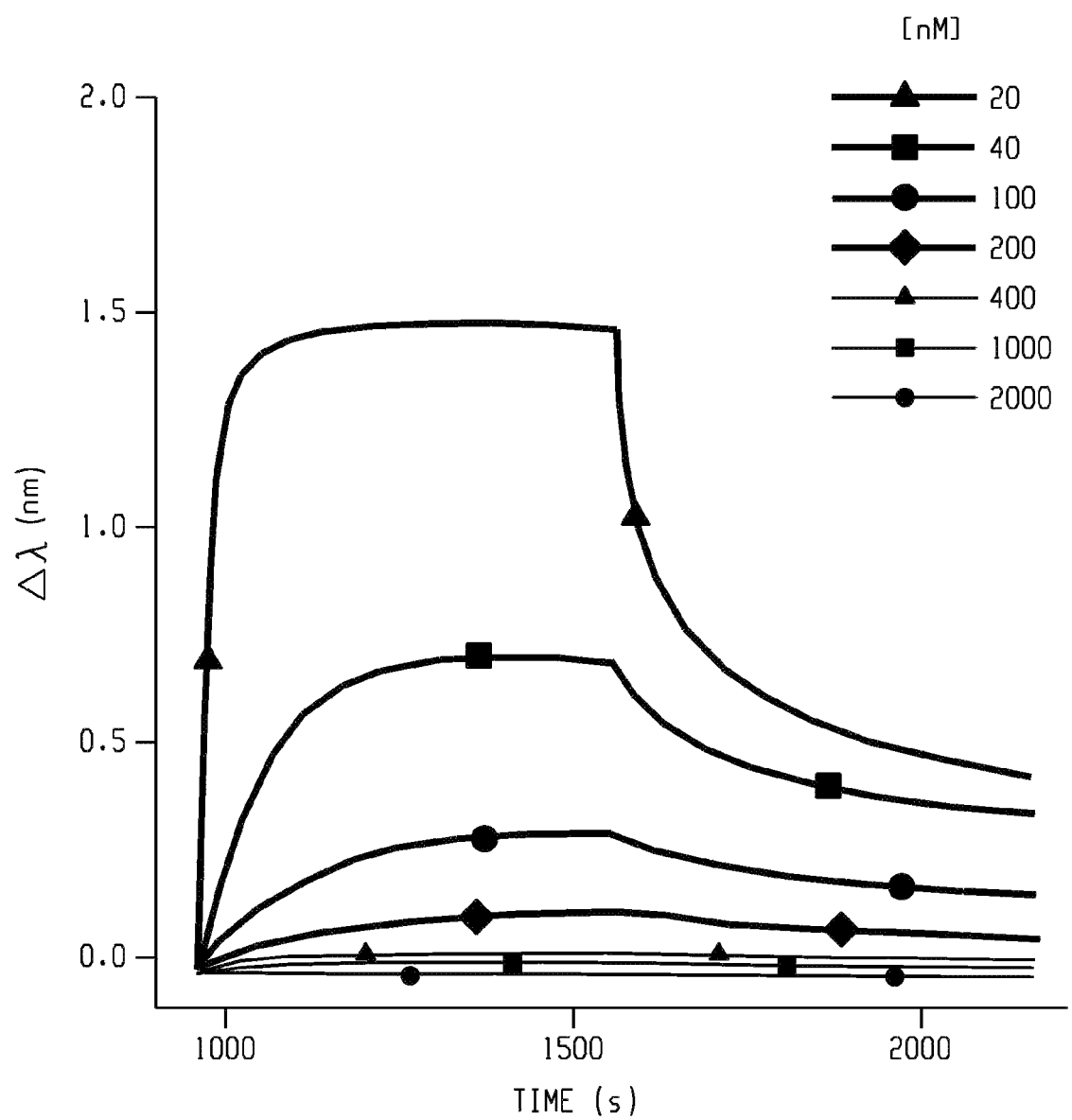
FIG. 41 is a plot showing binding kinetics—EB-TATE-BSA association/dissociation constants.
Figure 42:
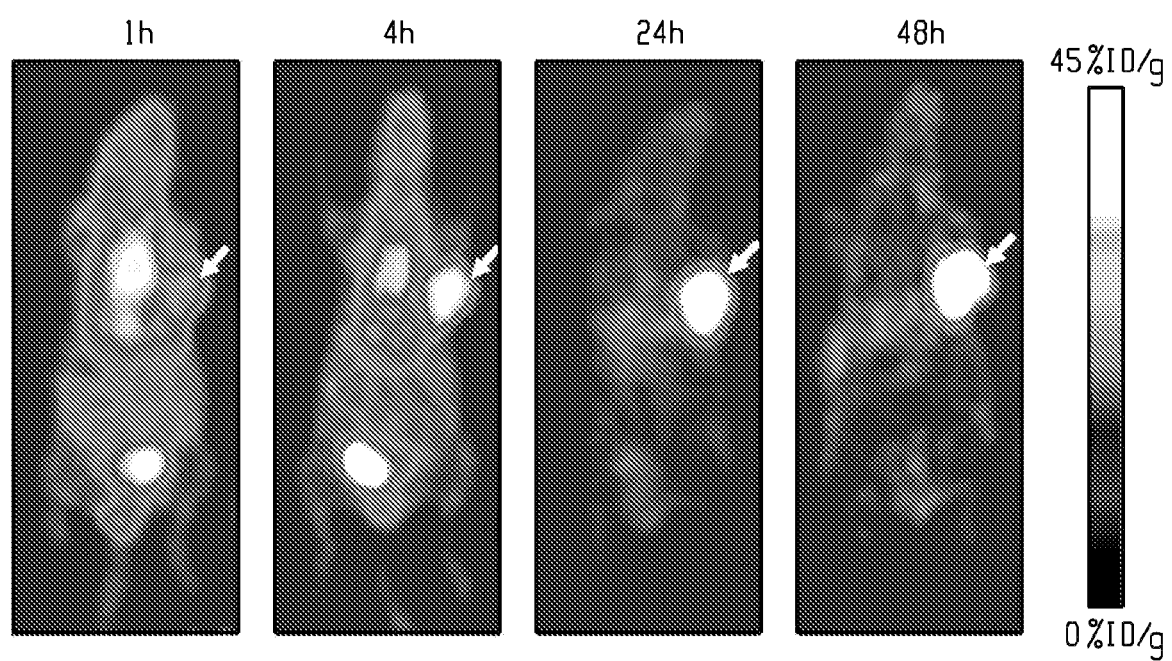
FIG. 42 is a set of PET images showing evaluation of $^{86}$Y-EB-TATE in HCT116$^{+}$ xenografts.
Figure 43:
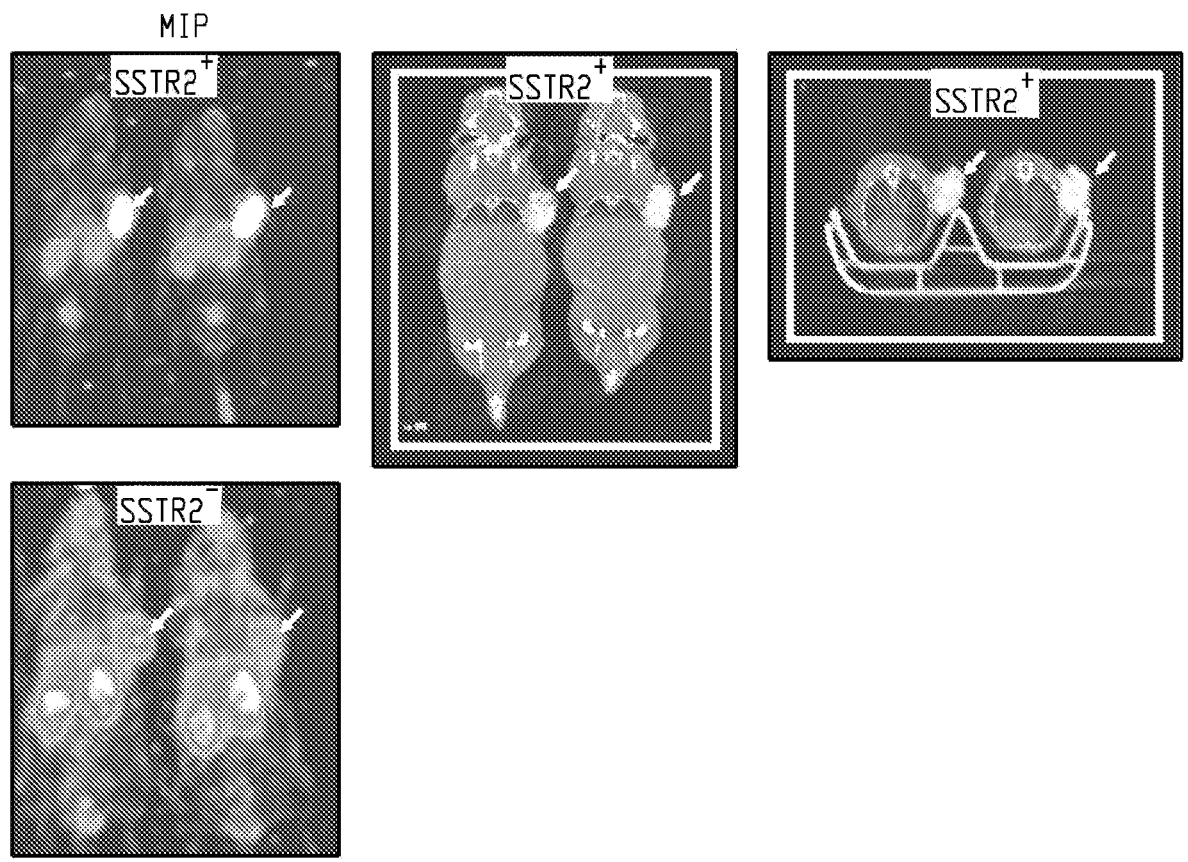
FIG. 43 is a set of PET images showing evaluation of $^{86}$Y-EB-TATE in HCT116$^{+/-}$ xenografts.
Figure 45A:
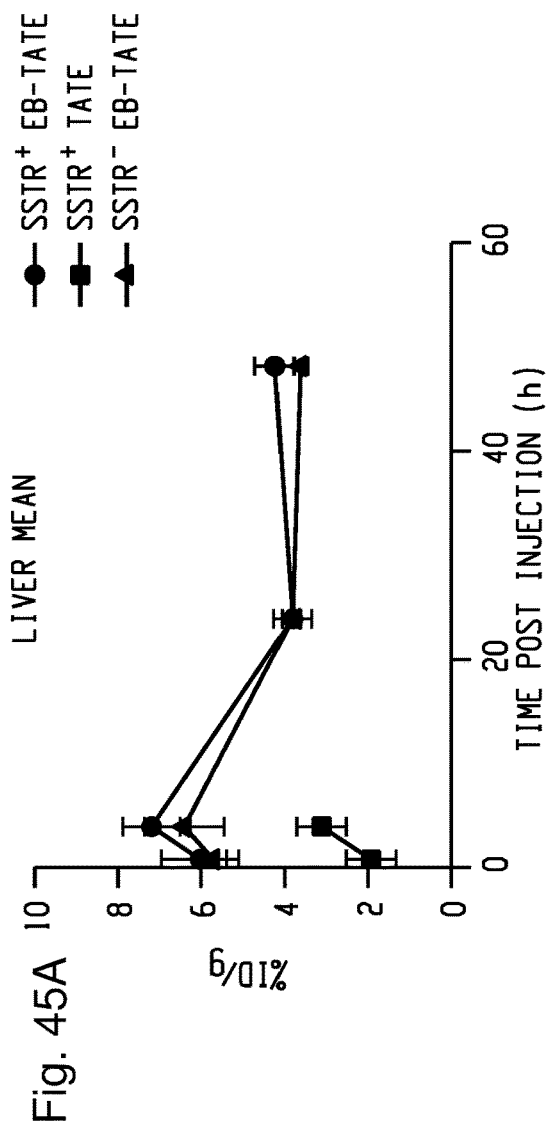
FIGS. 45A, 45B, and 45C are plots showing liver, kidney, and bladder TACs of $^{86}$Y-EB-TATE and $^{86}$Y-TATE.
Figure 45C:
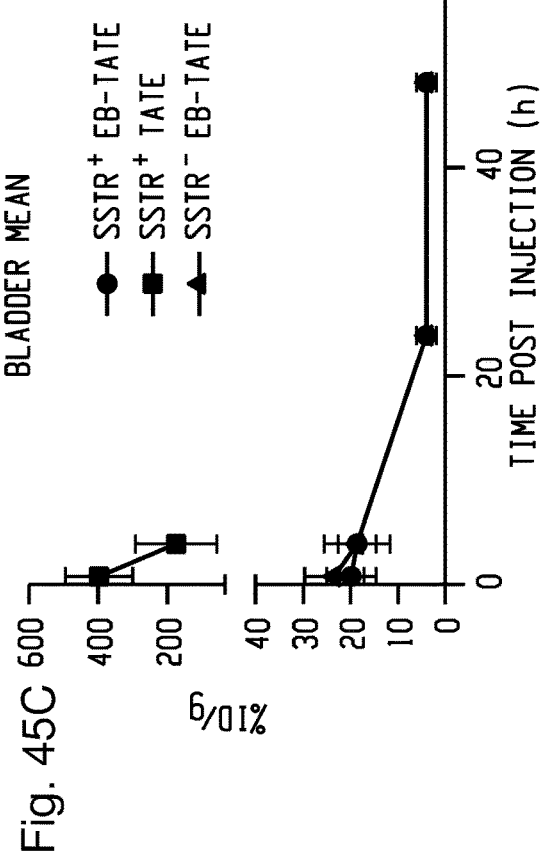
Figure 45B:
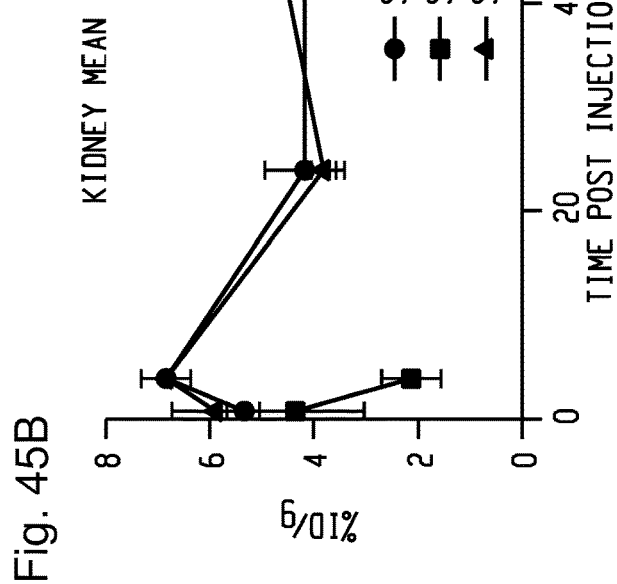
Figure 46:
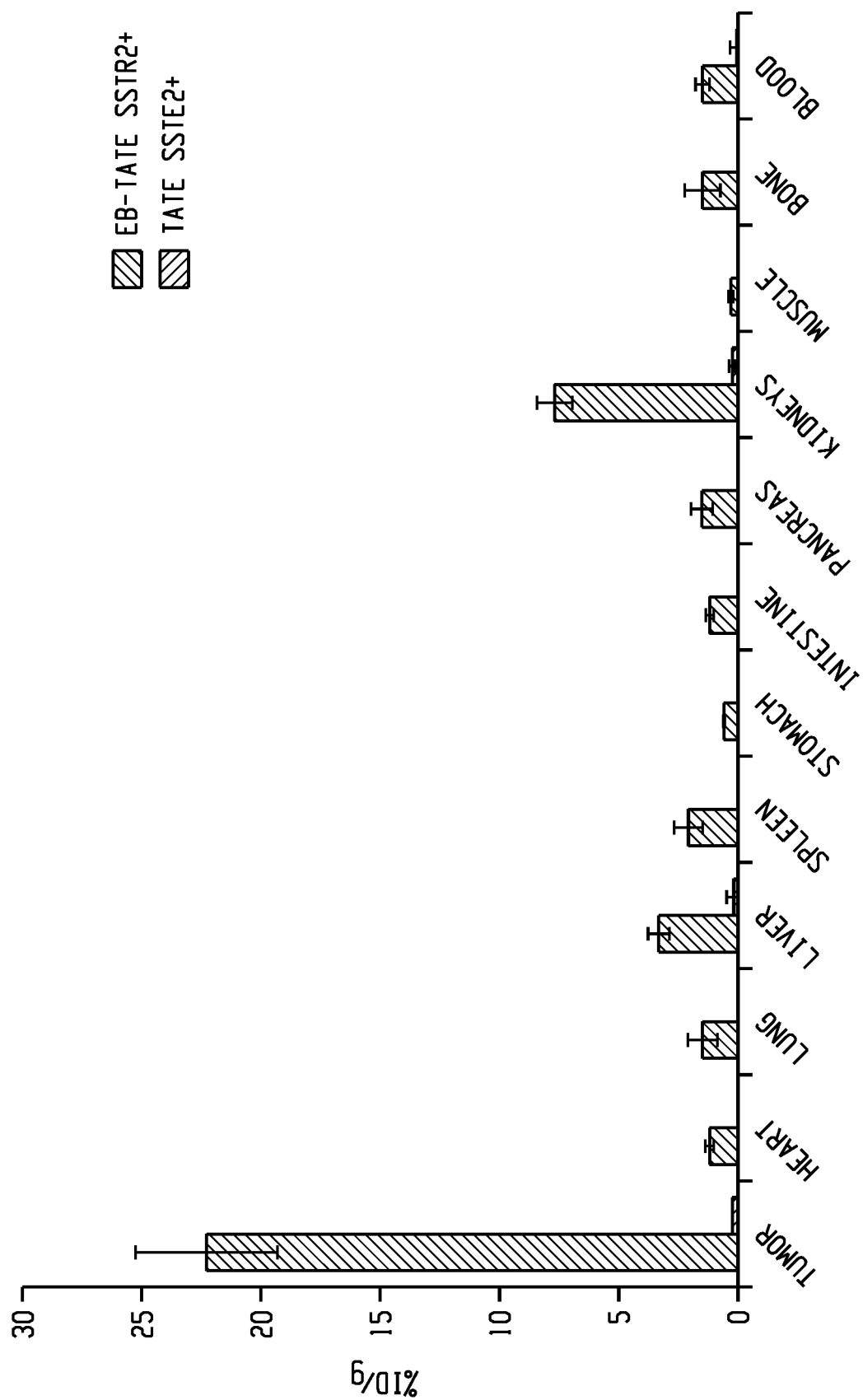
FIG. 46 is a diagram showing biodistribution of $^{86}$Y-EB-TATE vs. $^{86}$Y-TATE in HCT116$^{+}$ xenograft (SSTR2 positive tumors) 48 hours post-injection.
Figure 47:
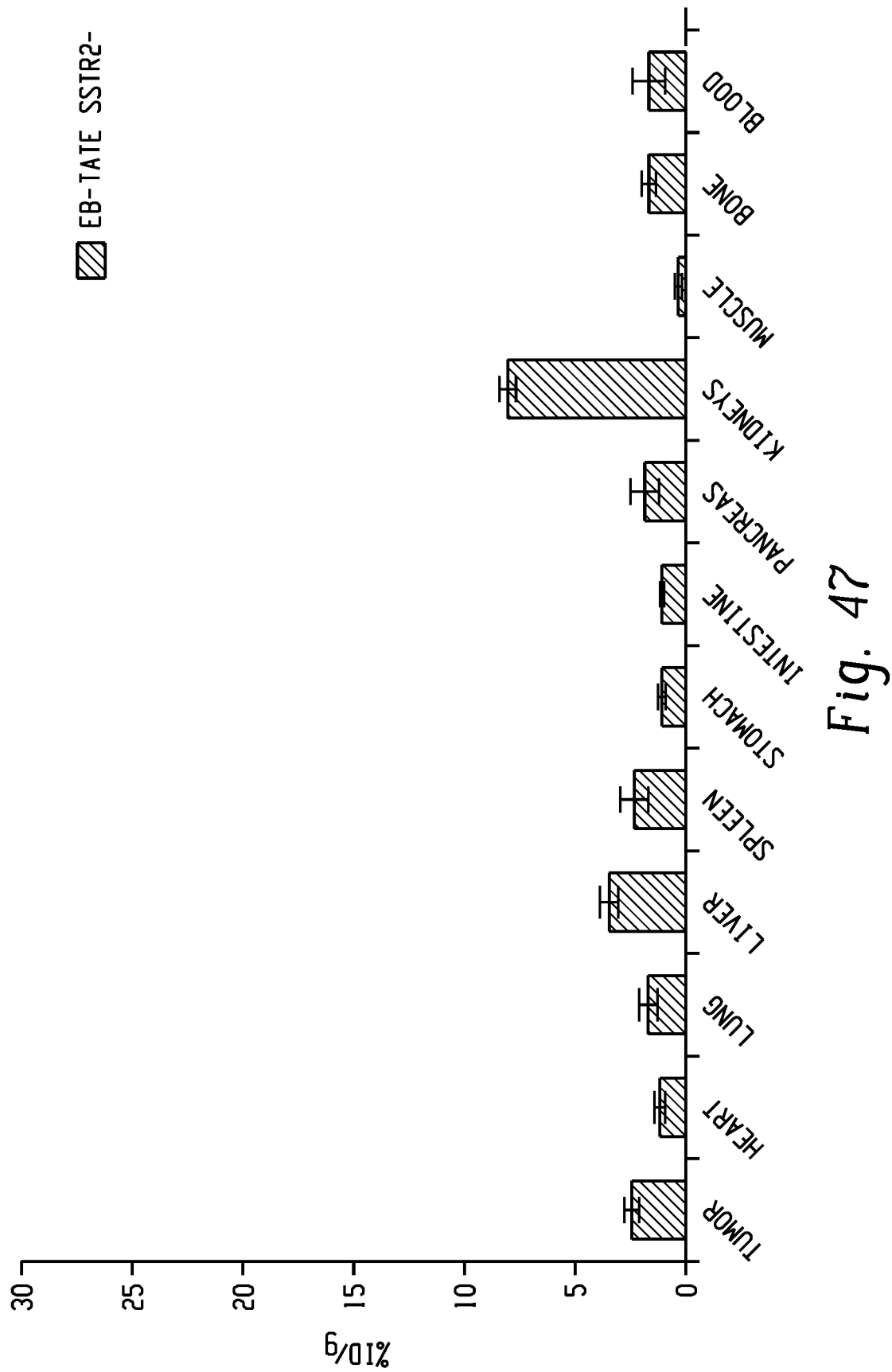
FIG. 47 is a diagram showing biodistribution of $^{86}$Y-EB-TATE E in HCT116$^{+}$ xenograft (SSTR2 positive tumors) 48 hours post-injection.
Figure 48:
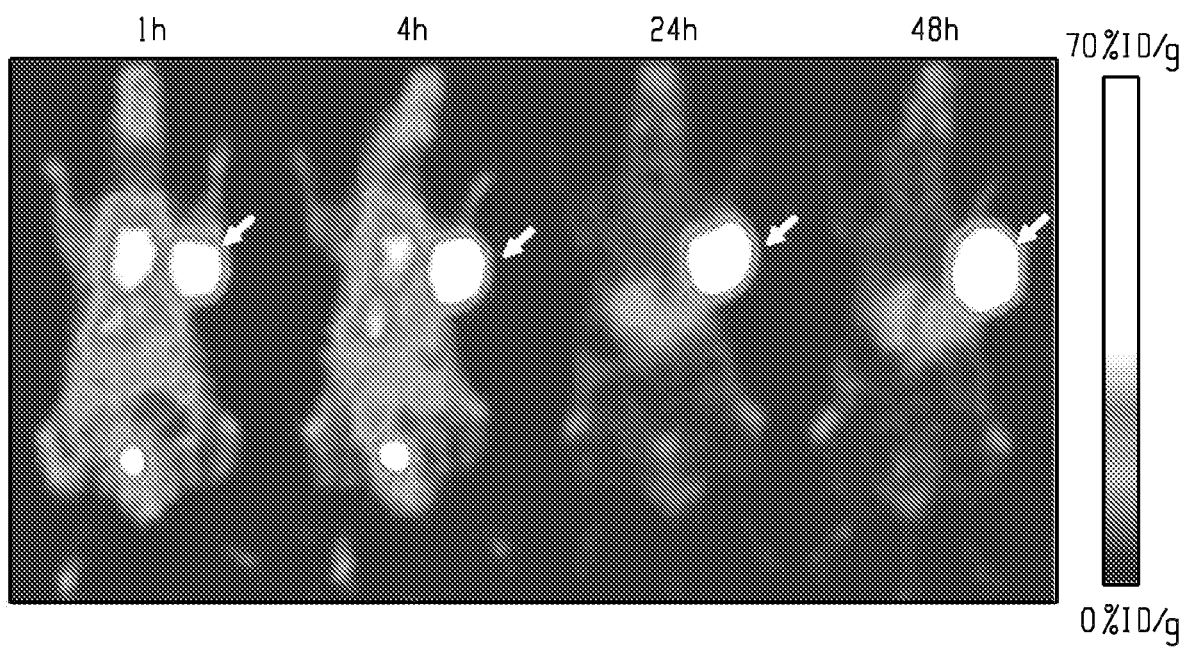
FIG. 48 is a set of PET images showing evaluation of $^{86}$Y-EB-TATE in AR42J xenografts.
Figure 49:
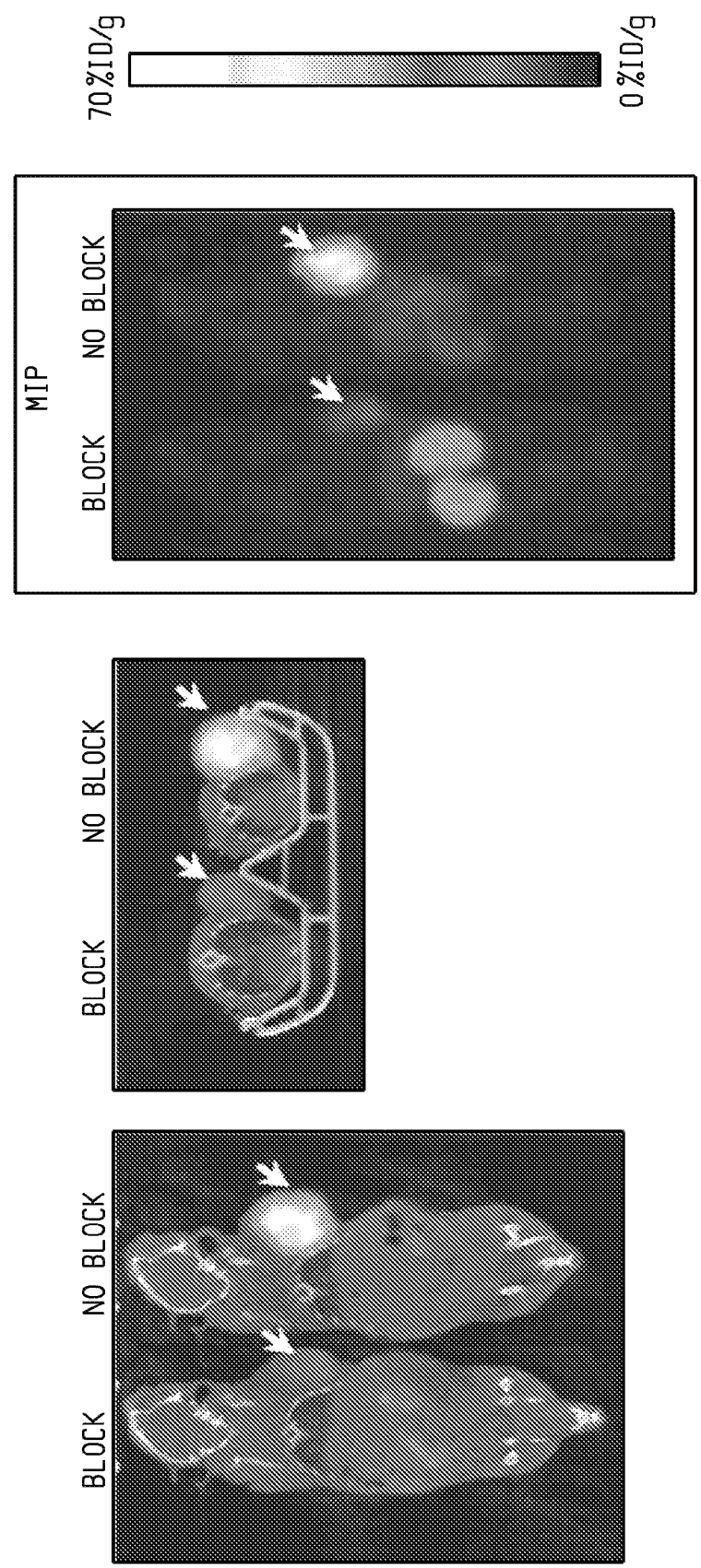
FIG. 49 is a set of PET images showing evaluation of $^{86}$Y-EB-TATE in AR42J xenografts 48 hours post-injection.
Figure 50B:
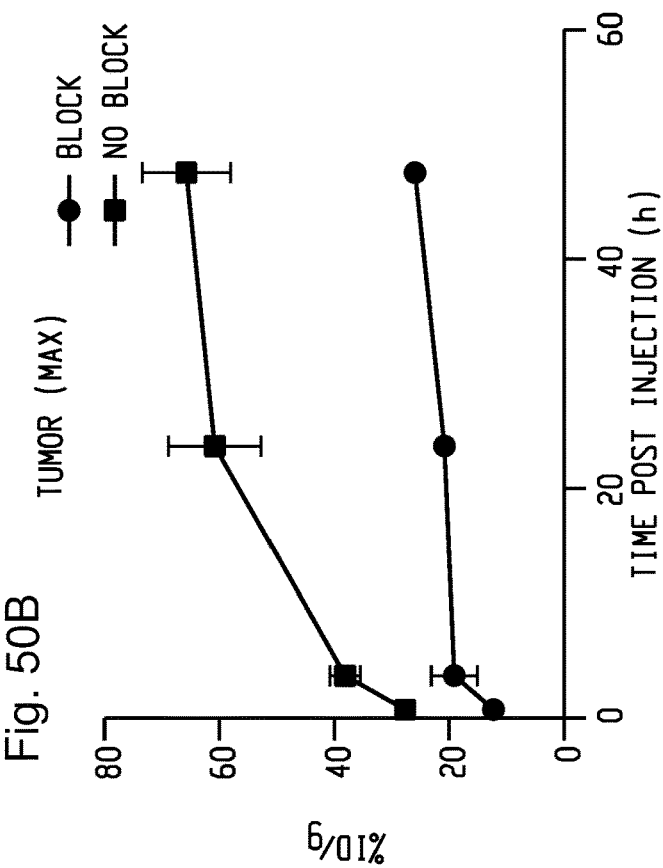
FIGS. 50A and 50B are plots showing $^{86}$Y-EB-TATE TACs in AR42J tumor model.
Figure 50A:
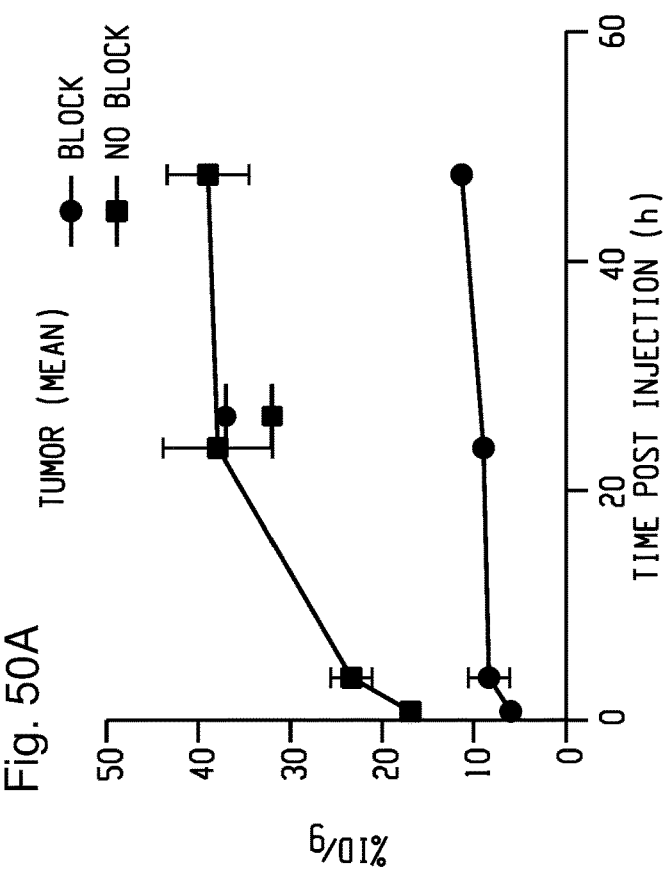
Figure 51:
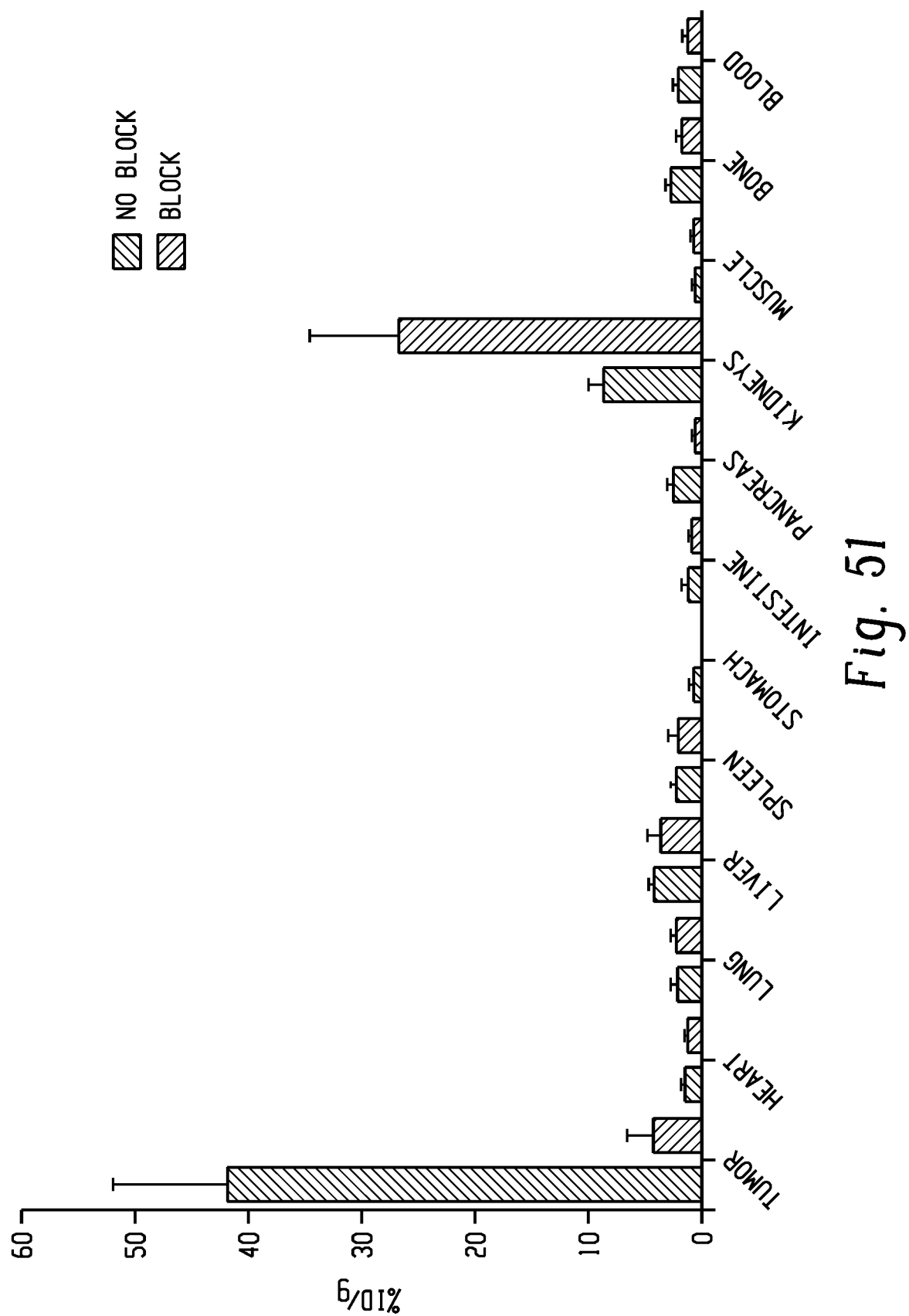
FIG. 51 is a diagram showing biodistribution of $^{86}$Y-EB-TATE in AR42J xenografts 48 hours post-injection.

The cell/internalization studies were repeated and comparable results as for $^{64}$Cu-EB-TATE and $^{64}$Cu-TATE derivatives were received (FIGS. 39A-B and 40A-B). Binding kinetics studies of unlabeled EB-TATE and bovine serum albumin were also performed. EB-TATE has high $K_{on}$ and low $K_{off}$ with μM $K_d$ affinity which is like Evans blue-albumin affinity (FIG. 41).

The resulting radiolabeled conjugate showed prolonged circulation half-life and enhanced tumor accumulation in somatostatin receptor positive tumors (FIGS. 42-43, 44A-D, 45A-C, 46, and 47A-B). Tumor uptake was markedly increased compared to the peptides without the "add-on" (FIGS. 42-43, 44A-D, 45A-C, 46, and 47A-B). $^{86}$Y-EB-TATE in AR42J xenografts was evaluated, which expresses higher SSTR2 levels and indeed got higher tumor uptake values (FIGS. 48-49, 50A-B, and 51). Attempt to block $^{86}$Y-EB-TATE in SSTR2-positive tumors were also successful (FIGS. 49, 50A-B, and 51).

Figure 52:
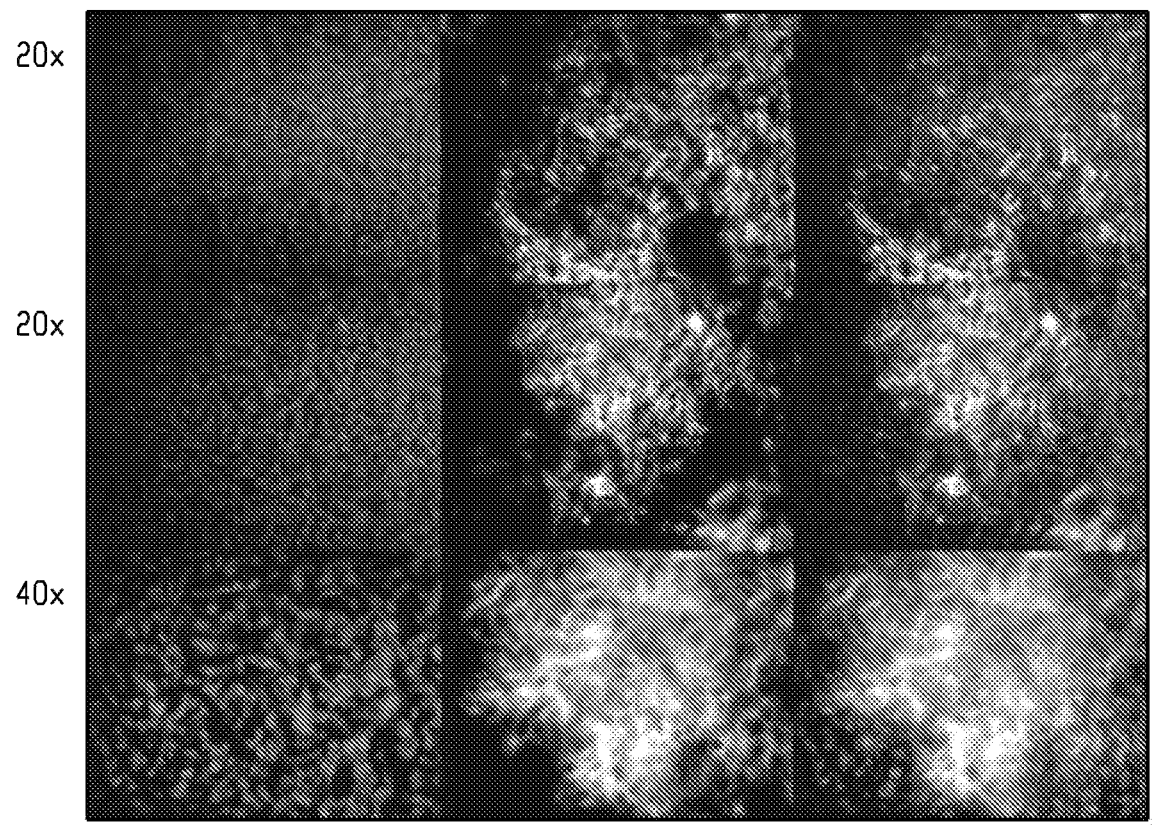
FIG. 52 is an image showing the results of immunofluorescent staining for HCT116 SSTR2$^{+}$ tumors.
Figure 53:
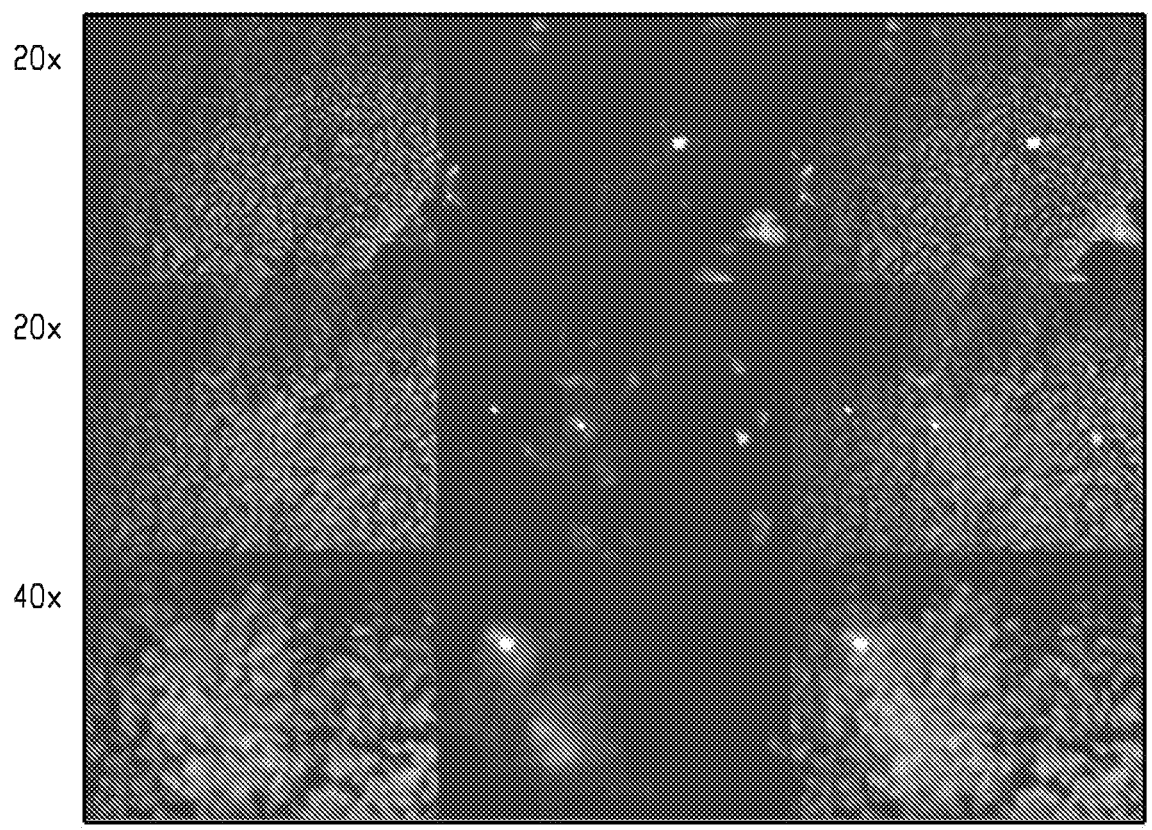
FIG. 53 is an image showing the results of immunofluorescent staining for HCT116 SSTR2$^{-}$ tumors.
Figure 54A:
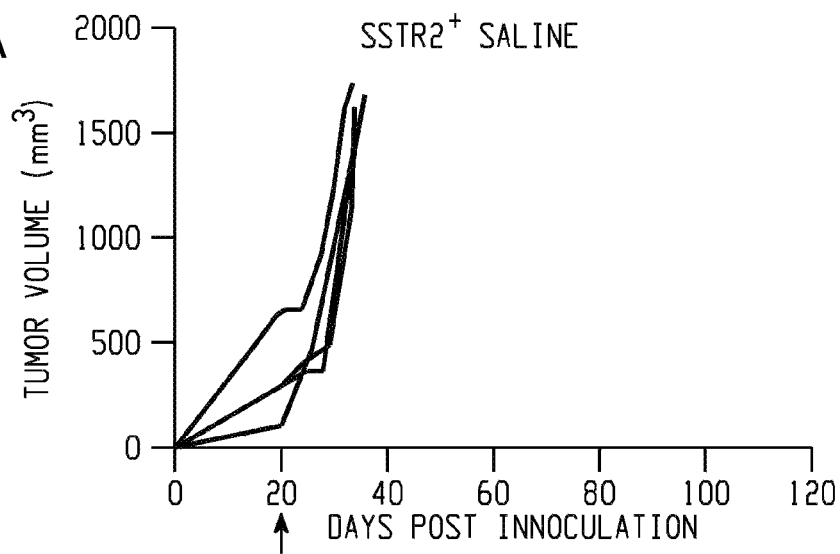
FIGS. 54A, 54B, 54C, 54D, 54E, and 54F are plots showing $^{90}$Y radiotherapy in HCT116 xenografts tumor growth curves.
Figure 54B:
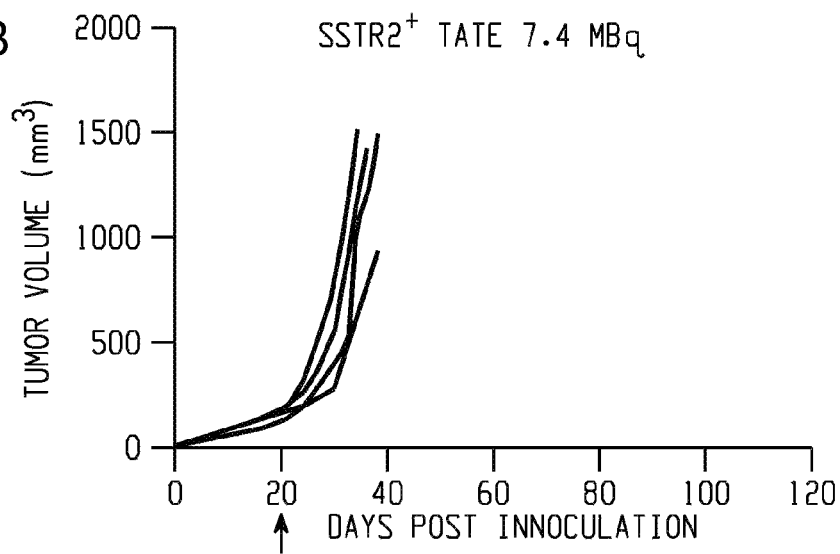
Figure 54C:
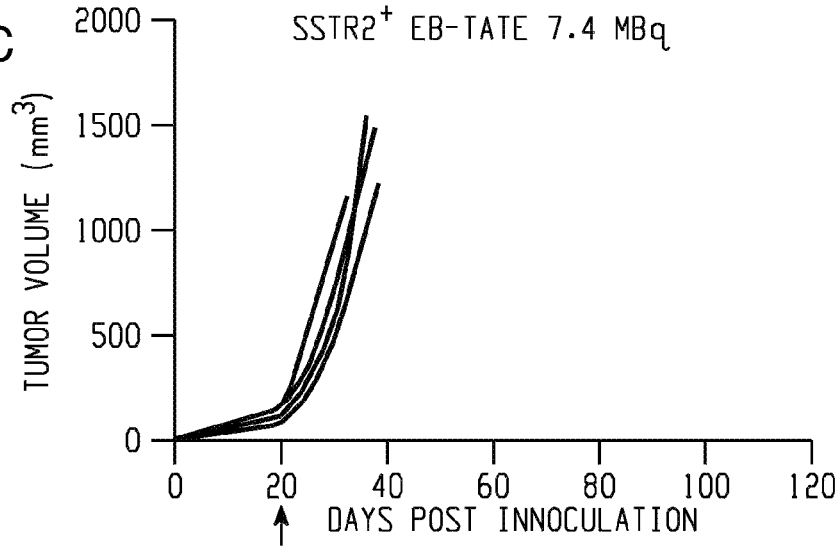
Figure 54D:
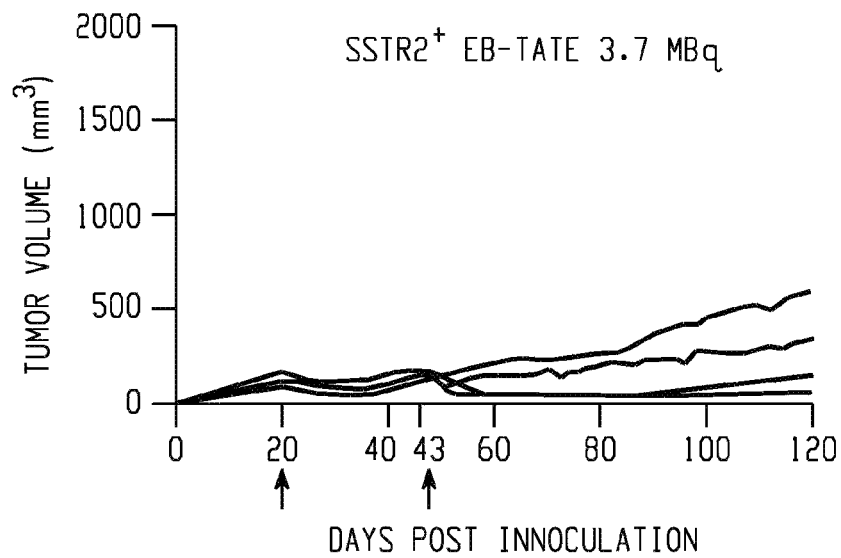
Figure 54E:
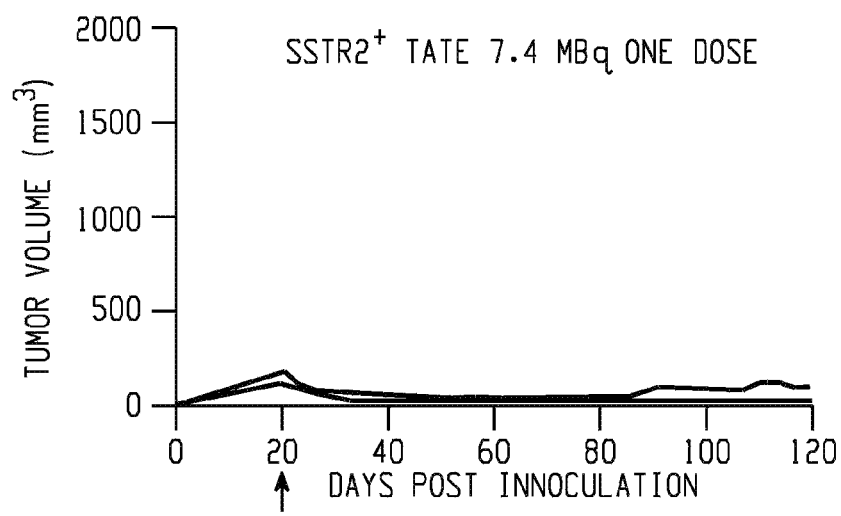
Figure 54F:
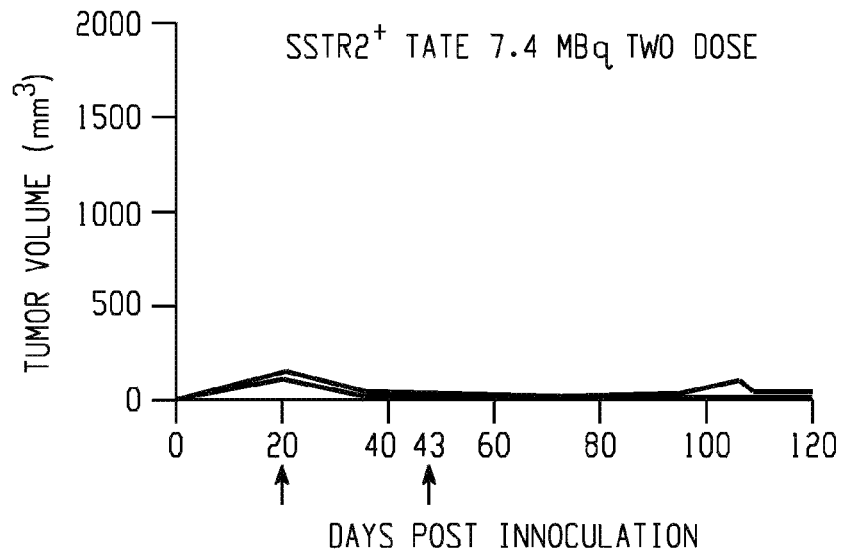
Figure 55:
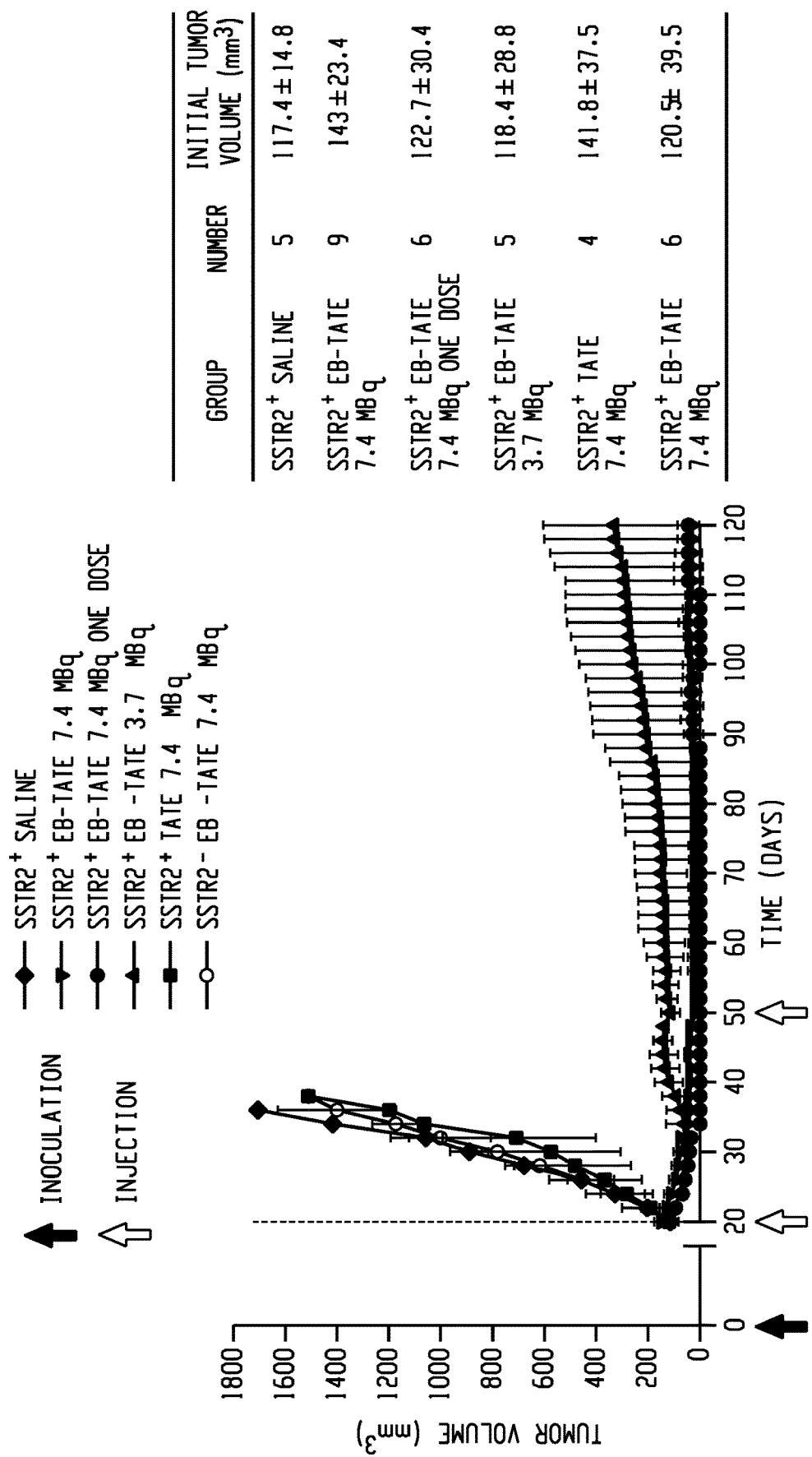
FIG. 55 is a plot showing $^{90}$Y radiotherapy in HCT116 xenografts tumor growth curve.
Figure 56:
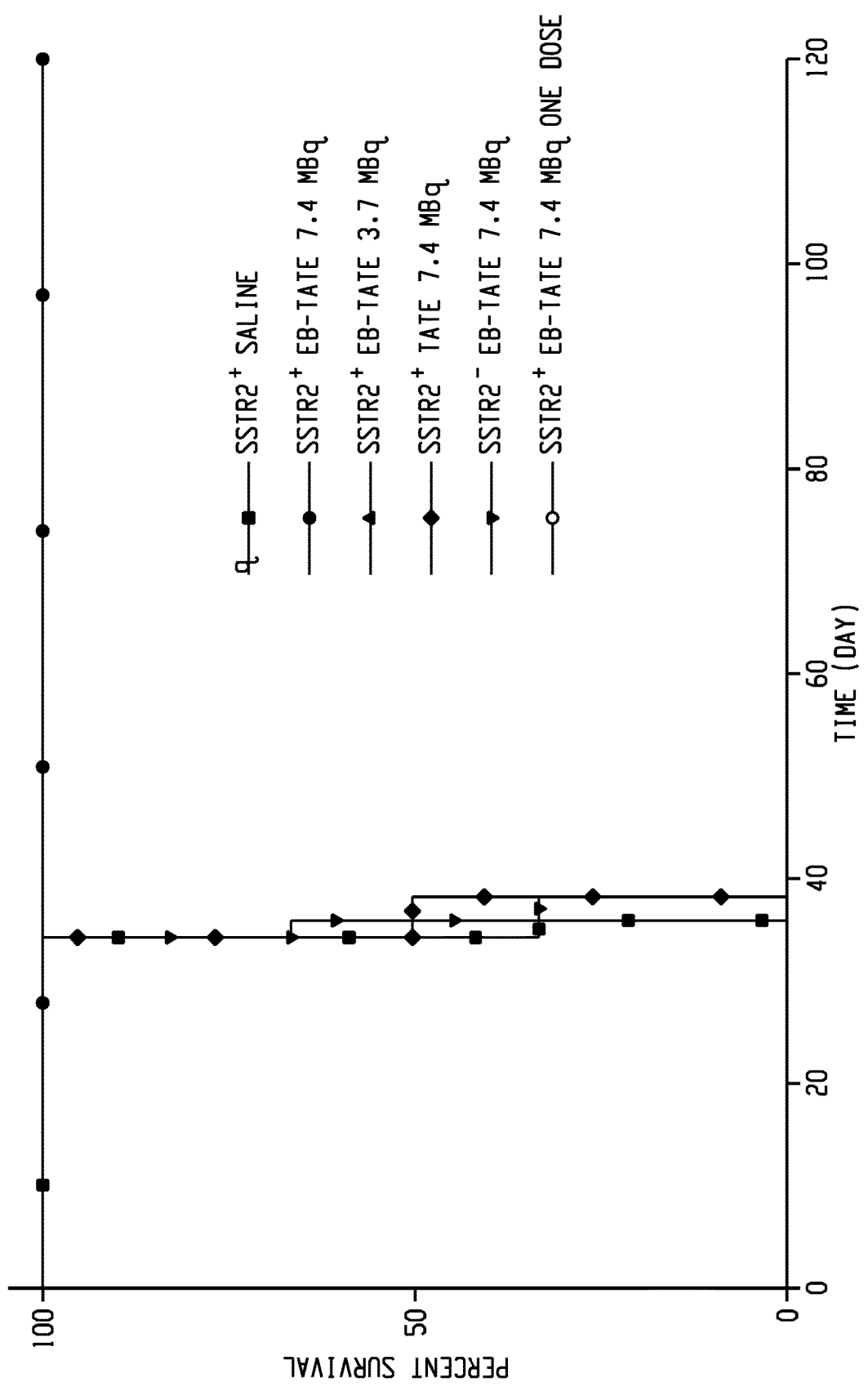
FIG. 56 is a plot showing $^{90}$Y radiotherapy in HCT116 xenografts survival curve.
Figure 57:
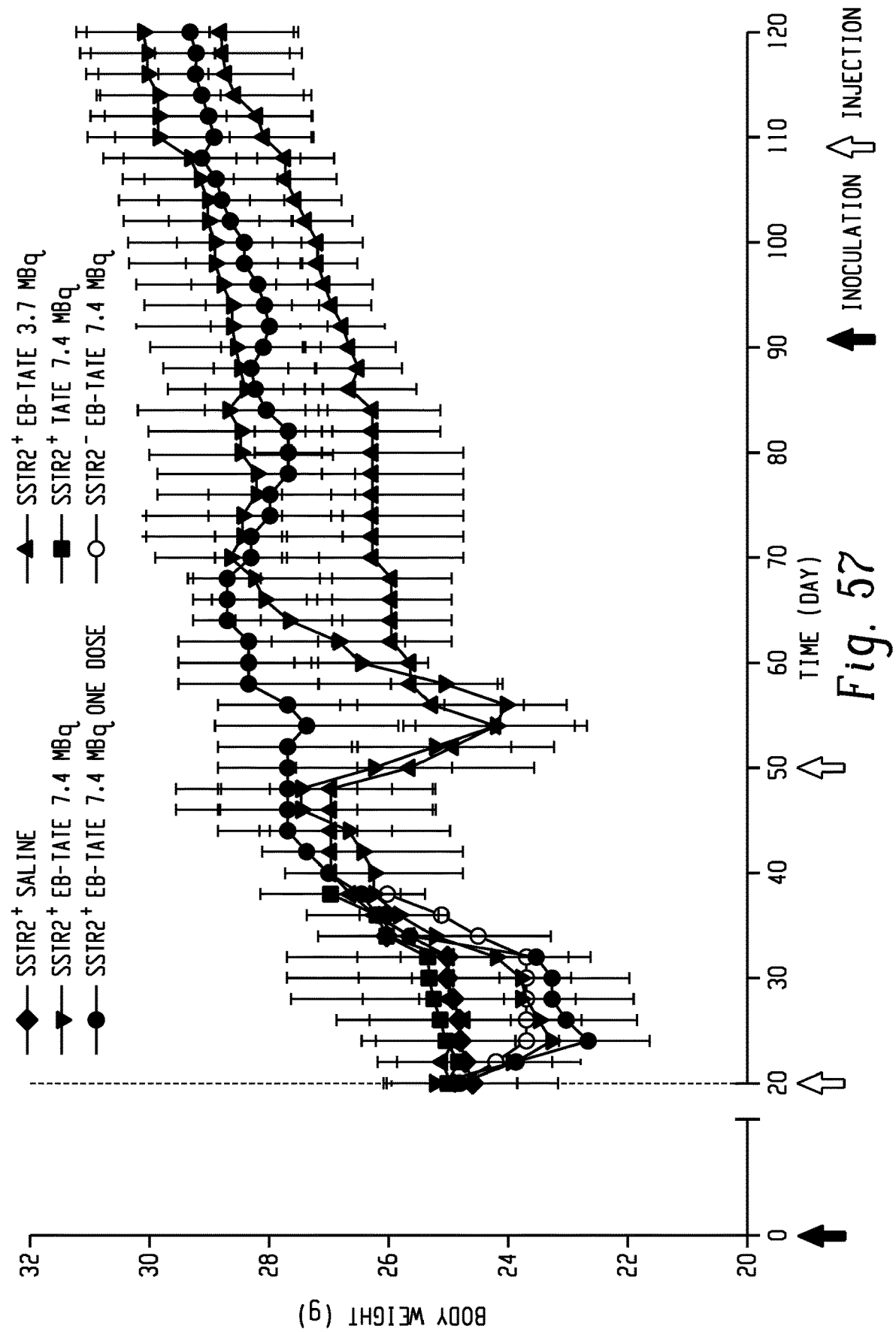
FIG. 57 is a plot showing $^{90}$Y radiotherapy in HCT116 xenografts body weight curve.
Figure 58A:
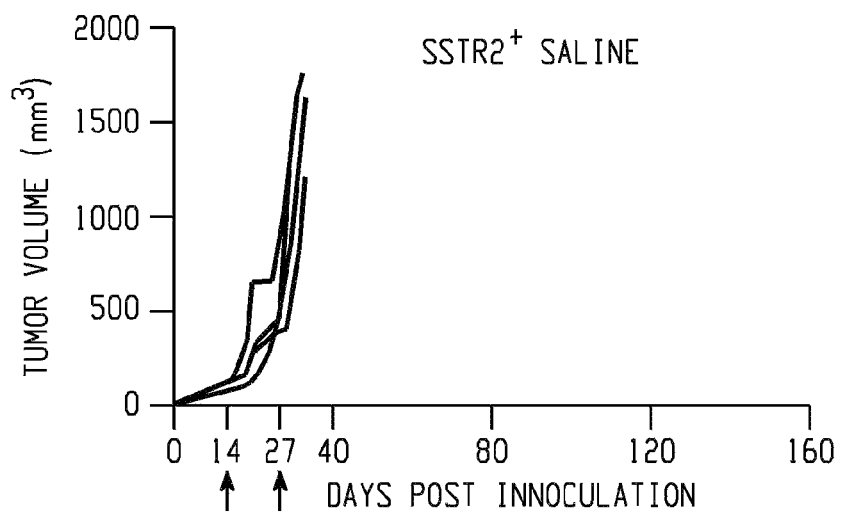
FIGS. 58A, 58B, 58C, 58D, 58E, and 58F are plots showing $^{90}$Y radiotherapy in HCT116 xenografts tumor growth curves.
Figure 58B:
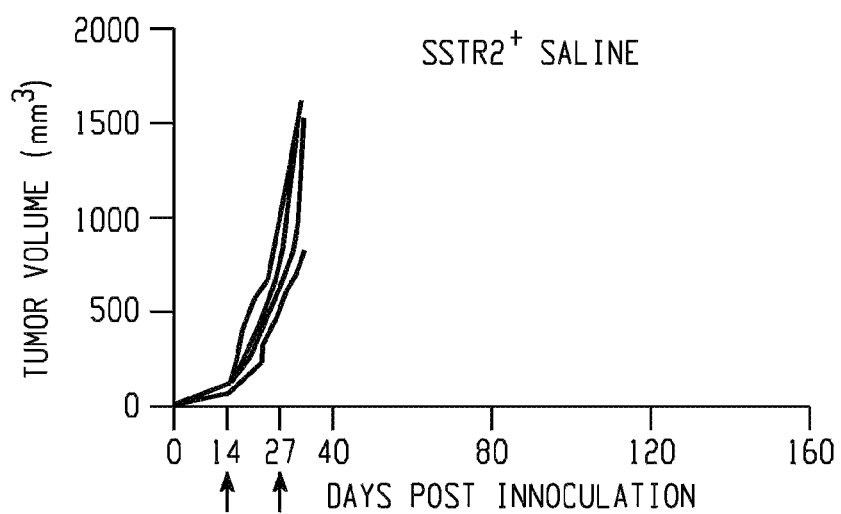
Figure 58C:
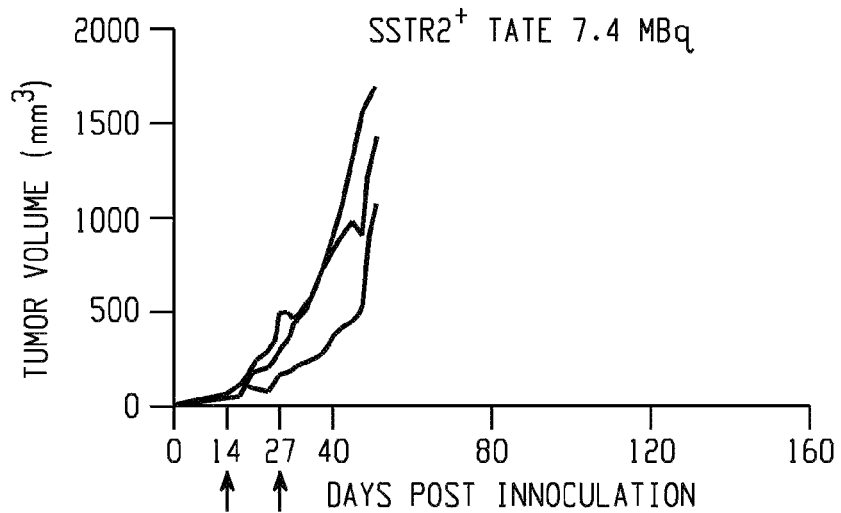
Figure 58D:
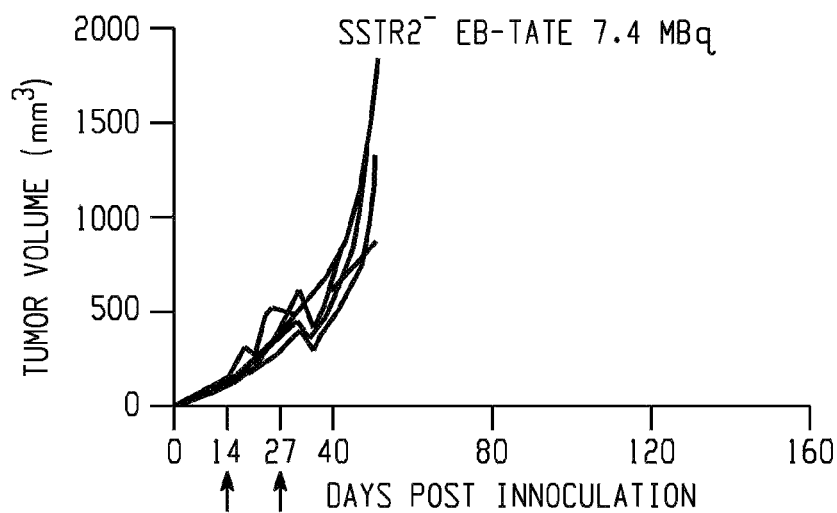
Figure 58E:
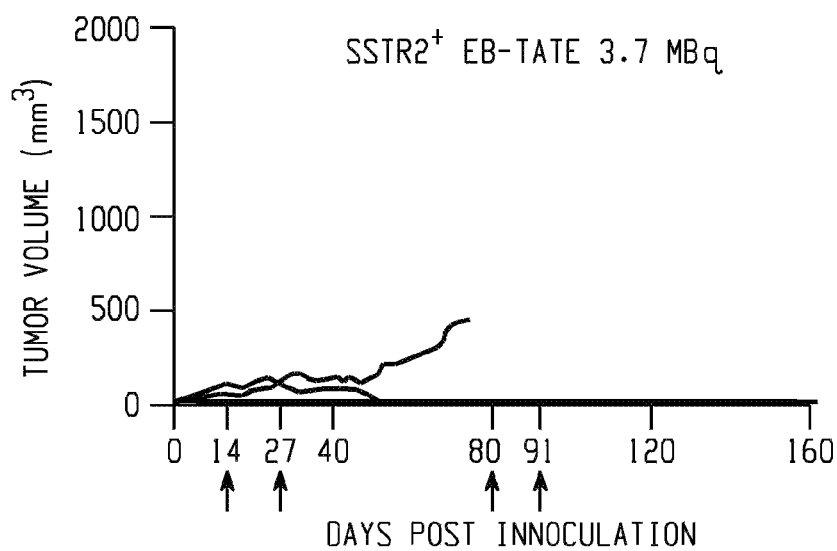
Figure 58F:
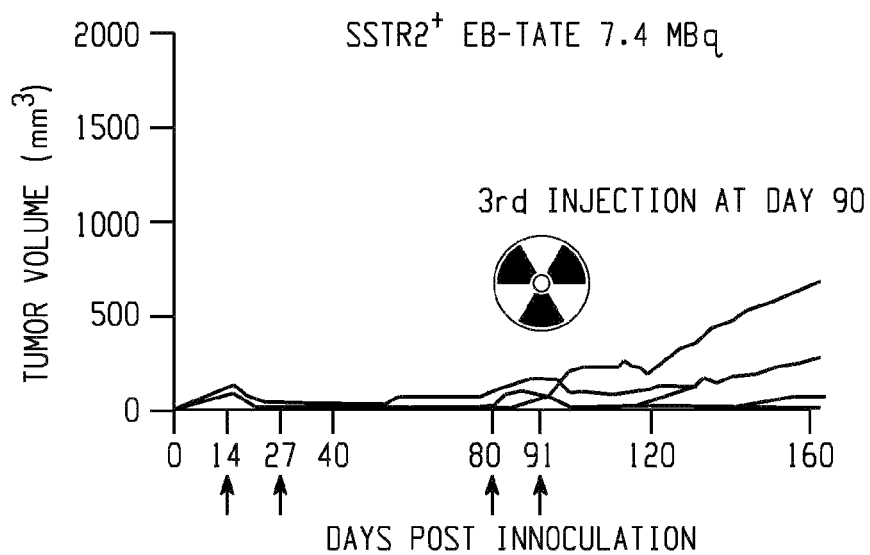

Immunofluorescence for tumor frozen sections indicated the receptor expression (FIGS. 52-53).

Figure 59:
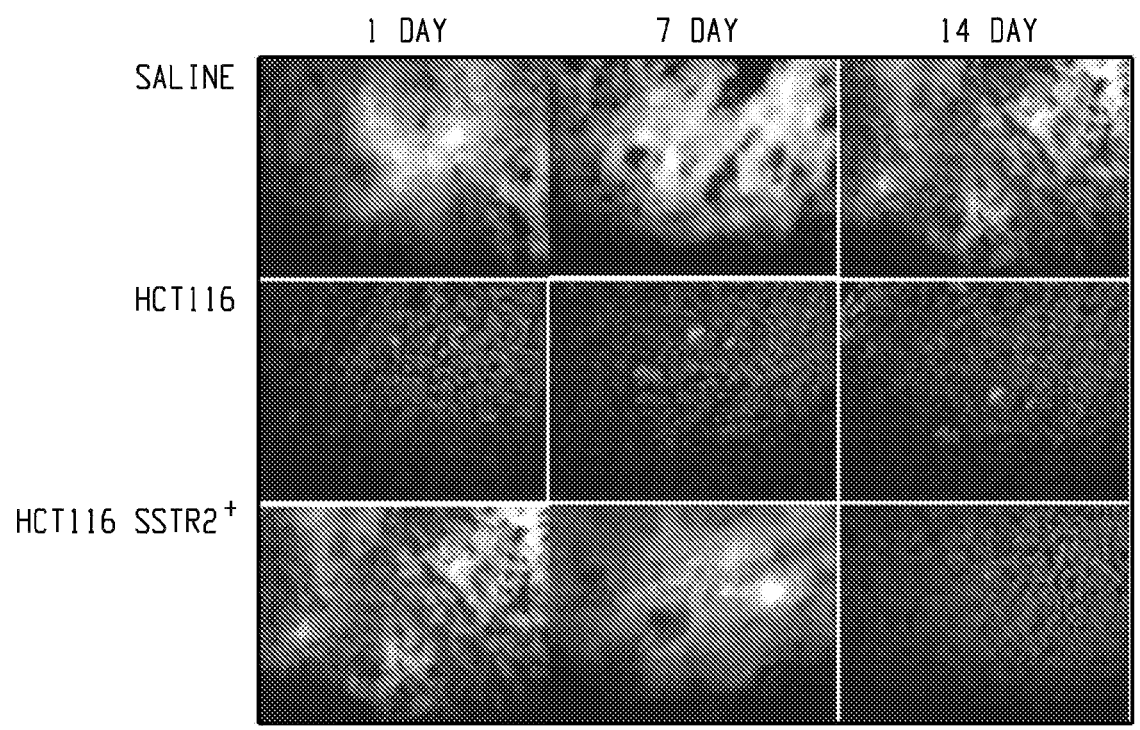
FIG. 59 is a set of images showing the results of immunofluorescent staining for HCT116 SSTR2$^{-}$ tumors as $^{90}$Y radiotherapy in HCT116 xenografts.
Figure 60:
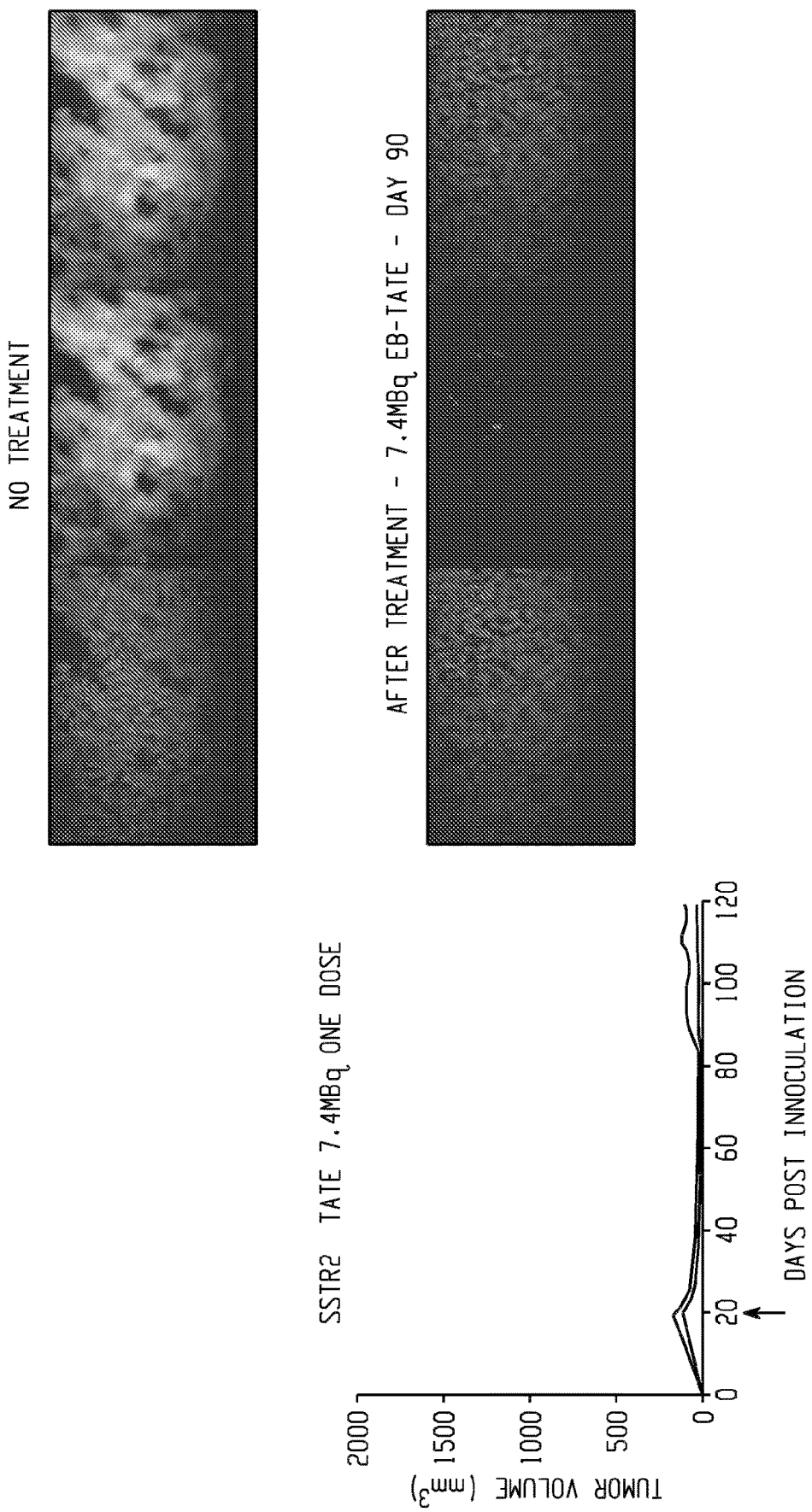
FIG. 60 is a set of images showing the results of immunofluorescent staining for SSTR2 as $^{90}$Y radiotherapy in HCT116 xenografts.
Figure 61:
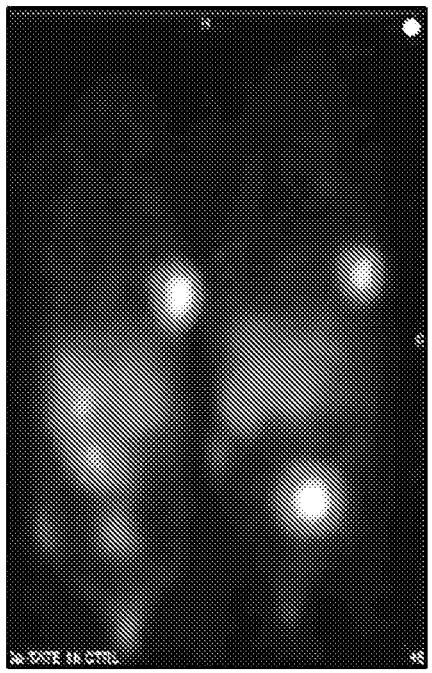
FIG. 61 is a set of PET images showing expression of SSTR2 in HCT116 SSTR2$^{+}$ tumors before and after treatment using $^{68}$Ga-DOTA-TATE imaging.
Figure 61:
Figure 63:
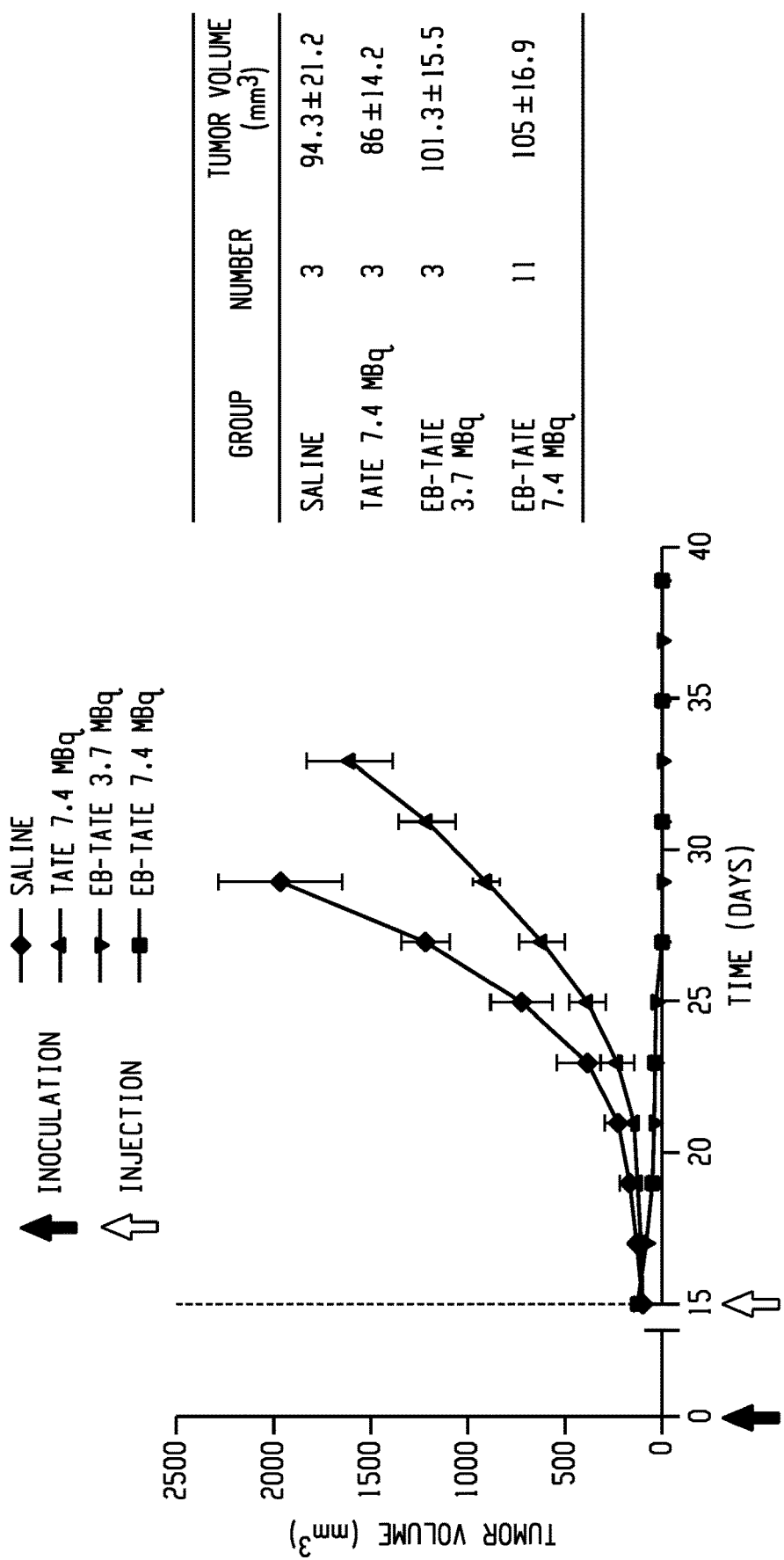
FIG. 63 is a plot showing $^{90}$Y radiotherapy in HCT116 xenografts tumor growth curve.
Figure 64:
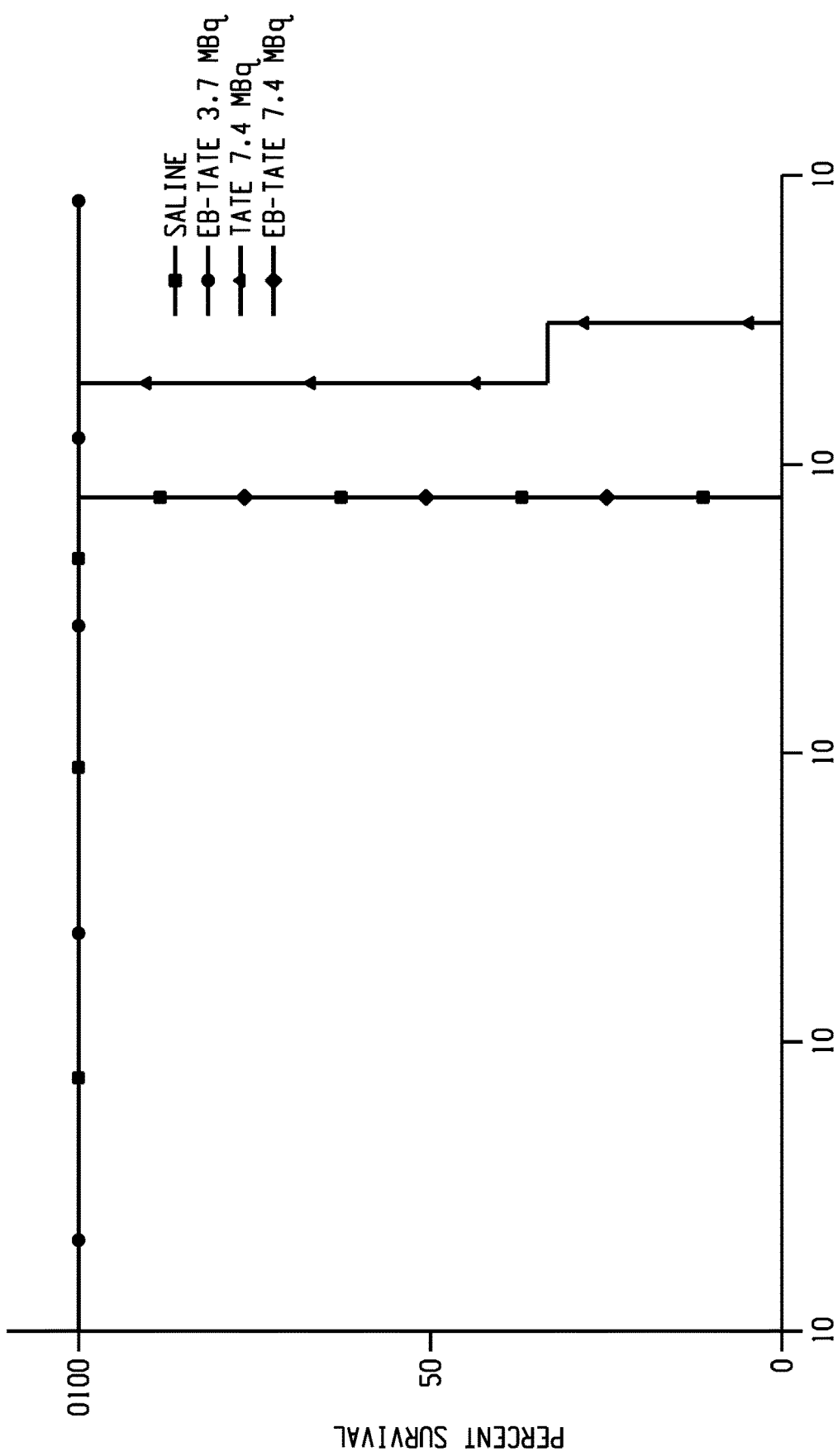
FIG. 64 is a plot showing $^{90}$Y radiotherapy in HCT116 xenografts survival curve.
Figure 65:
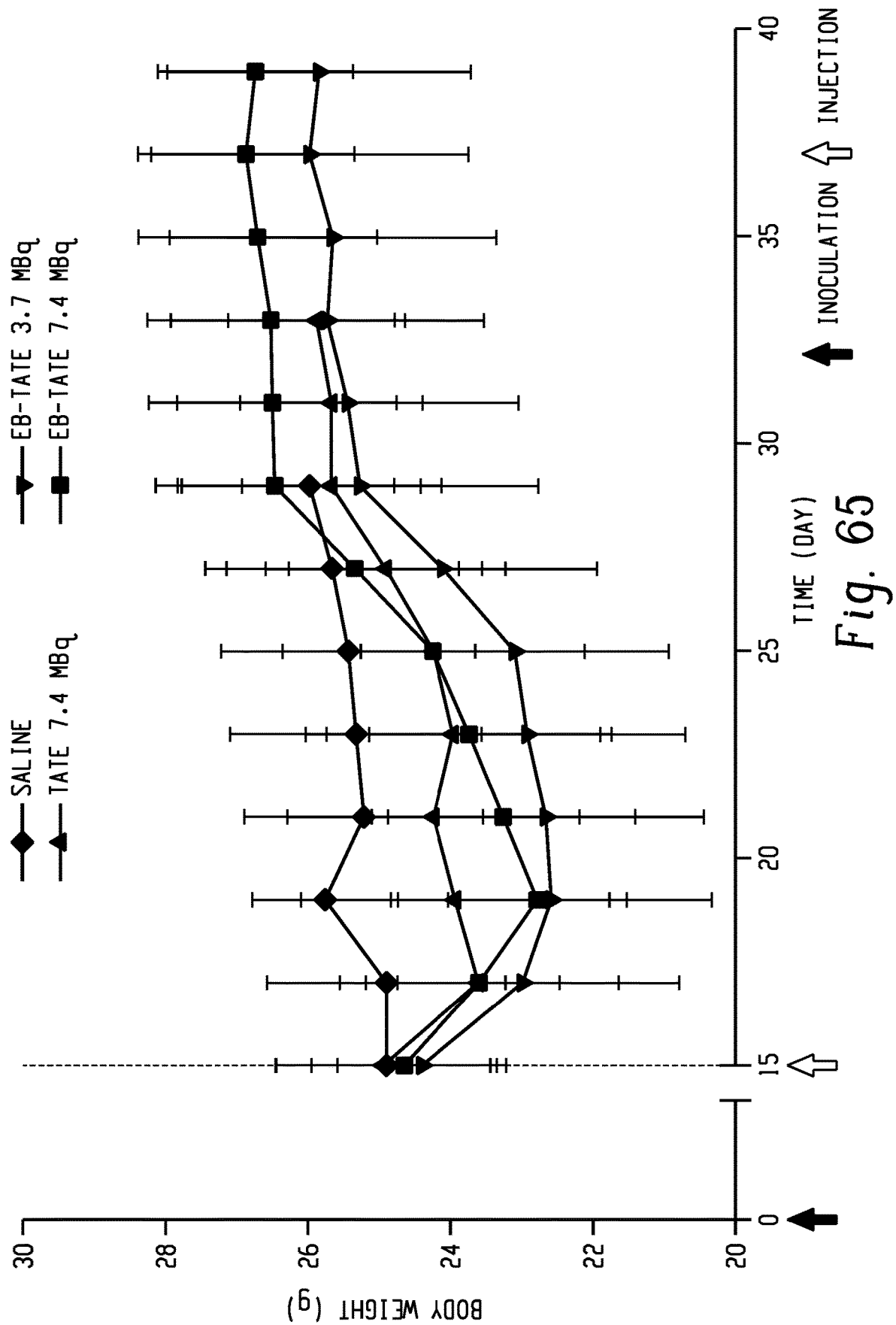
FIG. 65 is a plot showing $^{90}$Y radiotherapy in HCT116 xenografts body weight curve.
Figure 66:
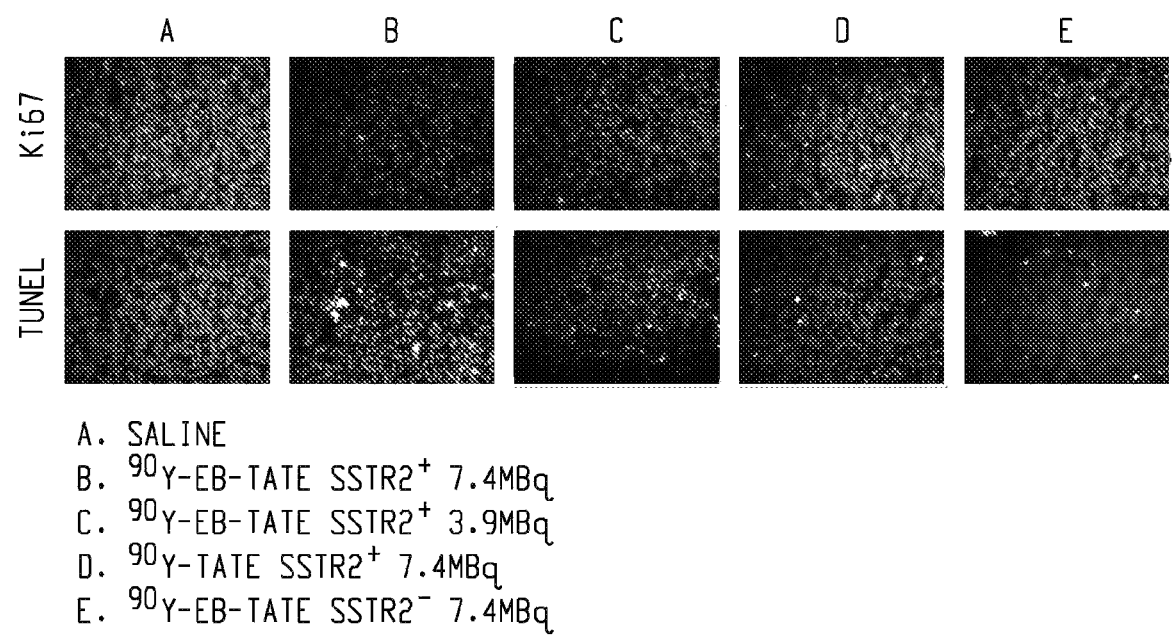
FIG. 66 is a set of images showing the results of staining experiments for Ki67 and TUNEL HCT116 xenografts.
Figure 67:
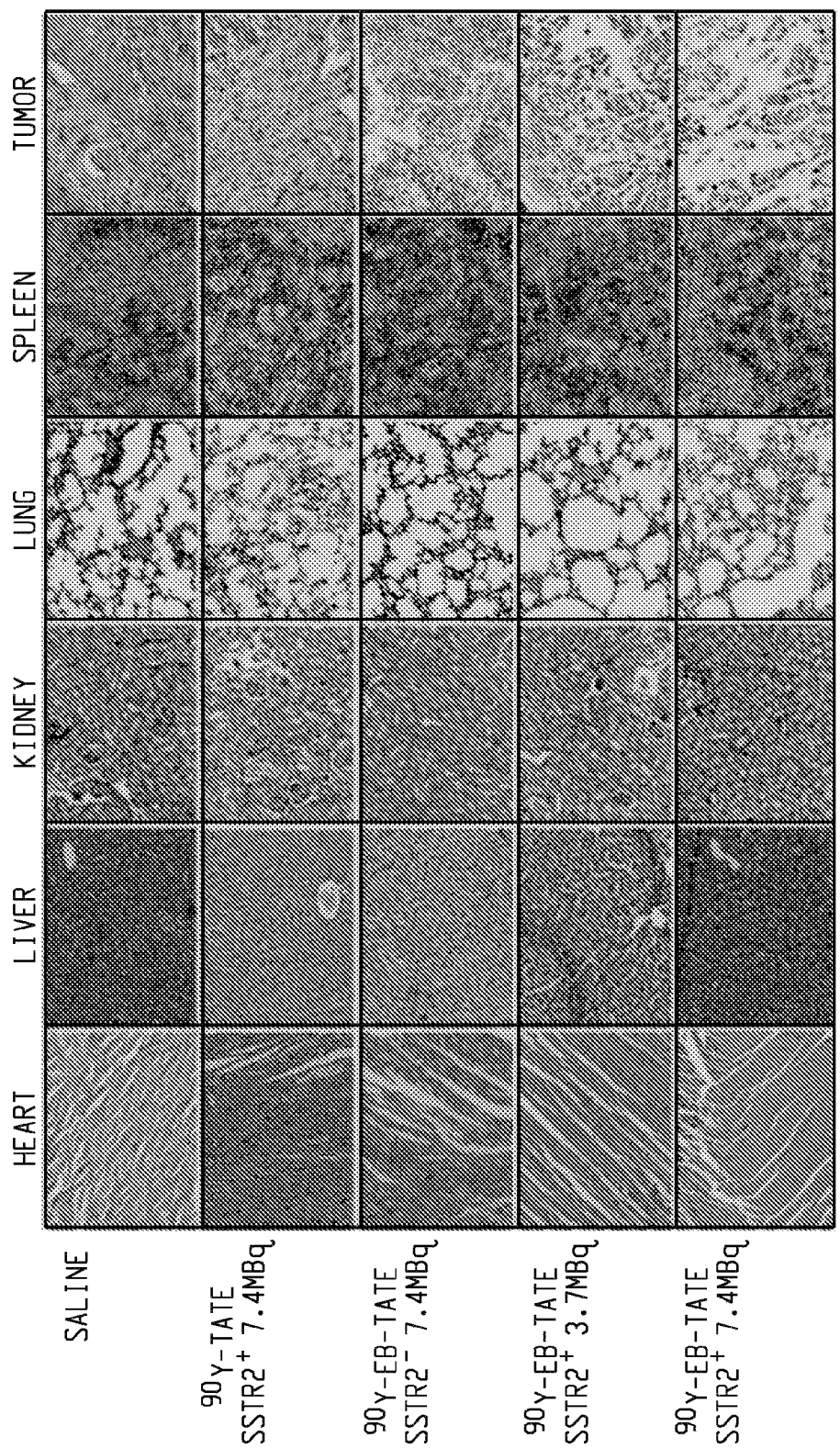
FIG. 67 is a set of images showing the results of H&E staining HCT116 xenografts.

Tumor radiotherapy experiments in mice using $^{90}$Y-EB-TATE was very successful (FIGS. 55-57, 58A-F, 59-61, 62A-D, and 63-65) and eliminated receptor positive tumors using one or two doses of $^{90}$Y-EB-TATE (FIGS. 55-57, 58A-F, 59-61, 62A-D, and 63-65). Three mice from the 7.4 MBq and one mouse from the 3.7 MBq from radiotherapy experiments presented in FIG. 58, slightly shown tumor re-growth. PET imaging using $^{68}$Ga-TATE and immunofluorescence staining confirmed that the tumor regrowth is SSTR2-independent (FIGS. 59-61). Less proliferation higher apoptosis in $^{90}$Y-EB-TATE treated groups than Saline and $^{90}$Y-TATE (Ki67, TUNEL and H&E staining accordingly, FIGS. 66-67) were observed.

Figure 68:
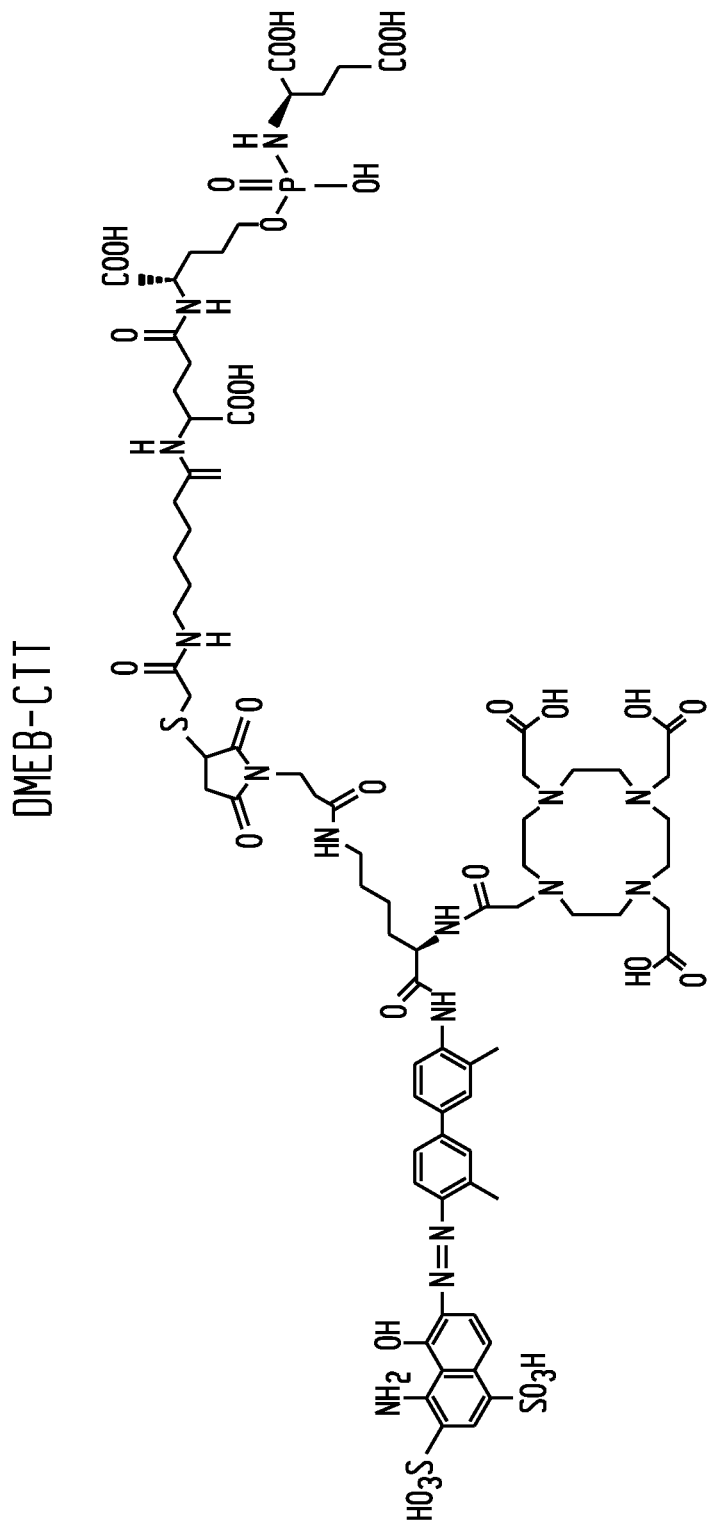
FIG. 68 shows the structure of DMEB-CTT.

The feasibility of the EB moiety by conjugation to a small molecule, CTT1298, prostate specific membrane antigen (PSMA) ligand (FIG. 68) was evaluated. This molecule was obtained from Cancer Targeted Technology (CTT) (http://www.cancertargetedechlology.com/management.html).

Figure 69:
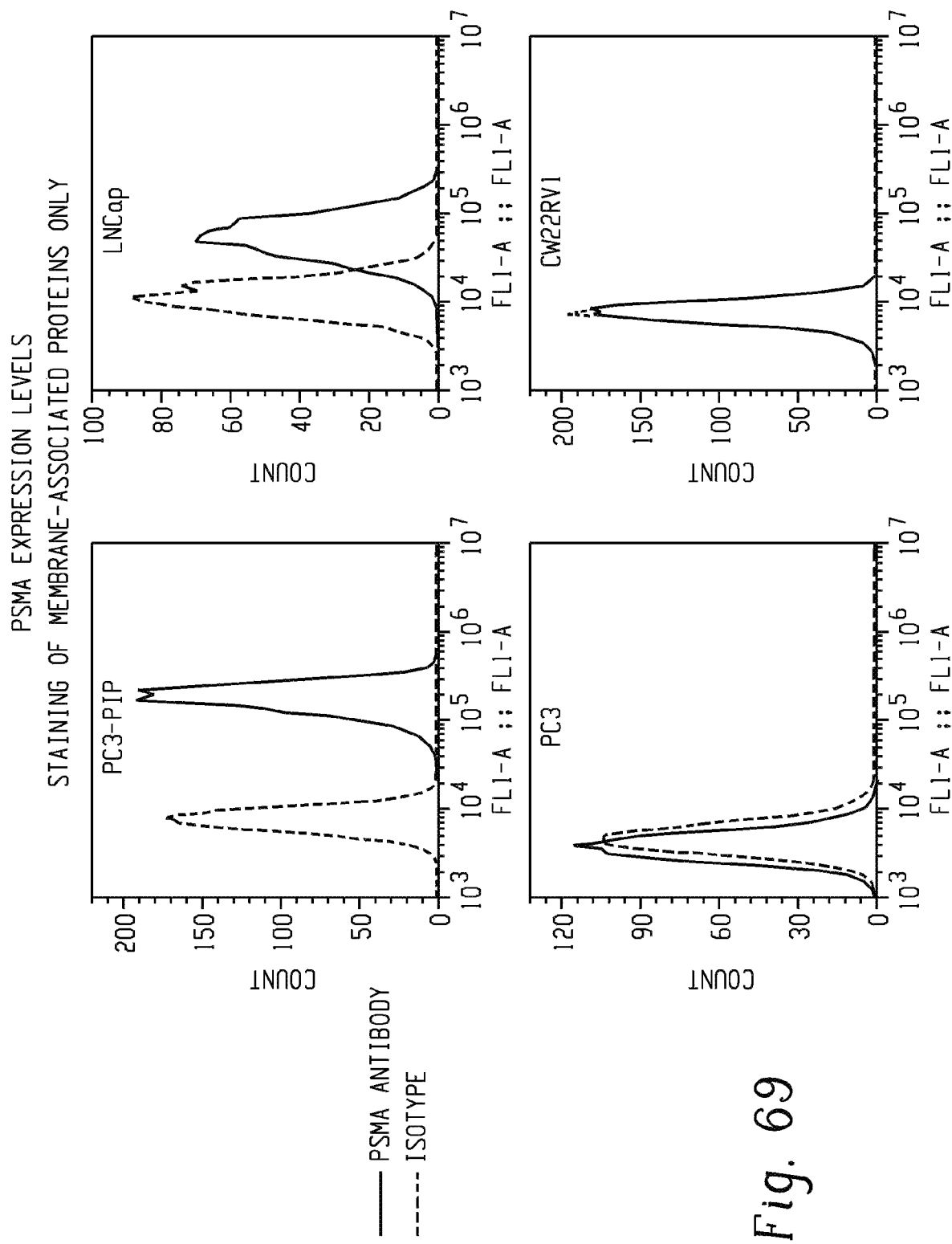
FIG. 69 are plots showing PSMA expression levels after staining of membrane-associated proteins only.
Figure 70A:
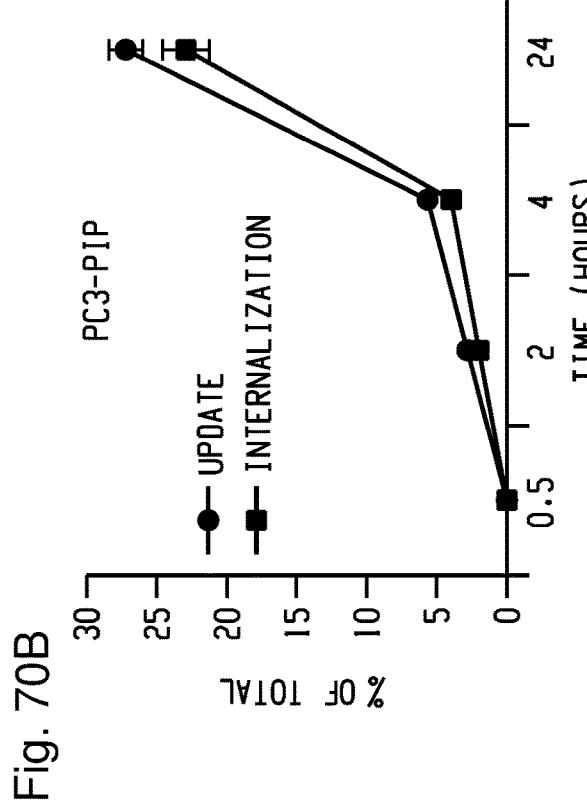
FIGS. 70A, 70B, 70C, and 70D are diagrams showing the results of $^{64}$Cu-EB-CTT cell uptake/internalization.
Figure 70B:
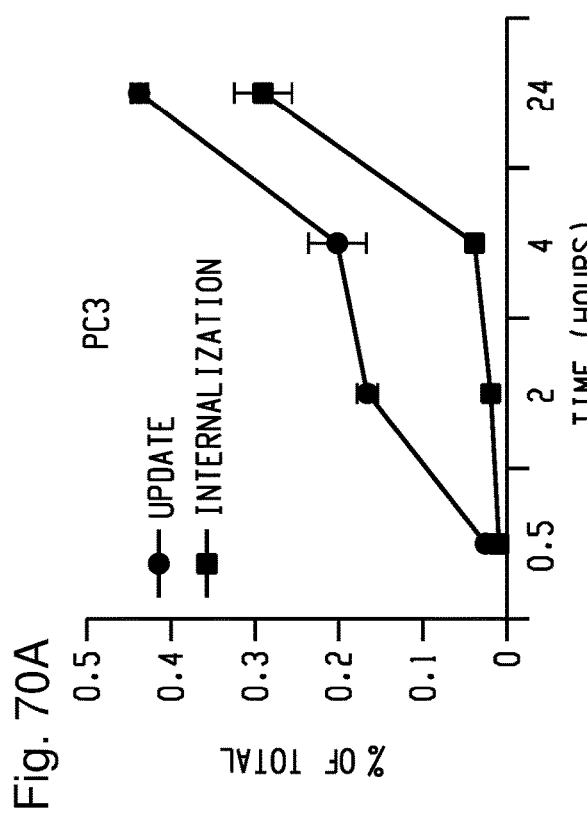
Figure 70C:
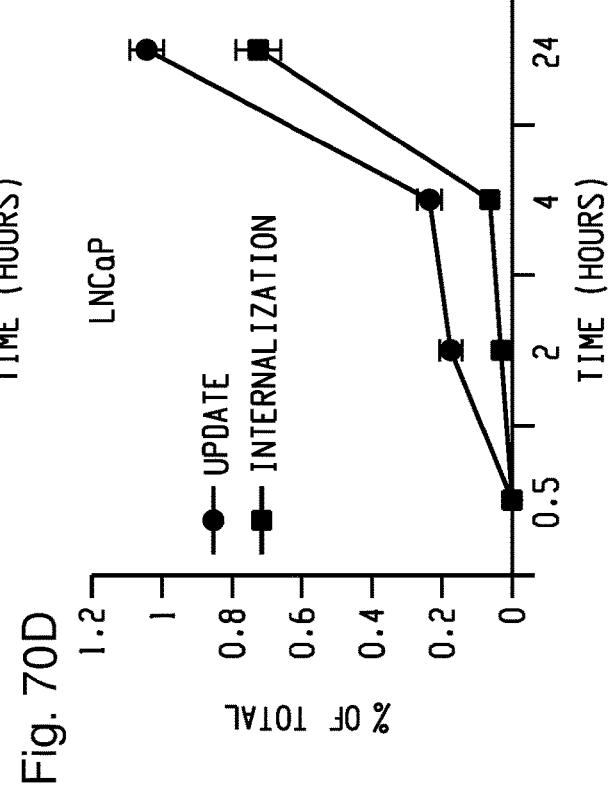
Figure 70D:
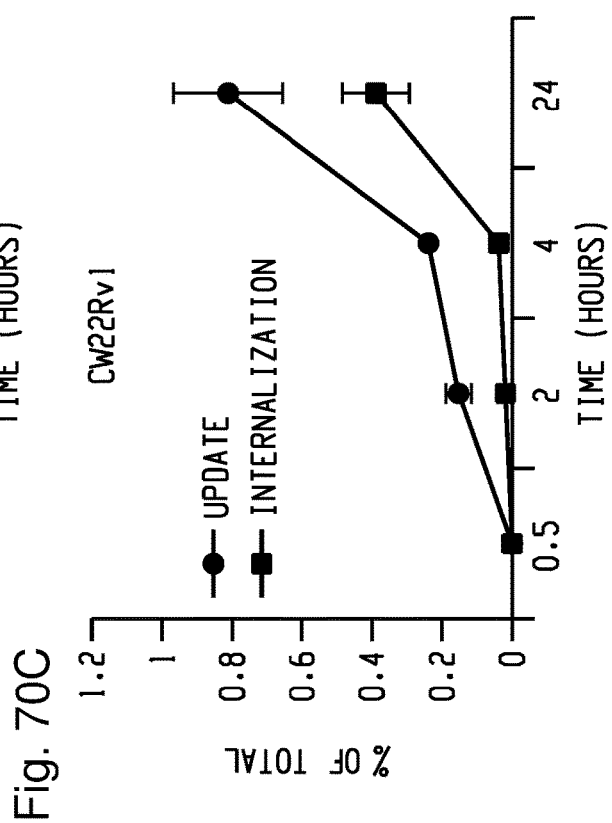
Figure 71:
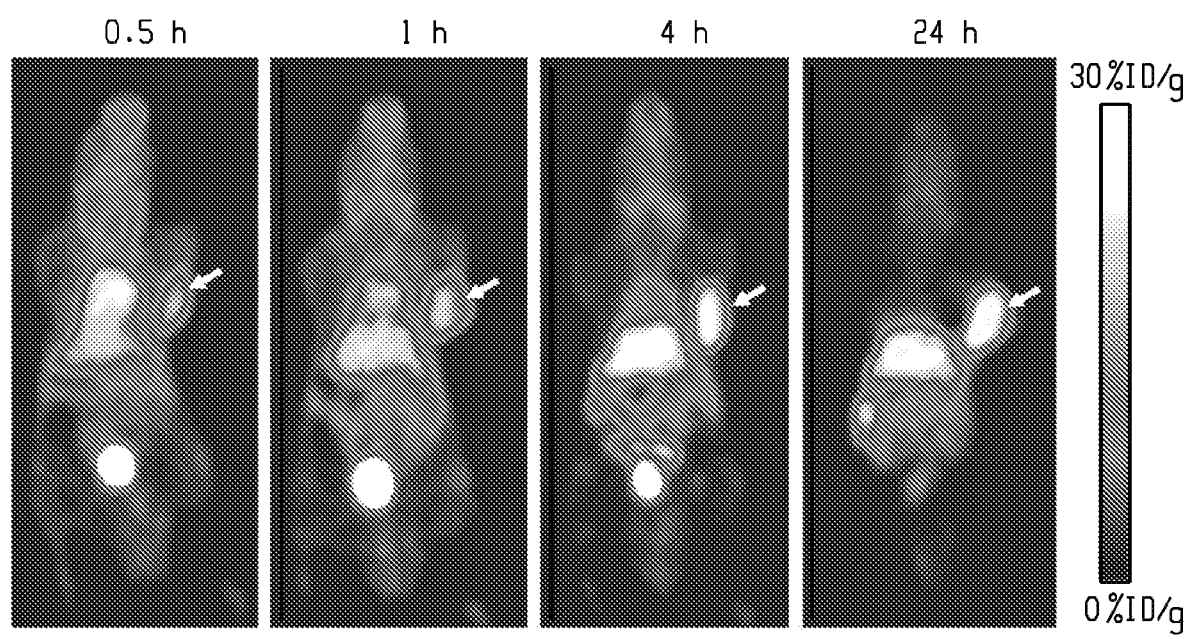
FIG. 71 is a set of PET images showing evaluation of $^{64}$Cu-EB-CTT in PC3-PIP xenograft.
Figure 72A:
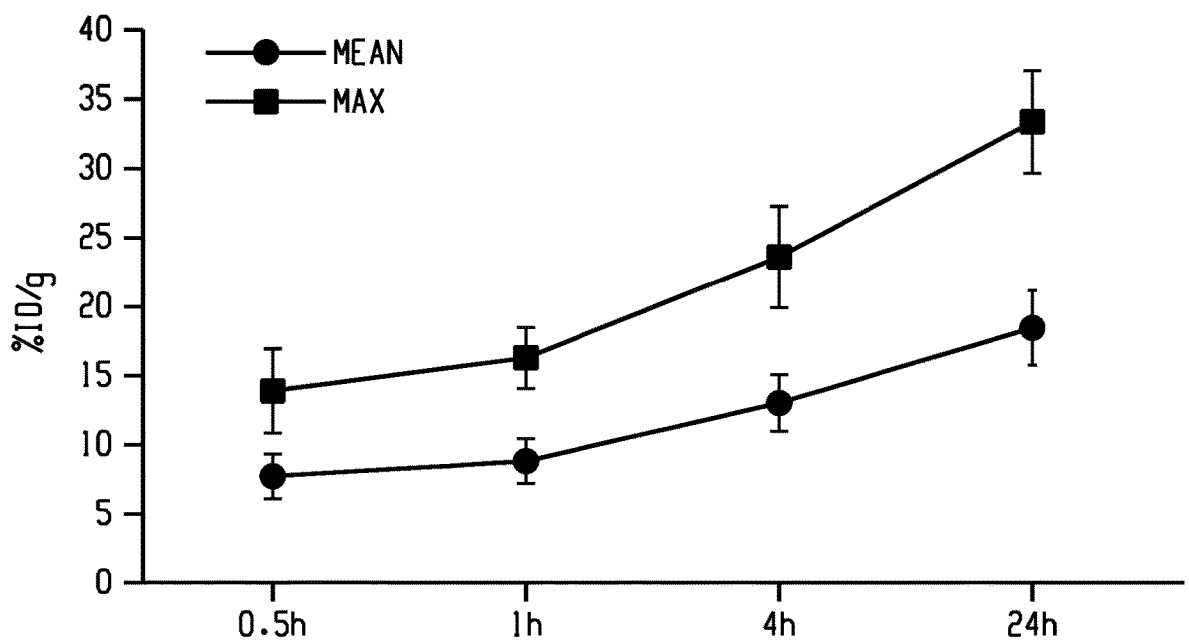
FIGS. 72A and 72B are plots showing tumor and blood TACs of $^{64}$Cu-EB-CTT.
Figure 72B:
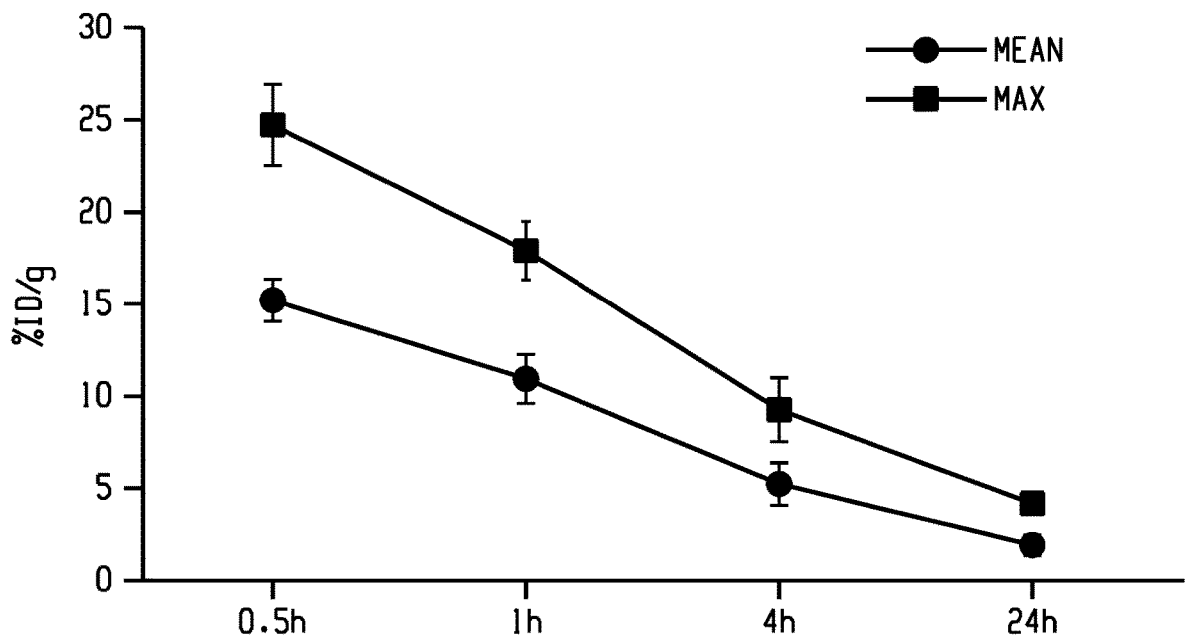
Figure 73:
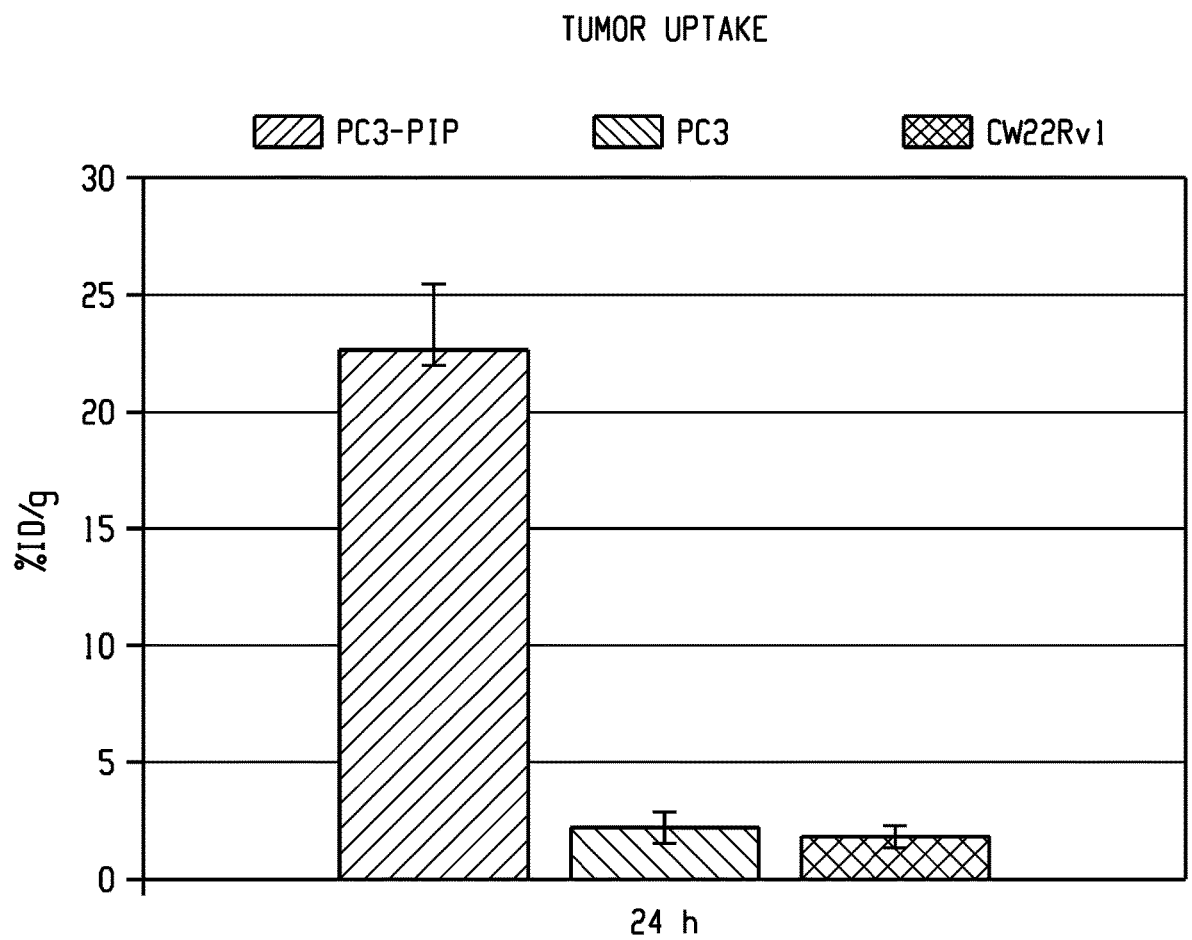
FIG. 73 is a diagram showing $^{64}$Cu-EB-CTT tumor uptake in different xenografts.
Figure 74:
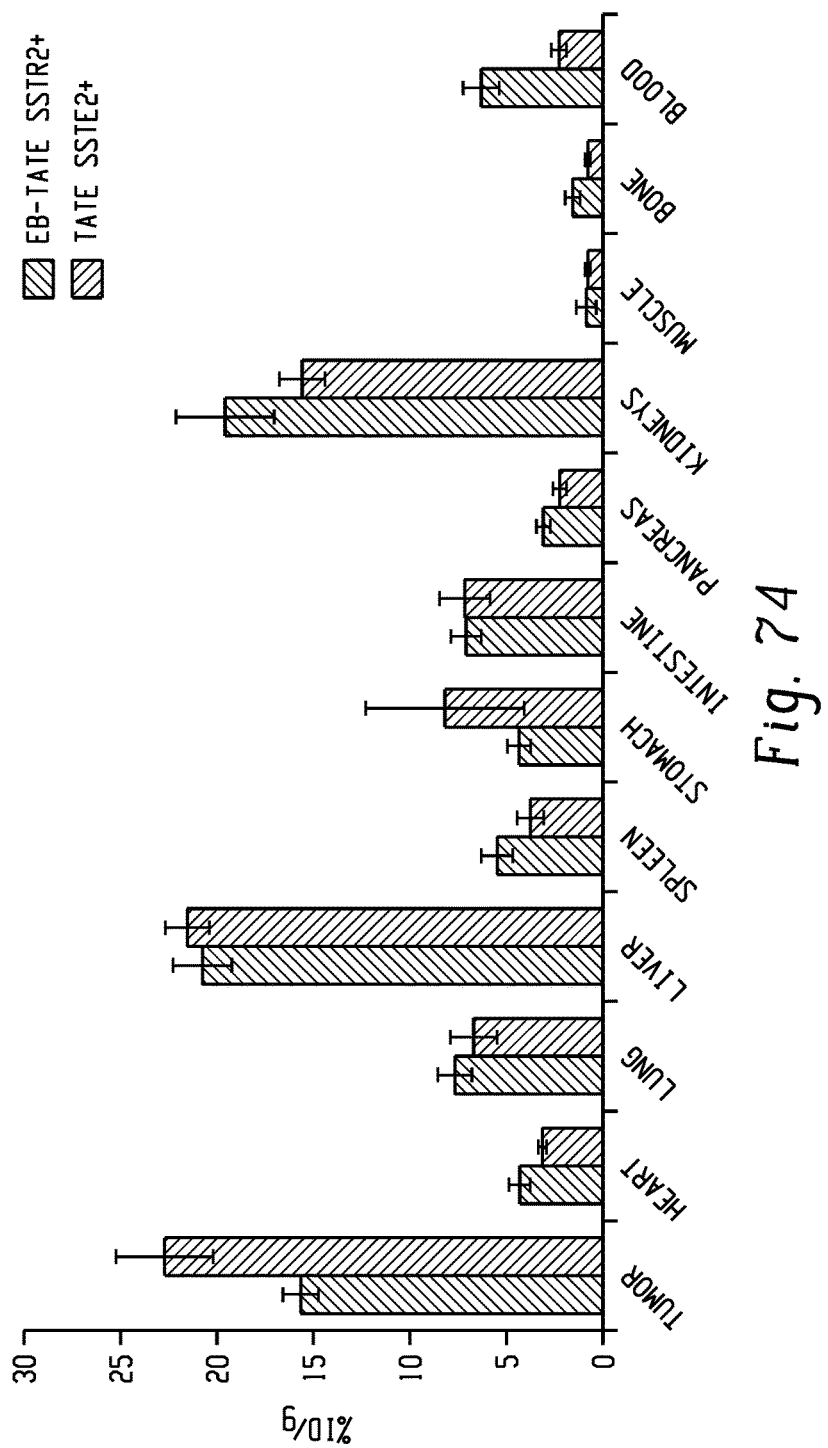
FIG. 74 is a diagram showing $^{64}$Cu-EB-CTT biodistribution in PC3-PIP xenograft.

PSMA expression in four cell lines and PC3-PIP (transfected cell, have high PSMA expression were tested. LNCaP has medium PSMA expression and PC3 and CW22Rv1 which have low PSMA expression (FIG. 69). Cell uptake/internalization showed that PC3-PIP have the highest uptake among the four cell lines with most of it internalized at all time points (FIGS. 70A-D). PET studies also showed high tumor accumulation for PC3-PIP in comparison to PC3 and Cw22RV1 xenografts (FIGS. 71, 72A-B, and 73-74). LNCaP xenografts need to be evaluated as well.

In conclusion, conjugation of our novel "add-on" molecules to TATE peptide and CTT1298 small molecule significantly improved both imaging and radiotherapy with these agents. These results show that our "add-on" improves blood half-life and tumor uptake, and can transform drugs into theranostic entities.

The present inventive concept has been described in terms of exemplary principles and embodiments, but those skilled in the art will recognize that variations may be made and equivalents substituted for what is described without departing from the scope and spirit of the disclosure as defined by the following claims.

What is claimed is:

1. A compound of Formula I or a pharmaceutically acceptable ester, amide, solvate, or salt thereof, or a salt of such an ester or amide or a solvate of such an ester amide or salt, Formula I

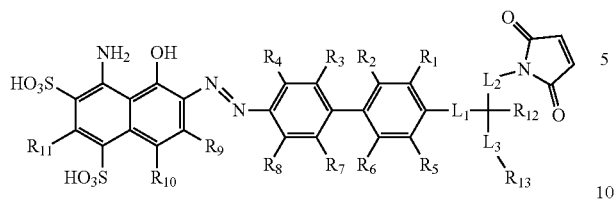

wherein:
$R_1, R_2, R_3, R_4, R_5, R_6, R_7, R_8, R_9, R_{10}$, and $R_{11}$ are chosen independently from hydrogen, halogen, hydroxyl, cyano, $C_1$-$C_6$alkoxy, $C_1$-$C_6$haloalkyl, and $C_1$-$C_6$haloalkoxy;
$R_{12}$ is hydrogen, $C_1$-$C_6$alkyl, or $C_1$-$C_6$haloalkyl;
$L_1$ is $(CH_2)_m$— wherein m is an integer from 0 to 12, wherein each $CH_2$ can be individually replaced with —O—, —NH(CO)—, or —(CO)—NH—, providing no two adjacent $CH_2$ groups are replaced;
$L_2$ is —$(CH_2)_m$— wherein n is an integer from 0 to 12, wherein each $CH_2$ can be individually replaced with —O—, —NH(CO)—, or —(CO)—NH—, providing no two adjacent $CH_2$ groups are replaced;
$L_3$ is —$(CH_2)_p$— wherein p is an integer from 0 to 12, wherein each $CH_2$ can be individually replaced with —O—, —NH(CO)—, or —(CO)—NH—, providing no two adjacent $CH_2$ groups are replaced; and
$R_{13}$ is a chelating group.

2. The compound of claim 1, wherein $L_1$ is —NH(CO)—.
3. The compound of claim 1, wherein $L_2$ is —$(CH_2)_4$—NH(CO)—$(CH_2)_2$—.
4. The compound of claim 1, wherein $L_3$ is NH(CO)$CH_2$—.
5. The compound of claim 1, wherein $R_1$ and $R_4$ are chosen independently from halogen, hydroxyl, cyano, $C_1$-$C_6$alkyl, $C_1$-$C_6$alkoxy, $C_1$-$C_6$haloalkyl, and $C_1$-$C_6$haloalkoxy.
6. The compound of claim 1, wherein $R_2, R_3, R_5, R_6, R_7, R_8, R_9, R_{10}$, and $R_{11}$ are each hydrogen.
7. The compound of claim 5, wherein $R_1$ and $R_4$ are chosen independently from $C_1$-$C_6$alkyl.
8. The compound of claim 7, wherein $R_1$ and $R_4$ are each methyl.
9. The compound of claim 1, wherein $R_{12}$ is hydrogen.
10. The compound of claim 1, wherein $R_{13}$ is selected from

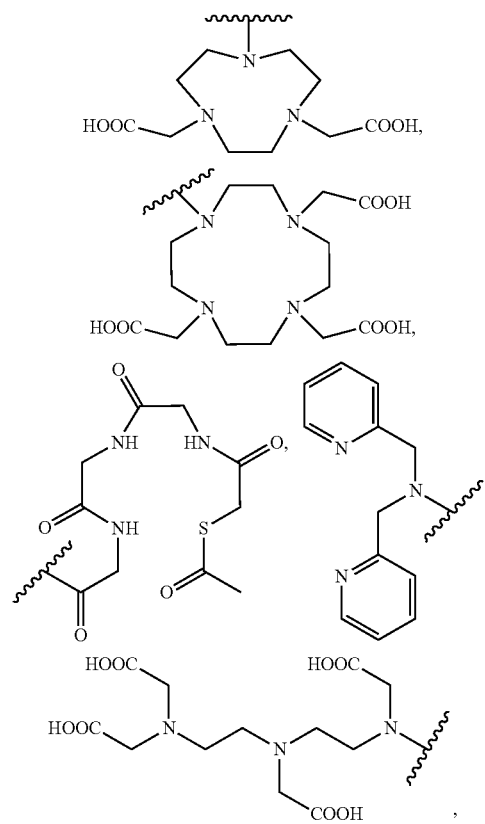

a crown ether, a cyclodextrin, or a porphyrin.

11. The compound of claim 1, wherein the compound of Formula I is a compound of Formula II:

Formula II

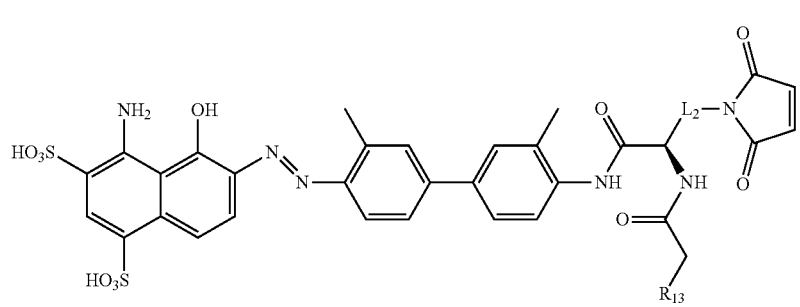

wherein:

$L_2$ is —$(CH_2)_n$— wherein n is an integer from 0 to 12, wherein each $CH_2$ can be individually replaced with —O—, —NH(CO)—, or —(CO)—NH—, providing no two adjacent $CH_2$ groups are replaced; and
$R_{13}$ is a chelating group.

12. The compound of claim 11, wherein $L_2$ is —$(CH_2)_4$—NH(CO)—$(CH_2)_2$—; and $R_{13}$ is selected from

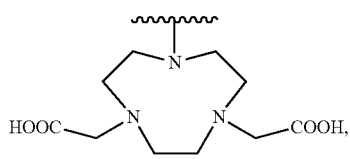

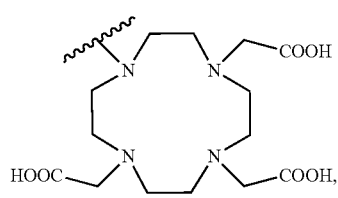

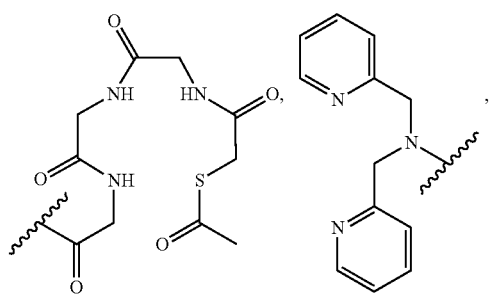

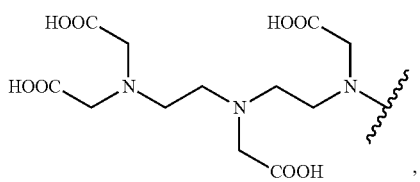

a crown ether, a cyclodextrin, or a porphyrin.

13. A compound of Formula III or a pharmaceutically acceptable ester, amide, solvate, or salt thereof, or a salt of such an ester or amide or a solvate of such an ester amide or salt, wherein:

$R_1$, $R_2$, $R_3$, $R_4$, $R_5$, $R_6$, $R_7$, $R_8$, $R_9$, $R_{10}$, and $R_{11}$ are chosen independently from hydrogen, halogen, hydroxyl, cyano, $C_1$-$C_6$alkoxy, $C_1$-$C_6$haloalkyl, and $C_1$-$C_6$haloalkoxy;

$R_{12}$ is hydrogen, $C_1$-$C_6$alkyl, or $C_1$-$C_6$haloalkyl;

$R_{14}$ is a peptide;

$L_1$ is —$(CH_2)_m$— wherein m is an integer from 0 to 12, wherein each $CH_2$ can be individually replaced with —O—, —NH(CO)—, or —(CO)—NH—, providing no two adjacent $CH_2$ groups are replaced;

$L_2$ is —$(CH_2)_n$— wherein n is an integer from 0 to 12, wherein each $CH_2$ can be individually replaced with —O—, —NH(CO)—, or —(CO)—NH—, providing no two adjacent $CH_2$ groups are replaced;

$L_3$ is —$(CH_2)_p$— wherein p is an integer from 0 to 12, wherein each $CH_2$ can be individually replaced with —O—, —NH(CO)—, or —(CO)—NH—, providing no two adjacent $CH_2$ groups are replaced; and $L_4$ is —$(CH_2)_q$— wherein q is an integer from 0 to 12, wherein each $CH_2$ can be individually replaced with —O—, —NH(CO)—, or —(CO)—NH—, providing no two adjacent $CH_2$ groups are replaced; and $R_{13}$ is a chelating group.

14. The compound of claim 13 wherein $L_1$ is —NH(CO)—, $R_1$ and $R_4$ are each methyl, and $R_2$, $R_3$, $R_5$, $R_6$, $R_7$, $R_8$, $R_9$, $R_{10}$, $R_{11}$, and $R_{12}$ are each hydrogen.

15. The compound of claim 13, wherein $R_{14}$ is a therapeutic peptide.

16. The compound of claim 13, wherein $R_{14}$ is a peptide capable of binding to a target cell or tissue.

17. The compound of claim 16, wherein $R_{14}$ is capable of binding to a tumor.

18. The compound of claim 16, wherein $R_{14}$ is selected from interferon alpha, GCSF, octreotate, bombesin, RGD, alpha-MSH, CTT1298, or aptamers.

19. The compound of claim 18, wherein $R_{14}$ is the cyclic peptide Arg-Gly-Asp-Phe-Lys.

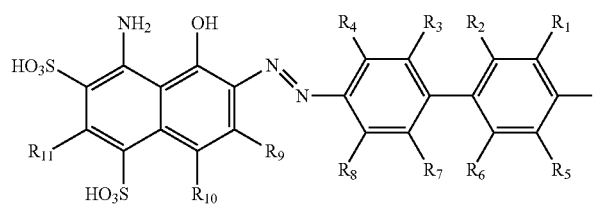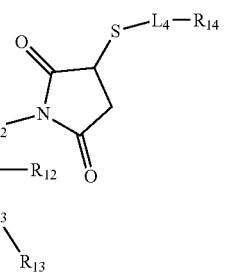

Formula III

20. The compound of claim 16 wherein $R_{14}$ is

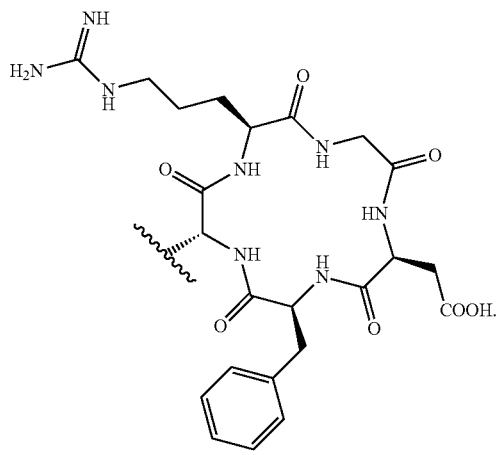 [SMILES: *[C@H]1NC(=O)[C@H](Cc2ccccc2)NC(=O)[C@H](CC(=O)O)NC(=O)CNC(=O)[C@H](CCCNC(=N)N)NC1=O]

21. The compound of claim 16, wherein $R_{14}$ further comprises a radionuclide.

22. The compound of claim 21, wherein the radionuclide is $^{18}F$, $^{76}Br$, $^{124}I$, $^{125}I$, or $^{131}I$.

23. The compound of claim 21, wherein $R_{14}$ is

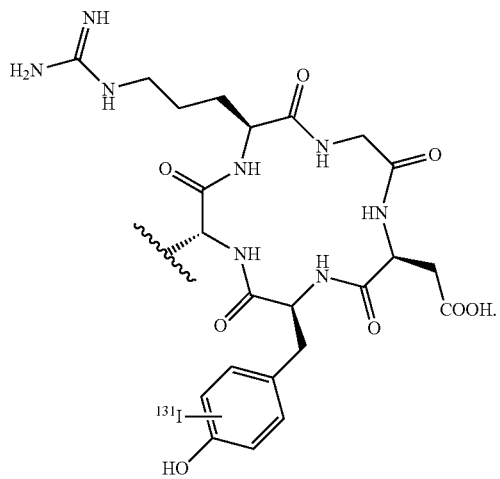

24. The compound of claim 13, wherein $R_{13}$ is selected from

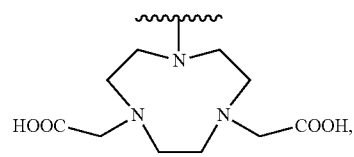

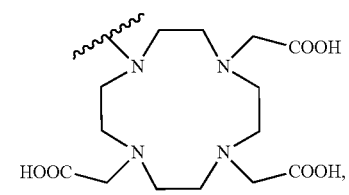

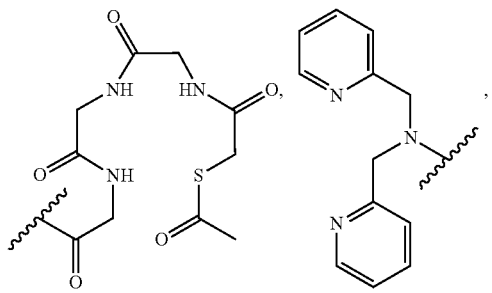

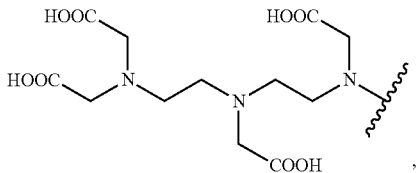

a crown ether, a cyclodextrin, or a porphyrin.

25. The compound of claim 13, wherein $R_{13}$ further comprises a radionuclide.

26. The compound of claim 25, wherein the radionuclide is $^{64}Cu$, $^{67}Cu$, $^{90}Y$, $_{86}Y$, $^{111}In$, $^{186}Re$, $^{188}Re$, $^{89}Zr$, $^{99}Tc$, $^{153}Sm$, $^{213}Bi$, $^{225}Ac$, or $^{223}Ra$.

27. The compound of claim 13, wherein the compound of Formula III is a compound of Formula IV:

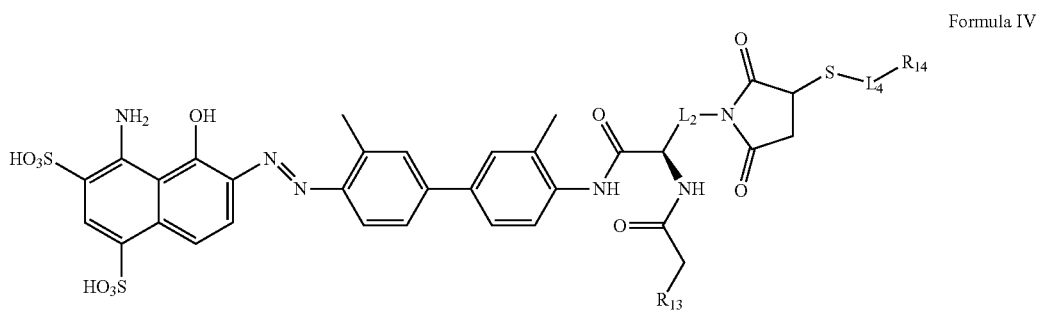

Formula IV wherein:

$R_{14}$ is a peptide;

$L_2$ is —$(CH_2)_n$— wherein n is an integer from 0 to 12, wherein each $CH_2$ can be individually replaced with —O—, —NH(CO)—, or —(CO)—NH—, providing no two adjacent $CH_2$ groups are replaced;

$L_4$ is —$(CH_2)_q$— wherein q is an integer from 0 to 12, wherein each $CH_2$ can be individually replaced with —O—, —NH(CO)—, or —(CO)—NH—, providing no two adjacent $CH_2$ groups are replaced; and $R_{13}$ is a chelating group.

28. The compound of claim 27, wherein $R_{14}$ is a peptide capable of binding to a target cell or tissue.

29. The compound of claim 28, wherein $R_{10}$ is capable of binding to a tumor.

30. The compound of claim 27, wherein $R_{14}$ is the cyclic peptide Arg-Gly-Asp-Phe-Lys.

31. The compound of claim 27 wherein $R_{14}$ is

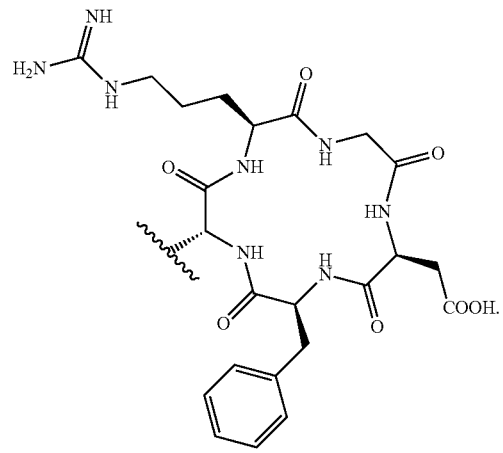 [SMILES: *[C@H]1NC(=O)[C@H](Cc2ccccc2)NC(=O)[C@H](CC(=O)O)NC(=O)CNC(=O)[C@H](CCCNC(=N)N)NC1=O]

32. The compound of claim 27, wherein
$L_2$ is —$(CH_2)_4$—NH(CO)—$(CH_2)_2$—; and
$L_4$-$R_{14}$ is

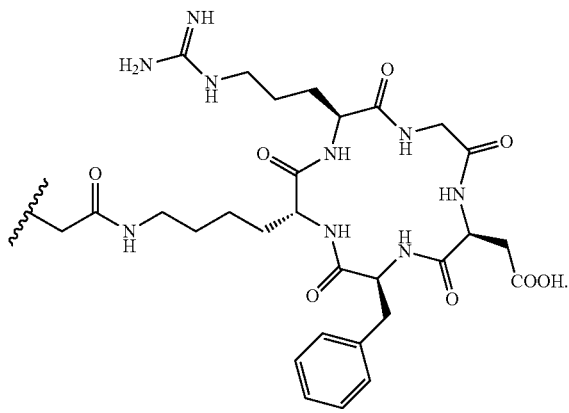 [SMILES: *CC(=O)NCCCC[C@H]1NC(=O)[C@H](Cc2ccccc2)NC(=O)[C@H](CC(=O)O)NC(=O)CNC(=O)[C@H](CCCNC(=N)N)NC1=O]

33. The compound of claim 27, wherein $R_{10}$ further comprises a radionuclide.

34. The compound of claim 33, wherein the radionuclide is $^{18}F$, $^{76}Br$, $^{124}I$, $^{125}I$, or $^{131}I$.

35. The compound of claim 33, wherein $R_{14}$ is

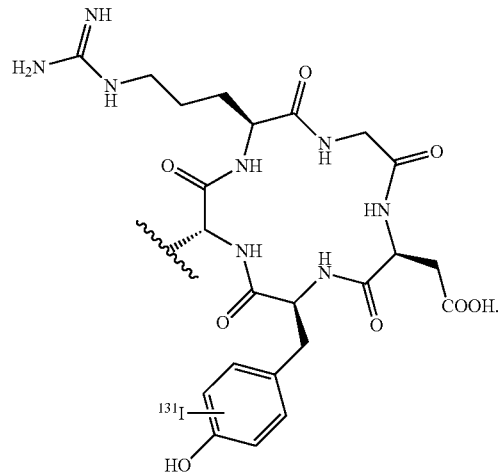

36. The compound of claim 27, wherein $R_{13}$ is selected from

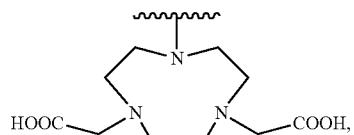

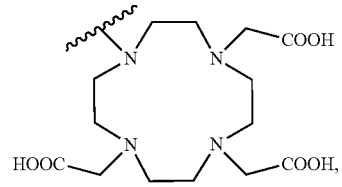

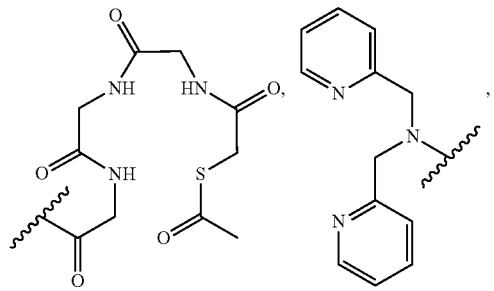

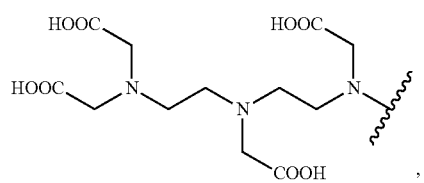

a crown ether, a cyclodextrin, or a porphyrin.

37. The compound of claim 27, wherein $R_{13}$ further comprises a radionuclide.

38. The compound of claim 37, wherein the radionuclide is $^{64}$Cu, $^{67}$Cu, $^{90}$Y, $^{86}$Y, $^{111}$In, $^{186}$Re, $^{188}$Re, $^{89}$Zr, $^{99}$Tc, $^{153}$Sm, $^{213}$Bi, $^{225}$Ac, or $^{223}$Ra.

39. A pharmaceutical composition comprising the compound of claim 13, together with a pharmaceutically acceptable carrier.

40. The composition of claim 39, wherein the pharmaceutically acceptable carrier is selected from the group consisting of binders, buffering agents, coloring agents, diluents, disintegrants, emulsifiers, flavorants, glidants, lubricants, preservatives, stabilizers, surfactants, tableting agents, wetting agents, and combinations thereof.

41. A method of treating or diagnosing cancer in a mammal, comprising administering to said mammal a therapeutically effective amount of a compound of claim 13, optionally in combination with one or more additional active ingredients.

42. The method of claim 41, wherein the one or more additional active ingredients are selected from the group consisting of doxorubicin, paclitaxel, docetaxel, cisplatin, camptothecin, temozolomide, avastin, Herceptin, Erbitux, and combinations thereof.

43. The compound of claim 16 wherein $R_{14}$ is

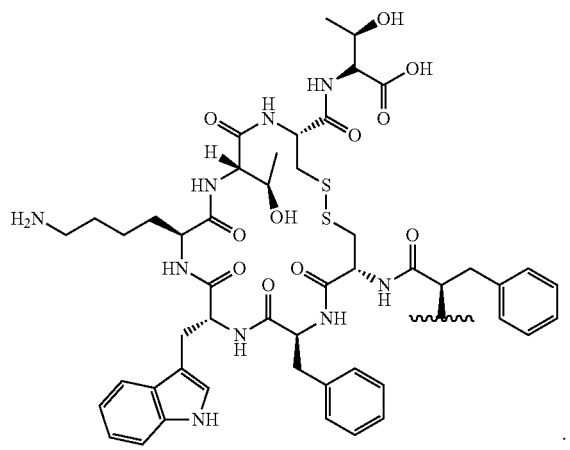

44. The compound of claim 27 wherein $R_{14}$ is

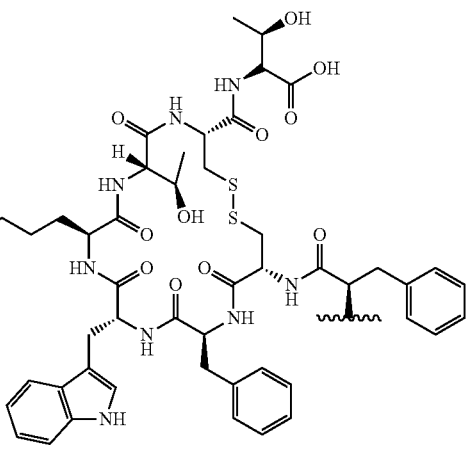

45. The compound of claim 16 wherein $R_{14}$ is

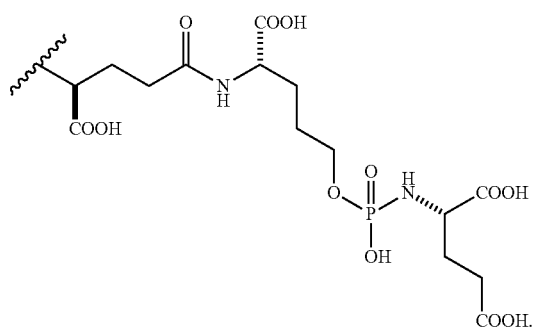

46. The compound of claim 27 wherein $R_{14}$ is

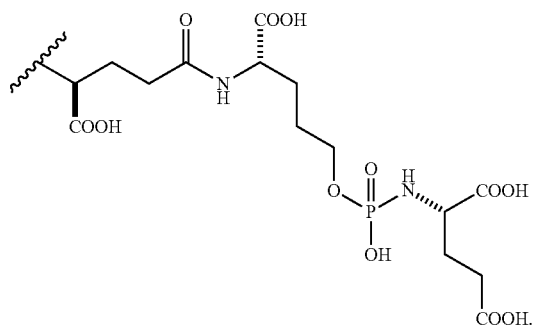

* * * * *